(12) United States Patent
Cao et al.

(10) Patent No.: US 11,104,732 B2
(45) Date of Patent: Aug. 31, 2021

(54) REDUCING IMMUNE INHIBITION INDUCED BY SIGLEC-15

(71) Applicant: Innovative Cellular Therapeutics Holdings, Ltd., Grand Cayman (KY)

(72) Inventors: Zhiyuan Cao, Shanghai (CN); Chengfei Pu, Shanghai (CN); Lei Xiao, Rockville, MD (US)

(73) Assignee: Innovative Cellular Therapeutics Holdings, Ltd.

(*) Notice: Subject to any disclaimer, the term of this patent is extended or adjusted under 35 U.S.C. 154(b) by 0 days.

(21) Appl. No.: 16/856,808

(22) Filed: Apr. 23, 2020

(65) Prior Publication Data
US 2020/0339683 A1    Oct. 29, 2020

Related U.S. Application Data

(60) Provisional application No. 62/845,631, filed on May 9, 2019, provisional application No. 62/837,932, filed on Apr. 24, 2019, provisional application No. 62/837,920, filed on Apr. 24, 2019.

(51) Int. Cl.
*C07K 16/28* (2006.01)
*C12N 5/0783* (2010.01)
*C07K 14/725* (2006.01)

(52) U.S. Cl.
CPC ...... *C07K 16/2803* (2013.01); *C07K 14/7051* (2013.01); *C12N 5/0636* (2013.01); *C07K 2317/24* (2013.01); *C07K 2317/622* (2013.01); *C07K 2319/02* (2013.01); *C07K 2319/03* (2013.01); *C07K 2319/33* (2013.01)

(58) Field of Classification Search
CPC ............ C07K 16/2803; C07K 14/7051; C07K 2317/24; C07K 2317/622; C07K 2319/02; C07K 2319/03; C07K 2319/33; C12N 5/0636
See application file for complete search history.

(56) References Cited

U.S. PATENT DOCUMENTS

| | | | |
|---|---|---|---|
| 2015/0037356 A1* | 2/2015 | Elvin | C07K 16/30 424/174.1 |
| 2018/0273601 A1* | 9/2018 | Adusumilli | A61K 39/0011 |

OTHER PUBLICATIONS

Cherassky et al. "Human CAR T cells with cell-intrinsic PD-1 checkpoint blockade resist tumor-mediated inhibition", J Clin Invest. Aug. 1, 2016; 126(8):3130-44 (Year: 2016).*
Shitara et al. "Regulatory T cells: a potential target in cancer immunotherapy", Ann N Y Acad Sci. Apr. 2018; 1417(1):104-115. (Year: 2018).*

* cited by examiner

*Primary Examiner* — Sharon X Wen
*Assistant Examiner* — Peter Johansen
(74) *Attorney, Agent, or Firm* — Lee & Hayes, P.C.

(57) ABSTRACT

The present disclosure relates to a modified cell comprising a polynucleotide encoding a secretable scFv binding SIGLEC-15 and/or encoding a dominant negative form of CD44. In embodiments, the modified cell further comprises an antigen-binding molecule, which for example, is a CAR comprising an antigen-binding domain, a transmembrane domain, and an intracellular signaling domain.

22 Claims, 12 Drawing Sheets
Specification includes a Sequence Listing.

REDUCING IMMUNE INHIBITION INDUCED BY SIGLEC-15

CROSS REFERENCE TO RELATED PATENT APPLICATIONS

This application claims the benefit of U.S. Provisional Application 62/837,932, filed Apr. 24, 2019, U.S. Provisional Application 62/837,920, filed Apr. 24, 2019, and U.S. Provisional Application 62/845,631, filed May 9, 2019, which are hereby incorporated by reference in their entirety.

SEQUENCE LISTING INFORMATION

A computer readable textfile, entitled "Sequence Listing.txt," created on or about Apr. 22, 2020, with a file size of about 312 KB, contains the sequence listing for this application and is hereby incorporated by reference in its entirety.

TECHNICAL FIELD

The present disclosure relates to compositions of agent-sensing immune cells and uses thereof in the treatment of diseases, including cancer.

BACKGROUND

T cell therapies have demonstrated efficacy and curative potential for treating cancers. For example, Chimeric Antigen Receptor (CAR) T cell therapy has achieved good clinical efficacy in cancer, such as B-ALL/CLL/lymphoma. However, use of these therapies has been limited by the presence of an immunosuppressive microenvironment. The immunosuppressive microenvironment includes immune inhibition on, for example, T cells, which is induced by immune inhibitors such as PD1. PD-1 is a negative coregulatory receptor on T cells and antigen-presenting cells. The PD-L1 is expressed by several cell types (e.g., tumor cells and other tissue cells), and appears to be dynamically regulated by the immune microenvironment. Therefore, there is a need to address immune tolerance induced by these immune inhibitors to improve the efficacy of T cell therapies.

SUMMARY

Embodiments relate to a modified cell comprising a polynucleotide encoding a secretable scFv binding SIGLEC-15 and/or encoding a dominant negative form of CD44. In embodiments, the modified cell comprises an antigen-binding molecule, which, for example, is a CAR comprising an antigen-binding domain, a transmembrane domain, and an intracellular signaling domain. Embodiments relate to a fusion protein comprising an scFv binding SIGLEC-15, a linker, an extracellular domain, a transmembrane domain, and a cytoplasmic domain, wherein the transmembrane domain is selected from a group consisting of a transmembrane domain of a receptor of IL15, IL2, IL7, IL6, IL12, IL18, IL21, IL23, IL 33, TNFα, TNFβ, IFNα, and IFNβ, and the cytoplasmic domain is selected from a group consisting of a cytoplasmic domain of receptor of the receptor of IL15, IL2, IL7, IL6, IL12, IL18, IL21, IL23, IL 33, TNFα, TNFβ, IFNα, and IFNβ, and the extracellular domain is selected from a group consisting of an extracellular domain of the receptor of IL15, IL2, IL7, IL6, IL12, IL18, IL21, IL23, IL 33, TNFα, TNFβ, IFNα, and IFNβ.

Embodiments also relate to a fusion protein comprising an extracellular domain, a transmembrane domain, and a cytoplasmic domain, the transmembrane domain being or comprising the transmembrane domain of Notch.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
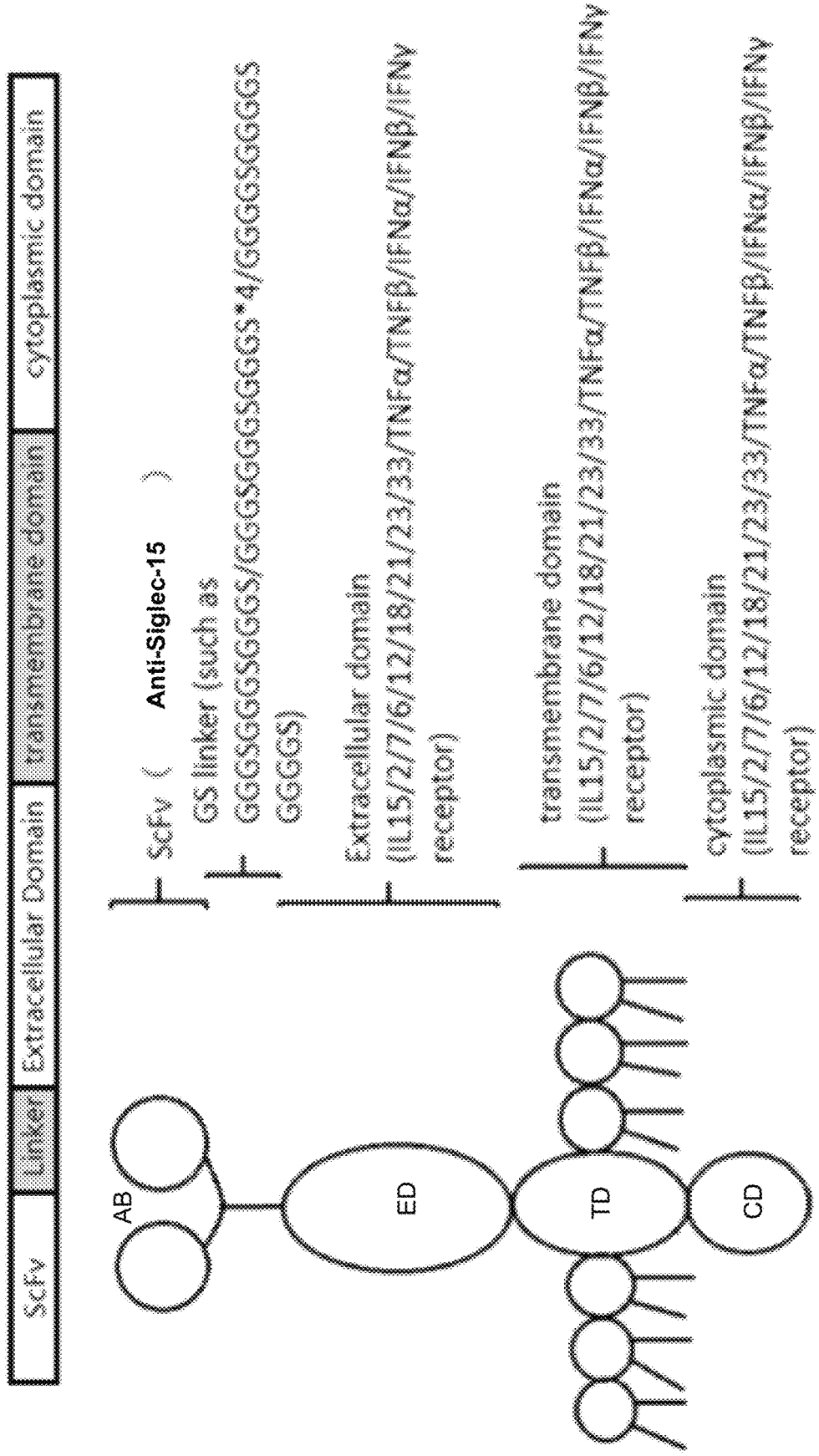
FIG. 1 shows a schematic diagram of an exemplary fusion protein.
Figure 2:
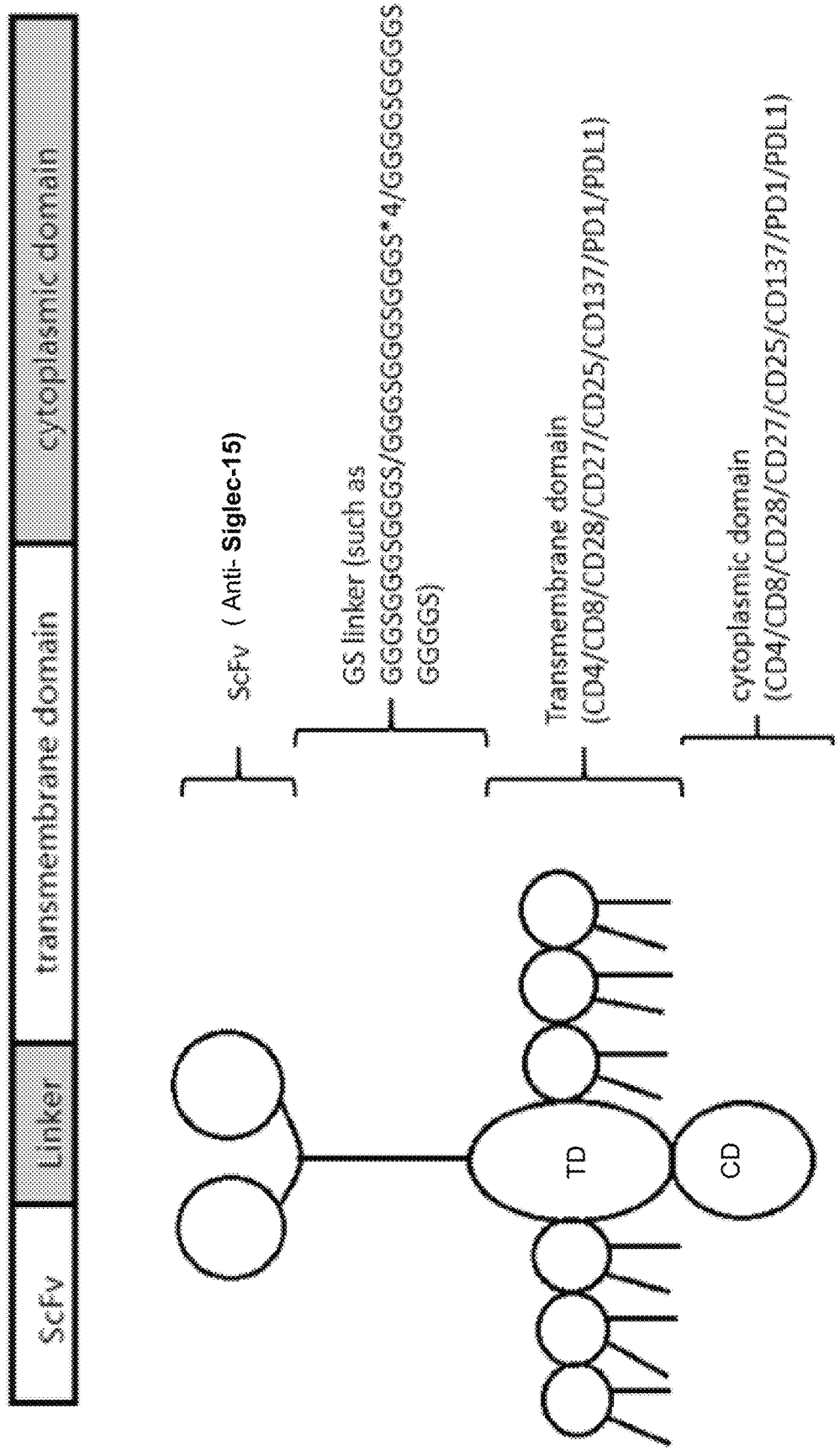
FIG. 2 shows a schematic diagram of another exemplary fusion protein.
Figure 3:
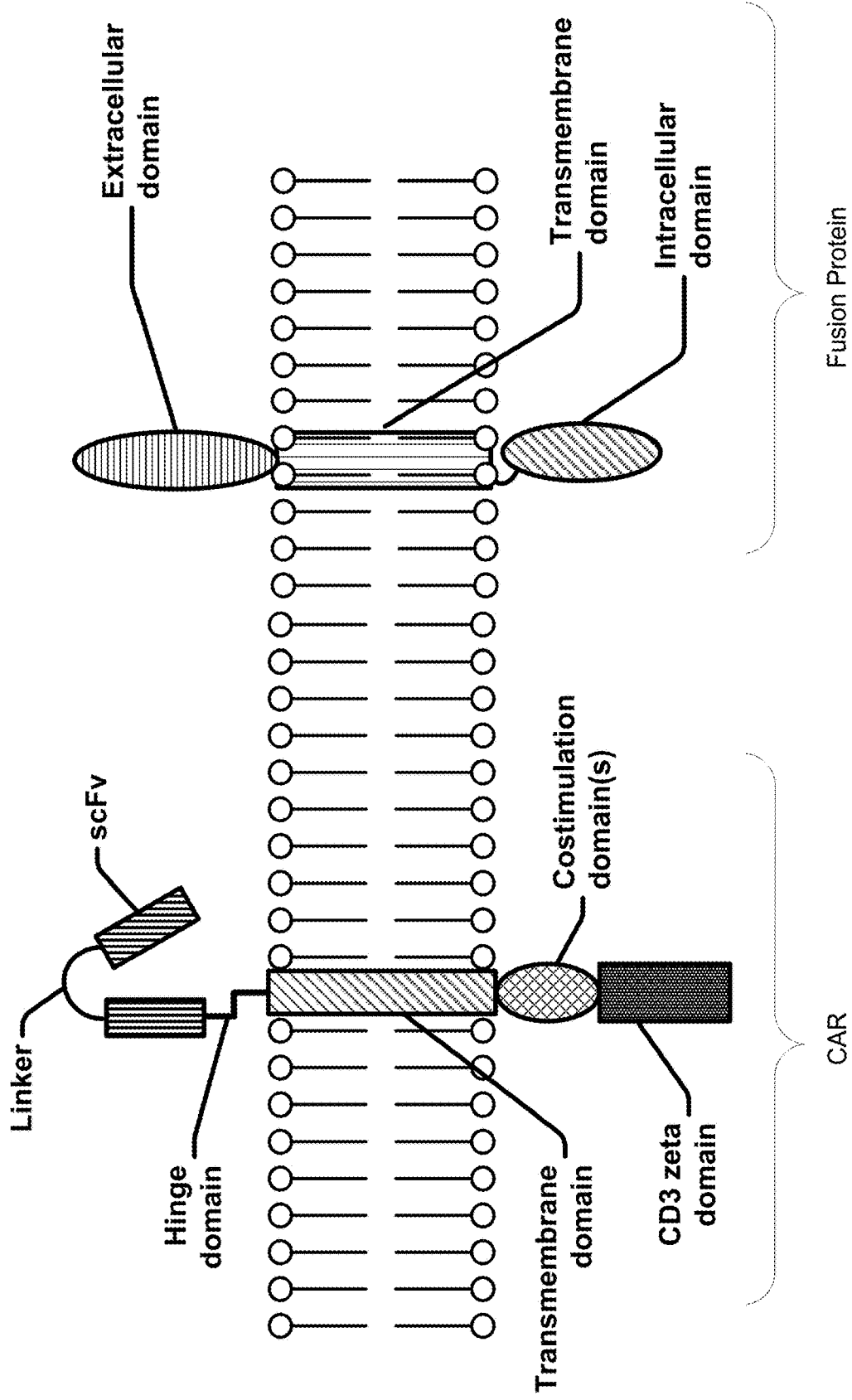
FIG. 3 shows a schematic diagram of an exemplary CAR molecule and a fusion protein.
Figure 4:
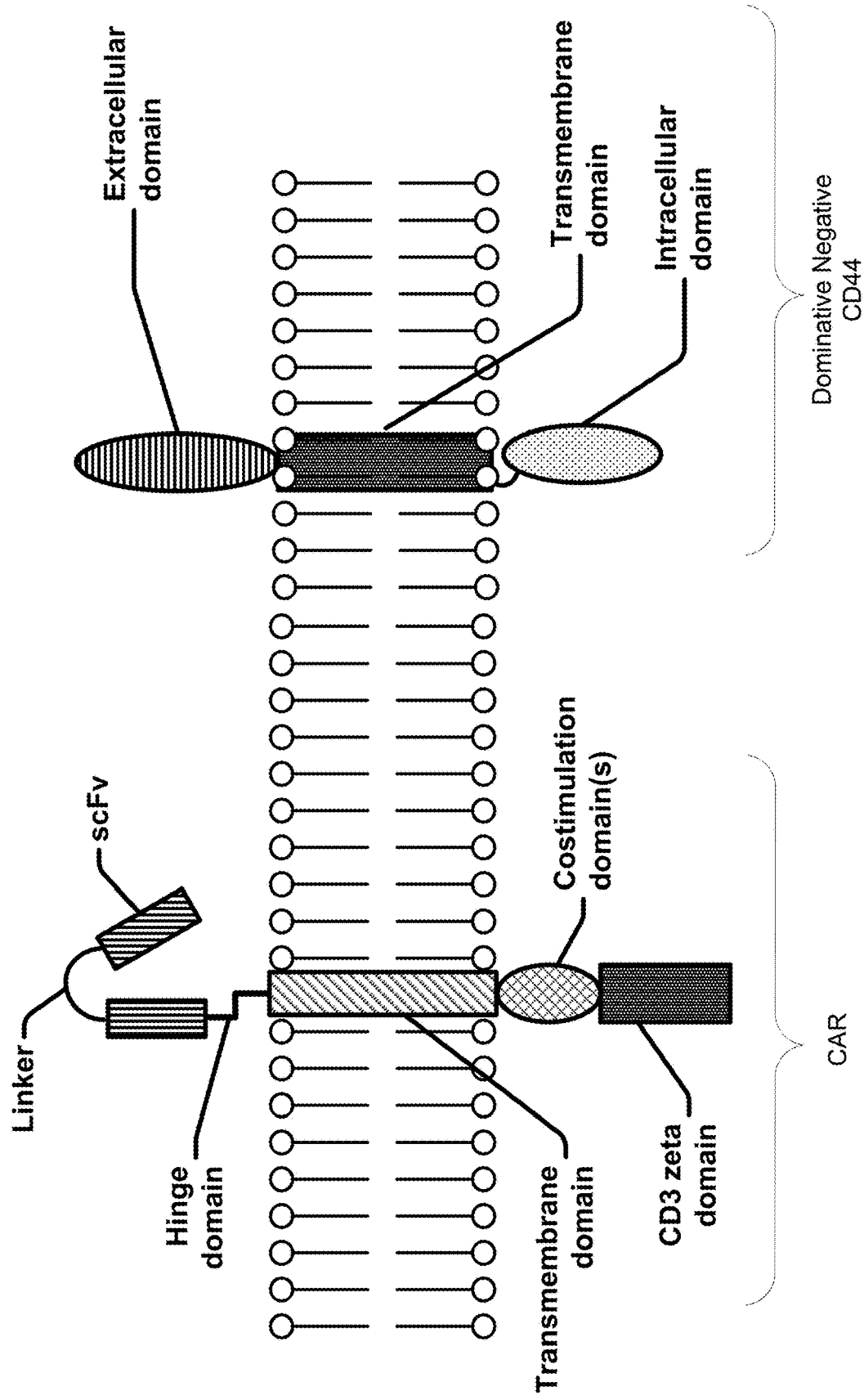
FIG. 4 shows a schematic diagram of an exemplary CAR molecule and a dominant negative CD44.
Figure 5:
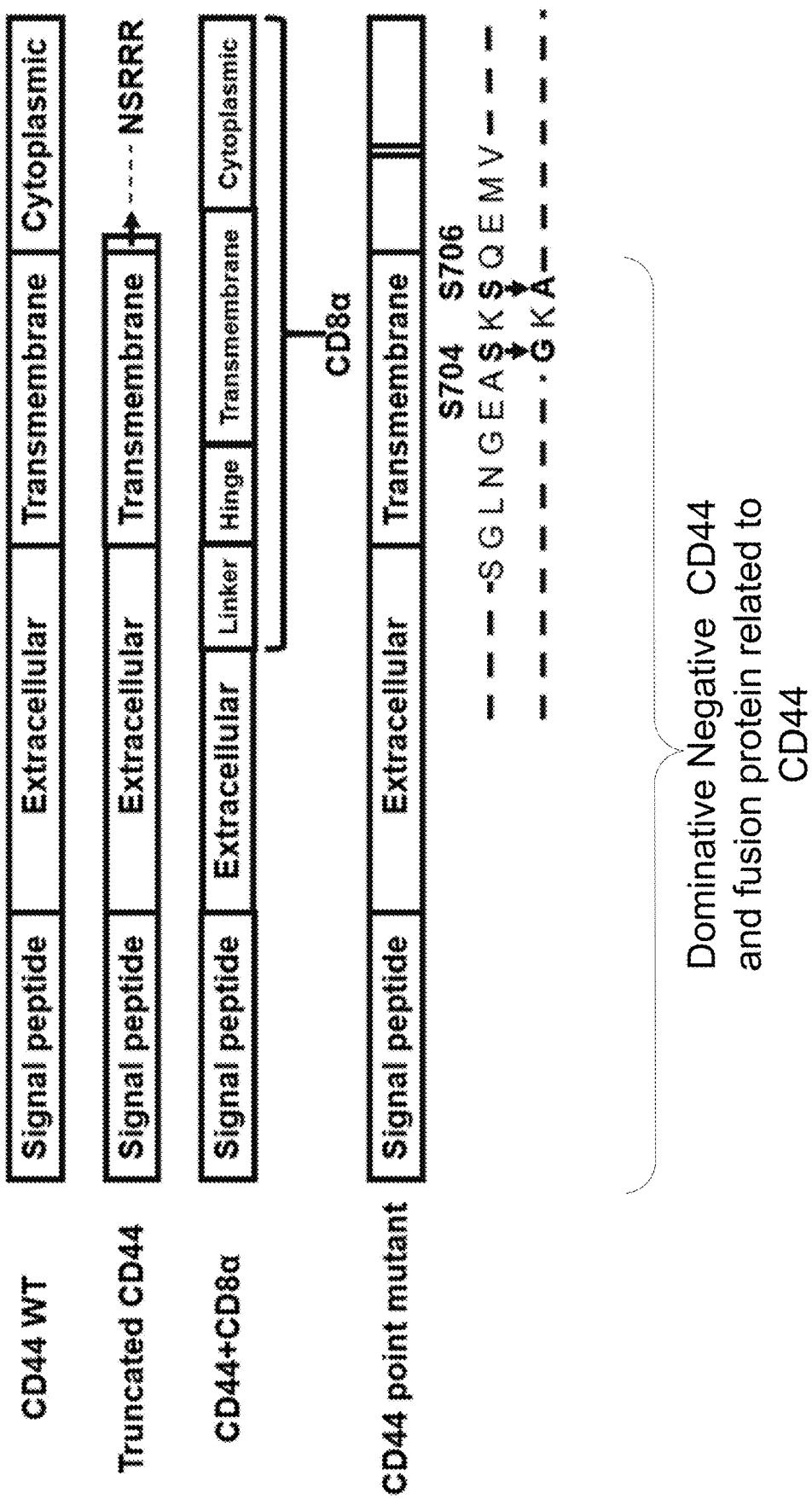
FIG. 5 shows schematic diagrams of exemplary constructs of dominant negative CD44.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and F(ab')$_2$ fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen-binding or variable region of the antibody. Other examples of antibody fragments include Fab, Fab', F(ab')$_2$, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute amino acid residues for antigen-binding and confer antigen-binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and A light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumors in the first place.

The term "auto-antigen" refers to an endogenous antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject that is subsequently re-introduced into the same subject.

The term "allogeneic" is used to describe a graft derived from a different subject of the same species. As an example, a donor subject may be related or unrelated to the recipient subject, but the donor subject has immune system markers that are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein, or (b) a peptide or polypeptide having an amino acid sequence that is substantially identical to a sequence of amino acids in a reference peptide or protein.

The term "co-stimulatory ligand," refers to a molecule on an antigen-presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor, and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules.

The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression" refers to the transcription and/or translation of a particular nucleotide sequence driven by its promoter.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables integration of the genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence, or a ribosome binding site is operably linked to a coding sequence if it is positioned so as to facilitate translation.

The term "under transcriptional control" refers to a promoter being operably linked to and in the correct location and orientation in relation to a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having a solid tumor or a hematological malignancy characterized by overexpression of the tumor antigen can be determined by standard assays known in the art.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, solid tumor antigens are also expressed at low levels on healthy tissue. Examples of solid tumor antigens and their related disease tumors are provided in Table 1.

TABLE 1

| Solid Tumor antigen | Disease tumor |
|---|---|
| PRLR | Breast Cancer |
| CLCA1 | colorectal Cancer |
| MUC12 | colorectal Cancer |
| GUCY2C | colorectal Cancer |
| GPR35 | colorectal Cancer |
| CR1L | Gastric Cancer |
| MUC 17 | Gastric Cancer |

TABLE 1-continued

| Solid Tumor antigen | Disease tumor |
|---|---|
| TMPRSS11B | esophageal Cancer |
| MUC21 | esophageal Cancer |
| TMPRSS11E | esophageal Cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC-15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesotelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomasb |
| EpCAM | Carcinomasa |
| EGFRvIII | Glioma—Glioblastoma |
| EGFR | Glioma—NSCL cancer |
| tMUC 1 | Cholangiocarcinoma, Pancreatic cancer, Breast Cancer |
| PSCA | pancreas, stomach, or prostate cancer |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein and refer to any human, or animal, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals, such as dogs, cats, mice, rats, and transgenic species thereof.

A subject in need of treatment or in need thereof includes a subject having a disease, condition, or disorder that needs to be treated. A subject in need thereof also includes a subject that needs treatment for prevention of a disease, condition, or disorder.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double-stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In embodiments, a polypeptide variant is distinguished from a reference polypeptide by one or more substitutions, which may be conservative or non-conservative. In embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control (regulatory) sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.05 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures.

The term "stimulatory molecule" refers to a molecule on a T cell that specifically binds a cognate stimulatory ligand present on an antigen presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to a treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, etc., of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as, for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

A "chimeric antigen receptor" (CAR) molecule is a recombinant polypeptide including at least an extracellular domain, a transmembrane domain and a cytoplasmic domain or intracellular domain. In embodiments, the domains of the CAR are on the same polypeptide chain, for example a chimeric fusion protein. In embodiments, the domains are on different polypeptide chains, for example the domains are not contiguous.

The extracellular domain of a CAR molecule includes an antigen-binding domain. The antigen-binding domain is for expanding and/or maintaining the modified cells, such as a CAR T cell or for killing a tumor cell, such as a solid tumor. In embodiments, the antigen-binding domain for expanding and/or maintaining modified cells binds an antigen, for example, a cell surface molecule or marker, on the surface of a WBC. In embodiments, the WBC is a granulocyte, monocyte and or lymphocyte. In embodiments, the WBC is a lymphocyte, for example, a B cell. In embodiments, the WBC is a B cell. In embodiments, the cell surface molecule of a B cell includes CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the B cell is CD19, CD20, CD22, or BCMA. In embodiments, the cell surface molecule of the B cell is CD19.

Modified cells (e.g., T-cells and NK cells) may be derived from a stem cell. The stem cells may be adult stem cells, embryonic stem cells, more particularly non-human stem cells, cord blood stem cells, progenitor cells, bone marrow stem cells, induced pluripotent stem cells, totipotent stem cells or hematopoietic stem cells. A modified cell may also be a dendritic cell, a NK-cell, a B-cell or a T-cell selected from the group consisting of inflammatory T-lymphocytes, cytotoxic T-lymphocytes, regulatory T-lymphocytes or helper T-lymphocytes. In another embodiment, Modified cells may be derived from the group consisting of CD4+T-lymphocytes and CD8+T-lymphocytes. Prior to expansion and genetic modification of the cells of the invention, a source of cells may be obtained from a subject through a variety of non-limiting methods. T cells may be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments of the present invention, any number of T cell lines available and known to those skilled in the art, may be used. In embodiments, modified cells may be derived from a healthy donor, from a patient diagnosed with cancer or from a patient diagnosed with an infection. In embodiments, modified cell is part of a mixed population of cells which present different phenotypic characteristics.

The term "stem cell" refers to any of certain types of cell which have the capacity for self-renewal and the ability to differentiate into other kind(s) of cell. For example, a stem cell gives rise either to two daughter stem cells (as occurs in vitro with embryonic stem cells in culture) or to one stem cell and a cell that undergoes differentiation (as occurs e.g. in hematopoietic stem cells, which give rise to blood cells). Different categories of stem cell may be distinguished on the basis of their origin and/or on the extent of their capacity for differentiation into other types of cell. For example, stem cell may include embryonic stem (ES) cells (i.e., pluripotent stem cells), somatic stem cells, Induced pluripotent stem cells, and any other types stem cells.

The pluripotent embryonic stem cells may be found in the inner cell mass of a blastocyst and have high innate capacity for differentiation. For example, pluripotent embryonic stem cells may have the potential to form any type of cell in the body. When grown in vitro for long periods of time, ES cells maintain pluripotency: progeny cells retain the potential for multilineage differentiation.

Somatic stem cells may include the fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a limited range of types of cell and have been described as multipotent. The 'tissue-specific' stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells, etc.).

Induced pluripotent stem cells (i.e., iPS cells or iPSCs) may include a type of pluripotent stem cell artificially derived from a non-pluripotent cell (e.g., an adult somatic cell) by inducing a expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells may be made from adult stomach, liver, skin cells and blood cells.

In embodiments, the antigen-binding domain for killing a tumor, binds an antigen on the surface of a tumor, for example a tumor antigen or tumor marker. Tumor antigens are proteins that are produced by tumor cells that elicit an immune response, particularly T cell mediated immune responses. Tumor antigens are well known in the art and include, for example, tumor associated MUC1 (tMUC1), a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, surviving, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, CD19, and mesothelin. For example, when the tumor antigen is CD19, the CAR thereof can be referred to as CD19CAR, which is a CAR molecule that includes a antigen-binding domain that binds CD19.

In embodiments, the extracellular antigen-binding domain of a CAR includes at least one scFv or at least a single domain antibody. As an example, there can be two scFvs on a CAR. The scFv includes a light chain variable (VL) region and a heavy chain variable (VH) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the GS linker having the amino acid sequence $(GGGGS)_3$ (SEQ ID NO: 120), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides and preferably comprised of about 20 or fewer amino acid residues. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

The cytoplasmic domain of the CAR molecules described herein includes one or more co-stimulatory domains and one or more signaling domains. The co-stimulatory and signaling domains function to transmit the signal and activate molecules, such as T cells, in response to antigen-binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule. In embodiments, the co-stimulatory molecules are cell surface molecules (other than antigens receptors or their ligands) that are required for activating a cellular response to an antigen.

In embodiments, the co-stimulatory domain includes the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds with CD83, or any combination thereof. In embodiments, the signaling domain includes a CD3 zeta domain derived from a T cell receptor.

The CAR molecules described herein also include a transmembrane domain. The incorporation of a transmembrane domain in the CAR molecules stabilizes the molecule. In embodiments, the transmembrane domain of the CAR molecules is the transmembrane domain of a CD28 or 4-1BB molecule.

Between the extracellular domain and the transmembrane domain of the CAR, there may be incorporated a spacer domain. As used herein, the term "spacer domain" generally means any oligo- or polypeptide that functions to link the transmembrane domain to the extracellular domain and/or the cytoplasmic domain on the polypeptide chain. A spacer domain may include up to 300 amino acids, preferably 10 to 100 amino acids, and most preferably 25 to 50 amino acids.

Embodiments relate to a modified cell comprising a binding molecule, and a dominant negative form of an inhibitory immune checkpoint molecule, wherein expression of the dominant negative form of the inhibitory immune checkpoint molecule is regulated by an inducible gene expression system. Embodiments relate to a polynucleotide encoding the binding molecule and/or the dominant negative form of the inhibitory immune checkpoint molecule. Embodiments relate to a pharmaceutical composition comprising the population of the modified cell. Embodiments relate to a kit comprising an effective amount of vector-free nucleic acids encoding the binding molecule and/or the dominant negative form of the inhibitory immune checkpoint molecule to render a population of immune cells specific for a tumor antigen expressed on the surface of the cells of a subject. Embodiments relate to a method of eliciting or enhancing T cell response, treating a subject in need thereof or enhancing cancer treatment thereof, the method comprising administering an effective amount of the composition or the kit to the subject.

Embodiments relate to a pharmaceutical composition comprising a population of the modified cells and a population of additional modified cells, wherein the modified cells bind a first antigen, and the additional modified cells bind a second antigen, which is different form the first antigen. In embodiments, the first antigen is a white blood cell antigen, and the second antigen is a solid tumor antigen. In embodiments, the second antigen is a white blood cell antigen, and the first antigen is a solid tumor antigen. In embodiments, the white blood cell antigen is CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the blood cell antigen is CD19, CD20, CD22, or BCMA. In embodiments, the solid tumor antigen is tMUC 1, PRLR, CLCA1, MUC12, GUCY2C, GPR35, CR1L, MUC 17, TMPRSS11B, MUC21, TMPRSS11E, CD207, SLC30A8, CFC1, SLC12A3, SSTR1, GPR27, FZD10, TSHR, SIGLEC-15, SLC6A3, KISS1R, CLDN18.2, QRFPR, GPR119, CLDN6, UPK2, ADAM12, SLC45A3, ACPP, MUC21, MUC16, MS4A12, ALPP, CEA, EphA2, FAP, GPC3, IL13-Rα2, Mesothelin, PSMA, ROR1, VEGFR-II, GD2, FR-α, ErbB2, EpCAM, EGFRvIII, B7-H3, or EGFR. In embodiments, the solid tumor antigen comprises tumor associated MUC1, ACPP, TSHR, GUCY2C, UPK2, CLDN18.2, PSMA, DPEP3, CXCRS, B7-H3, MUC16, CLDN6, Muc17, PRLR, and FZD10.

Embodiments relate to a method or use of polynucleotide, the method comprising providing a viral particle (e.g., AAV, lentivirus or their variants) comprising a vector genome, the vector genome comprising the polynucleotide encoding the binding molecule and/or the dominant negative form of the inhibitory immune checkpoint molecule, the polynucleotide operably linked to an expression control element conferring transcription of the polynucleotides; and administering an amount of the viral particle to a subject such that the polynucleotide is expressed in the subject, where the one or more molecules are overexpressed in cancer cells, associated with recruitment of immune cells, and/or associated with autoimmunity. In embodiments, the AAV preparation may include AAV vector particles, empty capsids and host cell impurities, thereby providing an AAV product substantially free of AAV empty capsids.

In embodiments, expression of the one or more molecules may be regulated by an inducible expression system. The inducible expression system allows for a temporal and spatial controlled activation and/or expression of genes. For example, Tetracycline-Controlled Transcriptional Activation is a method of inducible gene expression where transcription is reversibly turned on or off in the presence of the antibiotic tetracycline or one of its derivatives (e.g., doxycycline). For example, an inducible suicide gene expression system allows for a temporal and spatial controlled activation and/or expression of a suicide gene, which causes a cell to kill itself through apoptosis. In embodiments, the modified cells comprise a nucleic acid sequence encoding a reverse tetracycline transactivator (rtTA). In embodiments, expression of the one or more molecules is regulated by the rtTA, such that the one or more molecules are expressed in the presence of tetracycline. In embodiments, a concentration of tetracycline in the cell culture medium is not less than about 2 µg/ml. In embodiments, the tetracycline is selected from the group consisting of tetracycline, demeclocycline, meclocycline, doxycycline, lymecycline, methacycline, minocycline, oxytetracycline, rolitetracycline, and chlortetracycline. In embodiments, the tetracycline is doxycycline. In embodiments, the inducible suicide system is an HSV-TK system or an inducible caspase-9 system. In embodiments, the modified cells comprise a nucleic acid sequence encoding a suicide gene, such that when the modified cells are in the presence of a nucleoside analogue in a manner permitting expression of the suicide gene, to render the nucleoside analogue cytotoxic to the modified cells. In embodiments, the suicide gene is selected from the group consisting of thymidine kinase of herpes simplex virus, thymidine kinase of varicella zoster virus, and bacterial cytosine deaminase. In embodiments, the suicide gene is thymidine kinase of herpes simplex virus. In embodiments, the nucleoside analogue is selected from the group consisting of ganciclovir, acyclovir, buciclovir, famciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxyuridine, idoxuridine, AZT, AIU, dideoxycytidine, and araC. In embodiments, the nucleoside analogue is ganciclovir.

In embodiments, expression of the one or more molecules is regulated by one or more promoters. In embodiments, the polynucleotide comprises a promoter comprising a binding site for a transcription modulator that modulates the expression and/or secretion of the one or more molecules in the cell. For example, the transcription modulator is or includes Hif1a, NFAT, FOXP3, and/or NFkB. For example, the one or more molecules comprise at least one cytokine associated with an oxygen-sensitive polypeptide domain, and the oxygen-sensitive polypeptide domain comprises HIF VHL binding domain.

In embodiments, the polynucleotide may integrate into the genome of the modified cell and descendants of the modified cell will also express the polynucleotide, resulting in a stably transfected modified cell. In embodiments, the modified cell may express the polynucleotide encoding the CAR but the polynucleotide does not integrate into the genome of the modified cell such that the modified cell expresses the transiently transfected polynucleotide for a finite period of time (e.g., several days), after which the polynucleotide is lost through cell division or other factors. For example, the polynucleotide is present in the modified cell in a recombinant DNA construct, in an mRNA, or in a viral vector, and/or the polynucleotide is an mRNA, which is not integrated into the genome of the modified cell.

Embodiments relate to a method or use of polynucleotide. The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide; and administering an amount of the viral particle to the subject such that the polynucleotide is expressed in the subject. In embodiments, the AAV preparation may include AAV vector particles, empty capsids and host cell impurities, thereby providing an AAV product substantially free of AAV empty capsids. More information of the administration and preparation of the viral particle may be found at the U.S. Pat. No. 9,840,719 and Milani et al., Sci. Transl. Med. 11, eaav7325 (2019) 22 May 2019, which are incorporated herein by reference.

In embodiments, the bioreactor may be inoculated at a cell density of approximately $0.5 \times 10^6$ cells/mL with viability greater than 95%. When the cell density reaches approximately $1.0 \times 10^6$ cells/mL, the cells may be transfected with the PEI/DNA complexes (polyplexes) with a PEI to DNA ratio of 2:1. At the time of harvest, AAV from the cell culture in the bioreactor may be released using the Triton X-100 method. All solutions may be added directly to the bioreactor, and the lysate was centrifuged at 4000×g for 20 min. The supernatant may be stored at −80° C. for further processing. AAV may be further purified. For example, AAV samples (12.3 mL) may be purified by overlaying them on top of series of step gradients using 15, 25, 40 and 54% iodixanol concentrations containing 1, 5, 7 and 5 mL, respectively. The 15% iodixanol concentration also contains 1 M NaCl to avoid aggregation of AAV with other cellular proteins and negatively charged nuclear components. After the completion of centrifugation, 5 mL may be withdrawn from 2 mm below the 40/54 interface marked before starting the ultracentrifugation at 385,000×g for 1 h 45 min in Sorvall T-865 rotor in Sorvall Ultracentrifuge. The viral vectors may be then quantified. For example, vectors AAV infectivity may be determined by the gene transfer assay (GTA) using GFP as a reporter gene in all cases. AAV infectivity assay where sample may be diluted before addition to the cells to have the GFP positive cells in the range of 2-20% to assure that only single virus has entered the cell for GFP expression. The GFP-positive cells may be quantified by FACS using HEK293 cells in suspension. The AAV may be then administrated to a subject. For example, AAV may be diluted in 0.9% sterile NaCl saline solution (supplemented with 0.25% human serum albumin [HSA]) for infusion in patients and the final volume of infusion will be calculated based on the patient's weight as 3 mL/kg.

The term "expression or overexpression" refers to the transcription and/or translation of a particular nucleotide sequence into a precursor or mature protein, for example, driven by its promoter. "Overexpression" refers to the production of a gene product in transgenic organisms or cells that exceeds levels of production in normal or non-transformed organisms or cells. As defined herein, the term "expression" refers to expression or overexpression.

In embodiments, a T cell clone that expresses a TCR with a high affinity for the target antigen may be isolated. Tumor-infiltrating lymphocytes (TILs) or peripheral blood mononuclear cells (PBMCs) can be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRδ chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle, for example, a gammaretrovirus or lentivirus, can then be generated and tested for functionality (antigen specificity and functional avidity) and used to produce a clinical lot of the vector. An aliquot of the final product can then be used to transduce the target T cell population (generally purified from patient PBMCs), which is expanded before infusion into the patient.

Various methods may be implemented to obtain genes encoding tumor-reactive TCR. More information is provided in Kershaw et al., Clin Transl Immunology. 2014 May; 3(5): e16. In embodiments, specific TCR can be derived from spontaneously occurring tumor-specific T cells in patients. Antigens included in this category include the melanocyte differentiation antigens MART-1 and gp100, as well as the MAGE antigens and NY-ESO-1, with expression in a broader range of cancers. TCRs specific for viral-associated malignancies can also be isolated, as long as viral proteins are expressed by transformed cells. Malignancies in this category include liver and cervical cancer, associated with hepatitis and papilloma viruses, and Epstein-Barr virus-associated malignancies. In embodiments, target antigens of the TCR may include CEA (e.g., for colorectal cancer), gp100, MART-1, p53 (e.g., for Melanoma), MAGE-A3

(e.g., Melanoma, esophageal and synovial sarcoma), NY-ESO-1 (e.g., for Melanoma and sarcoma as well as Multiple myelomas).

In embodiments, preparation and transfusion of tumor infiltrating lymphocytes (TIL) may be implemented by the following. For example, tumor tissue comes from surgical or biopsy specimens, may be obtained under aseptic conditions and transported to the cell culture chamber in ice box. Necrotic tissue and adipose tissue may be removed. The tumor tissue may be cut into small pieces of about 1-3 cubic millimeter. Collagenase, hyaluronidase and DNA enzyme may be added, and digested overnight at 4° C. Filtering with 0.2 um filter, cells may be separated and collected by lymphocyte separation fluid, 1500 rpm for 5 min. Expanding the cells with a culture medium comprising PHA, 2-mercaptoethanol and CD3 monoclonal antibody, a small dose of IL-2 (10-20 IU/ml) may be added to induce activation and proliferation. According to the growth situation, the cell density may be carefully detected and maintained within the range of $0.5$-$2*10^6$/ml under the condition of 37° C. and 5% CO2 for 7-14 days. TIL positive cells have the ability to kill homologous cancer cell may be screened out by co-culture. The positive cells may be amplified in a serum-free medium containing a high dose of IL2 (5000-6000 IU/ml) until greater than $1*10^{11}$ TILs may be obtained. To administer TILs, they may be first collected in saline using continuous-flow centrifugation and then filtered through a platelet-administration set into a volume of 200-300 mL containing 5% albumin and 450 000 IU of IL-2. The TILs may be infused into patients through a central venous catheter over a period of 30-60 minutes. In embodiments, TILs may be often infused in two to four separate bags; the infusions may be separated by several hours.

In embodiments, expression of the polynucleotide is regulated or modulated by a synthetic Notch receptor comprising, from N-terminal to C-terminal and in covalent linkage: a) an extracellular domain comprising an antibody (e.g., a single-chain Fv (scFv) or a nanobody) that specifically binds to an antigen; b) a Notch regulatory region (NRR) and c) an intracellular domain comprising a transcriptional activator comprising a DNA binding domain. In embodiments, the Notch regulatory region comprises a Lin 12-Notch repeat, a heterodimerization domain comprising an S2 proteolytic cleavage site and a transmembrane domain comprising an S3 proteolytic cleavage site. The intracellular domain is heterologous to the Notch regulatory region. In embodiments, the transcriptional activator replaces a naturally-occurring intracellular notch domain, and binding of the antibody to the antigen induces cleavage at the S2 and S3 proteolytic cleavage sites, thereby releasing the intracellular domain. The release of the intracellular domain causes the transcriptional activator to induce expression of the polynucleotide encoding one or more target proteins in the modified cell. In embodiments, the modified cell comprises a polynucleotide encoding the synthetic Notch receptor and a polynucleotide encoding a transcriptional control element that is responsive to the transcriptional activator and operably linked to the polynucleotide encoding one or more target proteins (e.g., CAR and scFv targeting M2).

"Suicide gene" is a nucleic acid coding for a product, wherein the product causes cell death by itself or in the presence of other compounds. A representative example of such a therapeutic nucleic acid (suicide gene) is one which codes for thymidine kinase of herpes simplex virus (HSV-TK). Additional examples are thymidine kinase of varicella zoster virus and the bacterial gene cytosine deaminase which can convert 5-fluorocytosine to the highly toxic compound 5-fluorouracil.

In embodiment, the modified cell comprises an inducible gene expression system that comprises or is a lac system, a tetracycline system, or a galactose system. In embodiment, the expression of the dominant negative form of the inhibitory immune checkpoint molecule is regulated by Hif1a, NFAT, FOXP3, and/or NFkB.

In embodiment, the modified cell comprises a polynucleotide encoding the binding molecule and a dominant negative form of the inhibitory immune checkpoint molecule or a receptor thereof, wherein expression of the dominant negative form of the inhibitory immune checkpoint molecule is regulated by an inducible gene expression system.

In embodiment, the modified cell comprises a polynucleotide encoding the dominant negative form of the inhibitory immune checkpoint molecule or the receptor thereof, wherein expression of the dominant negative form of the inhibitory immune checkpoint molecule is regulated by an inducible gene expression system. In embodiments, the modified cell comprises a sequence listed in Table 7.

In embodiment, the polynucleotide comprises a polynucleotide encoding a NFAT promoter operatively associated with a nucleotide sequence encoding the inhibitory immune checkpoint molecule or the receptor thereof.

Embodiments relate to a modified cell comprising a polynucleotide encoding a secretable antibody binding SIGLEC-15 and/or encoding a dominant negative form of CD44. The antibody binding SIGLEC-15 can be a scFv. Embodiments relate to a modified cell comprising a polynucleotide encoding a secretable scFv binding SIGLEC-15 and/or encoding a secretable scFv binding CD44. In embodiments, the scFv binding SIGLEC-15 or CD44 is attached to the membrane of the modified cell as shown in FIG. 1.

Embodiments relate to a fusion protein comprising a scFv binding SIGLEC-15, a linker, an extracellular domain, a transmembrane domain, and a cytoplasmic domain, wherein the transmembrane domain is selected from a group consist of a transmembrane domain of a receptor of IL15, IL2, IL7, IL6, IL12, IL18, IL21, IL23, IL 33, TNFα, TNFβ, IFNα, and IFNβ, and the cytoplasmic domain is selected from a group consist of a cytoplasmic domain of receptor of the receptor of IL15, IL2, IL7, IL6, IL12, IL18, IL21, IL23, IL 33, TNFα, TNFβ, IFNα, and IFNβ, and the extracellular domain is selected from a group consist of an extracellular domain of the receptor of IL15, IL2, IL7, IL6, IL12, IL18, IL21, IL23, IL 33, TNFα, TNFβ, IFNα, and IFNβ. Embodiments relate to a fusion protein comprising a scFv binding SIGLEC-15, a linker, a transmembrane domain, and a cytoplasmic domain, wherein the transmembrane domain is selected from a group consist of a transmembrane domain of a receptor of CD4, CD8, CD28, CD27, CD25, CD137, PD1 and PDL1, and the cytoplasmic domain is selected from a group consist of a cytoplasmic domain of receptor of the receptor of CD4, CD8, CD28, CD27, CD25, CD137, PD1 and PDL1. Embodiments relate to a nucleic acid sequence encoding the fusion protein.

In embodiments, the binding domain is a scFv. In embodiments, the link is a GS linker. In embodiments, the scFv binds to one of the SEQ ID NOs: 85-89, the extracellular domain is or comprises a SEQ ID NO: 36-42, the transmembrane domain is or comprises one of the SEQ ID NOs: 43-49, and/or the cytoplasmic domain is or comprises one of the SEQ ID NO: 50-56; or the scFv binds to one of the SEQ ID NOs: 85-89, the liner is or comprises a SEQ ID NO: 83 and 84, the transmembrane domain is or comprises one of the SEQ ID NOs: 59-63, and/or the cytoplasmic domain is or comprises one of the SEQ ID NO: 64-70.

Embodiments relate to a nucleic acid sequence encoding a dominant negative form of SIGLEC-15 receptor on T cells or the dominant negative form of SIGLEC-15 receptor and CAR or modified TCR, wherein the modified SIGLEC-15 receptor and the CAR/TCR are expressed as gene products that are separate polypeptides. Embodiments relate to a nucleic acid sequence encoding a dominant negative form of SIGLEC-15 receptor on T cells (e.g., CD44) or the dominant negative form of CD44 and CAR or modified TCR, wherein the modified CD44 and the CAR/TCR are expressed as gene products that are separate polypeptides. Dominant negative mutations have an altered gene product that acts antagonistically to the wild-type allele. These mutations usually result in an altered molecular function (often inactive) and are characterized by a dominant or semi-dominant phenotype.

In embodiments, the dominant negative form of CD44 comprises a substitution or deletion as compared to a wild-type CD44 intracellular domain. SIGLEC-15 is a member of the SIGLEC gene family and has a typical sialic acid-binding immunoglobulin-type lectin structure, which plays a very important role in osteoclast differentiation and bone remodeling [1-4]. Expression of SIGLEC-15 is typically restricted to myeloid cells and is up-regulated in many human cancers. SIGLEC-15 is an immunosuppressive molecule that acts primarily on the tumor microenvironment and has no correlation with the PD-L1/PD-1 pathway. CD44 may be a potential functional ligand for SIGLEC-15 and is involved in the activation of T cells. The dominant negative receptor is constructed, that is, the extracellular segment of CD44 is retained, and its transmembrane or intracellular segment is modified to bind to SIGLEC-15, but the inhibitory signal cannot be transmitted through its cytoplasmic domain such as to enhance the anti-tumor activity of CAR-T cells.

Embodiments relate to a modified cell comprises the fusion protein or the nucleic acid sequence. Embodiments relate to a modified cell comprises a dominant negative form of CD44. In embodiments, the dominant negative form of CD44 is or comprises one of the SEQ ID NOS: 94-96. In embodiments, the modified cell is a T cell, NK cell, or dendritic cells.

Embodiments relate to a pharmaceutical composition comprising the population of the modified cells. Embodiments relate to a method of cause T cell response in a subject in need thereof and/or treating a tumor of the subject, the method comprising administering an effective amount of the composition to the subject.

Figure 11:
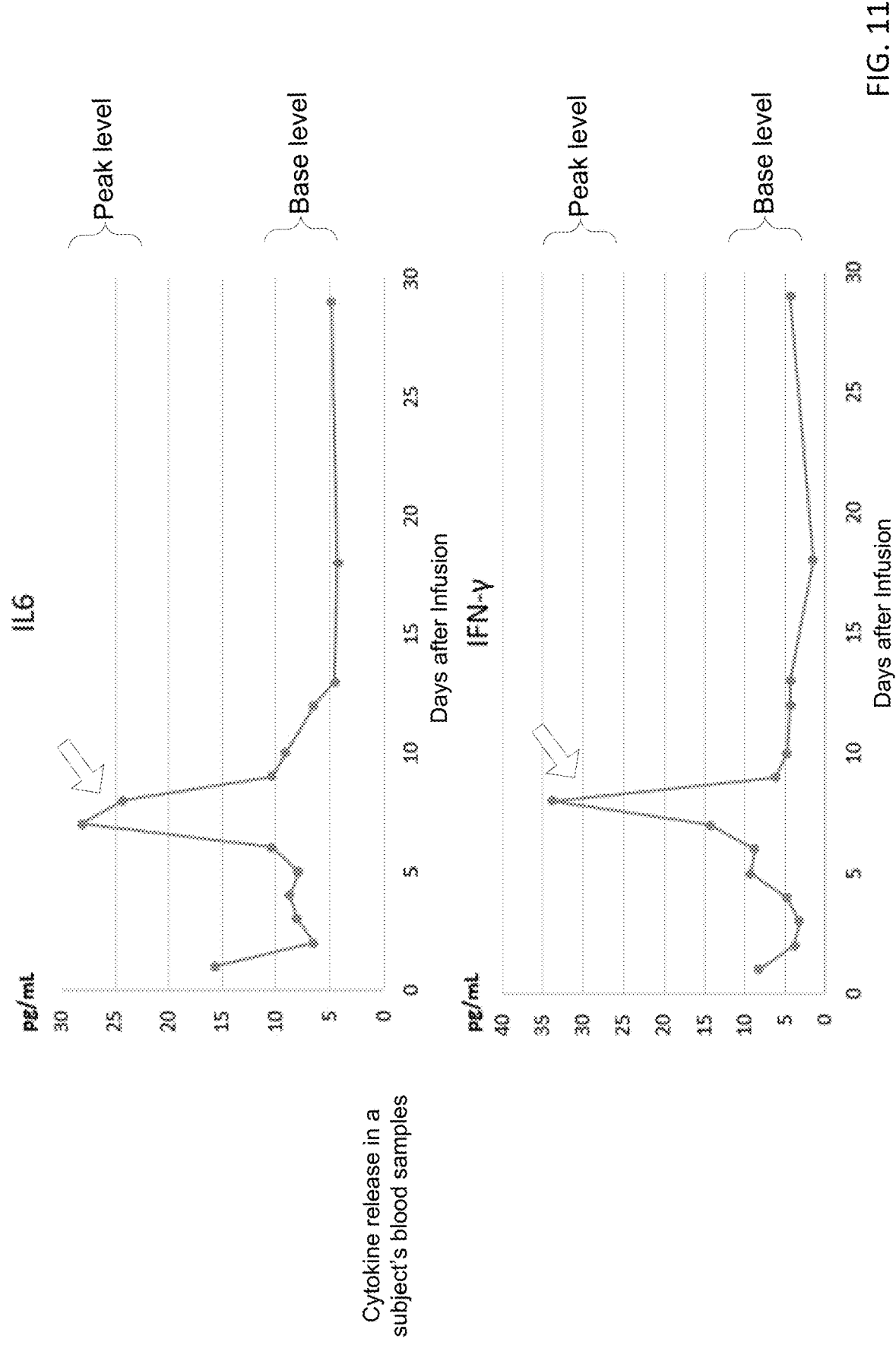
FIG. 11 shows a scheme of administering an agent (e.g., an inhibitor or inducer) in exemplary adoptive cell therapy. Arrows indicate the time when an agent (e.g., inhibitor or inducer) is administered to a subject, for example, at the peak of cytokine release.

Embodiments relate to a method of causing T cell response, treating a subject having cancer, enhancing cellular treatment on a subject having cancer, or inhibiting growth of tumor cells, the method comprising: administering an effective amount of modified cells comprising a binding molecule to the subject; and administering an effective amount of an inhibitor of an inhibitory immune checkpoint molecule (e.g., molecules associated with SIGLEC-15 and CD44 pathway) or a receptor thereof in response to a predetermined condition. In embodiments, the method further comprises intruding into cells with a plurality of nucleic acid sequences encoding the binding molecule to obtain the modified cells. In embodiments, the method further comprises monitoring cytokine releases of the subject in response to the CAR infusion; and wherein the administering the effective amount of the inhibitor of the inhibitory immune checkpoint molecule or the receptor thereof in response to the predetermined condition comprises administering the effective amount of the inhibitor of the inhibitory immune checkpoint molecule or the receptor thereof in response to determination that a level of one or more cytokines increases and/or reaches a peak level. In embodiments, the method further comprises terminating the administering of the inhibitor in response to determination that the level drops to a base level. In embodiments, the cytokine may include IL6 and/or IFNγ, as shown in FIG. 11.

In embodiments, the modified cell comprises a CAR. In embodiments, the CAR comprises an extracellular domain, a transmembrane domain, and an intracellular domain (e.g., 41-BB and CD3 zeta domain), the extracellular domain binds an antigen. In embodiments, the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

TABLE 2

| SEQ ID NO: | Identity |
| --- | --- |
| 1 | SP |
| 2 | Hinge & transmembrane domain |
| 3 | Co-stimulatory region |
| 4 | CD3-zeta |
| 5 | scFV Humanized CD19 |
| 6 | scFV CD19 |
| 7 | scFv FZD10 |
| 8 | scFv TSHR |
| 9 | scFv PRLR |
| 10 | scFv Muc 17 |
| 11 | scFv GUCY2C |
| 12 | scFv CD207 |
| 13 | Prolactin (ligand) |
| 14 | scFv CD3 |
| 15 | scFv CD4 |
| 16 | scFv CD4-2 |
| 17 | scFv CD5 |
| 18 | WTCD3zeta |
| 19 | WTCD3zeta-BCMACAR full length |
| 20 | BCMACAR |
| 21 | MUC1CAR |
| 22 | m19CAR-IRES-MUC1CAR |
| 23 | hCD19CAR-IRES-MUC1CAR |
| 24 | hCD22CAR-IRES-MUC1CAR |
| 25 | BCMACAR-IRES-MUC1CAR |
| 26 | mCD19CAR-2A-MUC1CAR |
| 27 | hCD19CAR-2A-MUC1CAR |
| 28 | hCD22CAR-2A-MUC1CAR |
| 29 | BCMA-2A-MUC1CAR |
| 30 | Tumor associated MUC1 scFv 1 |
| 31 | Tumor associated MUC1 scFv-1 VH |
| 32 | Tumor associated MUC1 scFv-1 VL |
| 33 | Tumor associated MUC1 scFv 2 |

TABLE 2-continued

| SEQ ID NO: | Identity |
|---|---|
| 34 | Tumor associated MUC1 scFv2 VH |
| 35 | Tumor associated MUC1 scFv2 VL |
| 36 | ED IL2 receptor |
| 37 | ED IL6 receptor |
| 38 | ED IL7 receptor |
| 39 | ED IL12 receptor |
| 40 | ED IL15 receptor |
| 41 | ED IL21 receptor |
| 42 | ED IL23 receptor |
| 43 | TM IL2 receptor |
| 44 | TM IL6 receptor |
| 45 | TM IL7 receptor |
| 46 | TM IL12 receptor |
| 47 | TM IL15 receptor |
| 48 | TM IL21 receptor |
| 49 | TM IL23 receptor |
| 50 | CD IL2 receptor |
| 51 | CD IL6 receptor |
| 52 | CD IL7 receptor |
| 53 | CD IL12 receptor |
| 54 | CD IL15 receptor |
| 55 | CD IL21 receptor |
| 56 | CD IL23 receptor |
| 57 | TM CD4 |
| 58 | TM CD8 |
| 59 | TM CD27 |
| 60 | TM CD28 |
| 61 | TM CD137 |
| 62 | TM PD1 |
| 63 | TM PDL1 |
| 64 | CD CD4 |
| 65 | CD CD8 |
| 66 | CD CD27 |
| 67 | CD CD28 |
| 68 | CD CD137 |
| 69 | CD PD1 |
| 70 | CD PDL1 |
| 71 | IL2 |
| 72 | IL6 |
| 73 | IL7 |
| 74 | IL12 |
| 75 | IL15 |
| 76 | IL21 |
| 77 | IL23 |
| 78 | IL33 |
| 79 | TNFα |
| 80 | TNFβ |
| 81 | Hif VHL-interaction domain: Hif amino acid 344-417 |
| 82 | Hif amino acid 380-603 |
| 83 | GS linker sequence |
| 84 | EA linker sequence |
| 85 | SIGLEC-15 antigen 1 |
| 86 | SIGLEC-15 antigen 2 |
| 87 | SIGLEC-15 antigen 3 |
| 88 | SIGLEC-15 antigen 4 |
| 89 | SIGLEC-15 antigen 5 |
| 90 | SIGLEC-15 antigen 6 |
| 91 | SIGLEC-15 antigen 7 |
| 92 | SIGLEC-15 antigen 8 |
| 93 | CD44 VVT aa |
| 94 | Truncated CD44 aa |
| 95 | CD44 + CD8α aa |
| 96 | CD44 point mutant aa |
| 97 | h-Notch transmembrane |
| 98 | m-Notch transmembrane |
| 99 | OX40 extracellular |
| 100 | CD40 extracelluar |
| 101 | 41-BB extracellular |
| 102 | Her2 extracellular |
| 103 | GITR extracellular |
| 104 | CD28 extracellular |
| 105 | ICOS extracellular |
| 106 | EGFR extracellular |
| 107 | CD27 extracellular |
| 108 | OPA1 |

TABLE 2-continued

| SEQ ID NO: | Identity |
|---|---|
| 109 | MKN1 |
| 110 | MKN2 |
| 111 | DNM1L |
| 112 | RUNX3 |
| 113 | EOMES |
| 114 | SIGLEC-15-P2A-EGFP |
| 115 | Anti-SIGLEC-15 scFv1 |
| 116 | Anti-SIGLEC-15 scFv2 |
| 117 | DNM1L |
| 118 | mCD19-P2A-DNM1L |
| 119 | P2A-DNM1L |

Note:
EM: Extracellular Domain;
TM: Transmembrane Domain;
CD: Cytoplasmic Domain Embodiments relate to a fusion protein comprising an extracellular domain, a transmembrane domain, and a cytoplasmic domain, the extracellular domain being or comprising the extracellular domain of at least one of OX40, CD40, 41-BB, GITR, ICOS, CD28, CD27, HER, or EGFR, the transmembrane domain being or comprising the transmembrane domain of an inducible molecule, and the cytoplasmic domain being or comprising at least one of OPA1, MKN1, MKN2, DNM1L, runx3, EOMES, TCF1, LEF1, Runx1, STAT3, TRAF6, ID3.

Embodiments relate to a fusion protein comprising an extracellular domain, a transmembrane domain, and a cytoplasmic domain, the transmembrane domain being or comprising the transmembrane domain of Notch. More information about Notch and its components may be found in U.S. Pat. No. 9,670,281, which incorporated herein by reference.

In embodiments, the extracellular domain comprises an extracellular domain of a receptor, an antibody, or a ligand. In embodiments, the receptor is a costimulatory molecule. In embodiments, the receptor is OX40, CD40, 41-BB, GITR, ICOS, CD28, CD27, HER, or EGFR. In embodiments, the ligand corresponds to the receptor. In embodiments, the receptor is a cytokine receptor, and the ligand is a cytokine. In embodiments, the antibody is an scFv targeting a tumor antigen. In embodiments, the cytoplasmic domain comprises a mitochondrial protein or a transcription factor. In embodiments, the cytoplasmic domain comprises at least one of OPA1, MKN1, MKN2, DNM1L, runx3, EOMES, TCF1, LEF1, Runx1, STAT3, TRAF6, and ID3. In embodiments, the cytoplasmic domain comprises at least one of a protein listed in Table 3.

In embodiments, the extracellular domain corresponds to an agent, and the transmembrane domain of Notch comprises a TACE cleavage site and a γ-secretase cleavage site such that binding of an extracellular domain to the agent induces cleavage at the TACE cleavage site and the γ-secretase cleavage site, thereby releasing the cytoplasmic domain. In embodiments, the agent is the receptor, and the extracellular domain comprises the ligand of the receptor. In embodiments, the extracellular domain comprises an extracellular domain of the receptor, and the agent is a ligand corresponding to the receptor. In embodiments, the agent is the tumor antigen, and the extracellular domain comprises an antibody against the tumor antigen.

In embodiments, the extracellular domain comprises at least one of SEQ ID NO: 38-46, the transmembrane domain comprises at least one of SEQ ID NO: 36 and 37, and the cytoplasmic domain comprises at least one of SEQ ID NO: 47-52.

Embodiments relate to a nucleic acid sequence encoding the fusion protein. Embodiments relate to a modified cell comprises a fusion protein described herein, for example one of embodiments 1-16 or the nucleic acid encoding a fusion protein described herein (one of embodiments 1-16). Embodiments relate to a pharmaceutical composition comprising the population of the modified cells. Embodiments relate to a method of cause T cell response in a subject in need thereof and/or treating a tumor of the subject, the method comprising administering an effective amount of the composition.

In embodiments, the modified cell comprises a CAR. In embodiments, the CAR comprises an extracellular domain, a transmembrane domain, and an intracellular domain, and the extracellular domain binds an antigen. In embodiments, the pharmaceutical composition, the modified cell, or the method of promoting a T cell response described herein include the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof. In embodiments, the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4. In embodiments, the cell is a T cell, macrophage, dendritic cell, or NK cell.

Figure 12:
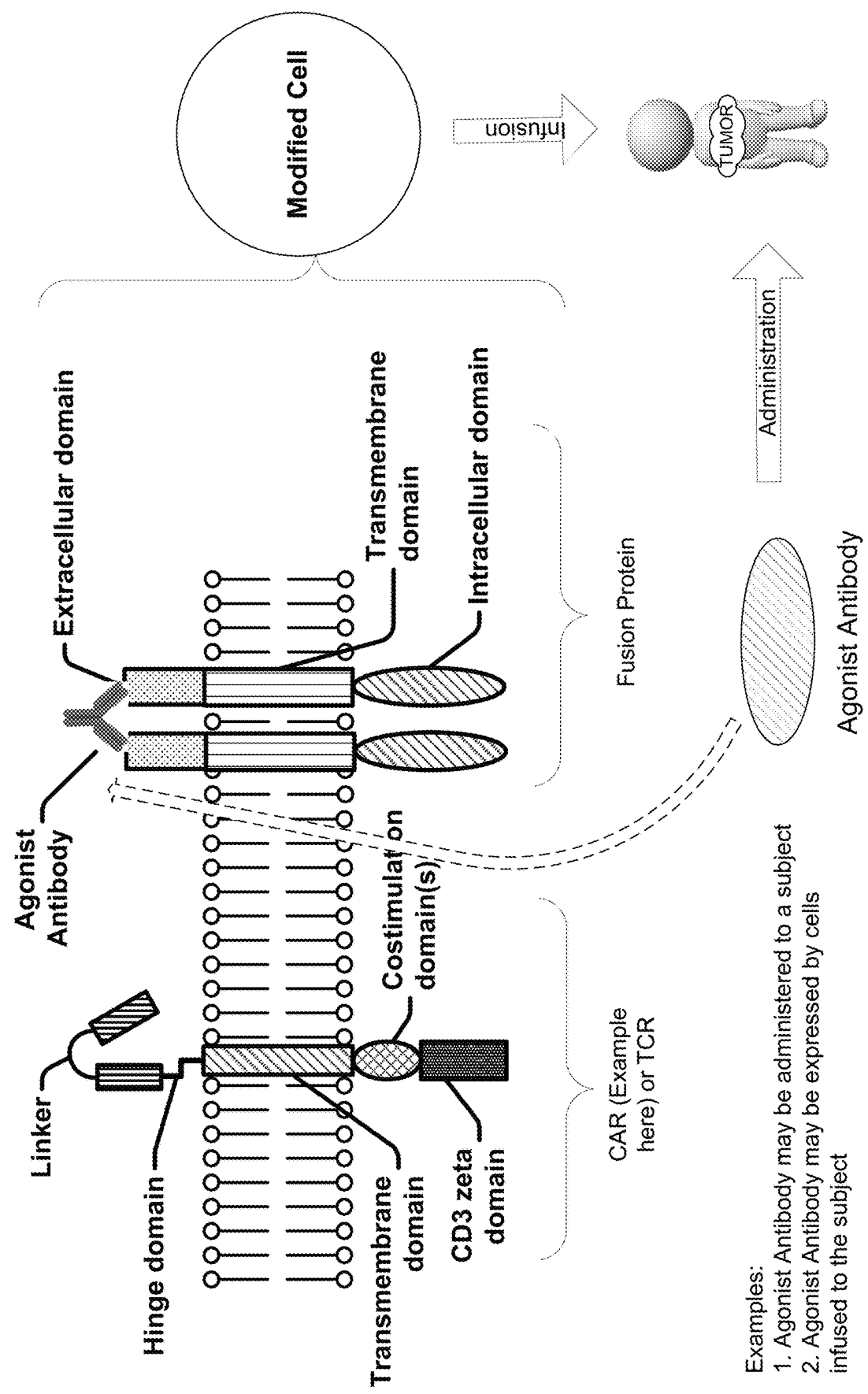
FIG. 12 shows a schematic diagram of exemplary structures of membrane proteins of a modified cell and uses thereof.

Embodiments relate to a fusion protein that can be activated by agonist antibodies to perform the specific desired functions. In an overexpressed fusion protein, the extracellular domain comprise a protein sequence that can be bound by an agonist antibody (that is, an antibody that binds the extracellular domain of the fusion protein), and the intracellular is the intracellular domain of another transmembrane protein. When using the agonist antibody, the extracellular segment is cross-linked by the agonist antibody, and the intracellular segment of the fusion protein forms a cluster that activates the downstream pathway. Examples of the fusion protein and the agonist antibody are shown in FIG. 12. An "agonist antibody," as used herein, is an antibody which activates a biological activity of the antigen it binds. In embodiments, during agonist antibody activation, partial dissociation of antibodies allows the antigen-binding fragment (Fab) arms of a single antibody to interact with more than two receptors in a dynamic fashion, resulting in the recruitment of multiple receptor monomers into a receptor oligomer where signaling activation can be triggered. In embodiments, antigen-presenting cells (APCs) acts as a scaffold to crosslink agonist antibody bound to a receptor (e.g., co stimulatory receptor), leading to receptor supercluster formation and increased agonist signaling. Some proteins (such as the proteins of the CD28 family and the TNF receptor family) have an agonist antibody for tumor therapy. More information about agonist antibodies and co-stimulatory molecules may be found at Nature Reviews Drug Discovery volume 17, pages 509-527 (2018), which is incorporated herein by reference in its entirety.

TABLE 3

| Group 1 | Group 1 | Group 1 | Group 1 | Group 2 | Group 3 | Group 4 |
|---|---|---|---|---|---|---|
| LEF1 | CXCR3 | FRC | T-bet | PI3K | ezh2 | PDCD1 |
| Gfi1 | Flt3 | FAO | GATA3 | Akt | kiaa1324 | PDL1 |
| δEF1/ZEB | Kit | Hif-1a | Blimp-1 | mTOR | fn1 | PDL2 |
| Ikaros | IL-7R | Hif-2a | Myc | Wnt | ITGA9 | CTLA4 |
| KLF2 | IL-4R | Vhl | HIF1 | Notch1 | SMDPD3A | LRBA |
| HEB | IL-9R | PHD1 | c-Myb | Notch2 | ITPRIPL2 | LAG3 |
| MAZR | PDGFRb | PHD2 | members of the E2A/HEB family | Activin | PRSS23 | Tim3 |
| Tox | gc (Il2rg) | PHD3 | members of the Ikaros family | BMP | CLECL1 | BILA |
| PU.1 | IL-2Ra (CD25) | FIH1 | Ets-family transcription factor PU.1 | TGFb | TBX21 | CD160 |
| HES1,2,3 | IL-2Rb | TET2 | Runx1 | IL7 | IKZF2 | 2B4 |
| Sox4 | PDGFRa | TET1 | GATA-2 | IL7Ra | EOMES | Foxp3 |
| E12, | Pdgfa | TET3 | TCF-1 (Tcf7) | IL12 | PRDM1 | ccr4 |
| E2-2 | Pdgfb | DNMT3 | RBPSuh | IL15 | BTLA | PVRIG |
| E47, | Pdgfc |  | Id3 | IL6 | CD244 | CD16B |
| MEF2 | Pdgfd |  | Id2 | IL2 | KL6 | SIVA1 |
| Nur77/Nor1 | TGF-b1 |  | Runx1 | MAPK | JUNB | CD33 |
| Ncoa4 | TGF-b2 |  | Runx3 | AMPK | FOSB | LAGLS9 |
| Basp2 | TGF-b3 |  | EBF | NF-Kb | FAM13A | CD122 |
| Pitx1 | BMP2 |  | Pax5 | NF-AT | BATF3 | IDO1 |
| Prdm16 | BMP4 |  | FOG-1 | AP-1 | KLRC1 | IDO2 |
| Ndn | BMP7 |  | GATA-3 | PI-3 kinase, Akt/PKB, and Ras/MAP | KLRC2 | CD45 |

TABLE 3-continued

| Group 1 | Group 1 | Group 1 | Group 2 | Group 3 | Group 4 |
|---|---|---|---|---|---|
| Irf6 | ActivinbetaA | GATA-2 | CCR7 | ZNF704 | CVPLBL |
| Dach1 | ALK-5 | GATA-1 | STAT1 | CTHRC1 | TNFAIP8L2 |
| Nr4a2 | BMPR-1A/B | Groucho/TLE/ Grg family proteins or Sin3A | STAT2 | FAXC | DNMT3A |
| Hoxa5 | BMPR-II | Helios | STAT3 | EGR1 | CEACAM-1 |
| Hoxb5 | TLR | NFAT | STAT4 | RBM47 | RUNX3 |
| FoxN1 | MyD88 | Bcl-6 | STAT5 | ENTPD1 | LEXM |
| Gli1,2,3 | SHH | BCL-6b (BAZF) | glut1 | SUV39H1 | PILRA |
| | Smoothen | HIF1 | | AKAP5 | PTNNS1L3 |
| | Ptch1 | c-Myc | | β-catenin | Fegr3a |
| | Fu | IRF4 | | PI3K | Nat8 |
| | Su(fu) | NF-kb | | GLUL | ccl9 |
| | Wnt1,3,4,5b,10b | ThPOK | | FAXC | HCK |
| | Smad | Oct3/4 | | | TREM2 |
| | CXCL10 | Nanog | | LNGM | CCL6 |
| | CXCL9 | Sox2 | | NUDT16 | CD36 |
| | INFa,b | KLF4 | | | IGF1 |
| | CXCR3 | FOXO1 | | | CTSS |
| | CCL5 | TSC1 | | | GZMC |
| | CCR5 | OxPhos | | | BATF |
| | CCR7 | Zbtb32 | | | CXCL2 |
| | SOCS1 | E2F2 | | | TNFAIP8L 3 |
| | SOCS2 | SMART | | | IL-1b |
| | SOCS3 | NCOR | | | IL-1a |
| | SOCS4 | | | | TRPV1 |
| | SOCS5 | | | | TRPV2 |
| | SOCS6 | | | | TRPV3 |
| | SOCS7 | | | | TRPV4 |
| | CIS | | | | Rgs1 |
| | | | | | PLSCR1 |
| | | | | | ITGB1 |
| | | | | | ITGB2 |
| | | | | | C3AR1 |
| | | | | | ITGA3 |
| | | | | | ITGA5 |
| | | | | | ITGAL |
| | | | | | CARD11 |
| | | | | | CD83 |

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:
1. A fusion protein comprising an extracellular domain, a transmembrane domain, and a cytoplasmic domain, the extracellular domain being or comprising an extracellular domain of at least one of OX40, CD40, 41-BB, GITR, ICOS, CD28, CD27, HER, or EGFR, the transmembrane domain being or comprising a transmembrane domain of an inducible molecule, and the cytoplasmic domain being or comprising at least one of OPA1, MKN1, MKN2, DNM1L, runx3, EOMES, TCF1, LEF1, Runx1, STAT3, TRAF6, or ID3.
2. A fusion protein comprising an extracellular domain, a transmembrane domain, and a cytoplasmic domain, the transmembrane domain being or comprising the transmembrane domain of Notch.
3. The fusion protein of embodiment 2, wherein the extracellular domain comprises an extracellular domain of a receptor, an antibody, or a ligand.
4. The fusion protein of embodiment 3, wherein the receptor is a costimulatory molecule.
5. The fusion protein of embodiment 3, wherein the receptor is OX40, CD40, 41-BB, GITR, ICOS, CD28, CD27, HER, or EGFR.
6. The fusion protein of embodiment 3, wherein the ligand corresponds to a receptor.
7. The fusion protein of embodiment 3, wherein the receptor is a cytokine receptor, and the ligand is a cytokine.
8. The fusion protein of embodiment 3, wherein the antibody is a scFv that targets a tumor antigen.
9. The fusion protein of one of embodiments 2-8, wherein the cytoplasmic domain comprises a mitochondrial protein or a transcription factor.
10. The fusion protein of embodiment 9, wherein the cytoplasmic domain comprises at least one of OPA1, MKN1, MKN2, DNM1L, runx3, EOMES, TCF1, LEF1, Runx1, STAT3, TRAF6, or ID3.
11. The fusion protein of embodiment 9, wherein the cytoplasmic domain comprises at least one of a protein listed in Table 3.
12. The fusion protein of one of embodiments 2-11, wherein the extracellular domain corresponds, to, interacts or associates with, and/or binds an agent, and the transmembrane domain of Notch comprises a TACE cleavage site and a y-secretase cleavage site such that binding of an extracellular domain to the agent induces cleavage at the TACE cleavage site and the y-secretase cleavage site, thereby releasing the cytoplasmic domain.

13. The fusion protein of embodiment 12, wherein the agent is a receptor, and the extracellular domain comprises a ligand of the receptor.
14. The fusion protein of embodiment 12, wherein the extracellular domain comprises an extracellular domain of a receptor, and the agent is a ligand of the receptor.
15. The fusion protein of embodiment 12, wherein the agent is a tumor antigen, and the extracellular domain comprises an antibody against the tumor antigen.
16. The fusion protein of embodiment 12, wherein the extracellular domain comprises an amino acid sequence of at least one of SEQ ID NO: 99-106, the transmembrane domain comprises an amino acid sequence of at least one of SEQ ID NO: 97 and 98, and the cytoplasmic domain comprises an amino acid sequence of at least one of SEQ ID NO: 108-113.
17. A nucleic acid encoding the fusion protein of one of embodiments 1-16.
18 A modified cell comprising the fusion protein of one of embodiments 1-16 or the nucleic acid sequence of embodiment 17.
19. A pharmaceutical composition comprising a population of the modified cells of embodiment 18.
20. A method of causing or promoting a T cell response in a subject in need thereof and/or treating a tumor of the subject, the method comprising administering an effective amount of the composition of embodiment 19 to the subject.
21. The pharmaceutical composition, the modified cell, and the method of one of embodiments 17-20, wherein the modified cell comprises a CAR.
22. The pharmaceutical composition, the modified cell, and the method of one of embodiments 17-20, wherein the CAR comprises an extracellular domain, a transmembrane domain, and an intracellular domain, and the extracellular domain binds an antigen.
23. The pharmaceutical composition, the modified cell, and the method of embodiment 23, wherein the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and a combination thereof.
24. The pharmaceutical composition, the modified cell, and the method of embodiment 23, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.
25. The pharmaceutical composition, the modified cell, and the method of embodiments 18-24, wherein the cell is a T cell, macrophage, dendritic cell, or NK cell.
26. A fusion protein comprising an scFv binding SIGLEC-15, a linker, an extracellular domain, a transmembrane domain, and a cytoplasmic domain, wherein the transmembrane domain is selected from a group consisting of a transmembrane domain of a receptor of IL15, IL2, IL7, IL6, IL12, IL18, IL21, IL23, IL 33, TNFα, TNFβ, IFNα, and IFNβ, and the cytoplasmic domain is selected from a group consisting of a cytoplasmic domain of receptor of the receptor of IL15, IL2, IL7, IL6, IL12, IL18, IL21, IL23, IL 33, TNFα, TNFβ, IFNα, and IFNβ, and the extracellular domain is selected from a group consisting of an extracellular domain of the receptor of IL15, IL2, IL7, IL6, IL12, IL18, IL21, IL23, IL 33, TNFα, TNFβ, IFNα, and IFNβ.
27. A fusion protein comprising an scFv binding SIGLEC-15, a linker, a transmembrane domain, and a cytoplasmic domain, wherein the transmembrane domain is selected from a group consisting of a transmembrane domain of a receptor of CD4, CD8, CD28, CD27, CD25, CD137, PD1, and PDL1, and the cytoplasmic domain is selected from a group consisting of a cytoplasmic domain of receptor of the receptor of CD4, CD8, CD28, CD27, CD25, CD137, PD1, and PDL1.
28. The fusion protein of one of embodiments 26 and 27, wherein the binding domain is an scFv.
29. The fusion protein of one of embodiments 26-28, wherein the link is a GS linker.
30. The fusion protein of one of embodiments 26-28, wherein the scFv binds one of the amino acid sequences of SEQ ID NOs: 85-89, the extracellular domain is or comprises one of amino acid sequences of SEQ ID NO: 36-42, the transmembrane domain is or comprises one of the amino acid sequences of SEQ ID NOs: 43-49, and/or the cytoplasmic domain is or comprises one of the amino acid sequences of SEQ ID NO: 50-56; or the scFv binds to one of the amino acid sequences of SEQ ID NOs: 85-89, the linker is or comprises SEQ ID NO: 83 or 84, the transmembrane domain is or comprises one of amino acid sequences of SEQ ID NOs: 59-63, and/or the cytoplasmic domain is or comprises one of the amino acid sequences of SEQ ID NOs: 64-70.
31. A nucleic acid sequence encoding the fusion protein of one of embodiments 26-30.
32. A nucleic acid sequence encoding a dominant negative form of SIGLEC-15 receptor on T cells or the dominant negative form of SIGLEC-15 receptor and CAR or modified TCR, wherein the modified SIGLEC-15 receptor and the CAR/TCR are expressed as gene products that are separate polypeptides.
33. A nucleic acid sequence encoding a dominant negative form of SIGLEC-15 receptor on T cells (e.g., CD44) or the dominant negative form of CD44 and CAR or modified TCR, wherein the modified CD44 and the CAR/TCR are expressed as gene products that are separate polypeptides.
34. The nucleic acid sequence of embodiment 33, wherein the dominant negative form of CD44 comprises a substitution or deletion in its intracellular domain as compared to a wild-type CD44.
35 A modified cell comprising the fusion protein of one of embodiments 1-6 or the nucleic acid sequence encoding one of the fusion proteins of embodiments 9-10.
36. A modified cell comprising a dominant negative form of CD44.
37. The modified cell of embodiment 35 or 36, wherein the dominant negative form of CD44 is or comprises one of the amino acid sequence of SEQ ID NOs: 94-96.
38. The modified cell of one of embodiments 35-37, wherein the modified cell is a T cell, NK cell, or dendritic cells.
39. A pharmaceutical composition comprising the population of the modified cells of embodiment 38.

40. A method of causing or promoting a T cell response in a subject in need thereof and/or treating a tumor of the subject, the method comprising administering an effective amount of the composition of embodiment 39 to the subject.

41. The pharmaceutical composition, the modified cell, and the method of one of embodiments 35-40, wherein the modified cell comprises a CAR.

42. The pharmaceutical composition, the modified cell, and the method of embodiment 41, wherein the CAR comprises an extracellular domain, a transmembrane domain, and an intracellular domain (e.g., 41-BB and CD3 zeta domain), the extracellular domain binds an antigen.

43. The pharmaceutical composition, the modified cell, and the method of embodiment 41 or 42, wherein the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and a combination thereof.

44. The pharmaceutical composition, the modified cell, and the method of embodiment 41 or 42, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

45. A recombinant antigen-binding protein or fragment thereof comprising the amino acid sequence of SEQ ID NO: 115 or 116.

46. The recombinant antigen-binding protein of embodiment 45, wherein said protein is an antibody.

47. The recombinant antigen-binding protein of embodiment 46, wherein the antibody is a human antibody.

48. The recombinant antigen-binding protein of embodiment 46, wherein said antibody or antigen-binding fragment thereof is intact Ig, Fab, F(ab')$_2$, Fv, or scFv.

49. The antigen-binding protein of embodiment 45, wherein said antigen-binding protein is a SIGLEC-15 agonist.

50. The antigen-binding protein of embodiment 45, wherein said antigen-binding protein is a SIGLEC-15 antagonist.

51. The antigen-binding protein of embodiment 45, wherein said antigen-binding protein is a chimeric antigen receptor (CAR).

52. A nucleic acid encoding an antigen-binding protein of embodiment 45 or at least one of the amino acid sequences of SEQ ID NOS: 115, 116, 94-96, and 100.

53. A vector comprising the nucleic acid of embodiment 52.

54. A modified cell comprising an antigen-binding protein of embodiment 45.

55. A modified cell comprising a nucleic acid of embodiment 52.

56. A modified cell comprising a vector of embodiment 53.

57. An antigen-binding protein of embodiment 45 conjugated to a therapeutic agent.

58. The antigen-binding protein of embodiment 57, wherein said therapeutic agent is a drug, toxin, radioisotope, protein, or peptide.

59. A pharmaceutical composition comprising an antigen-binding protein of embodiment 45.

60. A pharmaceutical composition comprising a nucleic acid of embodiment 52.

61. A pharmaceutical composition comprising a vector of embodiment 53.

62. A pharmaceutical composition comprising a cell that expresses an antigen-binding protein of embodiment 45.

63. A method of increasing a T cell response in a subject comprising administering to the subject a therapeutically effective amount of an antigen-binding protein or an antigen-binding fragment thereof of embodiment 45 or a nucleic acid that encodes the antigen-binding protein or an antigen-binding fragment thereof of embodiment 45.

64. The method of embodiment 63, wherein the antigen-binding protein or antigen-binding fragment thereof inhibits, reduces, modulates or abolishes signal transduction mediated by SIGLEC-15.

65. A method for treatment of a subject having a SIGLEC-15 positive disease, comprising administering to the subject a therapeutically effective amount of an antigen-binding protein or an antigen-binding fragment thereof of embodiment 45 or a nucleic acid that encodes the antigen-binding protein or an antigen-binding fragment thereof of embodiment 45.

66. The method of embodiment 65, wherein said antigen-binding protein or antigen-binding fragment thereof is a conjugate having a cytotoxic moiety linked thereto.

67. The method of embodiment 65, wherein the SIGLEC-15 positive disease is cancer.

68. A vector comprising a nucleic acid encoding a recombinant anti-SIGLEC-15 antigen-binding protein of embodiment 45 and a nucleic acid encoding a chimeric antigen receptor, wherein said recombinant anti-SIGLEC-15 antigen-binding protein is not identical to said chimeric antigen receptor.

69. A modified cell comprising the vector of embodiment 68.

68. A modified cell comprising a nucleic acid encoding a recombinant anti-SIGLEC-15 antigen-binding protein of embodiment 45 and a nucleic acid encoding a chimeric antigen receptor, wherein said recombinant anti-SIGLEC-15 antigen-binding protein is not identical to said chimeric antigen receptor.

70. A modified cell comprising a recombinant SIGLEC-15 antigen-binding protein of embodiment 45 and a chimeric antigen receptor, wherein said recombinant anti-SIGLEC-15 antigen-binding protein is not identical to said chimeric antigen receptor.

71. A vector or a cell comprising a vector that encodes a SIGLEC-15 antigen-binding protein of embodiment 45, wherein the recombinant anti-SIGLEC-15 antigen-binding protein is an antibody.

72. A vector or a cell of embodiment 71, wherein the recombinant SIGLEC-15 antigen-binding protein is a human antibody.

73. A vector or a cell of embodiment 71, wherein the recombinant SIGLEC-15 antigen-binding protein is an intact Ig, Fab, F(ab')2, Fv, or scFv.

74. A vector or cell of embodiment 71, wherein the recombinant SIGLEC-15 antigen-binding protein is a SIGLEC-15 agonist.

75. A vector or cell of embodiment 71, wherein the recombinant SIGLEC-15 antigen-binding protein is a SIGLEC-15 antagonist.

76. A vector or cell of embodiment 71, wherein the recombinant anti-SIGLEC-15 antigen-binding protein is a secretable protein.

77. A vector or cell of embodiment 71, wherein the chimeric antigen receptor specifically binds to CD-19.

78. A vector or cell of embodiment 71, wherein the chimeric antigen receptor can be inserted in a human T cell membrane.

79. The modified cell of any suitable preceding embodiments, wherein the modified cell is a T cell, NK cell, and/or DC.

80. A pharmaceutical composition comprising a vector or a cell of any of embodiments 70-79.

81. The pharmaceutical composition of embodiment 80 further comprising a pharmaceutically acceptable carrier.

82. A method of increasing a T cell response in a subject comprising administering to the subject a therapeutically effective amount of a vector or cell of any of embodiments 70-79, wherein the recombinant SIGLEC-15 antigen-binding protein is a SIGLEC-15 antagonist.

83. A method of increasing a T cell response in a subject comprising administering to the subject a therapeutically effective amount of a pharmaceutical composition comprising a vector or a cell of any of embodiments 70-79, wherein the recombinant SIGLEC-15 antigen-binding protein is a SIGLEC-15 antagonist.

84. The method of embodiment 83, wherein the recombinant SIGLEC-15 antigen-binding protein inhibits, reduces, modulates or abolishes signal transduction mediated by SIGLEC-15.

85. A method of decreasing a T cell response in a subject comprising administering to the subject a therapeutically effective amount of a vector or cell of any of embodiments 70-79, or a pharmaceutical composition of embodiment 80 or 81, wherein the recombinant SIGLEC-15 antigen-binding protein is a SIGLEC-15 agonist.

86. A method of decreasing a T cell response in a subject comprising administering to the subject a therapeutically effective amount of a vector or cell of any of embodiments 70-79, wherein the recombinant SIGLEC-15 antigen-binding protein is a SIGLEC-15 agonist.

87. A method of decreasing a T cell response in a subject comprising administering to the subject a therapeutically effective amount of a pharmaceutical composition of embodiment 80, wherein the recombinant SIGLEC-15 antigen-binding protein is a SIGLEC-15 agonist.

88. A method for treatment of a subject having a PD1-positive disease, comprising administering to the subject a therapeutically effective amount of a vector the encodes the or cell of any one of any of embodiments 70-79, or a pharmaceutical composition of embodiment 80 or 81.

89. A method for treatment of a subject having a SIGLEC-15-positive disease, comprising transducing at least one T cell of the subject with a nucleic acid encoding a recombinant anti-SIGLEC-15 antigen-binding protein and a nucleic acid encoding a chimeric antigen receptor, wherein said recombinant anti-SIGLEC-15 antigen-binding protein is not identical to said chimeric antigen receptor.

90. The method of embodiment 89, wherein the chimeric antigen receptor does not specifically bind to SIGLEC-15.

91. The method of embodiment 89, wherein the SIGLEC-15 positive disease is cancer.

92. A vector or a cell comprising a vector that encodes an antigen-binding protein of any of embodiments 70-79, wherein at least one of the anti-SIGLEC-15 antigen-binding protein and chimeric antigen receptor is conjugated to a therapeutic agent.

93. The vector or the cell of embodiment 92, wherein said therapeutic agent is a drug, toxin, radioisotope, protein, or peptide.

94. The modified cell or the method of any suitable preceding embodiments, wherein the modified cell is a T cell, NK cell, or dendritic cell.

95. A modified cell comprising a polynucleotide encoding a binding molecule, and a polynucleotide encoding an anti-SIGLEC-15 antigen-binding.

96. The modified cell of embodiment 95, wherein the anti-SIGLEC-15 antigen-binding protein is a secretable protein.

97. The modified cell of embodiment 95, wherein the anti-SIGLEC-15 antigen-binding protein is a secretable scFv.

98. The modified cell of embodiment 95, wherein the modified cell comprises a dominant negative form of PD-1.

99. The modified cell of any one of the preceding embodiments, wherein the cell or modified cell is a T cell derived from a healthy donor or a subject having cancer.

100. The modified cell of any of preceding embodiments, wherein the modified T cell comprises a dominant negative form of a receptor associated with CD44.

101. The modified cell of embodiment 100, wherein the modified CD44 lacks a functional CD44 intracellular domain for CD44 signal transduction, interferes with a pathway between CD44 of a human T cell of the human cells and SIGLEC-15 of a certain cell, comprises or is a CD44 extracellular domain or a CD44 transmembrane domain or a combination thereof, comprises a modified CD44 intracellular domain comprising a substitution or deletion as compared to a wild-type CD44 intracellular domain, or comprises or is a soluble receptor comprising a CD44 extracellular domain that binds to SIGLEC-15 of a certain cell.

102. The modified cell of embodiment 101, wherein an inhibitory effect of SIGLEC-15 on cytokine production of the human T cells of the population is less than an inhibitory effect of SIGLEC-15 on cytokine production of human T cells that do not comprise at least a part of the nucleic acid sequence that encodes the modified CD44.

103. The modified cell of any of preceding embodiments, wherein the modified cell is engineered to express and secrete a therapeutic agent such as a cytokine.

104. The modified cell of embodiment 103, wherein the therapeutic agent is or comprises IFN-γ.

105. The modified cell of embodiment 103, wherein the therapeutic agent is or comprises at least one of IL-6 or IFN-γ, IL-17, and CCL19.

106. The modified cell of embodiment 103, wherein the therapeutic agent is or comprises IL-15 or IL-12, or a combination thereof.

107. The modified cell of embodiment 103, wherein the therapeutic agent is or comprises a recombinant or native cytokine.

108. The modified cell of embodiment 103, wherein the therapeutic agent comprises an FC fusion protein associated with a small protein.

109. The modified cell of embodiment 108, wherein the small protein is or comprises IL-12, IL-15, IL-6 or IFN-γ.

110. The modified cell of embodiment 103, wherein the therapeutic agent is regulated by Hif1a, NFAT, FOXP3, and/or NFkB.

111. The modified cell of embodiment 108, wherein the small protein or the therapeutic agent is or comprises two or more recombinant or native cytokines are collected via 2A or /IRES component.
112. The nucleic acid, modified T cell or the method of any suitable preceding embodiments, wherein the modified T cell comprises a first targeting vector and a second targeting vector, the first targeting vector comprising a nucleic acid sequence encoding a CAR binding a blood antigen and the therapeutic agent, and the second targeting vector comprises a nucleic acid sequence encoding a CAR biding solid tumor antigen and a dominant negative form of the immune checkpoint molecule.
113. The nucleic acid, modified T cell or the method of any suitable preceding embodiments, wherein the modified T cell comprises a first targeting vector and a second targeting vector, the first targeting vector comprising a nucleic acid sequence encoding a CAR binding CD19 and the therapeutic agent, and the second targeting vector comprises a nucleic acid sequence encoding a CAR biding UPK2, ACPP, SIGLEC-15 or KISS1R and a dominant negative form of CD44.
114. The nucleic acid, modified T cell or the method of any suitable preceding embodiments, wherein the modified T cell comprises a first targeting vector and a second targeting vector, the first targeting vector comprising a nucleic acid sequence encoding a CAR binding a blood antigen, and the second targeting vector comprises a nucleic acid sequence encoding a CAR biding solid tumor antigen.
115. The nucleic acid, modified T cell or the method of any suitable preceding embodiments, wherein the modified T cell comprises a first targeting vector and a second targeting vector, the first targeting vector comprising a nucleic acid sequence encoding a CAR binding a B cell antigen, and the second targeting vector comprises a nucleic acid sequence encoding a CAR biding solid tumor antigen.
116. The nucleic acid, modified T cell or the method of any suitable preceding embodiments, wherein the solid tumor antigen is at least one of antigens listed in Table 1, and/or the B cell antigen is CD19, CD20, CD22, or BCMA.
117. The nucleic acid, modified T cell or the method of any suitable preceding embodiments, wherein the solid tumor antigen comprises at least one of antigens listed in Table 1.
118 A method of enhancing T cell expansion in a subject in need thereof, the method comprising administering an effective amount of the composition of T cells of any suitable preceding embodiments to the subject, the subject having a higher level of T cell expansion as compared with a subject that is administered an effective amount of the CAR T cells that do not have the CAR binding the B cell antigen.
119. The nucleic acid, modified T cell or the method any suitable preceding embodiments, wherein the modified T cell comprises a nucleic acid sequence encoding hTERT, SV40LT, or a combination thereof.
120. The nucleic acid, modified T cell or the method of any suitable preceding embodiments, wherein the modified T cell is more proliferable than T cells without nucleic acid sequence.
121. The isolated nucleic acid sequence, modified T cell or the method of any suitable preceding embodiments, wherein the proliferable cell remains functions of normal T cells/CAR T cells such as cell therapy functions.
122. The nucleic acid, modified T cell or the method any suitable preceding embodiments, wherein the T cell comprises a CAR and is cultured in the presence of an agent that is recognized by the extracellular domain of the CAR, thereby producing a modified CAR cell.
123. The nucleic acid, modified T cell or the method of any suitable preceding embodiments, wherein the integration of the nucleic acid sequence encoding hTERT, the nucleic acid encoding SV40LT, or a combination thereof includes genomic integration of the nucleic acid sequence encoding hTERT, a nucleic acid encoding SV40LT, or a combination thereof and constitutive expression of hTERT, SV40LT, or a combination thereof.
124. The nucleic acid sequence, modified T cell or the method of any suitable preceding embodiments, wherein expression of hTERT, SV40LT, or a combination thereof, is regulated by an inducible expression system such as a rtTA-TRE system.
125. The nucleic acid, modified T cell or the method of any suitable preceding embodiments, wherein modified T cell comprises a nucleic acid sequence encoding a suicide gene such as a an HSV-TK system.
126. The nucleic acid, modified T cell or the method of any suitable preceding embodiments, wherein the cell has a reduced graft-versus-host disease (GVHD) response in a bioincompatible human recipient as compared to the GVHD response of the primary human T cell.
127. The nucleic acid, modified T cell or the method of any suitable preceding embodiments, wherein the cell has reduced expression of endogenous TRAC gene.
128. A fusion protein comprising an extracellular domain, a transmembrane domain, and an intracellular domain, the extracellular domain derived from a first molecule, the intracellular domain derived from a second molecule, the first molecule different from the second molecule.
129. A fusion protein comprising an extracellular domain, a transmembrane domain, and an intracellular domain, the extracellular domain derived from a first molecule, the intracellular domain derived from a second molecule, the first molecule different from the second molecule, wherein the first molecule comprises a co-stimulatory domain, and the second molecule comprises a cytokine receptor.
130. An isolated nucleic acid encoding the fusion protein of embodiments 128 or 129.
131. A modified cell comprising the isolated nucleic acid of embodiment 130 or the fusion protein of embodiments 128 or 129.
132. A pharmaceutical composition comprising a population of the modified cells of embodiment 131.
133. A method of causing or promoting a T cell response in a subject in need thereof and/or treating a tumor of the subject, the method comprising administering an effective amount of the composition of embodiment 132 to the subject.
134. The method of embodiment 133, further comprising: administering an effective amount of an agonist antibody binding the extracellular domain.
135. The method of embodiment 134, wherein the binding of the extracellular domain with the agnostic antibody causes recruitment of multiple first molecules into a receptor oligomer in which signaling activation of the second molecule is triggered or enhanced.
136. The fusion protein, isolated nucleic acid, modified cell, pharmaceutical composition, or method of one of embodiments 128-135, wherein the extracellular domain binds to an agonist antibody, and wherein the agonist antibody is CDX 1140, SEA CD40, RO7009789, JNJ 64457107 (ADC1013), APX 005M, Chi Lob 7/4, TRX 518, MK 4166, MK 1248, GWN 323, INCAGN01876, BMS 986156, AMG 228, Tavolimab (MED10562), PF 04518600, BMS 986178, MOXR 0916, GSK 3174998, INCAGN01949, Utomilumab (PF 05082566), Urelumab (BMS 663513), GSK 3359609, JTX 2011, Theralizumab (TAB 08).

137. The fusion protein, isolated nucleic acid, modified cell, pharmaceutical composition, or method of one of embodiments 128-135, wherein the extracellular domain is an extracellular domain of a co-stimulatory molecule.

138. The fusion protein, isolated nucleic acid, modified cell, pharmaceutical composition, or method of one of embodiments 128-135, wherein the extracellular domain is an extracellular domain of OX40, CD40, 4-1BB, GITR, ICOS, CD28, CD27, HER2, or EGFR.

139. The fusion protein, isolated nucleic acid, modified cell, pharmaceutical composition, or method of one of embodiments 128-135, wherein: the extracellular domain is an extracellular domain of CD40, GITR, OX40, 41BB, ICOS, or CD28;
the co-stimulatory molecule is costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof; and/or the intracellular is an intracellular domain of a cytokine receptor.

140. The fusion protein, isolated nucleic acid, modified cell, pharmaceutical composition, or method of one of embodiments 128-135, wherein the second molecule is OX40, CD40, 4-1BB, GITR, ICOS, CD28, CD27, HER2, EGFR, IL10R, IL12R, IL18R1, IL23R, GP130, or IL15Ra.

141. The fusion protein, isolated nucleic acid, modified cell, pharmaceutical composition, or method of one of embodiments 128-135, wherein the intracellular domain is an intracellular domain of IL12R, IL18R1, IL23R, GP130, or IL15Ra.

142. The fusion protein, isolated nucleic acid, modified cell, pharmaceutical composition, or method of one of embodiments 128-141, wherein the transmembrane domain is an intracellular domain of OX40, CD40, 4-1BB, GITR, ICOS, CD28, CD27, HER2, EGFR, IL12R, IL18R1, IL23R, GP130, or IL15Ra.

143. The modified cell, pharmaceutical composition, or method of one of embodiments 131-135, wherein the modified cell is lymphocyte, leukocyte, or PBMC; or cells, NK cells, T cells, or dendritic cells.

144. The modified cell, pharmaceutical composition, or method of one of embodiments 131-143, wherein the modified cell further comprises a Chimeric antigen receptor (CAR) or a modified TCR.

145. The modified cell, pharmaceutical composition, or method of embodiment 144, wherein the TCR is a modified TCR.

146. The modified cell, pharmaceutical composition, or method of embodiment 144, wherein the TCR is derived from spontaneously occurring tumor-specific T cells in patients.

147. The modified cell, pharmaceutical composition, or method of embodiment 144, wherein the TCR binds a tumor antigen.

148. The modified cell, pharmaceutical composition, or method of embodiment 147, wherein the tumor antigen comprises CEA, gp100, MART-1, p53, MAGE-A3, or NY-ESO-1, or the TCR comprises TCRγ and TCRδ Chains or TCRα and TCRβ chains, or a combination thereof.

149. The modified cell, pharmaceutical composition, or method of embodiment 144, wherein the CAR comprises an extracellular domain, a transmembrane domain, and an intracellular domain, and wherein the extracellular domain binds an antigen.

150. The modified cell, pharmaceutical composition, or method of embodiment 149, wherein the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.

151. The modified cell, pharmaceutical composition, or method of embodiment 150, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Rα2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.

152. The modified cell, pharmaceutical composition, or method of one of embodiments 131-151, wherein the modified cell or the T cells comprise an additional CAR binding a solid tumor antigen, and the CAR binds an antigen of a white blood cell.

153. The modified cell, pharmaceutical composition, or method of one of embodiments 131-151, wherein the modified cell or the T cells comprise a dominant negative PD-1.

154. The modified cell, pharmaceutical composition, or method of one of embodiments 131-151, wherein the modified cell or the T cells comprise a modified PD-1 lacking a functional PD-1 intracellular domain.

155. The modified cell, pharmaceutical composition or method of one of embodiments 131-154, wherein the modified cell further comprises a nucleic acid encoding therapeutic agent.

156. The modified cell, pharmaceutical composition, or method of embodiment 155, wherein the isolated nucleic acid comprises a promoter comprising a binding site for a transcription modulator that modulates the expression and/or secretion of the therapeutic agent in the cell.

157. The modified cell, pharmaceutical composition, or method of embodiment 156, wherein the transcription modulator is or includes Hif1a, NFAT, FOXP3, and/or NFkB.

158. The modified cell, pharmaceutical composition, or method of embodiment 157, wherein the promoter is responsive to the transcription modulator.

159. The modified cell, pharmaceutical composition, or method of embodiment 157, wherein the promoter is operably linked to the nucleic acid encoding the therapeutic agent such that the promoter drives expression and/or secretion of the therapeutic agent in the cell.

160. The modified cell, pharmaceutical composition, or method of embodiment 157, wherein expression of the therapeutic agent is regulated by an inducible gene expression system.
161. The modified cell, pharmaceutical composition, or method of embodiment 160, wherein the inducible gene expression system comprises or is a lac system, a tetracycline system, or a galactose system.
162. The modified cell, pharmaceutical composition, or method of embodiment 160, wherein the inducible gene expression system comprises or is a tetracycline system.
163. The modified cell, pharmaceutical composition, or method of embodiment 162, wherein the inducible gene expression system comprises or is a tetracycline on system, and an inducer is tetracycline, doxycycline, or an analog thereof.
164. The modified cell, pharmaceutical composition, or method of one of embodiments 131-163, wherein the modified cell is a T cell derived from a primary human T cell isolated from a human donor.
165. The modified cell, pharmaceutical composition, or method of embodiment 164, wherein the cell has a reduced expression of endogenous TRAC gene.
166. The modified cell, pharmaceutical composition, or method of one of embodiments 131-163, wherein the modified cell is a T cell derived from a primary human T cell isolated from a subject having cancer.

The related sequences are provided in Table 2 as well as PCT Patent Applications Nos: PCT/CN2016/075061, PCT/CN2018/08891, and PCT/US19/13068, which are incorporated herein by reference in their entirety.

EXAMPLES

Figure 6:
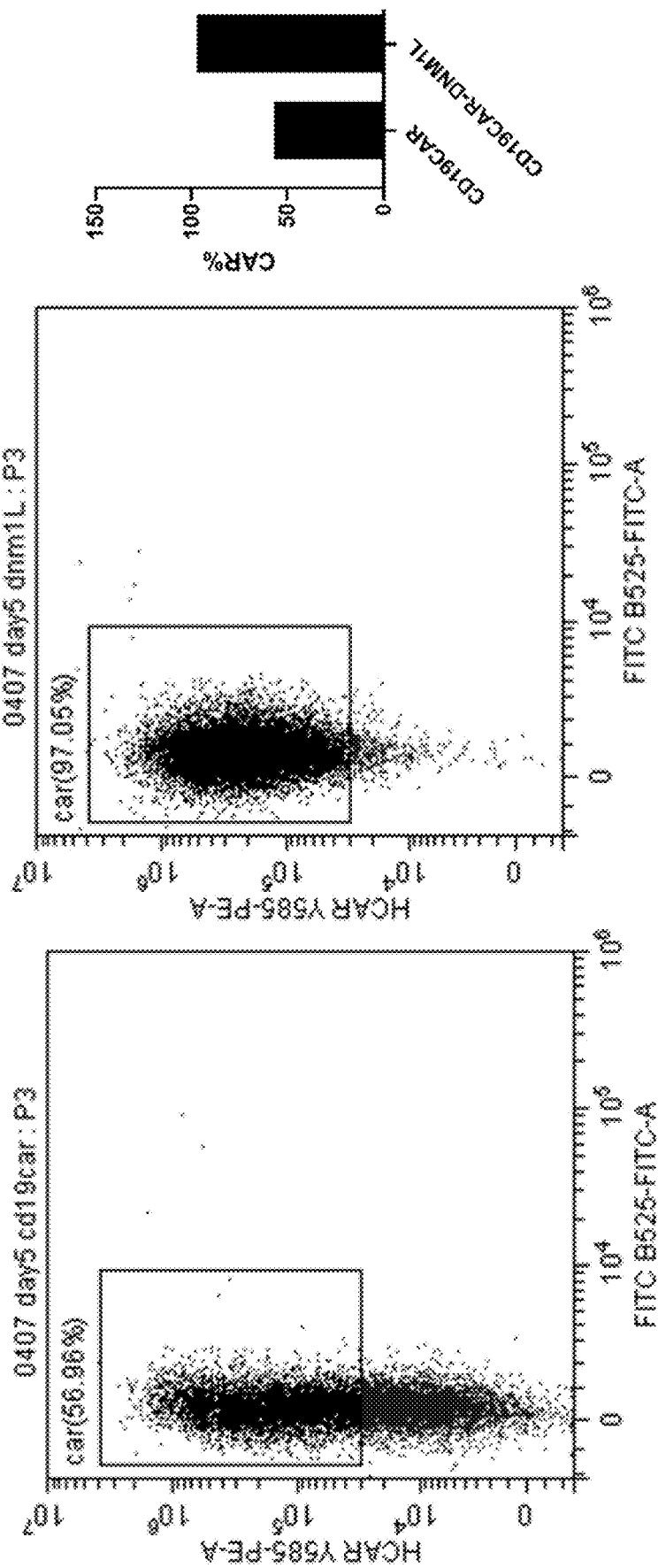
FIG. 6 shows flow cytometry results of CART cells that have been cultured to Day 5.

Lentiviral vectors that encode individual CAR molecules were generated and transfected into T cells, which are elaborated below. Techniques related to cell cultures, construction of cytotoxic T lymphocyte assay can be found in "Control of large, established tumor xenografts with genetically retargeted human T cells containing CD28 and CD137 domains," PNAS, Mar. 3, 2009, vol. 106, no. 9, 3360-3365 and "Chimeric Receptors Containing CD137 Signal Transduction Domains Mediate Enhanced Survival of T Cells and Increased Antileukemic Efficacy In Vivo," Molecular Therapy, August 2009, vol. 17, no. 8, 1453-1464, which are incorporated herein by reference in their entirety. FIG. 6 shows flow cytometry results of T cells comprising a polynucleotide encoding CD19CAR (scFv binding CD19: SEQ ID NO: 5) and CD19CAR-2a-DNM1L (SEQ ID NO: 118) that have been cultured to Day 5. Sequence information corresponding to various vectors in the Examples are provided in Table 2.

Figure 7:
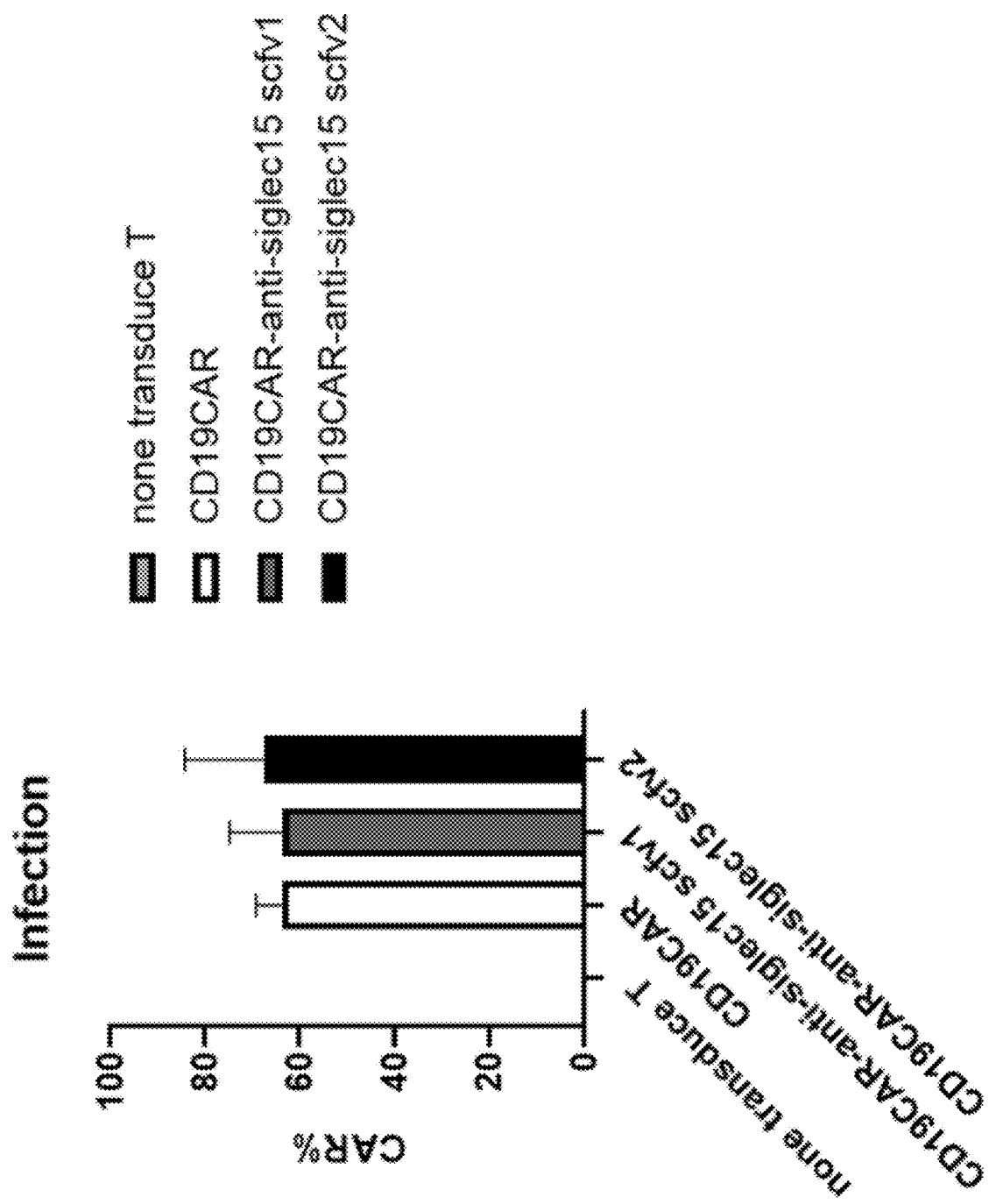
FIGS. 7, 8, 9, and 10 show CAR expression and functions of T cells comprising a CAR and T cells comprising a CAR and secretable SIGLEC-15 scFv.
Figure 8:
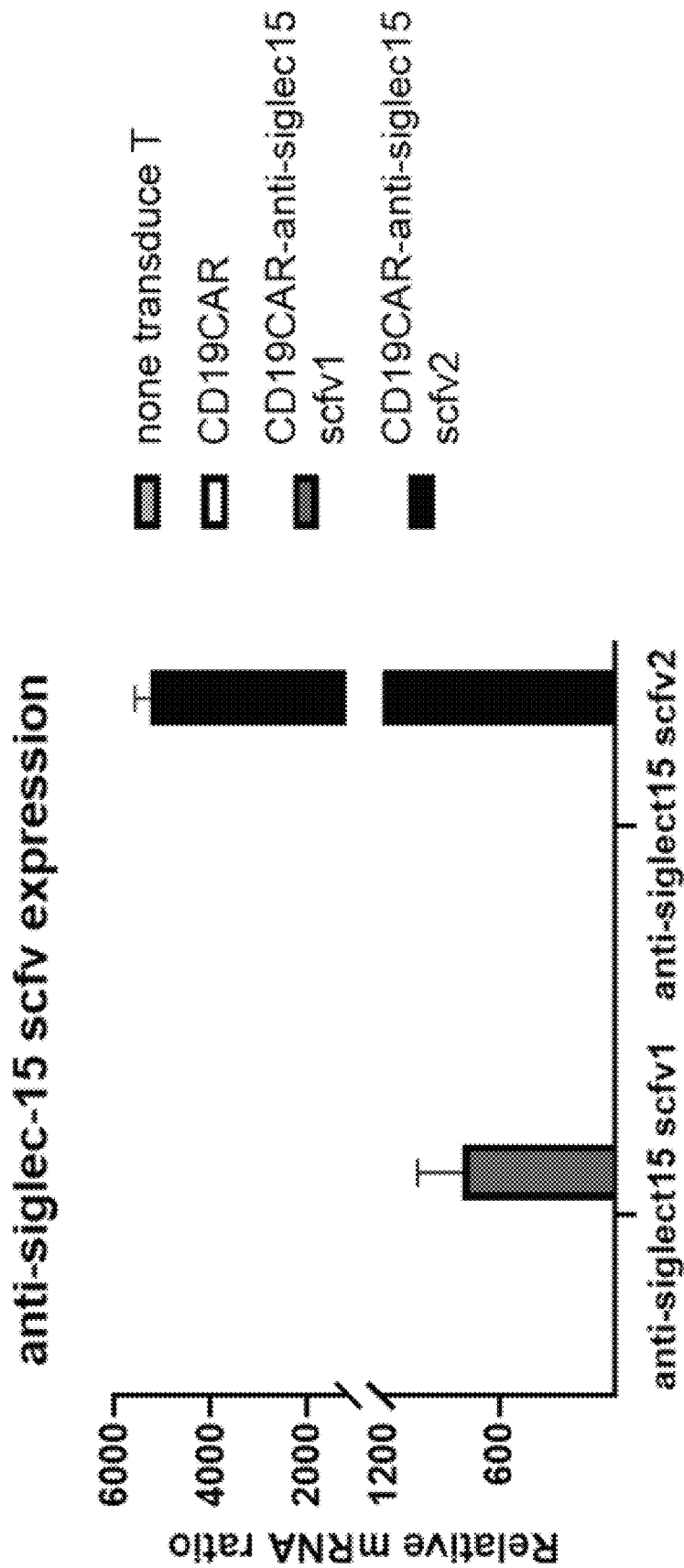

FIGS. 7-10 show CAR expression and functions of T cells comprising a CAR and T cells comprising a CAR and secretable SIGLEC-15 scFv. T cells from various donors were obtained and transfected with vectors comprising CD19 CAR (SEQ ID NO: 5) or CD19 CAR-anti-SIGLEC-15 scFvs (SEQ ID NO: 115 or 116). As shown in FIG. 7, transduction of polynucleotides encoding anti-SIGLEC-15 scFvs did not affect the expression of CAR, which indicates that CAR expression is normal. Further, as shown in FIG. 8, T cells comprising polynucleotides encoding anti-SIGLEC-15 SCFV-1 and SCFV-2 have significant mRNA expression compared to control.

Figure 9:
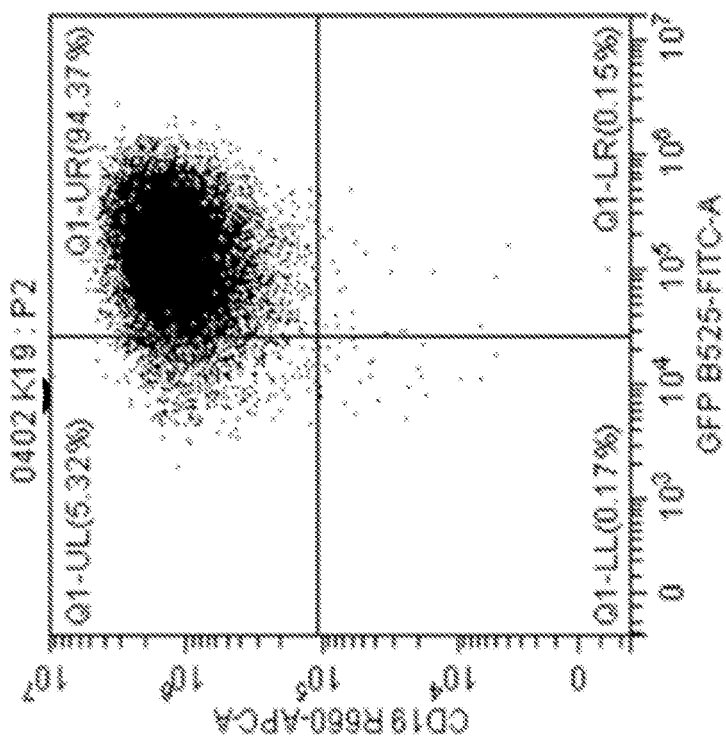
Figure 9:
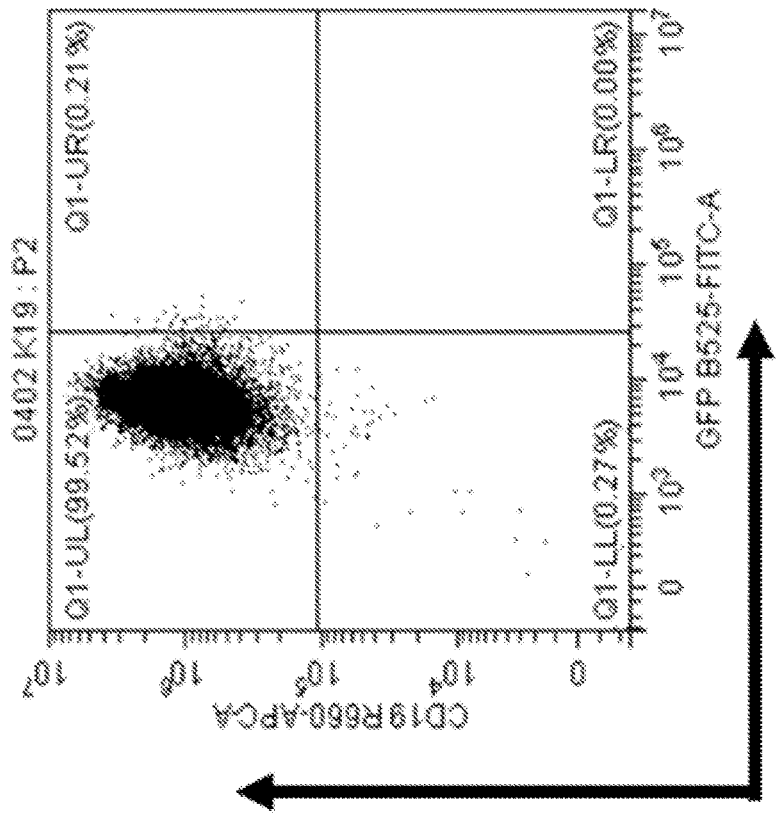
Figure 10:
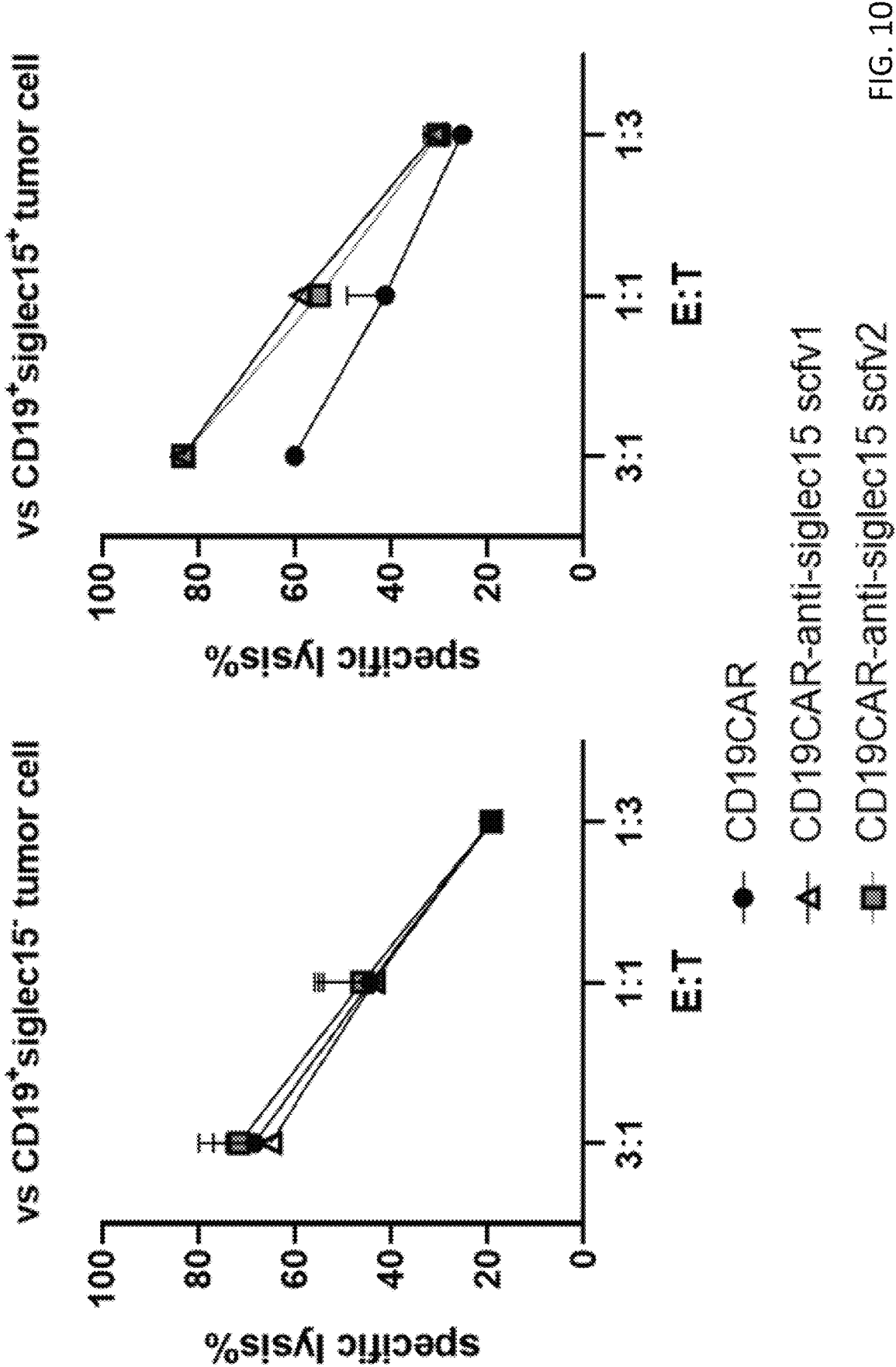

FIG. 9 shows flow cytometry results of the gene expression of tumor cells. The tumor cells comprising SIGLEC-15 and CD19+ does not express SIGLEC-15, while the tumor cells comprising CD19+ and SIGLEC-15+ express SIGLEC-15. FIG. 10 shows the killing function assay of T cells comprising CD19CAR and T cells comprising CD19CAR and secretable SIGLEC-15 scFv. Under different E:T ratios, various CART cells were co-cultured with SIGLEC-15-CD19+ and SIGLEC-15+-CD19+ tumor cells, and the function was determined by flow cytometry. As shown in FIG. 10, T cells comprising CD19 CAR and secretable SIGLEC-15 scFv showed enhanced killing of CD19+ and SIGLEC15+ tumor cells than T cells comprising CD19 CAR alone. These results demonstrate that secretable anti-SIGLEC-15 scFv blocked the SIGLEC-15-CD44 pathway to enhance the T cells' function.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A modified cell comprising a polynucleotide encoding an antibody binding SIGLEC-15, wherein the antibody is secretable or attached to the membrane of the modified cell, wherein the polynucleotide comprises a polynucleotide encoding at least one of SEQ ID NOS: 115 and 116.

2. The modified cell of claim 1, wherein the modified cell further comprises a dominant negative form of an immune checkpoint inhibitor selected from the group consisting of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRD, CD44, natural killer cell receptor 2B4 (2B4), and CD 160.

3. The modified cell of claim 1, wherein the modified T cell is engineered to express and secrete a therapeutic agent.

4. The modified cell of claim 3, wherein the therapeutic agent comprises at least one of IL-33, IL-1β, TNFα, MALP-2, IL1, IL17, G-CSF or GM-CSF, IL-6, IL-12, and IFN-γ.

5. The modified cell of claim 3, wherein the therapeutic agent is regulated by Hif1a, NFAT, FOXP3, and/or NFkB.

6. The modified cell of claim 1, wherein the modified cell comprises an antigen-binding molecule binding a tumor antigen, and the modified cell comprises a T cell derived from a healthy donor or a subject having cancer.

7. The modified cell of claim 6, wherein the antigen-binding molecule is a chimeric antigen receptor (CAR), which comprises an antigen-binding domain, a transmembrane domain, and an intracellular signaling domain.

8. The modified cell of claim 7, wherein the antigen-binding domain binds a tumor antigen selected from a group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGS5, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

9. The modified cell claim 8, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CD5, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

10. The modified cell of claim 6, wherein the antigen-binding molecule is a modified T cell receptor (TCR).

11. The modified cell of claim 10, wherein the TCR is derived from spontaneously occurring tumor-specific T cells in patients.

12. The modified cell of claim 11, wherein the TCR binds to a tumor antigen.

13. The modified cell of claim 12, wherein the tumor antigen comprises CEA, gp100, MART-1, p53, MAGE-A3, or NY-ESO-1.

14. The modified cell of claim 12, wherein the TCR comprises TCRγ and TCRδ chains, TCRα and TCRβ chains, or a combination thereof.

15. The modified cell of claim 1, wherein the cell is an immune cell.

16. The modified cell of claim 15, wherein the immune cell is a T cell or an NK cell.

17. The modified cell of claim 16, wherein the immune cell is a CD4+ T cell, a CD8+ T cell, or a combination thereof.

18. The modified cell of claim 3, wherein the therapeutic agent is a cytokine.

19. The modified cell of claim 1, wherein the polynucleotide further comprises at least one of SEQ ID NO: 117, 118, and 119.

20. A modified cell comprising a polynucleotide encoding at least one of SEQ ID NOS: 117, 118, and 119.

21. The modified cell of claim 20, wherein the modified cell comprises an antigen-binding molecule binding a tumor antigen, and the modified cell comprises a T cell derived from a healthy donor or a subject having cancer.

22. The modified cell of claim 21, wherein the antigen-binding molecule is a CAR or a modified TCR.

* * * * *

SEQUENCE LISTING

```
<160> NUMBER OF SEQ ID NOS: 120

<210> SEQ ID NO 1
<211> LENGTH: 21
<212> TYPE: PRT
<213> ORGANISM: Artificial Sequence
<220> FEATURE:
<223> OTHER INFORMATION: Synthesized

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 69
<212> TYPE: PRT
```

```
<213> ORGANISM: Artificial Sequence
<220> FEATURE:
<223> OTHER INFORMATION: Synthesized

<400> SEQUENCE: 2

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala Cys Asp
            35                  40                  45

Ile Tyr Ile Trp Ala Pro Leu Ala Gly Thr Cys Gly Val Leu Leu Leu
50                  55                  60

Ser Leu Val Ile Thr
65

<210> SEQ ID NO 3
<211> LENGTH: 42
<212> TYPE: PRT
<213> ORGANISM: Artificial Sequence
<220> FEATURE:
<223> OTHER INFORMATION: Synthesized

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 4
<211> LENGTH: 112
<212> TYPE: PRT
<213> ORGANISM: Artificial Sequence
<220> FEATURE:
<223> OTHER INFORMATION: Synthesized

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 242
<212> TYPE: PRT
<213> ORGANISM: Artificial Sequence
<220> FEATURE:
<223> OTHER INFORMATION: Synthesized
```

<400> SEQUENCE: 5

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Lys Tyr
            20                  25                  30

Leu Asn Trp Tyr Gln Gln Lys Pro Gly Lys Ala Pro Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Thr Leu Pro Tyr
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Glu
        115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
            180                 185                 190

Arg Asp Asn Ala Lys Asn Ser Leu Tyr Leu Gln Met Asn Ser Leu Arg
        195                 200                 205

Ala Glu Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser
```

<210> SEQ ID NO 6
<211> LENGTH: 242
<212> TYPE: PRT
<213> ORGANISM: Artificial Sequence
<220> FEATURE:
<223> OTHER INFORMATION: Synthesized

<400> SEQUENCE: 6

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110
```

```
Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
        130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
                195                 200                 205

Thr Asp Asp Thr Ala Ile Tyr Tyr Cys Ala Lys His Tyr Tyr Tyr Gly
            210                 215                 220

Gly Ser Tyr Ala Met Asp Tyr Trp Gly Gln Gly Thr Ser Val Thr Val
225                 230                 235                 240

Ser Ser

<210> SEQ ID NO 7
<211> LENGTH: 237
<212> TYPE: PRT
<213> ORGANISM: Artificial Sequence
<220> FEATURE:
<223> OTHER INFORMATION: Synthesized

<400> SEQUENCE: 7

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Gly Gly Gly Ser Gly Gly Gly Gly
            100                 105                 110

Gly Ser Gly Gly Gly Gly Ser Glu Val Gln Leu Gln Gln Ser Gly Ala
        115                 120                 125

Glu Leu Val Lys Pro Gly Ala Ser Val Lys Leu Ser Cys Thr Ala Ser
    130                 135                 140

Gly Phe Asn Ile Asn Asp Thr Tyr Met His Trp Val Lys Gln Arg Pro
145                 150                 155                 160

Glu Gln Gly Leu Glu Trp Ile Gly Arg Ile Asp Pro Ala Asn Gly Asn
                165                 170                 175

Thr Lys Tyr Asp Pro Lys Phe Gln Gly Lys Ala Thr Ile Thr Ala Asp
            180                 185                 190

Thr Ser Ser Asn Thr Ala Tyr Leu Gln Leu Ser Ser Leu Thr Ser Glu
        195                 200                 205

Asp Thr Ala Val Tyr Tyr Cys Ala Arg Gly Ala Arg Gly Ser Arg Phe
    210                 215                 220
```

Ala Tyr Trp Gly Gln Gly Thr Leu Val Thr Val Ser Ala
225                 230                 235

<210> SEQ ID NO 8
<211> LENGTH: 244
<212> TYPE: PRT
<213> ORGANISM: Artificial Sequence
<220> FEATURE:
<223> OTHER INFORMATION: Synthesized

<400> SEQUENCE: 8

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gly
            100                 105                 110

Gly Gly Ser Gly Gly Gly Gly Ser Gly Gly Gly Ser Glu Val Gln
            115                 120                 125

Leu Val Gln Ser Gly Ala Glu Val Lys Lys Pro Gly Gln Ser Leu Lys
        130                 135                 140

Ile Ser Cys Lys Ala Ser Gly Tyr Ser Leu Thr Asp Asn Trp Ile Gly
145                 150                 155                 160

Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
        195                 200                 205

Ser Ser Leu Lys Ala Ser Asp Thr Ala Ile Tyr Tyr Cys Val Gly Leu
    210                 215                 220

Asp Trp Asn Tyr Asn Pro Leu Arg Tyr Trp Gly Pro Gly Thr Leu Val
225                 230                 235                 240

Thr Val Ser Ser

<210> SEQ ID NO 9
<211> LENGTH: 252
<212> TYPE: PRT
<213> ORGANISM: Artificial Sequence
<220> FEATURE:
<223> OTHER INFORMATION: Synthesized

<400> SEQUENCE: 9

Asp Ile Val Leu Thr Gln Ser Pro Ala Ser Leu Ala Val Ser Leu Gly
1               5                   10                  15

Gln Gly Ala Thr Ile Ser Cys Arg Ala Ser Lys Ser Val Ser Thr Ser
            20                  25                  30

Gly Tyr Thr Tyr Met His Trp Tyr Gln Gln Lys Pro Gly Gln Pro Pro
        35                  40                  45

```
Lys Leu Leu Ile Tyr Leu Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Asp Ala Ala Thr Tyr Tyr Cys Gln His Ser Gly
             85                  90                  95

Glu Leu Pro Pro Ser Phe Gly Gly Gly Thr Lys Leu Glu Ile Lys Arg
            100                 105                 110

Ala Gly Gly Gly Gly Ser Gly Gly Gly Ser Gly Gly Gly Ser
            115                 120                 125

Glu Val Gln Leu Val Glu Ser Gly Gly Asp Leu Val Lys Pro Gly Gly
            130                 135                 140

Ser Leu Lys Leu Ser Cys Ala Val Ser Gly Phe Thr Phe Ser Ser Tyr
145                 150                 155                 160

Gly Met Ser Trp Val Arg Gln Thr Pro Asp Lys Arg Leu Glu Trp Val
                165                 170                 175

Ala Thr Val Ser Ser Gly Gly Thr Tyr Thr Tyr Tyr Pro Asp Ser Val
                180                 185                 190

Lys Gly Arg Phe Thr Ile Ser Arg Asp Asn Ala Lys Asn Thr Leu Tyr
                195                 200                 205

Leu Gln Met Ser Ser Leu Lys Ser Glu Asp Ser Ala Met Tyr Tyr Cys
            210                 215                 220

Ala Arg His Arg Gly Asn Tyr Tyr Ala Thr Tyr Tyr Tyr Ala Met Asp
225                 230                 235                 240

Tyr Trp Gly Gln Gly Thr Ser Val Thr Val Ser Ser
                245                 250
```

<210> SEQ ID NO 10
<211> LENGTH: 243
<212> TYPE: PRT
<213> ORGANISM: Artificial Sequence
<220> FEATURE:
<223> OTHER INFORMATION: Synthesized

<400> SEQUENCE: 10

```
Asp Val Gln Ile Thr Gln Ser Pro Ser Tyr Leu Ala Ala Ser Pro Gly
 1               5                  10                  15

Glu Thr Ile Thr Ile Asn Cys Arg Ala Ser Lys Ser Ile Ser Lys Tyr
                20                  25                  30

Leu Ala Trp Tyr Gln Glu Lys Pro Gly Lys Thr Asn Lys Leu Leu Ile
             35                  40                  45

Tyr Ser Gly Ser Thr Leu Gln Ser Gly Ile Pro Ser Arg Phe Ser Gly
         50                  55                  60

Ser Gly Ser Gly Thr Asp Phe Thr Leu Thr Ile Ser Ser Leu Glu Pro
 65                  70                  75                  80

Glu Asp Phe Ala Met Tyr Tyr Cys Gln Gln His Glu Tyr Pro Tyr
                 85                  90                  95

Thr Phe Gly Gly Gly Thr Lys Leu Glu Ile Lys Gly Gly Gly Gly Ser
            100                 105                 110

Gly Gly Gly Gly Ser Gly Gly Gly Ser Gln Val Gln Leu Gln Gln
            115                 120                 125

Pro Gly Ala Glu Leu Val Arg Pro Gly Ala Ser Val Lys Leu Ser Cys
            130                 135                 140

Lys Ala Ser Gly Tyr Thr Phe Thr Thr Tyr Trp Met Asn Trp Val Lys
145                 150                 155                 160
```

Gln Arg Pro Glu Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
            180                 185                 190

Thr Val Asp Lys Ser Ser Thr Ala Tyr Met Gln Leu Ser Ser Leu
        195                 200                 205

Thr Ser Glu Asp Ser Ala Val Tyr Tyr Cys Ala Arg Gly Pro Tyr Tyr
    210                 215                 220

Gly Thr Asn Pro Trp Phe Pro Tyr Trp Gly Gln Gly Thr Leu Val Thr
225                 230                 235                 240

Val Ser Ser

<210> SEQ ID NO 11
<211> LENGTH: 241
<212> TYPE: PRT
<213> ORGANISM: Artificial Sequence
<220> FEATURE:
<223> OTHER INFORMATION: Synthesized

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
        115                 120                 125

Trp Gly Ala Gly Leu Leu Lys Pro Ser Glu Thr Leu Ser Leu Thr Cys
130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
        195                 200                 205

Ala Ala Asp Thr Ala Val Tyr Tyr Cys Ala Arg Glu Arg Gly Tyr Thr
    210                 215                 220

Tyr Gly Asn Phe Asp His Trp Gly Gln Gly Thr Leu Val Thr Val Ser
225                 230                 235                 240

Ser

<210> SEQ ID NO 12
<211> LENGTH: 246
<212> TYPE: PRT
<213> ORGANISM: Artificial Sequence -continued

```
<220> FEATURE:
<223> OTHER INFORMATION: Synthesized

<400> SEQUENCE: 12

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Gly Gly Gly Gly Ser Gly Gly Gly Gly Ser Gly Gly Gly Gly
        115                 120                 125

Ser Gln Val Gln Leu Arg Gln Ser Gly Pro Glu Leu Val Lys Pro Gly
    130                 135                 140

Ala Ser Val Lys Met Ser Cys Lys Ala Ser Gly Tyr Thr Phe Thr Asp
145                 150                 155                 160

Tyr Val Ile Ser Trp Val Lys Gln Arg Thr Gly Gln Gly Leu Glu Trp
                165                 170                 175

Ile Gly Asp Ile Tyr Pro Gly Ser Gly Tyr Ser Phe Tyr Asn Glu Asn
            180                 185                 190

Phe Lys Gly Lys Ala Thr Leu Thr Ala Asp Lys Ser Ser Thr Thr Ala
        195                 200                 205

Tyr Met Gln Leu Ser Ser Leu Thr Ser Glu Asp Ser Ala Val Tyr Phe
    210                 215                 220

Cys Ala Thr Tyr Tyr Asn Tyr Pro Phe Ala Tyr Trp Gly Gln Gly Thr
225                 230                 235                 240

Leu Val Thr Val Ser Ala
                245

<210> SEQ ID NO 13
<211> LENGTH: 199
<212> TYPE: PRT
<213> ORGANISM: Artificial Sequence
<220> FEATURE:
<223> OTHER INFORMATION: Synthesized

<400> SEQUENCE: 13

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg
        35                  40                  45

Gly Phe Ile Thr Lys Ala Ile Asn Ser Cys His Thr Ser Ser Leu Ala
    50                  55                  60

Thr Pro Glu Asp Lys Glu Gln Ala Gln Gln Met Asn Gln Lys Asp Phe
65                  70                  75                  80

Leu Ser Leu Ile Val Ser Ile Leu Arg Ser Trp Asn Glu Pro Leu Tyr
```

```
                    85                  90                  95
His Leu Val Thr Glu Val Arg Gly Met Gln Glu Ala Pro Glu Ala Ile
                100                 105                 110

Leu Ser Lys Ala Val Glu Ile Glu Glu Gln Thr Lys Arg Leu Leu Glu
            115                 120                 125

Gly Met Glu Leu Ile Val Ser Gln Val His Pro Glu Thr Lys Glu Asn
        130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Lys Cys Arg
                180                 185                 190

Ile Ile His Asn Asn Asn Cys
                195

<210> SEQ ID NO 14
<211> LENGTH: 240
<212> TYPE: PRT
<213> ORGANISM: Artificial Sequence
<220> FEATURE:
<223> OTHER INFORMATION: Synthesized

<400> SEQUENCE: 14

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
                100                 105                 110

Gly Gly Gly Gly Gly Ser Gly Gly Gly Ser Gly Gly Gly Gly Ser
            115                 120                 125

Asp Ile Val Met Thr Gln Ser Pro Asp Ser Leu Ala Val Ser Leu Gly
        130                 135                 140

Glu Arg Ala Thr Ile Asn Cys Lys Ser Ser Gln Ser Leu Leu Asn Ser
145                 150                 155                 160

Arg Thr Arg Lys Asn Tyr Leu Ala Trp Tyr Gln Gln Lys Pro Gly Gln
                165                 170                 175

Pro Pro Lys Leu Leu Ile Tyr Trp Ala Ser Thr Arg Glu Ser Gly Val
                180                 185                 190

Pro Asp Arg Phe Ser Gly Ser Gly Ser Gly Thr Asp Phe Thr Leu Thr
            195                 200                 205

Ile Ser Ser Leu Gln Ala Glu Asp Val Ala Val Tyr Tyr Cys Thr Gln
        210                 215                 220

Ser Phe Ile Leu Arg Thr Phe Gly Gln Gly Thr Lys Val Glu Ile Lys
225                 230                 235                 240
```

```
<210> SEQ ID NO 15
<211> LENGTH: 281
<212> TYPE: PRT
<213> ORGANISM: Artificial Sequence
<220> FEATURE:
<223> OTHER INFORMATION: Synthesized

<400> SEQUENCE: 15

Met Asn Val Pro Thr Gln Leu Leu Gly Leu Leu Leu Trp Leu Thr
1               5                   10                  15

Gly Gly Lys Cys Asp Ile Gln Met Thr Gln Ser Pro Ala Ser Leu Ser
                20                  25                  30

Ala Ser Leu Glu Glu Ile Val Thr Ile Thr Cys Lys Ala Ser Gln Ala
            35                  40                  45

Ile Asp Ala Tyr Leu Ser Trp Tyr Gln Gln Lys Pro Gly Lys Ser Pro
50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys Gly
        115                 120                 125

Gly Gly Gly Gly Ser Gly Gly Gly Gly Ser Gly Gly Gly Gly Ser Met
    130                 135                 140

Ala Val Leu Val Leu Leu Leu Cys Leu Leu Ile Phe Pro Ser Cys Val
145                 150                 155                 160

Leu Ser Gln Val Gln Leu Lys Glu Ser Gly Pro Gly Leu Val Gln Pro
                165                 170                 175

Ser Gln Thr Leu Ser Leu Thr Cys Thr Val Ser Gly Ser Ser Leu Thr
            180                 185                 190

Ser Asn Ser Val Ser Trp Ile Arg Gln Pro Pro Gly Lys Gly Leu Glu
        195                 200                 205

Trp Met Gly Val Ile Trp Ser Asn Gly Asp Ala Asp Tyr Asn Ser Ala
    210                 215                 220

Ile Lys Ser Arg Leu Ser Ile Ser Arg Asp Thr Ser Lys Ser Gln Val
225                 230                 235                 240

Phe Leu Lys Met Asn Ser Leu Gln Thr Glu Asp Thr Ala Met Tyr Phe
                245                 250                 255

Cys Ala Ser Pro Tyr Tyr Gly Tyr Tyr Phe Pro Phe Asp Tyr Trp Gly
            260                 265                 270

Gln Gly Val Met Val Thr Val Ser Ser
        275                 280

<210> SEQ ID NO 16
<211> LENGTH: 285
<212> TYPE: PRT
<213> ORGANISM: Artificial Sequence
<220> FEATURE:
<223> OTHER INFORMATION: Synthesized

<400> SEQUENCE: 16

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
                20                  25                  30
```

```
Ser Leu Gly Gln Arg Ala Thr Ile Ser Cys Arg Ala Ser Gln Ser Val
            35                  40                  45

Ser Ile Ser Ser His Asp Leu Met Gln Trp Tyr Gln Gln Lys Pro Gly
        50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Ile Ala Thr Tyr Tyr Cys Gln
            100                 105                 110

Gln Ser Lys Asp Asp Pro Tyr Thr Phe Gly Ala Gly Thr Lys Leu Glu
            115                 120                 125

Leu Lys Gly Gly Gly Gly Ser Gly Gly Gly Ser Gly Gly Gly
        130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
        195                 200                 205

Gly Leu Glu Trp Val Ala Thr Ile Ser Tyr Asp Gly Ser Ile Thr Tyr
        210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
            275                 280                 285

<210> SEQ ID NO 17
<211> LENGTH: 242
<212> TYPE: PRT
<213> ORGANISM: Artificial Sequence
<220> FEATURE:
<223> OTHER INFORMATION: Synthesized

<400> SEQUENCE: 17

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45

Tyr Trp Thr Ser Thr Arg His Thr Gly Val Pro Asp Arg Phe Thr Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Phe Cys His Gln Tyr Asn Ser Tyr Asn Thr
                85                  90                  95

Phe Gly Ser Gly Thr Lys Leu Glu Ile Lys Gly Gly Gly Gly Ser
            100                 105                 110
```

Gly Gly Gly Gly Ser Gly Gly Gly Ser Gln Val Thr Leu Lys Glu
            115                 120                 125

Ser Gly Pro Val Leu Val Lys Pro Thr Glu Thr Leu Thr Leu Thr Cys
130                 135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Val Tyr Tyr Asn Pro Ser Leu Lys Ser Arg Leu Thr
            180                 185                 190

Ile Thr Lys Asp Ala Ser Lys Asp Gln Val Ser Leu Lys Leu Ser Ser
            195                 200                 205

Val Thr Ala Ala Asp Thr Ala Val Tyr Tyr Cys Val Arg Arg Arg Ala
210                 215                 220

Thr Gly Thr Gly Phe Asp Tyr Trp Gly Gln Gly Thr Leu Val Thr Val
225                 230                 235                 240

Ser Ser

<210> SEQ ID NO 18
<211> LENGTH: 339
<212> TYPE: DNA
<213> ORGANISM: Homo sapiens

<400> SEQUENCE: 18
agagtgaagt tcagcaggag cgcagacgcc cccgcgtacc agcagggcca gaaccagctc      60
tataacgagc tcaatctagg acgaagagag gagtacgatg ttttggacaa gaggcgtggc     120
cgggaccctg agatgggggg aaagccgaga aggaagaacc ctcaggaagg cctgtacaat     180
gaactgcaga agataagat ggcggaggcc tacagtgaga ttgggatgaa aggcgagcgc      240
cggaggggca aggggcacga tggcctttac cagggtctca gtacagccac caaggacacc     300
tacgacgccc ttcacatgca ggccctgccc cctcgctaa                           339

<210> SEQ ID NO 19
<211> LENGTH: 1689
<212> TYPE: DNA
<213> ORGANISM: Artificial Sequence
<220> FEATURE:
<223> OTHER INFORMATION: Synthesized

<400> SEQUENCE: 19
cggctccggt gcccgtcagt gggcagagcg cacatcgccc acagtccccg agaagttggg      60
gggaggggtc ggcaattgaa ccggtgccta gagaaggtgg cgcggggtaa actgggaaag    120
tgatgtcgtg tactggctcc gccttttttcc gagggtggg ggagaaccgt atataagtgc     180
agtagtcgcc gtgaacgttc ttttttcgcaa cgggtttgcc gccagaacac aggatccgcc    240
accatggcct taccagtgac cgccttgctc ctgccgctgg ccttgctgct ccacgccgcc    300
aggccggaca tccagctcac ccagtccccg agctcgctgt ccgcctccgt gggagatcgg    360
gtcaccatca cgtgccgcgc cagccagtcg atttcctcct acctgaactg gtaccaacag    420
aagcccggaa aagccccgaa gcttctcatc tacgccgcct cgagcctgca gtcaggagtg    480
ccctcacggt tctccggctc cggttccggt actgatttca ccctgaccat tcctccctg    540 caaccggagg acttcgctac ttactactgc cagcagtcgt actccacccc ctacactttc    600
ggacaaggca ccaaggtcga aatcaagggt ggcggtggct cgggcggtgg tgggtcgggt    660
ggcggcggat ctgaagtgca attggtggaa tcaggggag gacttgtgca gcctggagga    720

-continued

```
tcgctgagac tgtcatgtgc cgtgtccggc tttgccctgt ccaaccacgg gatgtcctgg    780
gtccgccgcg cgcctggaaa gggcctcgaa tgggtgtcgg gtattgtgta cagcggtagc    840
acctactatg ccgcatccgt gaaggggaga ttcaccatca gccgggacaa ctccaggaac    900
actctgtacc tccaaatgaa ttcgctgagg ccagaggaca ctgccatcta ctactgctcc    960
gcgcatggcg gagagtccga cgtctgggga caggggacca ccgtgaccgt gtctagcacc   1020
acgacgccag cgccgcgacc accaacaccg gcgcccacca tcgcgtcgca gcccctgtcc   1080
ctgcgcccag aggcgtgccg gccagcggcg gggggcgcag tgcacacgag ggggctggac   1140
ttcgcctgtg atatctacat ctgggcgccc ttggccggga cttgtggggt ccttctcctg   1200
tcactggtta tcacccttta ctgcaaacgg ggcagaaaga aactcctgta tatattcaaa   1260
caaccattta tgagaccagt acaaactact caagaggaag atggctgtag ctgccgattt   1320
ccagaagaag aagaaggagg atgtgaactg agagtgaagt tcagcaggag cgcagacgcc   1380
cccgcgtacc agcagggcca gaaccagctc tataacgagc tcaatctagg acgaagagag   1440
gagtacgatg tttttggaca agaggcgtgg cgggaccctg gatggggggg aaagccgaga   1500
aggaagaacc ctcaggaagg cctgtacaat gaactgcaga agataagat ggcggaggcc    1560 tacagtgaga ttgggatgaa aggcgagcgc cggaggggca aggggcacga tggcctttac   1620
cagggtctca gtacagccac caaggacacc tacgacgccc ttcacatgca ggccctgccc   1680
cctcgctaa                                                            1689
```

<210> SEQ ID NO 20
<211> LENGTH: 1446
<212> TYPE: DNA
<213> ORGANISM: Artificial Sequence
<220> FEATURE:
<223> OTHER INFORMATION: Synthesized

<400> SEQUENCE: 20

```
atggccttac cagtgaccgc cttgctcctg ccgctggcct tgctgctcca cgccgccagg     60
ccggacatcc agctcaccca gtccccgagc tcgctgtccg cctccgtggg agatcgggtc    120
accatcacgt gccgcgccag ccagtcgatt tcctcctacc tgaactggta ccaacagaag    180
cccggaaaag cccgaagct tctcatctac gccgcctcga gcctgcagtc aggagtgccc    240
tcacggttct ccggctccgg ttccggtact gatttcaccc tgaccatttc ctccctgcaa    300
ccggaggact cgctactta ctactgccag cagtcgtact ccacccccta cactttcgga    360
caaggcacca aggtcgaaat caaggtggc ggtggctcgg gcggtggtgg gtcgggtggc    420
ggcggatctg aagtgcaatt ggtggaatca gggggaggac ttgtgcagcc tggaggatcg    480
ctgagactgt catgtgccgt gtccggcttt gccctgtcca ccacgggat gtcctgggtc    540 cgccgcgcgc ctggaaaggg cctcgaatgg gtgtcgggta ttgtgtacag cggtagcacc    600
tactatgccg catccgtgaa ggggagattc accatcagcc gggacaactc caggaacact    660
ctgtacctcc aaatgaattc gctgaggcca gaggacactg ccatctacta ctgctccgcg    720
catggcggag agtccgacgt ctggggacag gggaccaccg tgaccgtgtc tagcaccacg    780
acgccagcgc cgcgaccacc aacaccggcg cccaccatcg cgtcgcagcc cctgtccctg    840
cgcccagagg cgtgccggcc agcggcgggg gcgcagtgc acacgagggg gctggacttc    900
gcctgtgata tctacatctg ggcgcccttg gccgggactt gtgggtcct tctcctgtca    960 ctggttatca cccctttactg caaacggggc agaaagaaac tcctgtatat attcaaacaa   1020
```

```
ccatttatga gaccagtaca aactactcaa gaggaagatg gctgtagctg ccgatttcca   1080
gaagaagaag aaggaggatg tgaactgaga gtgaagttca gcaggagcgc agacgccccc   1140
gcgtacaagc agggccagaa ccagctctat aacgagctca atctaggacg aagagaggag   1200
tacgatgttt tggacaagag gcgtggccgg gaccctgaga tgggggggaaa gccgagaagg   1260 aagaaccctc aggaaggcct gtacaatgaa ctgcagaaag ataagatggc ggaggcctac   1320
agtgagattg ggatgaaagg cgagcgccgg aggggcaagg ggcacgatgg cctttaccag   1380
ggtctcagta cagccaccaa ggacacctac gacgcccttc acatgcaggc cctgccccct   1440
cgctaa                                                              1446
```

<210> SEQ ID NO 21
<211> LENGTH: 1467
<212> TYPE: DNA
<213> ORGANISM: Artificial Sequence
<220> FEATURE:
<223> OTHER INFORMATION: Synthesized

<400> SEQUENCE: 21

```
atggccttac cagtgaccgc cttgctcctg ccgctggcct tgctgctcca cgccgccagg    60
ccggacatcg tgatgaccca gtccccctcc agcctgacga tgacagccgg cgagaaggtg   120
acaatgatct gtaagtccag ccagagcctg ctgaacagcg gcgaccagaa gaactacctg   180
acctggtacc agcagaagcc tggccagccc cccaagctgc tgatcttctg ggccagcaca   240
agggagagcg gcgtgcccga cagattcaca ggcagcggca gcggcaccga cttcacactg   300
accatttcct ccgtgcaggc cgaggacctc gccgtgtact actgccagaa cgactactcc   360
taccccctga cattcggcgc cggcaccaaa ctggagctga aggtggcgg tggctcgggc   420 ggtggtgggt cgggtggcgg cggatctcag gtgcagctcc agcagtccga tgccgagctg   480
gtgaagcccg gaagcagcgt caagatcagc tgtaaggcct ccggctacac cttcacagac   540
cacgccatcc actgggtgaa gcagaagccc gagcagggcc tggagtggat cggccacttt   600
agccccggaa acaccgacat caagtacaac gacaagttca agggcaaggc caccctgacc   660
gtggacagga gcagcagcac cgcctacatg cagctgaaca gcctgacaag cgaggacagc   720
gccgtgtact ctgcaagac ctccaccttc ttcttcgact actggggcca gggaaccacc   780
ctgacagtgt ccagcaccac gacgccagcg ccgcgaccac caacaccggc gccaccatc   840 gcgtcgcagc ccctgtccct gcgcccagag gcgtgccggc cagcggcggg gggcgcagtg   900
cacacgaggg ggctggactt cgcctgtgat atctacatct gggcgccctt ggccgggact   960
tgtggggtcc ttctcctgtc actggttatc accctttact gcaaacgggg cagaaagaaa  1020
ctcctgtata tattcaaaca accatttatg agaccagtac aaaactactca agaggaagat  1080 ggctgtagct gccgatttcc agaagaagaa gaaggaggat gtgaactgag agtgaagttc  1140
agcaggagcg cagacgcccc cgcgtacaag cagggccaga accagctcta taacgagctc  1200
aatctaggac gaagagagga gtacgatgtt ttggacaaga ggcgtggccg ggaccctgag  1260 atgggggga agccgagaag gaagaaccct caggaaggcc tgtacaatga actgcagaaa  1320
gataagatgg cggaggccta cagtgagatt gggatgaaag gcgagcgccg gaggggcaag  1380
gggcacgatg gcctttacca gggtctcagt acagccacca aggacaccta cgacgccctt  1440
cacatgcagg ccctgccccc tcgctaa                                      1467
```

<210> SEQ ID NO 22
<211> LENGTH: 3533

```
<212> TYPE: DNA
<213> ORGANISM: Artificial Sequence
<220> FEATURE:
<223> OTHER INFORMATION: Synthesized

<400> SEQUENCE: 22
atggccttac cagtgaccgc cttgctcctg ccgctggcct tgctgctcca cgccgccagg      60
ccggacatcc agatgacaca gactacatcc tccctgtctg cctctctggg agacagagtc     120
accatcagtt gcagggcaag tcaggacatt agtaaatatt taaattggta tcagcagaaa     180
ccagatggaa ctgttaaact cctgatctac catacatcaa gattacactc aggagtccca     240
tcaaggttca gtggcagtgg gtctggaaca gattattctc tcaccattag caacctggag     300
caagaagata ttgccactta cttttgccaa cagggtaata cgcttccgta cacgttcgga     360
ggggggacca agctggagat cacaggtggc ggtggctcgg cggtggtggg gtcgggtggc     420
ggcggatctg aggtgaaact gcaggagtca ggacctggcc tggtggcgcc ctcacagagc     480
ctgtccgtca catgcactgt ctcaggggtc tcattacccg actatggtgt aagctggatt     540
cgccagcctc cacgaaaggg tctggagtgg ctggagtaa tatgggtag tgaaaccaca       600
tactataatt cagctctcaa atccagactg accatcatca aggacaactc caagagccaa     660
gttttcttaa aaatgaacag tctgcaaact gatgacacag ccatttacta ctgtgccaaa     720
cattattact acggtggtag ctatgctatg gactactggg gccaaggaac ctcagtcacc     780
gtctcctcaa ccacgacgcc agcgccgcga ccaccaacac cggcgcccac catcgcgtcg     840
cagcccctgt ccctgcgccc agaggcgtgc cggccagcgg cggggggcgc agtgcacacg     900
aggggggctgg acttcgcctg tgatatctac atctgggcgc ccttggccgg acttgtggg      960
gtccttctcc tgtcactggt tatcaccctt tactgcaaac ggggcagaaa gaaactcctg    1020
tatatattca acaaccatt tatgagacca gtacaaacta ctcaagagga gatggctgt      1080
agctgccgat ttccagaaga agaagaagga ggatgtgaac tgagagtgaa gttcagcagg    1140
agcgcagacg ccccgcgta caagcagggc cagaaccagc tctataacga gctcaatcta    1200
ggacgaagag aggagtacga tgttttggac aagaggcgtg gccgggaccc tgagatgggg    1260
ggaaagccga aaggaagaa ccctcaggaa ggcctgtaca tgaactgca gaaagataag      1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc ccctcgcta atctagaggc gcgccctct ccctccccc cccctaacgt       1500
tactggccga agccgcttgg aataaggccg gtgtgcgttt gtctatatgt tattttccac    1560
catattgccg tcttttggca atgtgagggc ccggaaacct ggccctgtct tcttgacgag    1620
cattcctagg ggtctttccc ctctcgccaa aggaatgcaa ggtctgttga atgtcgtgaa    1680
ggaagcagtt cctctggaag cttcttgaag acaaacaacg tctgtagcga cccttcgcag    1740
gcagcggaac cccccacctg cgacaggtg cctctgcggc caaaagccac gtgtataaga    1800
tacacctgca aaggcggcac aaccccagtg ccacgttgtg agttggatag ttgtggaaag    1860
agtcaaatgg ctctcctcaa gcgtattcaa caaggggctg aaggatgccc agaaggtacc    1920
ccattgtatg ggatctgatc tggggcctcg gtacacatgc tttacatgtg tttagtcgag    1980
gttaaaaaaa cgtctaggcc cccgaacca cggggacgtg gttttccttt gaaaaacacg    2040
atgataatat ggccacaacc catatgatgg ccttaccagt gaccgccttg ctcctgccgc    2100
tggccttgct gctccacgcc gccaggccgg acatcgtgat gacccagtcc ccctccagcc    2160
```

```
tgacagtgac agccggcgag aaggtgacaa tgatctgtaa gtccagccag agcctgctga       2220
acagcggcga ccagaagaac tacctgacct ggtaccagca gaagcctggc cagcccccca       2280
agctgctgat cttctgggcc agcacaaggg agagcggcgt gcccgacaga ttcacaggca       2340
gcggcagcgg caccgacttc acactgacca tttcctccgt gcaggccgag gacctcgccg       2400
tgtactactg ccagaacgac tactcctacc ccctgacatt cggcgccggc accaaactgg       2460
agctgaaggg tggcggtggc tcgggcggtg gtgggtcggg tggcggcgga tctcaggtgc       2520
agctccagca gtccgatgcc gagctggtga agcccggaag cagcgtcaag atcagctgta       2580
aggcctccgg ctacaccttc acagaccacg ccatccactg ggtgaagcag aagcccgagc       2640
agggcctgga gtggatcggc actttagcc ccggaaacac cgacatcaag tacaacgaca       2700
agttcaaggg caaggccacc ctgaccgtgg acaggagcag cagcaccgcc tacatgcagc       2760
tgaacagcct gacaagcgag gacagcgccg tgtacttctg caagacctcc accttcttct       2820
tcgactactg gggccaggga accacccctga cagtgtccag caccacgacg ccagcgccgc       2880
gaccaccaac accggcgccc accatcgcgt cgcagcccct gtccctgcgc ccagaggcgt       2940
gccggccagc ggcgggggc gcagtgcaca cgagggggct ggacttcgcc tgtgatatct       3000
acatctgggc gcccttggcc gggacttgtg gggtccttct cctgtcactg gttatcaccc       3060
tttactgcaa acggggcaga aagaaactcc tgtatatatt caaacaacca tttatgagac       3120
cagtacaaac tactcaagag gaagatggct gtagctgccg atttccagaa gaagaagaag       3180
gaggatgtga actgagagtg aagttcagca ggagcgcaga cgcccccgcg tacaagcagg       3240
gccagaacca gctctataac gagctcaatc taggacgaag agaggagtac gatgttttgg       3300
acaagaggcg tggccgggac cctgagatgg ggggaaagcc gagaaggaag aaccctcagg       3360
aaggcctgta caatgaactg cagaaagata agatggcgga ggcctacagt gagattggga       3420
tgaaaggcga gcgccggagg ggcaaggggc acgatggcct ttaccagggt ctcagtacag       3480
ccaccaagga cacctacgac gcccttcaca tgcaggccct gccccctcgc taa            3533
```

<210> SEQ ID NO 23
<211> LENGTH: 3533
<212> TYPE: DNA
<213> ORGANISM: Artificial Sequence
<220> FEATURE:
<223> OTHER INFORMATION: Synthesized

<400> SEQUENCE: 23

```
atggccttac cagtgaccgc cttgctcctg ccgctggcct tgctgctcca cgccgccagg        60
ccggatatcc agatgaccca gagcccgagc agcctgagcg cgagcgtggg tgatcgcgtg       120
accattacct gcagggcaag tcaggacatt agtaaatatt taaattggta tcagcagaaa       180
ccgggtaaag cgccgaaact gttaatttat catacatcaa gattacactc aggcgtgccg       240
tcgcgtttta gcggctcggg ttcgggcacc gatttaccc tgaccatctc gagcttgcag       300
ccggaggact cgccaccta ctattgccaa cagggtaata cgcttccgta cacgttcggt       360
cagggcacca aagtggagat caaaggtggc ggtggctcgg gcggtggtgg gtcgggtggc       420
ggcggatctg aggtgcagct ggtggagtct gggggaggct tggtacagcc tggggggtcc       480
ctgagactct cctgtgcagc ctctggagtg tccctgcctg attatggcgt gtcctgggtc       540
cgccaggctc cagggaaggg gctgagtggg gtttcagtga tctggggcag cgagacaacc       600
tactacaaca gcgccctgaa gtcccgattc accatctcca gagacaatgc caagaactca       660
ctgtatctgc aaatgaacag cctgagagcc gaggacacgg ctgtgtatta ctgtgcgaag       720
```

```
cactactact acggcggcag ctacgctatg gactactggg gccaaggaac cctggtcacc    780
gtgtcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900
aggggggctgg acttcgcctg tgatatctac atctgggcgc ccttggccgg acttgtggg    960
gtccttctcc tgtcactggt tatcacccctt tactgcaaac ggggcagaaa gaaactcctg   1020
tatatattca acaaccatt tatgagacca gtacaaacta ctcaagagga agatggctgt    1080
agctgccgat ttccagaaga agaagaagga ggatgtgaac tgagagtgaa gttcagcagg    1140
agcgcagacg ccccccgcgta caagcagggc cagaaccagc tctataacga gctcaatcta   1200
ggacgaagag aggagtacga tgttttggac aagaggcgtg gccgggaccc tgagatgggg    1260
ggaaagccga aaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgcta atctagaggc gcgcccctct ccctcccccc ccctaacgt    1500
tactggccga agccgcttgg aataaggccg gtgtgcgttt gtctatatgt tatttccac    1560
catattgccg tcttttggca atgtgagggc ccggaaacct ggccctgtct tcttgacgag    1620
cattcctagg ggtctttccc ctctcgccaa aggaatgcaa ggtctgttga atgtcgtgaa    1680
ggaagcagtt cctctggaag cttcttgaag acaaacaacg tctgtagcga cccttttgcag   1740
gcagcggaac cccccaccctg gcgacaggtg cctctgcggc caaaagccac gtgtataaga   1800
tacacctgca aaggcggcac aaccccagtg ccacgttgtg agttggatag ttgtggaaag    1860
agtcaaatgg ctctcctcaa gcgtattcaa caagggggctg aaggatgccc agaaggtacc   1920
ccattgtatg ggatctgatc tggggcctcg gtacacatgc tttacatgtg tttagtcgag    1980
gttaaaaaaa cgtctaggcc ccccgaacca cggggacgtg gttttccttt gaaaaacacg    2040
atgataatat ggccacaacc catatgatgg ccttaccagt gaccgccttg ctcctgccgc    2100
tggccttgct gctccacgcc gccaggccgg acatcgtgat gacccagtcc ccctccagcc   2160
tgacagtgac agccggcgag aaggtgacaa tgatctgtaa gtccagccag agcctgctga    2220
acagcggcga ccagaagaac tacctgacct ggtaccagca gaagcctggc cagcccccca    2280
agctgctgat cttctgggcc agcacaaggg agagcggcgt gcccgacaga ttcacaggca    2340
gcggcagcgg caccgacttc acactgacca tttcctccgt gcaggccgag gacctcgccg    2400
tgtactactg ccagaacgac tactcctacc ccctgacatt cggcgccggc accaaactgg    2460
agctgaaggg tggcggtggc tcgggcggtg gtgggtcggg tggcggcgga tctcaggtgc    2520
agctccagca gtccgatgcc gagctggtga agccggaag cagcgtcaag atcagctgta    2580
aggcctccgg ctacaccttc acagaccacg ccatccactg ggtgaagcag aagcccgagc    2640
agggcctgga gtggatcggc cactttagcc ccggaaacac cgacatcaag tacaacgaca    2700
agttcaaggg caaggccacc ctgaccgtgg acaggagcag cagcaccgcc tacatgcagc    2760
tgaacagcct gacaagcgag gacagcgccg tgtacttctg caagacctcc accttcttct    2820
tcgactactg ggccaggga accaccctga cagtgtccag caccacgacg ccagcgccgc    2880
gaccaccaac accggcgccc accatcgcgt cgcagcccct gtccctgcgc ccagaggcgt    2940
gccgccagc ggcgggggc gcagtgcaca cgagggggct ggacttcgcc tgtgatatct    3000
acatctgggc gcccttggcc gggacttgtg gggtccttct cctgtcactg gttatcaccc   3060
```

| | |
|---|---:|
| tttactgcaa acggggcaga agaaactcc tgtatatatt caaacaacca tttatgagac | 3120 |
| cagtacaaac tactcaagag gaagatggct gtagctgccg atttccagaa gaagaagaag | 3180 |
| gaggatgtga actgagagtg aagttcagca ggagcgcaga cgccccgcg tacaagcagg | 3240 |
| gccagaacca gctctataac gagctcaatc taggacgaag agaggagtac gatgttttgg | 3300 |
| acaagaggcg tggccgggac cctgagatgg ggggaaagcc gagaaggaag aaccctcagg | 3360 |
| aaggcctgta caatgaactg cagaaagata agatggcgga ggcctacagt gagattggga | 3420 |
| tgaaaggcga gcgccggagg ggcaaggggc acgatggcct ttaccagggt ctcagtacag | 3480 |
| ccaccaagga cacctacgac gcccttcaca tgcaggccct gccccctcgc taa | 3533 |

<210> SEQ ID NO 24
<211> LENGTH: 3545
<212> TYPE: DNA
<213> ORGANISM: Artificial Sequence
<220> FEATURE:
<223> OTHER INFORMATION: Synthesized

<400> SEQUENCE: 24

| | |
|---|---:|
| atggccttac cagtgaccgc cttgctcctg ccgctggcct tgctgctcca cgccgccagg | 60 |
| ccggatatcc agatgaccca gagcccaagc tccctgtccg cctctgtggg cgacagggtg | 120 |
| accatcacat gccgcgccag ccagacaatc tggtcctacc tgaactggta tcagcagaga | 180 |
| cccggcaagg cccctaatct gctgatctac gcagcatcta gcctgcagtc tggagtgccc | 240 |
| tcccggttct ctggaagagg atccggaacc gacttcaccc tgacaatctc ctctctgcag | 300 |
| gccgaggact cgccacata ctattgccag cagagctatt ccatccctca gacctttggc | 360 |
| cagggcacaa agctggagat caagggcggc ggcggctctg gaggaggagg aagcggagga | 420 |
| ggaggatccc aggtgcagct gcagcagagc ggaccaggac tggtgaagcc ctcccagacc | 480 |
| ctgtctctga catgtgccat cagcggcgat tccgtgagct ccaacagcgc cgcctggaat | 540 |
| tggatccggc agtctcccag cagaggactg gagtggctgg aaggaccta ctatcgctcc | 600 |
| aagtggtaca acgattatgc cgtgtctgtg aagagccgga tcaccatcaa ccctgacaca | 660 |
| tctaagaatc agttcagcct gcagctgaat tccgtgaccc cagaggacac agccgtgtac | 720 |
| tattgtgcaa gggaggtgac cggcgacctg gaggatgcct ttgacatctg gggccagggc | 780 |
| accatggtga cagtgtctag caccacgacg ccagcgccgc gaccaccaac accggcgccc | 840 |
| accatcgcgt cgcagccct gtccctgcgc ccagaggcgt gccggccagc ggcggggggc | 900 |
| gcagtgcaca gagggggct ggacttcgcc tgtgatatct acatctgggc gcccttggcc | 960 |
| gggacttgtg gggtccttct cctgtcactg gttatcaccc tttactgcaa acggggcaga | 1020 |
| aagaaactcc tgtatatatt caaacaacca tttatgagac cagtacaaac tactcaagag | 1080 |
| gaagatggct gtagctgccg atttccagaa gaagaagaag gaggatgtga actgagagtg | 1140 |
| aagttcagca ggagcgcaga cgccccgcg tacaagcagg gccagaacca gctctataac | 1200 |
| gagctcaatc taggacgaag agaggagtac gatgttttgg acaagaggcg tggccgggac | 1260 |
| cctgagatgg ggggaaagcc gagaaggaag aaccctcagg aaggcctgta caatgaactg | 1320 |
| cagaaagata agatggcgga ggcctacagt gagattggga tgaaaggcga gcgccggagg | 1380 |
| ggcaaggggc acgatggcct ttaccagggt ctcagtacag ccaccaagga cacctacgac | 1440 |
| gcccttcaca tgcaggccct gccccctcgc taatctagag gcgcgccct ctccctcccc | 1500 |
| cccccctaac gttactggcc gaagccgctt ggaataaggc cggtgtgcgt ttgtctatat | 1560 |
| gttattttcc accatattgc cgtcttttgg caatgtgagg gcccggaaac ctggccctgt | 1620 | cttcttgacg agcattccta ggggtctttc ccctctcgcc aaaggaatgc aaggtctgtt    1680 gaatgtcgtg aaggaagcag ttcctctgga agcttcttga agacaaacaa cgtctgtagc    1740 gacccttttgc aggcagcgga acccccacc tggcgacagg tgcctctgcg gccaaaagcc    1800 acgtgtataa gatacacctg caaaggcggc acaaccccag tgccacgttg tgagttggat    1860 agttgtggaa agagtcaaat ggctctcctc aagcgtattc aacaaggggc tgaaggatgc    1920 ccagaaggta ccccattgta tgggatctga tctggggcct cggtacacat gctttacatg    1980 tgtttagtcg aggttaaaaa aacgtctagg ccccccgaac cacggggacg tggttttcct    2040 ttgaaaaaca cgatgataat atggccacaa cccatatgat ggccttacca gtgaccgcct    2100 tgctcctgcc gctggccttg ctgctccacg ccgccaggcc ggacatcgtg atgacccagt    2160 cccctccag cctgacagtg acagccgcg agaaggtgac aatgatctgt aagtccagcc    2220 agagcctgct gaacagcggc gaccagaaga actacctgac ctggtaccag cagaagcctg    2280 gccagccccc caagctgctg atcttctggg ccagcacaag ggagagcggc gtgcccgaca    2340 gattcacagg cagcggcagc ggcaccgact tcacactgac catttcctcc gtgcaggccg    2400 aggacctcgc cgtgtactac tgccagaacg actactccta ccccctgaca ttcggcgccg    2460 gcaccaaact ggagctgaag ggtggcggtg gctcgggcgg tggtgggtcg ggtggcggcg    2520 gatctcaggt gcagctccag cagtccgatg ccgagctggt gaagcccgga agcagcgtca    2580 agatcagctg taaggcctcc ggctacacct tcacagacca cgccatccac tgggtgaagc    2640 agaagcccga gcagggcctg gagtggatcg gccactttag ccccggaaac accgacatca    2700 agtacaacga caagttcaag ggcaaggcca ccctgaccgt ggacaggagc agcagcaccg    2760 cctacatgca gctgaacagc ctgacaagcg aggacagcgc cgtgtacttc tgcaagacct    2820 ccaccttctt cttcgactac tggggccagg gaaccaccct gacagtgtcc agcaccacga    2880 cgccagcgcc gcgaccacca caccggcgcg ccaccatcgc gtcgcagccc ctgtccctgc    2940 gcccagaggc gtgccggcca gcggcggggg gcgcagtgca cacgaggggg ctggacttcg    3000 cctgtgatat ctacatctgg gcgcccttgg ccgggacttg tggggtcctt ctcctgtcac    3060 tggttatcac cctttactgc aaacggggca gaaagaaact cctgtatata ttcaaacaac    3120 catttatgag accagtacaa actactcaag aggaagatgg ctgtagctgc cgatttccag    3180 aagaagaaga aggaggatgt gaactgagag tgaagttcag caggagcgca gacgcccccg    3240 cgtacaagca gggccagaac cagctctata cgagctcaa tctaggacga agagaggagt    3300 acgatgtttt ggacaagagg cgtggccggg accctgagat ggggggaaag ccagaaggaa    3360 agaaccctca ggaaggcctg tacaatgaac tgcagaaaga taagatggcg gaggcctaca    3420 gtgagattgg gatgaaaggc gagcgccgga ggggcaaggg gcacgatggc ctttaccagg    3480 gtctcagtac agccaccaag gacacctacg acgcccttca catgcaggcc ctgccccctc    3540 gctaa                                                                3545

<210> SEQ ID NO 25
<211> LENGTH: 3518
<212> TYPE: DNA
<213> ORGANISM: Artificial Sequence
<220> FEATURE:
<223> OTHER INFORMATION: Synthesized

<400> SEQUENCE: 25
atggccttac cagtgaccgc cttgctcctg ccgctggcct tgctgctcca cgccgccagg      60

| | |
|---|---|
| ccggacatcc agctcaccca gtccccgagc tcgctgtccg cctccgtggg agatcgggtc | 120 |
| accatcacgt gccgcgccag ccagtcgatt tcctcctacc tgaactggta ccaacagaag | 180 |
| cccggaaaag ccccgaagct tctcatctac gccgcctcga gcctgcagtc aggagtgccc | 240 |
| tcacggttct ccggctccgg ttccggtact gatttcaccc tgaccatttc ctccctgcaa | 300 |
| ccggaggact cgctactta ctactgccag cagtcgtact ccacccccta cactttcgga | 360 |
| caaggcacca aggtcgaaat caagggtggc ggtggctcgg gcggtggtgg gtcgggtggc | 420 |
| ggcggatctg aagtgcaatt ggtggaatca gggggaggac ttgtgcagcc tggaggatcg | 480 |
| ctgagactgt catgtgccgt gtccggcttt gccctgtcca accacgggat gtcctgggtc | 540 |
| cgccgcgcgc ctggaaaggg cctcgaatgg gtgtcgggta ttgtgtacag cggtagcacc | 600 |
| tactatgccg catccgtgaa ggggagattc accatcagcc gggacaactc caggaacact | 660 |
| ctgtacctcc aaatgaattc gctgaggcca gaggacactg ccatctacta ctgctccgcg | 720 |
| catggcggag agtccgacgt ctggggacag ggaccaccg tgaccgtgtc tagcaccacg | 780 |
| acgccagcgc cgcgaccacc aacaccggcg cccaccatcg cgtcgcagcc cctgtccctg | 840 |
| cgcccagagg cgtgccggcc agcggcgggg ggcgcagtgc acacgagggg gctggacttc | 900 |
| gcctgtgata tctacatctg gcgcccttg gccgggactt gtggggtcct tctcctgtca | 960 |
| ctggttatca ccctttactg caaacggggc agaagaaac tcctgtatat attcaaacaa | 1020 |
| ccatttatga gaccagtaca aactactcaa gaggaagatg gctgtagctg ccgatttcca | 1080 |
| gaagaagaag aaggaggatg tgaactgaga gtgaagttca gcaggagcgc agacgccccc | 1140 |
| gcgtacaagc agggccagaa ccagctctat aacgagctca atctaggacg aagagaggag | 1200 |
| tacgatgttt tggacaagag gcgtggccgg gaccctgaga tgggggaaa gccgagaagg | 1260 |
| aagaaccctc aggaaggcct gtacaatgaa ctgcagaaag ataagatggc ggaggcctac | 1320 |
| agtgagattg ggatgaaagg cgagcgccgg aggggcaagg ggcacgatgg cctttaccag | 1380 |
| ggtctcagta cagccaccaa ggacacctac gacgcccttc acatgcaggc cctgccccct | 1440 |
| cgctaatcta gaggcgcgcc cctctccctc cccccccct aacgttactg gccgaagccg | 1500 |
| cttggaataa ggccggtgtg cgtttgtcta tatgttattt tccaccatat tgccgtcttt | 1560 |
| tggcaatgtg agggcccgga aacctggccc tgtcttcttg acgagcattc ctaggggtct | 1620 |
| ttcccctctc gccaaaggaa tgcaaggtct gttgaatgtc gtgaaggaag cagttcctct | 1680 |
| ggaagcttct tgaagacaaa caacgtctgt agcgaccctt gcaggcagc ggaaccccc | 1740 |
| acctggcgac aggtgcctct gcggccaaaa gccacgtgta taagatacac ctgcaaaggc | 1800 |
| ggcacaaccc cagtgccacg ttgtgagttg gatagttgtg gaaagagtca aatggctctc | 1860 |
| ctcaagcgta ttcaacaagg ggctgaagga tgcccagaag gtaccccatt gtatgggatc | 1920 |
| tgatctgggg cctcggtaca catgctttac atgtgtttag tcgaggttaa aaaaacgtct | 1980 |
| aggccccccg aaccacgggg acgtggtttt cctttgaaaa acacgatgat aatatggcca | 2040 |
| caacccatat gatggcctta ccagtgaccg ccttgctcct gccgctggcc ttgctgctcc | 2100 |
| acgccgccag gccggacatc gtgatgaccc agtccccctc cagcctgaca gtgacagccg | 2160 |
| gcgagaaggt gacaatgatc tgtaagtcca gccagagcct gctgaacagc ggcgaccaga | 2220 |
| agaactacct gacctggtac cagcagaagc ctggccagcc cccaagctg ctgatcttct | 2280 |
| gggccagcac aagggagagc ggcgtgcccg acagattcac aggcagcggc agcggcaccg | 2340 |
| acttcacact gaccatttcc tccgtgcagg ccgaggacct cgccgtgtac tactgccaga | 2400 |
| acgactactc ctaccccctg acattcggcg ccggcaccaa actggagctg aagggtggcg | 2460 |

```
gtggctcggg cggtggtggg tcgggtggcg gcggatctca ggtgcagctc cagcagtccg   2520
atgccgagct ggtgaagccc ggaagcagcg tcaagatcag ctgtaaggcc tccggctaca   2580
ccttcacaga ccacgccatc cactgggtga agcagaagcc cgagcagggc ctggagtgga   2640
tcggccactt tagccccgga aacaccgaca tcaagtacaa cgacaagttc aagggcaagg   2700
ccaccctgac cgtggacagg agcagcagca ccgcctacat gcagctgaac agcctgacaa   2760
gcgaggacag cgccgtgtac ttctgcaaga cctccacctt cttcttcgac tactggggcc   2820
agggaaccac cctgacagtg tccagcacca cgacgccagc gccgcgacca ccaacaccgg   2880
cgcccaccat cgcgtcgcag cccctgtccc tgcgcccaga ggcgtgccgg ccagcggcgg   2940
ggggcgcagt gcacacgagg gggctggact cgcctgtga tatctacatc tgggcgccct   3000
tggccgggac ttgtgggtc cttctcctgt cactggttat cacccttta ctgcaaacggg   3060 gcagaaagaa actcctgtat atattcaaac aaccatttat gagaccagta caaactactc   3120
aagaggaaga tggctgtagc tgccgatttc cagaagaaga agaaggagga tgtgaactga   3180
gagtgaagtt cagcaggagc gcagacgccc ccgcgtacaa gcagggccag aaccagctct   3240
ataacgagct caatctagga cgaagagagg agtacgatgt tttggacaag aggcgtggcc   3300
gggaccctga tgggggga aagccgagaa ggaagaaccc tcaggaaggc ctgtacaatg   3360
aactgcagaa agataagatg gcggaggcct acagtgagat tgggatgaaa ggcgagcgcc   3420
ggaggggcaa ggggcacgat ggcctttacc agggtctcag tacagccacc aaggacacct   3480
acgacgccct tcacatgcag gccctgcccc ctcgctaa                            3518
```

<210> SEQ ID NO 26
<211> LENGTH: 2994
<212> TYPE: DNA
<213> ORGANISM: Artificial Sequence
<220> FEATURE:
<223> OTHER INFORMATION: Synthesized

<400> SEQUENCE: 26

```
atggccttac cagtgaccgc cttgctcctg ccgctggcct tgctgctcca cgccgccagg     60
ccggacatcc agatgacaca gactacatcc tccctgtctg cctctctggg agacagagtc    120
accatcagtt gcagggcaag tcaggacatt agtaaatatt taaattggta tcagcagaaa    180
ccagatggaa ctgttaaact cctgatctac catacatcaa gattacactc aggagtccca    240
tcaaggttca gtggcagtgg gtctggaaca gattattctc tcaccattag caacctggag    300
caagaagata ttgccactta cttttgccaa cagggtaata cgcttccgta cacgttcgga    360 gggggggacca agctggagat cacaggtggc ggtggctcgg gcggtggtgg gtcgggtggc    420
ggcggatctg aggtgaaact gcaggagtca ggacctggcc tggtggcgcc ctcacagagc    480
ctgtccgtca catgcactgt ctcagggtc tcattacccg actatggtgt aagctggatt    540
cgccagcctc cacgaaaggg tctggagtgg ctggagtaa tatggggtag tgaaaccaca    600
tactataatt cagctctcaa atccagactg accatcatca aggacaactc caagagccaa    660
gttttcttaa aaatgaacag tctgcaaact gatgacacag ccatttacta ctgtgccaaa    720
cattattact acggtggtag ctatgctatg gactactggg gccaaggaac ctcagtcacc    780
gtctcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900
agggggctgg acttcgcctg tgatatctac atctgggcgc ccttggccgg gacttgtggg    960
```

```
gtccttctcc tgtcactggt tatcacccett tactgcaaac ggggcagaaa gaaactcctg    1020
tatatattca acaaccatt tatgagacca gtacaaacta ctcaagagga agatggctgt      1080
agctgccgat ttccagaaga agaagaagga ggatgtgaac tgagagtgaa gttcagcagg    1140
agcgcagacg ccccgcgta caagcagggc cagaaccagc tctataacga gctcaatcta     1200
ggacgaagag aggagtacga tgttttggac aagaggcgtg gccgggaccc tgagatgggg    1260
ggaaagccga gaaggaagaa ccctcaggaa ggcctgtaca atgaactgca gaaagataag    1320
atggcggagg cctacagtga gattgggatg aaaggcgagc gccggagggg caaggggcac    1380
gatggccttt accagggtct cagtacagcc accaaggaca cctacgacgc ccttcacatg    1440
caggccctgc cccctcgctc tagagccacg aacttctctc tgttaaagca agcaggagac    1500
gtggaagaaa ccccggtcc tcatatgatg gccttaccag tgaccgcctt gctcctgccg     1560
ctggccttgc tgctccacgc cgccaggcg gacatcgtga tgacccagtc cccctccagc     1620
ctgacagtga cagccggcga gaaggtgaca atgatctgta agtccagcca gagcctgctg    1680
aacagcggcg accagaagaa ctacctgacc tggtaccagc agaagcctgg ccagccccc    1740 aagctgctga tcttctgggc cagcacaagg gagagcggcg tgcccgacag attcacaggc    1800
agcggcagcg gcaccgactt cacactgacc atttcctccg tgcaggccga ggacctcgcc   1860
gtgtactact gccagaacga ctactcctac cccctgacat tcggcgccgg caccaaactg    1920
gagctgaagg gtggcggtgg ctcgggcggt ggtgggtcgg gtggcggcgg atctcaggtg    1980
cagctccagc agtccgatgc cgagctggtg aagcccggaa gcagcgtcaa gatcagctgt    2040
aaggcctccg gctacacctt cacagaccac gccatccact gggtgaagca gaagcccgag    2100
cagggcctgg agtggatcgg ccactttagc cccggaaaca ccgacatcaa gtacaacgac    2160
aagttcaagg gcaaggccac cctgaccgtg gacaggagca gcagcaccgc ctacatgcag    2220
ctgaacagcc tgacaagcga ggacagcgcc gtgtacttct gcaagacctc caccttcttc    2280
ttcgactact ggggccaggg aaccaccctg acagtgtcca gcaccacgac gccagcgccg    2340
cgaccaccaa caccggcgcc caccatcgcg tcgcagcccc tgtccctgcg cccagaggcg    2400
tgccggccag cggcgggggg cgcagtgcac acgaggggc tggacttcgc ctgtgatatc    2460
tacatctggg cgcccttggc cgggacttgt ggggtccttc tcctgtcact ggttatcacc    2520
ctttactgca acggggcag aaagaaactc ctgtatatat tcaaacaacc atttatgaga    2580
ccagtacaaa ctactcaaga ggaagatggc tgtagctgcc gatttccaga agaagaagaa    2640
ggaggatgtg aactgagagt gaagttcagc aggagcgcag acgcccccgc gtacaagcag    2700
ggccagaacc agctctataa cgagctcaat ctaggacgaa gagaggagta cgatgttttg    2760
gacaagaggc gtggccggga ccctgagatg ggggaaagc cgagaaggaa gaaccctcag    2820
gaaggcctgt acaatgaact gcagaaagat aagatggcgg aggcctacag tgagattggg    2880
atgaaaggcg agcgccggag gggcaagggg cacgatggcc tttaccaggg tctcagtaca    2940
gccaccaagg acacctacga cgcccttcac atgcaggccc tgcccctcg ctaa          2994
```

<210> SEQ ID NO 27
<211> LENGTH: 2994
<212> TYPE: DNA
<213> ORGANISM: Artificial Sequence
<220> FEATURE:
<223> OTHER INFORMATION: Synthesized

<400> SEQUENCE: 27

```
atggccttac cagtgaccgc cttgctcctg ccgctggcct tgctgctcca cgccgccagg    60
```

```
ccggatatcc agatgaccca gagcccgagc agcctgagcg cgagcgtggg tgatcgcgtg    120
accattacct gcagggcaag tcaggacatt agtaaatatt taaattggta tcagcagaaa    180
ccgggtaaag cgccgaaact gttaatttat catacatcaa gattacactc aggcgtgccg    240
tcgcgtttta gcggctcggg ttcgggcacc gattttaccc tgaccatctc gagcttgcag    300
ccggaggact tcgccaccta ctattgccaa cagggtaata cgcttccgta cacgttcggt    360
cagggcacca aagtggagat caaaggtggc ggtggctcgg gcggtggtgg gtcgggtggc    420
ggcggatctg aggtgcagct ggtggagtct gggggaggct tggtacagcc tggggggtcc    480
ctgagactct cctgtgcagc ctctggagtg tccctgcctg attatggcgt gtcctgggtc    540
cgccaggctc cagggaaggg gctggagtgg gtttcagtga tctggggcag cgagacaacc    600
tactacaaca cgcccctgaa gtcccgattc accatctcca gagacaatgc caagaactca    660
ctgtatctgc aaatgaacag cctgagagcc gaggacacgg ctgtgtatta ctgtgcgaag    720
cactactact acggcggcag ctacgctatg gactactggg gccaaggaac cctggtcacc    780
gtgtcctcaa ccacgacgcc agcgccgcga ccaccaacac cggcgcccac catcgcgtcg    840
cagcccctgt ccctgcgccc agaggcgtgc cggccagcgg cggggggcgc agtgcacacg    900
agggggctgg acttcgcctg tgatatctac atctgggcgc ccttggccgg acttgtgggg    960
gtccttctcc tgtcactggt tatcaccctt tactgcaaac ggggcagaaa gaaactcctg   1020
tatatattca acaaccatt tatgagacca gtacaaacta ctcaagagga gatggctgt    1080 agctgccgat ttccagaaga agaagaagga ggatgtgaac tgagagtgaa gttcagcagg   1140
agcgcagacg cccccgcgta caagcagggc cagaaccagc tctataacga gctcaatcta   1200
ggacgaagag aggagtacga tgttttggac aagaggcgtg gccggacccc tgagatgggg   1260
ggaaagccga aaggaagaa ccctcaggaa ggcctgtaca tgaactgca gaaagataag    1320 atggcggagg cctacagtga gattgggatg aaaggcgagc gccggagggg caaggggcac   1380
gatggccttt accagggtct cagtacagcc accaaggaca cctacgacgc ccttcacatg   1440 caggcccctgc cccctcgctc tagagccacg aacttctctc tgttaaagca agcaggagac   1500
gtggaagaaa accccggtcc tcatatgatg gccttaccag tgaccgcctt gctcctgccg   1560
ctggccttgc tgctccacgc cgccaggccg gacatcgtga tgacccagtc ccctccagc    1620 ctgacagtga cagccggcga aaggtgaca atgatctgta gtccagcca gagcctgctg    1680 aacagcggcg accagaagaa ctacctgacc tggtaccagc agaagcctgg ccagccccc    1740 aagctgctga tcttctgggc cagcacaagg gagagcggtc tgcccgacag attcacaggc   1800
agcggcagcg gcaccgactt cacactgacc atttcctccg tgcaggccga ggacctcgcc   1860
gtgtactact gccagaacga ctactcctac ccctgacat cggcgccgg caccaaactg   1920 gagctgaagg gtggcggtgg ctcggcggt ggtgggtcgg gtggcggcgg atctcaggtg    1980
cagctccagc agtccgatgc cgagctggtg aagcccggaa gcagcgtcaa gatcagctgt   2040
aaggcctccg gctacacctt cacagaccac gccatccact gggtgaagca agagcccgag   2100
cagggcctgg agtggatcgg ccactttagc cccggaaaca ccgacatcaa gtacaacgac   2160
aagttcaagg gcaaggccac cctgaccgtg gacaggagca gcaccgc ctacatgcag    2220 ctgaacagcc tgacaagcga ggacagcgcc gtgtacttct gcaagacctc caccttcttc   2280
ttcgactact ggggccaggg aaccaccctg acagtgtcca gcaccacgac gccagcgccg   2340
cgaccaccaa caccggcgcc caccatcgcg tcgcagcccc tgtccctgcg cccagaggcg   2400
```

| | |
|---|---|
| tgccggccag cggcggggggg cgcagtgcac acgaggggggc tggacttcgc ctgtgatatc | 2460 |
| tacatctggg cgcccttggc cgggacttgt ggggtccttc tcctgtcact ggttatcacc | 2520 |
| ctttactgca aacggggcag aaagaaactc ctgtatatat tcaaacaacc atttatgaga | 2580 |
| ccagtacaaa ctactcaaga ggaagatggc tgtagctgcc gatttccaga agaagaagaa | 2640 |
| ggaggatgtg aactgagagt gaagttcagc aggagcgcag acgcccccgc gtacaagcag | 2700 |
| ggccagaacc agctctataa cgagctcaat ctaggacgaa gagaggagta cgatgttttg | 2760 |
| gacaagaggc gtggccggga ccctgagatg ggggaaagc cgagaaggaa gaaccctcag | 2820 |
| gaaggcctgt acaatgaact gcagaaagat aagatggcgg aggcctacag tgagattggg | 2880 |
| atgaaaggcg agcgccggag gggcaagggg cacgatggcc tttaccaggg tctcagtaca | 2940 |
| gccaccaagg acacctacga cgcccttcac atgcaggccc tgccccctcg ctaa | 2994 |

<210> SEQ ID NO 28
<211> LENGTH: 3009
<212> TYPE: DNA
<213> ORGANISM: Artificial Sequence
<220> FEATURE:
<223> OTHER INFORMATION: Synthesized

<400> SEQUENCE: 28

| | |
|---|---|
| atggccttac cagtgaccgc cttgctcctg ccgctggcct tgctgctcca cgccgccagg | 60 |
| ccggatatcc agatgaccca gagcccaagc tccctgtccg cctctgtggg cgacagggtg | 120 |
| accatcacat gccgcgccag ccagacaatc tggtcctacc tgaactggta tcagcagaga | 180 |
| cccggcaagg cccctaatct gctgatctac gcagcatcta gcctgcagtc tggagtgccc | 240 |
| tcccggttct ctggaagagg atccggaacc gacttcaccc tgacaatctc ctctctgcag | 300 |
| gccgaggact cgccacata ctattgccag cagagctatt ccatccctca gacctttggc | 360 |
| cagggcacaa agctggagat caagggcggc ggcggctctg gaggaggagg aagcggagga | 420 |
| ggaggatccc aggtgcagct gcagcagagc ggaccaggac tggtgaagcc ctcccagacc | 480 |
| ctgtctctga catgtgccat cagcggcgat tccgtgagct ccaacagcgc cgcctggaat | 540 |
| tggatccggc agtctcccag cagaggactg gagtggctgg aaggacccta ctatcgctcc | 600 |
| aagtggtaca acgattatgc cgtgtctgtg aagagccgga tcaccatcaa ccctgacaca | 660 |
| tctaagaatc agttcagcct gcagctgaat tccgtgaccc cagaggacac agccgtgtac | 720 |
| tattgtgcaa gggaggtgac cggcgacctg aggatgcct tgacatctg ggccagggc | 780 |
| accatggtga cagtgtctag caccacgacg ccagcgccgc gaccaccaac accggcgccc | 840 |
| accatcgcgt cgcagccct gtccctgcgc ccagaggcgt gccggccagc ggcgggggggc | 900 |
| gcagtgcaca cgagggggct ggacttcgcc tgtgatatct acatctgggc gcccttggcc | 960 |
| gggacttgtg ggtccttct cctgtcactg gttatcaccc tttactgcaa acggggcaga | 1020 |
| aagaaactcc tgtatatatt caaacaacca tttatgagac cagtacaaac tactcaagag | 1080 |
| gaagatggct gtagctgccg atttccagaa gaagaagaag aggatgtga actgagagtg | 1140 |
| aagttcagca ggagcgcaga cgcccccgcg tacaagcagg ccagaacca gctctataac | 1200 |
| gagctcaatc taggacgaag agaggagtac gatgttttgg acaagaggcg tggccgggac | 1260 |
| cctgagatgg ggggaaagcc gagaaggaag aaccctcagg aaggcctgta caatgaactg | 1320 |
| cagaaagata agatggcgga ggcctacagt gagattggga tgaaaggcga gcgccggagg | 1380 |
| ggcaaggggc acgatggcct ttaccagggt ctcagtacag ccaccaagga cacctacgac | 1440 |
| gcccttcaca tgcaggccct gccccctcgc taatctagag ccacgaactt ctctctgtta | 1500 |

```
aagcaagcag gagacgtgga agaaaacccc ggtcctcata tgatggcctt accagtgacc   1560
gccttgctcc tgccgctggc cttgctgctc cacgccgcca ggccggacat cgtgatgacc   1620
cagtccccct ccagcctgac agtgacagcg gcgagaagg tgacaatgat ctgtaagtcc    1680
agccagagcc tgctgaacag cggcgaccag aagaactacc tgacctggta ccagcagaag   1740
cctggccagc cccccaagct gctgatcttc tgggccagca aggggagag cggcgtgccc    1800 gacagattca caggcagcgg cagcggcacc gacttcacac tgaccatttc ctccgtgcag   1860
gccgaggacc tcgccgtgta ctactgccag aacgactact cctaccccct gacattcggc   1920
gccggcacca aactggagct gaaggggtgg ggtggctcgg gcgtggtgg gtcgggtggc    1980 ggcggatctc aggtgcagct ccagcagtcc gatgccgagc tggtgaagcc cggaagcagc   2040
gtcaagatca gctgtaaggc ctccggctac accttcacag accacgccat ccactgggtg   2100
aagcagaagc ccgagcaggg cctggagtgg atcggccact ttagccccgg aaacaccgac   2160
atcaagtaca cgacaagtt caagggcaag gccaccctga ccgtggacag gagcagcagc    2220
accgcctaca tgcagctgaa cagcctgaca agcgaggaca cgccgtgta cttctgcaag    2280 acctccacct tcttcttcga ctactgggc cagggaacca ccctgacagt gtccagcacc    2340
acgacgccag cgccgcgacc accaacaccg gcgcccacca tcgcgtcgca gccctgtcc    2400 ctgcgcccag aggcgtgccg gccagcgcg ggggcgcag tgcacacgag ggggctggac     2460
ttcgcctgtg atatctacat ctgggcgccc ttggccggga cttgtggggt ccttctcctg   2520
tcactggtta tcacccttta ctgcaaacgg ggcagaaaga aactcctgta tatattcaaa   2580
caaccattta tgagaccagt acaaactact caagaggaag atggctgtag ctgccgattt   2640
ccagaagaag aagaaggagg atgtgaactg agagtgaagt tcagcaggag cgcagacgcc   2700
cccgcgtaca gcagggcca gaaccagctc tataacgagc tcaatctagg acgaagagag   2760
gagtacgatg tttggacaa gaggcgtggc cgggaccctg agatgggggg aaagccgaga    2820
aggaagaacc ctcaggaagg cctgtacaat gaactgcaga agataagat ggcggaggcc    2880 tacagtgaga ttgggatgaa aggcgagcgc cggaggggca aggggcacga tggcctttac   2940
cagggtctca gtacagccac caaggacacc tacgacgccc ttcacatgca ggccctgccc   3000
cctcgctaa                                                           3009
```

<210> SEQ ID NO 29
<211> LENGTH: 2982
<212> TYPE: DNA
<213> ORGANISM: Artificial Sequence
<220> FEATURE:
<223> OTHER INFORMATION: Synthesized

<400> SEQUENCE: 29

```
atggccttac cagtgaccgc cttgctcctg ccgctggcct tgctgctcca cgccgccagg    60
ccggacatcc agctcaccca gtccccgagc tcgctgtccg cctccgtggg agatcgggtc   120
accatcacgt gccgcgccag ccagtcgatt tcctcctacc tgaactggta ccaacagaag   180
cccggaaaag ccccgaagct tctcatctac gccgcctcga gcctgcagtc aggagtgccc   240
tcacggttct ccggctccgg ttccggtact gatttcaccc tgaccatttc ctccctgcaa   300
ccggaggact cgctacttta ctactgccag cagtcgtact ccaccccta cactttcgga   360 caaggcacca aggtcgaaat caaggggtgg ggtggctcgg gcgtggtgg gtcgggtggc    420 ggcggatctg aagtgcaatt ggtggaatca gggggaggac ttgtgcagcc tggaggatcg    480
```

```
ctgagactgt catgtgccgt gtccggcttt gccctgtcca accacgggat gtcctgggtc      540
cgccgcgcgc ctggaaaggg cctcgaatgg gtgtcgggta ttgtgtacag cggtagcacc      600
tactatgccg catccgtgaa ggggagattc accatcagcc gggacaactc caggaacact      660
ctgtacctcc aaatgaattc gctgaggcca gaggacactg ccatctacta ctgctccgcg      720
catggcggag agtccgacgt ctggggacag gggaccaccg tgaccgtgtc tagcaccacg      780
acgccagcgc cgcgaccacc aacaccggcg cccaccatcg cgtcgcagcc cctgtccctg      840
cgcccagagg cgtgccggcc agcggcgggg ggcgcagtgc acacgagggg gctggacttc      900
gcctgtgata tctacatctg ggcgcccttg gccgggactt gtggggtcct tctcctgtca      960
ctggttatca ccctttactg caaacggggc agaaagaaac tcctgtatat attcaaacaa     1020
ccatttatga gaccagtaca aactactcaa gaggaagatg gctgtagctg ccgatttcca     1080
gaagaagaag aaggaggatg tgaactgaga gtgaagttca gcaggagcgc agacgccccc     1140
gcgtacaagc agggccagaa ccagctctat aacgagctca atctaggacg aagagaggag     1200
tacgatgttt tggacaagag gcgtggccgg accctgaga tggggggaaa gccgagaagg      1260
aagaaccctc aggaaggcct gtacaatgaa ctgcagaaag ataagatggc ggaggcctac     1320
agtgagattg gatgaaagg cgagcgccgg aggggcaagg gcacgatgg cctttaccag       1380 ggtctcagta cagccaccaa ggacacctac gacgcccttc acatgcaggc cctgccccct     1440
cgctaatcta gagccacgaa cttctctctg ttaaagcaag caggagacgt ggaagaaaac     1500
cccggtcctc atatgatggc cttaccagtg accgccttgc tcctgccgct ggccttgctg     1560
ctccacgccg ccaggccgga catcgtgatg acccagtccc cctccagcct gacagtgaca     1620
gccggcgaga aggtgacaat gatctgtaag tccagccaga gcctgctgaa cagcggcgac     1680
cagaagaact acctgacctg gtaccagcag aagcctggcc agcccccaa gctgctgatc      1740 ttctgggcca gcacaaggga gagcggcgtg cccgacagat tcacaggcag cggcagcggc     1800
accgacttca cactgaccat ttcctccgtg caggccgagg acctcgccgt gtactactgc     1860
cagaacgact actcctaccc cctgacattc ggcgccggca ccaaactgga gctgaagggt     1920
ggcggtggct cgggcggtgg tgggtcgggt ggcggcggat ctcaggtgca gctccagcag     1980
tccgatgccg agctggtgaa gcccggaagc agcgtcaaga tcagctgtaa ggcctccggc     2040
tacaccttca cagaccacgc catccactgg gtgaagcaga agcccgagca gggcctggag     2100
tggatcggcc actttagccc cggaaacacc gacatcaagt acaacgacaa gttcaagggc     2160
aaggccaccc tgaccgtgga caggagcagc agcaccgcct acatgcagct gaacagcctg     2220
acaagcgagg acagcgccgt gtacttctgc aagacctcca ccttcttctt cgactactgg     2280
ggccagggaa ccaccctgac agtgtccagc accacgacgc cagcgccgcg accaccaaca     2340
ccggcgccca ccatcgcgtc gcagcccctg tccctgcgcc cagaggcgtg ccggccagcg     2400
gcggggggcg cagtgcacac gagggggctg gacttcgcct gtgatatcta catctgggcg     2460
cccttggccg ggacttgtgg ggtccttctc ctgtcactgg ttatcaccct ttactgcaaa     2520
cggggcagaa agaaactcct gtatatattc aaacaaccat ttatgagacc agtacaaact     2580
actcaagagg aagatggctg tagctgccga tttccagaag aagaagaagg aggatgtgaa     2640
ctgagagtga agttcagcag gagcgcagac gccccgcgt acaagcaggg ccagaaccag      2700
ctctataacg agctcaatct aggacgaaga gaggagtacg atgttttgga caagaggcgt     2760
ggccgggacc ctgagatggg gggaaagccg agaaggaaga accctcagga aggcctgtac     2820
aatgaactgc agaaagataa gatggcggag gcctacagtg agattgggat gaaaggcgag     2880
```

```
cgccggaggg gcaaggggca cgatggcctt taccagggtc tcagtacagc caccaaggac    2940
acctacgacg cccttcacat gcaggccctg ccccctcgct aa                      2982
```

<210> SEQ ID NO 30
<211> LENGTH: 244
<212> TYPE: PRT
<213> ORGANISM: Artificial Sequence
<220> FEATURE:
<223> OTHER INFORMATION: Synthesized

<400> SEQUENCE: 30

```
Asp Ile Val Met Thr Gln Ser Pro Ser Ser Leu Thr Val Thr Ala Gly
1               5                   10                  15

Glu Lys Val Thr Met Ile Cys Lys Ser Ser Gln Ser Leu Leu Asn Ser
            20                  25                  30

Gly Asp Gln Lys Asn Tyr Leu Thr Trp Tyr Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Tyr Ser Tyr Pro Leu Thr Phe Gly Ala Gly Thr Lys Leu Glu Leu
            100                 105                 110

Lys Gly Gly Gly Gly Ser Gly Gly Gly Ser Gly Gly Gly Gly Ser
        115                 120                 125

Gln Val Gln Leu Gln Gln Ser Asp Ala Glu Leu Val Lys Pro Gly Ser
    130                 135                 140

Ser Val Lys Ile Ser Cys Lys Ala Ser Gly Tyr Thr Phe Thr Asp His
145                 150                 155                 160

Ala Ile His Trp Val Lys Gln Lys Pro Glu Gln Gly Leu Glu Trp Ile
                165                 170                 175

Gly His Phe Ser Pro Gly Asn Thr Asp Ile Lys Tyr Asn Asp Lys Phe
            180                 185                 190

Lys Gly Lys Ala Thr Leu Thr Val Asp Arg Ser Ser Ser Thr Ala Tyr
        195                 200                 205

Met Gln Leu Asn Ser Leu Thr Ser Glu Asp Ser Ala Val Tyr Phe Cys
    210                 215                 220

Lys Thr Ser Thr Phe Phe Asp Tyr Trp Gly Gln Gly Thr Thr Leu
225                 230                 235                 240

Thr Val Ser Ser
```

<210> SEQ ID NO 31
<211> LENGTH: 116
<212> TYPE: PRT
<213> ORGANISM: Artificial Sequence
<220> FEATURE:
<223> OTHER INFORMATION: Synthesized

<400> SEQUENCE: 31

```
Gln Val Gln Leu Gln Gln Ser Asp Ala Glu Leu Val Lys Pro Gly Ser
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
```

```
                    35                  40                  45
Gly His Phe Ser Pro Gly Asn Thr Asp Ile Lys Tyr Asn Asp Lys Phe
        50                  55                  60
Lys Gly Lys Ala Thr Leu Thr Val Asp Arg Ser Ser Thr Ala Tyr
65                  70                  75                  80
Met Gln Leu Asn Ser Leu Thr Ser Glu Asp Ser Ala Val Tyr Phe Cys
                85                  90                  95
Lys Thr Ser Thr Phe Phe Phe Asp Tyr Trp Gly Gln Gly Thr Thr Leu
                100                 105                 110
Thr Val Ser Ser
        115

<210> SEQ ID NO 32
<211> LENGTH: 113
<212> TYPE: PRT
<213> ORGANISM: Artificial Sequence
<220> FEATURE:
<223> OTHER INFORMATION: Synthesized

<400> SEQUENCE: 32

Asp Ile Val Met Thr Gln Ser Pro Ser Ser Leu Thr Val Thr Ala Gly
1               5                   10                  15
Glu Lys Val Thr Met Ile Cys Lys Ser Ser Gln Ser Leu Leu Asn Ser
                20                  25                  30
Gly Asp Gln Lys Asn Tyr Leu Thr Trp Tyr Gln Gln Lys Pro Gly Gln
            35                  40                  45
Pro Pro Lys Leu Leu Ile Phe Trp Ala Ser Thr Arg Glu Ser Gly Val
    50                  55                  60
Pro Asp Arg Phe Thr Gly Ser Gly Ser Gly Thr Asp Phe Thr Leu Thr
65                  70                  75                  80
Ile Ser Ser Val Gln Ala Glu Asp Leu Ala Val Tyr Tyr Cys Gln Asn
                85                  90                  95
Asp Tyr Ser Tyr Pro Leu Thr Phe Gly Ala Gly Thr Lys Leu Glu Leu
                100                 105                 110
Lys

<210> SEQ ID NO 33
<211> LENGTH: 246
<212> TYPE: PRT
<213> ORGANISM: Artificial Sequence
<220> FEATURE:
<223> OTHER INFORMATION: Synthesized

<400> SEQUENCE: 33

Asp Ile Val Met Thr Gln Ala Ala Phe Ser Asn Pro Val Thr Leu Gly
1               5                   10                  15
Thr Ser Ala Ser Ile Ser Cys Arg Ser Ser Lys Ser Leu Leu His Ser
                20                  25                  30
Asn Gly Ile Thr Tyr Phe Phe Trp Tyr Leu Gln Lys Pro Gly Leu Ser
            35                  40                  45
Pro Gln Leu Leu Ile Tyr Gln Met Ser Asn Leu Ala Ser Gly Val Pro
    50                  55                  60
Asp Arg Phe Ser Ser Gly Ser Gly Thr Asp Phe Thr Leu Arg Ile
65                  70                  75                  80
Ser Arg Val Glu Ala Glu Asp Val Gly Val Tyr Tyr Cys Ala Gln Asn
                85                  90                  95
Leu Glu Leu Pro Pro Thr Phe Gly Gly Gly Thr Lys Leu Glu Ile Lys
```

```
                    100                 105                 110
Arg Ala Gly Gly Gly Ser Gly Gly Gly Ser Gly Gly Gly
            115                 120                 125

Ser Glu Val Lys Leu Val Glu Ser Gly Gly Leu Val Gln Pro Gly
    130                 135                 140

Gly Ser Met Lys Leu Ser Cys Val Ala Ser Gly Phe Thr Phe Ser Asn
145                 150                 155                 160

Tyr Trp Met Asn Trp Val Arg Gln Ser Pro Glu Lys Gly Leu Glu Trp
                165                 170                 175

Val Ala Glu Ile Arg Leu Lys Ser Asn Asn Tyr Thr Thr His Tyr Ala
            180                 185                 190

Glu Ser Val Lys Gly Arg Phe Thr Ile Ser Arg Asp Asp Ser Lys Ser
        195                 200                 205

Ser Val Ser Leu Gln Met Asn Asn Leu Arg Val Glu Asp Thr Gly Ile
    210                 215                 220

Tyr Tyr Cys Thr Arg His Tyr Tyr Phe Asp Tyr Trp Gly Gln Gly Thr
225                 230                 235                 240

Thr Leu Thr Val Ser Ser
                245

<210> SEQ ID NO 34
<211> LENGTH: 117
<212> TYPE: PRT
<213> ORGANISM: Artificial Sequence
<220> FEATURE:
<223> OTHER INFORMATION: Synthesized

<400> SEQUENCE: 34

Glu Val Lys Leu Val Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Ser Pro Glu Lys Gly Leu Glu Trp Val
        35                  40                  45

Ala Glu Ile Arg Leu Lys Ser Asn Asn Tyr Thr Thr His Tyr Ala Glu
    50                  55                  60

Ser Val Lys Gly Arg Phe Thr Ile Ser Arg Asp Asp Ser Lys Ser Ser
65                  70                  75                  80

Val Ser Leu Gln Met Asn Asn Leu Arg Val Glu Asp Thr Gly Ile Tyr
                85                  90                  95

Tyr Cys Thr Arg His Tyr Tyr Phe Asp Tyr Trp Gly Gln Gly Thr Thr
            100                 105                 110

Leu Thr Val Ser Ser
        115

<210> SEQ ID NO 35
<211> LENGTH: 114
<212> TYPE: PRT
<213> ORGANISM: Artificial Sequence
<220> FEATURE:
<223> OTHER INFORMATION: Synthesized

<400> SEQUENCE: 35

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30
```

Asn Gly Ile Thr Tyr Phe Phe Trp Tyr Leu Gln Lys Pro Gly Leu Ser
            35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Gly Thr Asp Phe Thr Leu Arg Ile
 65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

Arg Ala

<210> SEQ ID NO 36
<211> LENGTH: 219
<212> TYPE: PRT
<213> ORGANISM: Homo sapiens

<400> SEQUENCE: 36

Glu Leu Cys Asp Asp Asp Pro Pro Glu Ile Pro His Ala Thr Phe Lys
 1               5                  10                  15

Ala Met Ala Tyr Lys Glu Gly Thr Met Leu Asn Cys Glu Cys Lys Arg
            20                  25                  30

Gly Phe Arg Arg Ile Lys Ser Gly Ser Leu Tyr Met Leu Cys Thr Gly
            35                  40                  45

Asn Ser Ser His Ser Ser Trp Asp Asn Gln Cys Gln Cys Thr Ser Ser
 50                  55                  60

Ala Thr Arg Asn Thr Thr Lys Gln Val Thr Pro Gln Pro Glu Glu Gln
 65                  70                  75                  80

Lys Glu Arg Lys Thr Thr Glu Met Gln Ser Pro Met Gln Pro Val Asp
                85                  90                  95

Gln Ala Ser Leu Pro Gly His Cys Arg Glu Pro Pro Pro Trp Glu Asn
            100                 105                 110

Glu Ala Thr Glu Arg Ile Tyr His Phe Val Val Gly Gln Met Val Tyr
            115                 120                 125

Tyr Gln Cys Val Gln Gly Tyr Arg Ala Leu His Arg Gly Pro Ala Glu
            130                 135                 140

Ser Val Cys Lys Met Thr His Gly Lys Thr Arg Trp Thr Gln Pro Gln
145                 150                 155                 160

Leu Ile Cys Thr Gly Glu Met Glu Thr Ser Gln Phe Pro Gly Glu Glu
                165                 170                 175

Lys Pro Gln Ala Ser Pro Glu Gly Arg Pro Glu Ser Glu Thr Ser Cys
            180                 185                 190

Leu Val Thr Thr Thr Asp Phe Gln Ile Gln Thr Glu Met Ala Ala Thr
            195                 200                 205

Met Glu Thr Ser Ile Phe Thr Thr Glu Tyr Gln
            210                 215

<210> SEQ ID NO 37
<211> LENGTH: 346
<212> TYPE: PRT
<213> ORGANISM: Homo sapiens

<400> SEQUENCE: 37

Leu Ala Pro Arg Arg Cys Pro Ala Gln Glu Val Ala Arg Gly Val Leu
 1               5                  10                  15

Thr Ser Leu Pro Gly Asp Ser Val Thr Leu Thr Cys Pro Gly Val Glu

```
            20                  25                  30
Pro Glu Asp Asn Ala Thr Val His Trp Val Leu Arg Lys Pro Ala Ala
         35                  40                  45
Gly Ser His Pro Ser Arg Trp Ala Gly Met Gly Arg Arg Leu Leu Leu
     50                  55                  60
Arg Ser Val Gln Leu His Asp Ser Gly Asn Tyr Ser Cys Tyr Arg Ala
 65                  70                  75                  80
Gly Arg Pro Ala Gly Thr Val His Leu Leu Val Asp Val Pro Pro Glu
                 85                  90                  95
Glu Pro Gln Leu Ser Cys Phe Arg Lys Ser Pro Leu Ser Asn Val Val
            100                 105                 110
Cys Glu Trp Gly Pro Arg Ser Thr Pro Ser Leu Thr Thr Lys Ala Val
        115                 120                 125
Leu Leu Val Arg Lys Phe Gln Asn Ser Pro Ala Glu Asp Phe Gln Glu
    130                 135                 140
Pro Cys Gln Tyr Ser Gln Glu Ser Gln Lys Phe Ser Cys Gln Leu Ala
145                 150                 155                 160
Val Pro Glu Gly Asp Ser Ser Phe Tyr Ile Val Ser Met Cys Val Ala
                165                 170                 175
Ser Ser Val Gly Ser Lys Phe Ser Lys Thr Gln Thr Phe Gln Gly Cys
            180                 185                 190
Gly Ile Leu Gln Pro Asp Pro Pro Ala Asn Ile Thr Val Thr Ala Val
        195                 200                 205
Ala Arg Asn Pro Arg Trp Leu Ser Val Thr Trp Gln Asp Pro His Ser
    210                 215                 220
Trp Asn Ser Ser Phe Tyr Arg Leu Arg Phe Glu Leu Arg Tyr Arg Ala
225                 230                 235                 240
Glu Arg Ser Lys Thr Phe Thr Thr Trp Met Val Lys Asp Leu Gln His
                245                 250                 255
His Cys Val Ile His Asp Ala Trp Ser Gly Leu Arg His Val Val Gln
            260                 265                 270
Leu Arg Ala Gln Glu Glu Phe Gly Gln Gly Glu Trp Ser Glu Trp Ser
        275                 280                 285
Pro Glu Ala Met Gly Thr Pro Trp Thr Glu Ser Arg Ser Pro Pro Ala
    290                 295                 300
Glu Asn Glu Val Ser Thr Pro Met Gln Ala Leu Thr Thr Asn Lys Asp
305                 310                 315                 320
Asp Asp Asn Ile Leu Phe Arg Asp Ser Ala Asn Ala Thr Ser Leu Pro
                325                 330                 335
Val Gln Asp Ser Ser Ser Val Pro Leu Pro
            340                 345

<210> SEQ ID NO 38
<211> LENGTH: 219
<212> TYPE: PRT
<213> ORGANISM: Homo sapiens

<400> SEQUENCE: 38

Glu Ser Gly Tyr Ala Gln Asn Gly Asp Leu Glu Asp Ala Glu Leu Asp
 1               5                  10                  15
Asp Tyr Ser Phe Ser Cys Tyr Ser Gln Leu Glu Val Asn Gly Ser Gln
             20                  25                  30
His Ser Leu Thr Cys Ala Phe Glu Asp Pro Asp Val Asn Ile Thr Asn
         35                  40                  45
```

```
Leu Glu Phe Glu Ile Cys Gly Ala Leu Val Glu Val Lys Cys Leu Asn
 50                  55                  60

Phe Arg Lys Leu Gln Glu Ile Tyr Phe Ile Glu Thr Lys Lys Phe Leu
 65                  70                  75                  80

Leu Ile Gly Lys Ser Asn Ile Cys Val Lys Val Gly Glu Lys Ser Leu
                 85                  90                  95

Thr Cys Lys Lys Ile Asp Leu Thr Thr Ile Val Lys Pro Glu Ala Pro
                100                 105                 110

Phe Asp Leu Ser Val Val Tyr Arg Glu Gly Ala Asn Asp Phe Val Val
                115                 120                 125

Thr Phe Asn Thr Ser His Leu Gln Lys Lys Tyr Val Lys Val Leu Met
130                 135                 140

His Asp Val Ala Tyr Arg Gln Glu Lys Asp Glu Asn Lys Trp Thr His
145                 150                 155                 160

Val Asn Leu Ser Ser Thr Lys Leu Thr Leu Leu Gln Arg Lys Leu Gln
                165                 170                 175

Pro Ala Ala Met Tyr Glu Ile Lys Val Arg Ser Ile Pro Asp His Tyr
                180                 185                 190

Phe Lys Gly Phe Trp Ser Glu Trp Ser Pro Ser Tyr Tyr Phe Arg Thr
                195                 200                 205

Pro Glu Ile Asn Asn Ser Ser Gly Glu Met Asp
                210                 215

<210> SEQ ID NO 39
<211> LENGTH: 522
<212> TYPE: PRT
<213> ORGANISM: Homo sapiens

<400> SEQUENCE: 39

Cys Arg Thr Ser Glu Cys Cys Phe Gln Asp Pro Tyr Pro Asp Ala
 1               5                  10                  15

Asp Ser Gly Ser Ala Ser Gly Pro Arg Asp Leu Arg Cys Tyr Arg Ile
                 20                  25                  30

Ser Ser Asp Arg Tyr Glu Cys Ser Trp Gln Tyr Glu Gly Pro Thr Ala
                 35                  40                  45

Gly Val Ser His Phe Leu Arg Cys Cys Leu Ser Ser Gly Arg Cys Cys
 50                  55                  60

Tyr Phe Ala Ala Gly Ser Ala Thr Arg Leu Gln Phe Ser Asp Gln Ala
 65                  70                  75                  80

Gly Val Ser Val Leu Tyr Thr Val Thr Leu Trp Val Glu Ser Trp Ala
                 85                  90                  95

Arg Asn Gln Thr Glu Lys Ser Pro Glu Val Thr Leu Gln Leu Tyr Asn
                100                 105                 110

Ser Val Lys Tyr Glu Pro Pro Leu Gly Asp Ile Lys Val Ser Lys Leu
                115                 120                 125

Ala Gly Gln Leu Arg Met Glu Trp Glu Thr Pro Asp Asn Gln Val Gly
130                 135                 140

Ala Glu Val Gln Phe Arg His Arg Thr Pro Ser Ser Pro Trp Lys Leu
145                 150                 155                 160

Gly Asp Cys Gly Pro Gln Asp Asp Thr Glu Ser Cys Leu Cys Pro
                165                 170                 175

Leu Glu Met Asn Val Ala Gln Glu Phe Gln Leu Arg Arg Arg Gln Leu
                180                 185                 190

Gly Ser Gln Gly Ser Ser Trp Ser Lys Trp Ser Ser Pro Val Cys Val
                195                 200                 205
```

Pro Pro Glu Asn Pro Pro Gln Pro Gln Val Arg Phe Ser Val Glu Gln
    210                 215                 220

Leu Gly Gln Asp Gly Arg Arg Leu Thr Leu Lys Glu Gln Pro Thr
225                 230                 235                 240

Gln Leu Glu Leu Pro Glu Gly Cys Gln Gly Leu Ala Pro Gly Thr Glu
            245                 250                 255

Val Thr Tyr Arg Leu Gln Leu His Met Leu Ser Cys Pro Cys Lys Ala
            260                 265                 270

Lys Ala Thr Arg Thr Leu His Leu Gly Lys Met Pro Tyr Leu Ser Gly
        275                 280                 285

Ala Ala Tyr Asn Val Ala Val Ile Ser Ser Asn Gln Phe Gly Pro Gly
        290                 295                 300

Leu Asn Gln Thr Trp His Ile Pro Ala Asp Thr His Thr Glu Pro Val
305                 310                 315                 320

Ala Leu Asn Ile Ser Val Gly Thr Asn Gly Thr Thr Met Tyr Trp Pro
            325                 330                 335

Ala Arg Ala Gln Ser Met Thr Tyr Cys Ile Glu Trp Gln Pro Val Gly
            340                 345                 350

Gln Asp Gly Gly Leu Ala Thr Cys Ser Leu Thr Ala Pro Gln Asp Pro
        355                 360                 365

Asp Pro Ala Gly Met Ala Thr Tyr Ser Trp Ser Arg Glu Ser Gly Ala
    370                 375                 380

Met Gly Gln Glu Lys Cys Tyr Tyr Ile Thr Ile Phe Ala Ser Ala His
385                 390                 395                 400

Pro Glu Lys Leu Thr Leu Trp Ser Thr Val Leu Ser Thr Tyr His Phe
            405                 410                 415

Gly Gly Asn Ala Ser Ala Ala Gly Thr Pro His His Val Ser Val Lys
            420                 425                 430

Asn His Ser Leu Asp Ser Val Ser Val Asp Trp Ala Pro Ser Leu Leu
        435                 440                 445

Ser Thr Cys Pro Gly Val Leu Lys Glu Tyr Val Val Arg Cys Arg Asp
    450                 455                 460

Glu Asp Ser Lys Gln Val Ser Glu His Pro Val Gln Pro Thr Glu Thr
465                 470                 475                 480

Gln Val Thr Leu Ser Gly Leu Arg Ala Gly Val Ala Tyr Thr Val Gln
            485                 490                 495

Val Arg Ala Asp Thr Ala Trp Leu Arg Gly Val Trp Ser Gln Pro Gln
            500                 505                 510

Arg Phe Ser Ile Glu Val Gln Val Ser Asp
        515                 520

<210> SEQ ID NO 40
<211> LENGTH: 175
<212> TYPE: PRT
<213> ORGANISM: Homo sapiens

<400> SEQUENCE: 40

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile

```
                    50                  55                  60
Arg Asp Pro Ala Leu Val His Gln Arg Pro Ala Pro Pro Ser Thr Val
65                  70                  75                  80

Thr Thr Ala Gly Val Thr Pro Gln Pro Glu Ser Leu Ser Pro Ser Gly
                85                  90                  95

Lys Glu Pro Ala Ala Ser Pro Ser Ser Asn Asn Thr Ala Ala Thr
            100                 105                 110

Thr Ala Ala Ile Val Pro Gly Ser Gln Leu Met Pro Ser Lys Ser Pro
            115                 120                 125

Ser Thr Gly Thr Thr Glu Ile Ser Ser His Glu Ser Ser His Gly Thr
            130                 135                 140

Pro Ser Gln Thr Thr Ala Lys Asn Trp Glu Leu Thr Ala Ser Ala Ser
145                 150                 155                 160

His Gln Pro Pro Gly Val Tyr Pro Gln Gly His Ser Asp Thr Thr
                165                 170                 175

<210> SEQ ID NO 41
<211> LENGTH: 213
<212> TYPE: PRT
<213> ORGANISM: Homo sapiens

<400> SEQUENCE: 41

Cys Pro Asp Leu Val Cys Tyr Thr Asp Tyr Leu Gln Thr Val Ile Cys
1               5                   10                  15

Ile Leu Glu Met Trp Asn Leu His Pro Ser Thr Leu Thr Leu Thr Trp
                20                  25                  30

Gln Asp Gln Tyr Glu Glu Leu Lys Asp Glu Ala Thr Ser Cys Ser Leu
            35                  40                  45

His Arg Ser Ala His Asn Ala Thr His Ala Thr Tyr Thr Cys His Met
        50                  55                  60

Asp Val Phe His Phe Met Ala Asp Asp Ile Phe Ser Val Asn Ile Thr
65                  70                  75                  80

Asp Gln Ser Gly Asn Tyr Ser Gln Glu Cys Gly Ser Phe Leu Leu Ala
                85                  90                  95

Glu Ser Ile Lys Pro Ala Pro Pro Phe Asn Val Thr Val Thr Phe Ser
            100                 105                 110

Gly Gln Tyr Asn Ile Ser Trp Arg Ser Asp Tyr Glu Asp Pro Ala Phe
            115                 120                 125

Tyr Met Leu Lys Gly Lys Leu Gln Tyr Glu Leu Gln Tyr Arg Asn Arg
            130                 135                 140

Gly Asp Pro Trp Ala Val Ser Pro Arg Arg Lys Leu Ile Ser Val Asp
145                 150                 155                 160

Ser Arg Ser Val Ser Leu Leu Pro Leu Glu Phe Arg Lys Asp Ser Ser
                165                 170                 175

Tyr Glu Leu Gln Val Arg Ala Gly Pro Met Pro Gly Ser Ser Tyr Gln
            180                 185                 190

Gly Thr Trp Ser Glu Trp Ser Asp Pro Val Ile Phe Gln Thr Gln Ser
            195                 200                 205

Glu Glu Leu Lys Glu
    210

<210> SEQ ID NO 42
<211> LENGTH: 332
<212> TYPE: PRT
<213> ORGANISM: Homo sapiens
```

```
<400> SEQUENCE: 42

Gly Ile Thr Asn Ile Asn Cys Ser Gly His Ile Trp Val Glu Pro Ala
1               5                   10                  15

Thr Ile Phe Lys Met Gly Met Asn Ile Ser Ile Tyr Cys Gln Ala Ala
            20                  25                  30

Ile Lys Asn Cys Gln Pro Arg Lys Leu His Phe Tyr Lys Asn Gly Ile
        35                  40                  45

Lys Glu Arg Phe Gln Ile Thr Arg Ile Asn Lys Thr Thr Ala Arg Leu
    50                  55                  60

Trp Tyr Lys Asn Phe Leu Glu Pro His Ala Ser Met Tyr Cys Thr Ala
65                  70                  75                  80

Glu Cys Pro Lys His Phe Gln Glu Thr Leu Ile Cys Gly Lys Asp Ile
                85                  90                  95

Ser Ser Gly Tyr Pro Pro Asp Ile Pro Asp Glu Val Thr Cys Val Ile
                100                 105                 110

Tyr Glu Tyr Ser Gly Asn Met Thr Cys Thr Trp Asn Ala Gly Lys Leu
            115                 120                 125

Thr Tyr Ile Asp Thr Lys Tyr Val Val His Val Lys Ser Leu Glu Thr
130                 135                 140

Glu Glu Glu Gln Gln Tyr Leu Thr Ser Ser Tyr Ile Asn Ile Ser Thr
145                 150                 155                 160

Asp Ser Leu Gln Gly Gly Lys Lys Tyr Leu Val Trp Val Gln Ala Ala
                165                 170                 175

Asn Ala Leu Gly Met Glu Glu Ser Lys Gln Leu Gln Ile His Leu Asp
            180                 185                 190

Asp Ile Val Ile Pro Ser Ala Ala Val Ile Ser Arg Ala Glu Thr Ile
        195                 200                 205

Asn Ala Thr Val Pro Lys Thr Ile Ile Tyr Trp Asp Ser Gln Thr Thr
    210                 215                 220

Ile Glu Lys Val Ser Cys Glu Met Arg Tyr Lys Ala Thr Thr Asn Gln
225                 230                 235                 240

Thr Trp Asn Val Lys Glu Phe Asp Thr Asn Phe Thr Tyr Val Gln Gln
                245                 250                 255

Ser Glu Phe Tyr Leu Glu Pro Asn Ile Lys Tyr Val Phe Gln Val Arg
            260                 265                 270

Cys Gln Glu Thr Gly Lys Arg Tyr Trp Gln Pro Trp Ser Ser Leu Phe
        275                 280                 285

Phe His Lys Thr Pro Glu Thr Val Pro Gln Val Thr Ser Lys Ala Phe
    290                 295                 300

Gln His Asp Thr Trp Asn Ser Gly Leu Thr Val Ala Ser Ile Ser Thr
305                 310                 315                 320

Gly His Leu Thr Ser Asp Asn Arg Gly Asp Ile Gly
                325                 330

<210> SEQ ID NO 43
<211> LENGTH: 19
<212> TYPE: PRT
<213> ORGANISM: Homo sapiens

<400> SEQUENCE: 43

Val Ala Val Ala Gly Cys Val Phe Leu Leu Ile Ser Val Leu Leu Leu
1               5                   10                  15

Ser Gly Leu
```

```
<210> SEQ ID NO 44
<211> LENGTH: 21
<212> TYPE: PRT
<213> ORGANISM: Homo sapiens

<400> SEQUENCE: 44

Thr Phe Leu Val Ala Gly Gly Ser Leu Ala Phe Gly Thr Leu Leu Cys
1               5                   10                  15

Ile Ala Ile Val Leu
            20

<210> SEQ ID NO 45
<211> LENGTH: 25
<212> TYPE: PRT
<213> ORGANISM: Homo sapiens

<400> SEQUENCE: 45

Pro Ile Leu Leu Thr Ile Ser Ile Leu Ser Phe Phe Ser Val Ala Leu
1               5                   10                  15

Leu Val Ile Leu Ala Cys Val Leu Trp
            20                  25

<210> SEQ ID NO 46
<211> LENGTH: 25
<212> TYPE: PRT
<213> ORGANISM: Homo sapiens

<400> SEQUENCE: 46

Trp Leu Ile Phe Phe Ala Ser Leu Gly Ser Phe Leu Ser Ile Leu Leu
1               5                   10                  15

Val Gly Val Leu Gly Tyr Leu Gly Leu
            20                  25

<210> SEQ ID NO 47
<211> LENGTH: 23
<212> TYPE: PRT
<213> ORGANISM: Homo sapiens

<400> SEQUENCE: 47

Val Ala Ile Ser Thr Ser Thr Val Leu Leu Cys Gly Leu Ser Ala Val
1               5                   10                  15

Ser Leu Leu Ala Cys Tyr Leu
            20

<210> SEQ ID NO 48
<211> LENGTH: 21
<212> TYPE: PRT
<213> ORGANISM: Homo sapiens

<400> SEQUENCE: 48

Gly Trp Asn Pro His Leu Leu Leu Leu Leu Leu Val Ile Val Phe
1               5                   10                  15

Ile Pro Ala Phe Trp
            20

<210> SEQ ID NO 49
<211> LENGTH: 21
<212> TYPE: PRT
<213> ORGANISM: Homo sapiens

<400> SEQUENCE: 49

Leu Leu Leu Gly Met Ile Val Phe Ala Val Met Leu Ser Ile Leu Ser
1               5                   10                  15
```

```
Leu Ile Gly Ile Phe
            20

<210> SEQ ID NO 50
<211> LENGTH: 13
<212> TYPE: PRT
<213> ORGANISM: Homo sapiens

<400> SEQUENCE: 50

Thr Trp Gln Arg Arg Gln Arg Lys Ser Arg Arg Thr Ile
1               5                  10

<210> SEQ ID NO 51
<211> LENGTH: 82
<212> TYPE: PRT
<213> ORGANISM: Homo sapiens

<400> SEQUENCE: 51

Arg Phe Lys Lys Thr Trp Lys Leu Arg Ala Leu Lys Glu Gly Lys Thr
1               5                  10                  15

Ser Met His Pro Pro Tyr Ser Leu Gly Gln Leu Val Pro Glu Arg Pro
            20                  25                  30

Arg Pro Thr Pro Val Leu Val Pro Leu Ile Ser Pro Pro Val Ser Pro
        35                  40                  45

Ser Ser Leu Gly Ser Asp Asn Thr Ser Ser His Asn Arg Pro Asp Ala
    50                  55                  60

Arg Asp Pro Arg Ser Pro Tyr Asp Ile Ser Asn Thr Asp Tyr Phe Phe
65                  70                  75                  80

Pro Arg

<210> SEQ ID NO 52
<211> LENGTH: 195
<212> TYPE: PRT
<213> ORGANISM: Homo sapiens

<400> SEQUENCE: 52

Lys Lys Arg Ile Lys Pro Ile Val Trp Pro Ser Leu Pro Asp His Lys
1               5                  10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45

Asp Ile Gln Ala Arg Asp Glu Val Glu Gly Phe Leu Gln Asp Thr Phe
    50                  55                  60

Pro Gln Gln Leu Glu Glu Ser Glu Lys Gln Arg Leu Gly Gly Asp Val
65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Ser Arg Ser Leu Asp Cys Arg Glu
        115                 120                 125

Ser Gly Lys Asn Gly Pro His Val Tyr Gln Asp Leu Leu Leu Ser Leu
    130                 135                 140

Gly Thr Thr Asn Ser Thr Leu Pro Pro Pro Phe Ser Leu Gln Ser Gly
145                 150                 155                 160

Ile Leu Thr Leu Asn Pro Val Ala Gln Gly Gln Pro Ile Leu Thr Ser
```

```
                    165                 170                 175
Leu Gly Ser Asn Gln Glu Glu Ala Tyr Val Thr Met Ser Ser Phe Tyr
                180                 185                 190

Gln Asn Gln
        195

<210> SEQ ID NO 53
<211> LENGTH: 92
<212> TYPE: PRT
<213> ORGANISM: Homo sapiens

<400> SEQUENCE: 53

Asn Arg Ala Ala Arg His Leu Cys Pro Pro Leu Pro Thr Pro Cys Ala
1               5                   10                  15

Ser Ser Ala Ile Glu Phe Pro Gly Gly Lys Glu Thr Trp Gln Trp Ile
            20                  25                  30

Asn Pro Val Asp Phe Gln Glu Glu Ala Ser Leu Gln Glu Ala Leu Val
        35                  40                  45

Val Glu Met Ser Trp Asp Lys Gly Glu Arg Thr Glu Pro Leu Glu Lys
50                  55                  60

Thr Glu Leu Pro Glu Gly Ala Pro Glu Leu Ala Leu Asp Thr Glu Leu
65                  70                  75                  80

Ser Leu Glu Asp Gly Asp Arg Cys Lys Ala Lys Met
                85                  90

<210> SEQ ID NO 54
<211> LENGTH: 39
<212> TYPE: PRT
<213> ORGANISM: Homo sapiens

<400> SEQUENCE: 54

Lys Ser Arg Gln Thr Pro Pro Leu Ala Ser Val Glu Met Glu Ala Met
1               5                   10                  15

Glu Ala Leu Pro Val Thr Trp Gly Thr Ser Ser Arg Asp Glu Asp Leu
            20                  25                  30

Glu Asn Cys Ser His His Leu
        35

<210> SEQ ID NO 55
<211> LENGTH: 285
<212> TYPE: PRT
<213> ORGANISM: Homo sapiens

<400> SEQUENCE: 55

Ser Leu Lys Thr His Pro Leu Trp Arg Leu Trp Lys Lys Ile Trp Ala
1               5                   10                  15

Val Pro Ser Pro Glu Arg Phe Phe Met Pro Leu Tyr Lys Gly Cys Ser
            20                  25                  30

Gly Asp Phe Lys Lys Trp Val Gly Ala Pro Phe Thr Gly Ser Ser Leu
        35                  40                  45

Glu Leu Gly Pro Trp Ser Pro Glu Val Pro Ser Thr Leu Glu Val Tyr
50                  55                  60

Ser Cys His Pro Pro Arg Ser Pro Ala Lys Arg Leu Gln Leu Thr Glu
65                  70                  75                  80

Leu Gln Glu Pro Ala Glu Leu Val Glu Ser Asp Gly Val Pro Lys Pro
                85                  90                  95

Ser Phe Trp Pro Thr Ala Gln Asn Ser Gly Gly Ser Ala Tyr Ser Glu
            100                 105                 110
```

-continued

Glu Arg Asp Arg Pro Tyr Gly Leu Val Ser Ile Asp Thr Val Thr Val
            115                 120                 125

Leu Asp Ala Glu Gly Pro Cys Thr Trp Pro Cys Ser Cys Glu Asp Asp
130                 135                 140

Gly Tyr Pro Ala Leu Asp Leu Asp Ala Gly Leu Glu Pro Ser Pro Gly
145                 150                 155                 160

Leu Glu Asp Pro Leu Leu Asp Ala Gly Thr Thr Val Leu Ser Cys Gly
            165                 170                 175

Cys Val Ser Ala Gly Ser Pro Gly Leu Gly Pro Leu Gly Ser Leu
            180                 185                 190

Leu Asp Arg Leu Lys Pro Pro Leu Ala Asp Gly Glu Asp Trp Ala Gly
            195                 200                 205

Gly Leu Pro Trp Gly Gly Arg Ser Pro Gly Val Ser Glu Ser Glu
            210                 215                 220

Ala Gly Ser Pro Leu Ala Gly Leu Asp Met Asp Thr Phe Asp Ser Gly
225                 230                 235                 240

Phe Val Gly Ser Asp Cys Ser Ser Pro Val Glu Cys Asp Phe Thr Ser
            245                 250                 255

Pro Gly Asp Glu Gly Pro Pro Arg Ser Tyr Leu Arg Gln Trp Val Val
            260                 265                 270

Ile Pro Pro Pro Leu Ser Ser Pro Gly Pro Gln Ala Ser
            275                 280                 285

<210> SEQ ID NO 56
<211> LENGTH: 253
<212> TYPE: PRT
<213> ORGANISM: Homo sapiens

<400> SEQUENCE: 56

Asn Arg Ser Phe Arg Thr Gly Ile Lys Arg Arg Ile Leu Leu Leu Ile
1               5                   10                  15

Pro Lys Trp Leu Tyr Glu Asp Ile Pro Asn Met Lys Asn Ser Asn Val
            20                  25                  30

Val Lys Met Leu Gln Glu Asn Ser Glu Leu Met Asn Asn Asn Ser Ser
            35                  40                  45

Glu Gln Val Leu Tyr Val Asp Pro Met Ile Thr Glu Ile Lys Glu Ile
50                  55                  60

Phe Ile Pro Glu His Lys Pro Thr Asp Tyr Lys Lys Glu Asn Thr Gly
65                  70                  75                  80

Pro Leu Glu Thr Arg Asp Tyr Pro Gln Asn Ser Leu Phe Asp Asn Thr
            85                  90                  95

Thr Val Val Tyr Ile Pro Asp Leu Asn Thr Gly Tyr Lys Pro Gln Ile
            100                 105                 110

Ser Asn Phe Leu Pro Glu Gly Ser His Leu Ser Asn Asn Glu Ile
            115                 120                 125

Thr Ser Leu Thr Leu Lys Pro Pro Val Asp Ser Leu Asp Ser Gly Asn
            130                 135                 140

Asn Pro Arg Leu Gln Lys His Pro Asn Phe Ala Phe Ser Val Ser Ser
145                 150                 155                 160

Val Asn Ser Leu Ser Asn Thr Ile Phe Leu Gly Glu Leu Ser Leu Ile
            165                 170                 175

Leu Asn Gln Gly Glu Cys Ser Ser Pro Asp Ile Gln Asn Ser Val Glu
            180                 185                 190

Glu Glu Thr Thr Met Leu Leu Glu Asn Asp Ser Pro Ser Glu Thr Ile

```
                195                 200                 205
Pro Glu Gln Thr Leu Leu Pro Asp Glu Phe Val Ser Cys Leu Gly Ile
            210                 215                 220
Val Asn Glu Glu Leu Pro Ser Ile Asn Thr Tyr Phe Pro Gln Asn Ile
225                 230                 235                 240
Leu Glu Ser His Phe Asn Arg Ile Ser Leu Leu Glu Lys
                245                 250

<210> SEQ ID NO 57
<211> LENGTH: 22
<212> TYPE: PRT
<213> ORGANISM: Homo sapiens

<400> SEQUENCE: 57

Met Ala Leu Ile Val Leu Gly Gly Val Ala Gly Leu Leu Leu Phe Ile
1               5                   10                  15
Gly Leu Gly Ile Phe Phe
            20

<210> SEQ ID NO 58
<211> LENGTH: 21
<212> TYPE: PRT
<213> ORGANISM: Homo sapiens

<400> SEQUENCE: 58

Ile Tyr Ile Trp Ala Pro Leu Ala Gly Thr Cys Gly Val Leu Leu Leu
1               5                   10                  15
Ser Leu Val Ile Thr
            20

<210> SEQ ID NO 59
<211> LENGTH: 21
<212> TYPE: PRT
<213> ORGANISM: Homo sapiens

<400> SEQUENCE: 59

Ile Leu Val Ile Phe Ser Gly Met Phe Leu Val Phe Thr Leu Ala Gly
1               5                   10                  15
Ala Leu Phe Leu His
            20

<210> SEQ ID NO 60
<211> LENGTH: 27
<212> TYPE: PRT
<213> ORGANISM: Homo sapiens

<400> SEQUENCE: 60

Phe Trp Val Leu Val Val Val Gly Gly Val Leu Ala Cys Tyr Ser Leu
1               5                   10                  15
Leu Val Thr Val Ala Phe Ile Ile Phe Trp Val
            20                  25

<210> SEQ ID NO 61
<211> LENGTH: 27
<212> TYPE: PRT
<213> ORGANISM: Homo sapiens

<400> SEQUENCE: 61

Ile Ile Ser Phe Phe Leu Ala Leu Thr Ser Thr Ala Leu Leu Phe Leu
1               5                   10                  15
Leu Phe Phe Leu Thr Leu Arg Phe Ser Val Val
```

-continued

```
                20                  25

<210> SEQ ID NO 62
<211> LENGTH: 21
<212> TYPE: PRT
<213> ORGANISM: Homo sapiens

<400> SEQUENCE: 62

Val Gly Val Val Gly Gly Leu Leu Gly Ser Leu Val Leu Leu Val Trp
1               5                   10                  15

Val Leu Ala Val Ile
            20

<210> SEQ ID NO 63
<211> LENGTH: 21
<212> TYPE: PRT
<213> ORGANISM: Homo sapiens

<400> SEQUENCE: 63

Thr His Leu Val Ile Leu Gly Ala Ile Leu Leu Cys Leu Gly Val Ala
1               5                   10                  15

Leu Thr Phe Ile Phe
            20

<210> SEQ ID NO 64
<211> LENGTH: 40
<212> TYPE: PRT
<213> ORGANISM: Homo sapiens

<400> SEQUENCE: 64

Cys Val Arg Cys Arg His Arg Arg Gln Ala Glu Arg Met Ser Gln
1               5                   10                  15

Ile Lys Arg Leu Leu Ser Glu Lys Lys Thr Cys Gln Cys Pro His Arg
            20                  25                  30

Phe Gln Lys Thr Cys Ser Pro Ile
        35                  40

<210> SEQ ID NO 65
<211> LENGTH: 32
<212> TYPE: PRT
<213> ORGANISM: Homo sapiens

<400> SEQUENCE: 65

Leu Tyr Cys Asn His Arg Asn Arg Arg Val Cys Lys Cys Pro Arg
1               5                   10                  15

Pro Val Val Lys Ser Gly Asp Lys Pro Ser Leu Ser Ala Arg Tyr Val
            20                  25                  30

<210> SEQ ID NO 66
<211> LENGTH: 48
<212> TYPE: PRT
<213> ORGANISM: Homo sapiens

<400> SEQUENCE: 66

Gln Arg Arg Lys Tyr Arg Ser Asn Lys Gly Glu Ser Pro Val Glu Pro
1               5                   10                  15

Ala Glu Pro Cys His Tyr Ser Cys Pro Arg Glu Glu Gly Ser Thr
            20                  25                  30

Ile Pro Ile Gln Glu Asp Tyr Arg Lys Pro Glu Pro Ala Cys Ser Pro
        35                  40                  45
```

<210> SEQ ID NO 67
<211> LENGTH: 41
<212> TYPE: PRT
<213> ORGANISM: Homo sapiens

<400> SEQUENCE: 67

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 68
<211> LENGTH: 42
<212> TYPE: PRT
<213> ORGANISM: Homo sapiens

<400> SEQUENCE: 68

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 69
<211> LENGTH: 97
<212> TYPE: PRT
<213> ORGANISM: Homo sapiens

<400> SEQUENCE: 69

Cys Ser Arg Ala Ala Arg Gly Thr Ile Gly Ala Arg Arg Thr Gly Gln
1               5                   10                  15

Pro Leu Lys Glu Asp Pro Ser Ala Val Pro Val Phe Ser Val Asp Tyr
            20                  25                  30

Gly Glu Leu Asp Phe Gln Trp Arg Glu Lys Thr Pro Glu Pro Pro Val
        35                  40                  45

Pro Cys Val Pro Glu Gln Thr Glu Tyr Ala Thr Ile Val Phe Pro Ser
    50                  55                  60

Gly Met Gly Thr Ser Ser Pro Ala Arg Arg Gly Ser Ala Asp Gly Pro
65                  70                  75                  80

Arg Ser Ala Gln Pro Leu Arg Pro Glu Asp Gly His Cys Ser Trp Pro
                85                  90                  95

Leu

<210> SEQ ID NO 70
<211> LENGTH: 31
<212> TYPE: PRT
<213> ORGANISM: Homo sapiens

<400> SEQUENCE: 70

Arg Leu Arg Lys Gly Arg Met Met Asp Val Lys Lys Cys Gly Ile Gln
1               5                   10                  15

Asp Thr Asn Ser Lys Lys Gln Ser Asp Thr His Leu Glu Glu Thr
            20                  25                  30

<210> SEQ ID NO 71
<211> LENGTH: 153
<212> TYPE: PRT

<213> ORGANISM: Homo sapiens

<400> SEQUENCE: 71

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 72
<211> LENGTH: 212
<212> TYPE: PRT
<213> ORGANISM: Homo sapiens

<400> SEQUENCE: 72

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
```

```
            195                 200                 205

Leu Arg Gln Met
    210

<210> SEQ ID NO 73
<211> LENGTH: 177
<212> TYPE: PRT
<213> ORGANISM: Homo sapiens

<400> SEQUENCE: 73

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 74
<211> LENGTH: 219
<212> TYPE: PRT
<213> ORGANISM: Homo sapiens

<400> SEQUENCE: 74

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125
```

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
                180                 185                 190

Ile Lys Leu Cys Ile Leu Leu His Ala Phe Arg Ile Arg Ala Val Thr
            195                 200                 205

Ile Asp Arg Val Met Ser Tyr Leu Asn Ala Ser
            210                 215

<210> SEQ ID NO 75
<211> LENGTH: 162
<212> TYPE: PRT
<213> ORGANISM: Homo sapiens

<400> SEQUENCE: 75

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
                20                  25                  30

Val Phe Ile Leu Gly Cys Phe Ser Ala Gly Leu Pro Lys Thr Glu Ala
            35                  40                  45

Asn Trp Val Asn Val Ile Ser Asp Leu Lys Lys Ile Glu Asp Leu Ile
50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 76
<211> LENGTH: 155
<212> TYPE: PRT
<213> ORGANISM: Homo sapiens

<400> SEQUENCE: 76

Met Glu Arg Ile Val Ile Cys Leu Met Val Ile Phe Leu Gly Thr Leu
1               5                   10                  15

Val His Lys Ser Ser Ser Gln Gly Gln Asp Arg His Met Ile Arg Met
                20                  25                  30

Arg Gln Leu Ile Asp Ile Val Asp Gln Leu Lys Asn Tyr Val Asn Asp
            35                  40                  45

Leu Val Pro Glu Phe Leu Pro Ala Pro Glu Asp Val Glu Thr Asn Cys
50                  55                  60

```
Glu Trp Ser Ala Phe Ser Cys Phe Gln Lys Ala Gln Leu Lys Ser Ala
65                  70                  75                  80

Asn Thr Gly Asn Asn Glu Arg Ile Ile Asn Val Ser Ile Lys Lys Leu
                85                  90                  95

Lys Arg Lys Pro Pro Ser Thr Asn Ala Gly Arg Arg Gln Lys His Arg
            100                 105                 110

Leu Thr Cys Pro Ser Cys Asp Ser Tyr Glu Lys Lys Pro Pro Lys Glu
            115                 120                 125

Phe Leu Glu Arg Phe Lys Ser Leu Leu Gln Lys Met Ile His Gln His
            130                 135                 140

Leu Ser Ser Arg Thr His Gly Ser Glu Asp Ser
145                 150                 155
```

<210> SEQ ID NO 77
<211> LENGTH: 189
<212> TYPE: PRT
<213> ORGANISM: Homo sapiens

<400> SEQUENCE: 77

```
Met Leu Gly Ser Arg Ala Val Met Leu Leu Leu Leu Pro Trp Thr
1                   5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr
50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
            115                 120                 125

Leu Gly Leu Ser Gln Leu Leu Gln Pro Glu Gly His His Trp Glu Thr
            130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185
```

<210> SEQ ID NO 78
<211> LENGTH: 270
<212> TYPE: PRT
<213> ORGANISM: Homo sapiens

<400> SEQUENCE: 78

```
Met Lys Pro Lys Met Lys Tyr Ser Thr Asn Lys Ile Ser Thr Ala Lys
1                   5                   10                  15

Trp Lys Asn Thr Ala Ser Lys Ala Leu Cys Phe Lys Leu Gly Lys Ser
                20                  25                  30

Gln Gln Lys Ala Lys Glu Val Cys Pro Met Tyr Phe Met Lys Leu Arg
            35                  40                  45
```

```
Ser Gly Leu Met Ile Lys Lys Glu Ala Cys Tyr Phe Arg Arg Glu Thr
    50                  55                  60

Thr Lys Arg Pro Ser Leu Lys Thr Gly Arg Lys His Lys Arg His Leu
65                  70                  75                  80

Val Leu Ala Ala Cys Gln Gln Gln Ser Thr Val Glu Cys Phe Ala Phe
                85                  90                  95

Gly Ile Ser Gly Val Gln Lys Tyr Thr Arg Ala Leu His Asp Ser Ser
                100                 105                 110

Ile Thr Gly Ile Ser Pro Ile Thr Glu Tyr Leu Ala Ser Leu Ser Thr
                115                 120                 125

Tyr Asn Asp Gln Ser Ile Thr Phe Ala Leu Glu Asp Glu Ser Tyr Glu
130                 135                 140

Ile Tyr Val Glu Asp Leu Lys Lys Asp Glu Lys Lys Asp Lys Val Leu
145                 150                 155                 160

Leu Ser Tyr Tyr Glu Ser Gln His Pro Ser Asn Glu Ser Gly Asp Gly
                165                 170                 175

Val Asp Gly Lys Met Leu Met Val Thr Leu Ser Pro Thr Lys Asp Phe
                180                 185                 190

Trp Leu His Ala Asn Asn Lys Glu His Ser Val Glu Leu His Lys Cys
                195                 200                 205

Glu Lys Pro Leu Pro Asp Gln Ala Phe Phe Val Leu His Asn Met His
                210                 215                 220

Ser Asn Cys Val Ser Phe Glu Cys Lys Thr Asp Pro Gly Val Phe Ile
225                 230                 235                 240

Gly Val Lys Asp Asn His Leu Ala Leu Ile Lys Val Asp Ser Ser Glu
                245                 250                 255

Asn Leu Cys Thr Glu Asn Ile Leu Phe Lys Leu Ser Glu Thr
                260                 265                 270

<210> SEQ ID NO 79
<211> LENGTH: 177
<212> TYPE: PRT
<213> ORGANISM: Homo sapiens

<400> SEQUENCE: 79

Gly Pro Gln Arg Glu Glu Phe Pro Arg Asp Leu Ser Leu Ile Ser Pro
1               5                   10                  15

Leu Ala Gln Ala Val Arg Ser Ser Ser Arg Thr Pro Ser Asp Lys Pro
                20                  25                  30

Val Ala His Val Val Ala Asn Pro Gln Ala Glu Gly Gln Leu Gln Trp
            35                  40                  45

Leu Asn Arg Arg Ala Asn Ala Leu Leu Ala Asn Gly Val Glu Leu Arg
50                  55                  60

Asp Asn Gln Leu Val Val Pro Ser Glu Gly Leu Tyr Leu Ile Tyr Ser
65                  70                  75                  80

Gln Val Leu Phe Lys Gly Gln Gly Cys Pro Ser Thr His Val Leu Leu
                85                  90                  95

Thr His Thr Ile Ser Arg Ile Ala Val Ser Tyr Gln Thr Lys Val Asn
                100                 105                 110

Leu Leu Ser Ala Ile Lys Ser Pro Cys Gln Arg Glu Thr Pro Glu Gly
                115                 120                 125

Ala Glu Ala Lys Pro Trp Tyr Glu Pro Ile Tyr Leu Gly Gly Val Phe
                130                 135                 140

Gln Leu Glu Lys Gly Asp Arg Leu Ser Ala Glu Ile Asn Arg Pro Asp
145                 150                 155                 160
```

Tyr Leu Asp Phe Ala Glu Ser Gly Gln Val Tyr Phe Gly Ile Ile Ala
                165                 170                 175

Leu

<210> SEQ ID NO 80
<211> LENGTH: 205
<212> TYPE: PRT
<213> ORGANISM: Homo sapiens

<400> SEQUENCE: 80

Met Thr Pro Pro Glu Arg Leu Phe Leu Pro Arg Val Cys Gly Thr Thr
1               5                   10                  15

Leu His Leu Leu Leu Gly Leu Leu Val Leu Leu Pro Gly Ala
            20                  25                  30

Gln Gly Leu Pro Gly Val Gly Leu Thr Pro Ser Ala Ala Gln Thr Ala
        35                  40                  45

Arg Gln His Pro Lys Met His Leu Ala His Ser Thr Leu Lys Pro Ala
    50                  55                  60

Ala His Leu Ile Gly Asp Pro Ser Lys Gln Asn Ser Leu Leu Trp Arg
65                  70                  75                  80

Ala Asn Thr Asp Arg Ala Phe Leu Gln Asp Gly Phe Ser Leu Ser Asn
                85                  90                  95

Asn Ser Leu Leu Val Pro Thr Ser Gly Ile Tyr Phe Val Tyr Ser Gln
            100                 105                 110

Val Val Phe Ser Gly Lys Ala Tyr Ser Pro Lys Ala Thr Ser Ser Pro
        115                 120                 125

Leu Tyr Leu Ala His Glu Val Gln Leu Phe Ser Ser Gln Tyr Pro Phe
    130                 135                 140

His Val Pro Leu Leu Ser Ser Gln Lys Met Val Tyr Pro Gly Leu Gln
145                 150                 155                 160

Glu Pro Trp Leu His Ser Met Tyr His Gly Ala Ala Phe Gln Leu Thr
                165                 170                 175

Gln Gly Asp Gln Leu Ser Thr His Thr Asp Gly Ile Pro His Leu Val
            180                 185                 190

Leu Ser Pro Ser Thr Val Phe Phe Gly Ala Phe Ala Leu
        195                 200                 205

<210> SEQ ID NO 81
<211> LENGTH: 74
<212> TYPE: PRT
<213> ORGANISM: Homo sapiens

<400> SEQUENCE: 81

Gly Ile Ile Gln His Asp Leu Ile Phe Ser Leu Gln Gln Thr Glu Cys
1               5                   10                  15

Val Leu Lys Pro Val Glu Ser Ser Asp Met Lys Met Thr Gln Leu Phe
            20                  25                  30

Thr Lys Val Glu Ser Glu Asp Thr Ser Ser Leu Phe Asp Lys Leu Lys
        35                  40                  45

Lys Glu Pro Asp Ala Leu Thr Leu Leu Ala Pro Ala Ala Gly Asp Thr
    50                  55                  60

Ile Ile Ser Leu Asp Phe Gly Ser Asn Asp
65                  70

<210> SEQ ID NO 82
<211> LENGTH: 224

<212> TYPE: PRT
<213> ORGANISM: Homo sapiens

<400> SEQUENCE: 82

Ser Glu Asp Thr Ser Ser Leu Phe Asp Lys Leu Lys Glu Pro Asp
1               5                   10                  15

Ala Leu Thr Leu Leu Ala Pro Ala Ala Gly Asp Thr Ile Ile Ser Leu
            20                  25                  30

Asp Phe Gly Ser Asn Asp Thr Glu Thr Asp Asp Gln Gln Leu Glu Glu
        35                  40                  45

Val Pro Leu Tyr Asn Asp Val Met Leu Pro Ser Pro Asn Glu Lys Leu
    50                  55                  60

Gln Asn Ile Asn Leu Ala Met Ser Pro Leu Pro Thr Ala Glu Thr Pro
65                  70                  75                  80

Lys Pro Leu Arg Ser Ser Ala Asp Pro Ala Leu Asn Gln Glu Val Ala
                85                  90                  95

Leu Lys Leu Glu Pro Asn Pro Glu Ser Leu Glu Leu Ser Phe Thr Met
            100                 105                 110

Pro Gln Ile Gln Asp Gln Thr Pro Ser Pro Ser Asp Gly Ser Thr Arg
        115                 120                 125

Gln Ser Ser Pro Glu Pro Asn Ser Pro Ser Glu Tyr Cys Phe Tyr Val
    130                 135                 140

Asp Ser Asp Met Val Asn Glu Phe Lys Leu Glu Leu Val Glu Lys Leu
145                 150                 155                 160

Phe Ala Glu Asp Thr Glu Ala Lys Asn Pro Phe Ser Thr Gln Asp Thr
                165                 170                 175

Asp Leu Asp Leu Glu Met Leu Ala Pro Tyr Ile Pro Met Asp Asp Asp
            180                 185                 190

Phe Gln Leu Arg Ser Phe Asp Gln Leu Ser Pro Leu Glu Ser Ser Ser
        195                 200                 205

Ala Ser Pro Glu Ser Ala Ser Pro Gln Ser Thr Val Thr Val Phe Gln
    210                 215                 220

<210> SEQ ID NO 83
<211> LENGTH: 10
<212> TYPE: PRT
<213> ORGANISM: Artificial Sequence
<220> FEATURE:
<223> OTHER INFORMATION: Syntheized

<400> SEQUENCE: 83

Gly Gly Gly Gly Ser Gly Gly Gly Gly Ser
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Syntheized

<400> SEQUENCE: 84

Glu Ala Ala Ala Arg Glu Ala Ala Ala Arg
1               5                   10

<210> SEQ ID NO 85
<211> LENGTH: 750
<212> TYPE: PRT
<213> ORGANISM: Homo sapiens

```
<400> SEQUENCE: 85

Gly Ala Cys Ala Thr Cys Gly Thr Gly Ala Thr Gly Ala Cys Cys Cys
1               5                   10                  15

Ala Gly Thr Cys Cys Cys Thr Cys Thr Gly Thr Cys Thr Thr Thr
                20                  25                  30

Ala Cys Cys Cys Gly Thr Thr Ala Cys Ala Cys Cys Cys Gly Gly Thr
                35                  40                  45

Gly Ala Ala Cys Cys Cys Gly Cys Ala Gly Cys Ala Thr Thr Ala
            50                  55                  60

Gly Cys Thr Gly Thr Ala Gly Gly Thr Cys Cys Ala Cys Cys Ala Ala
65                  70                  75                  80

Gly Thr Cys Thr Thr Thr Ala Cys Thr Gly Cys Ala Cys Ala Gly Cys
                85                  90                  95

Ala Ala Cys Gly Gly Cys Ala Ala Cys Ala Cys Cys Thr Ala Thr Thr
                100                 105                 110

Thr Ala Thr Ala Cys Thr Gly Gly Thr Thr C

Ala Ala Ala Gly Cys Cys Cys Gly Gly Cys Ala Gly Cys Ala Gly Cys
            420                 425                 430

Gly Thr Cys Ala Ala Gly Gly Thr Gly Ala Gly Cys Thr Gly Cys Ala
            435                 440                 445

Ala Gly Gly Cys Cys Ala Gly Cys Gly Gly Cys Thr Ala Cys Ala Cys
            450                 455                 460

Cys Thr Thr Cys Ala Cys Cys Gly Ala Thr Thr Ala Cys Gly Ala Cys
465                 470                 475                 480

Ala Thr Gly Cys Ala Cys Thr Gly Gly Thr Gly Ala Gly Ala Cys
            485                 490                 495

Ala Ala Gly Cys Thr Cys Cys Gly Gly Thr Cys Ala Ala Gly Gly
            500                 505                 510

Thr Thr Thr Ala Gly Ala Gly Thr Gly Gly Ala Thr Cys Gly Gly Cys
            515                 520                 525

Ala Cys Ala Ala Thr Cys Gly Ala Cys Cys Cys Gly Ala Gly Ala
            530                 535                 540

Cys Cys Gly Gly Cys Gly Gly Cys Ala Cys Ala Gly Cys Cys Thr Ala
545                 550                 555                 560

Cys Ala Ala Cys Cys Ala Gly Ala Ala Gly Thr Thr Thr Ala Ala Gly
            565                 570                 575

Gly Gly Thr Cys Gly Thr Gly Cys Cys Ala Cys Thr Thr Thr Ala Ala
            580                 585                 590

Cys Ala Gly Cys Cys Gly Ala Thr Cys Gly Thr Thr Cys Cys Ala Cys
            595                 600                 605

Cys Ala Gly Cys Ala Cys Cys Gly Cys Cys Thr Ala Cys Ala Thr Gly
            610                 615                 620

Gly Ala Gly Cys Thr Gly Ala Gly Cys Thr Cys Thr Thr Thr Ala Ala
625                 630                 635                 640

Gly Gly Thr Cys Cys Gly Ala Gly Gly Ala Cys Ala Cys Cys Gly Cys
            645                 650                 655

Thr Gly Thr Gly Thr Ala Cys Thr Ala Thr Thr Gly Cys Ala Cys Cys
            660                 665                 670

Ala Gly Cys Thr Thr Cys Thr Ala Thr Thr Ala Cys Ala Cys Cys Thr
            675                 680                 685

Ala Cys Ala Gly Cys Ala Ala Cys Thr Ala Cys Gly Ala Cys Gly Thr
            690                 695                 700

Gly Gly Gly Cys Thr Thr Thr Gly Cys Cys Thr Ala Cys Thr Gly Gly
705                 710                 715                 720

Gly Gly Cys Cys Ala Ala Gly G

```
                35                  40                  45
Gly Ala Gly Cys Cys Gly Cys Thr Ala Gly Cys Ala Thr Cys Ala
            50                  55                  60
Gly Cys Thr Gly Thr Cys Gly Thr Ala Gly Cys Ala Cys Ala Ala
65                  70                  75                  80
Gly Thr Cys Cys Thr Thr Ala Thr Ala Cys Ala Cys Thr Cys Cys
                85                  90                  95
Ala Ala Cys Gly Gly Cys Ala Ala Cys Ala Cys Thr Ala Thr Thr
            100                 105                 110
Thr Ala Thr Ala Cys Thr Gly Gly Thr Thr Cys Cys Thr Cys Ala
            115                 120                 125
Gly Ala Ala Cys Cys Cys Gly Gly Cys Cys Ala Gly Thr Cys Cys
            130                 135                 140
Cys Cys Cys Cys Ala Gly Cys Thr Gly Cys Thr Gly Ala Thr Cys
145                 150                 155                 160
Ala Thr Cys Gly Thr Ala Thr Gly Ala Gly Cys Ala Ala Thr Thr
                165                 170                 175
Ala Gly Cys Cys Thr Cys Cys Gly Cys Gly Thr Gly Cys Cys Cys
            180                 185                 190
Gly Ala Thr Ala Gly Ala Thr Thr Ala Gly Cys Gly Gly Cys Ala
            195                 200                 205
Gly Cys Gly Gly Thr Ala Gly Cys Gly Gly Cys Ala Cys Cys Gly
            210                 215                 220
Cys Thr Thr Thr Ala Cys Thr Thr Thr Ala Ala Ala Gly Ala Thr Cys
225                 230                 235                 240
Thr Cys Thr Cys Gly Thr Gly Thr Gly Gly Ala Gly Gly Cys Cys Gly
            245                 250                 255
Ala Gly Gly Ala Cys Gly Thr Gly Gly Thr Gly Thr Gly Thr Ala
            260                 265                 270
Cys Thr Ala Cys Thr Gly Cys Ala Thr Gly Cys Ala Gly Cys Ala Thr
            275                 280                 285
Thr Thr Ala Gly Ala Gly Thr Ala Cys Cys Cys Thr Thr Cys Ala
            290                 295                 300
Cys Cys Thr Thr Gly Gly Cys Gly Gly Cys Gly Gly Cys Ala Cys
305                 310                 315                 320
Cys Ala Ala Gly Gly Thr Gly Gly Ala Gly Ala Thr Cys Ala Ala Ala
            325                 330                 335
Gly Gly Cys Gly Gly Cys Gly Gly Ala Gly Gly Ala Ala Gly Cys Gly
            340                 345                 350
Gly Cys Gly Gly Cys Gly Gly Cys Gly Gly Cys Thr Cys Cys Gly Gly
            355                 360                 365
Cys Gly Gly Cys Gly Gly Ala Gly Gly Cys Thr Cys Cys Gly Ala Gly
            370                 375                 380
Ala Thr Thr Cys Ala Gly Cys Thr Cys Ala Gly Cys Ala Gly Ala
385                 390                 395                 400
Gly Cys Gly Gly Cys Gly Cys Cys Gly Ala Gly Thr Gly Ala Ala
            405                 410                 415
Ala Ala Ala Ala Cys Cys Cys Gly Gly Cys Thr Cys Thr Cys Cys
            420                 425                 430
Gly Thr Gly Ala Ala Gly Gly Thr Gly Thr Cys Thr Thr Gly Thr Ala
            435                 440                 445
Ala Gly Gly Cys Cys Ala Gly Cys Gly Gly Cys Thr Ala Cys Ala Cys
450                 455                 460
```

-continued

Cys Thr Thr Cys Ala Cys Ala Gly Ala Cys Thr Ala Cys Gly Ala Cys
465                 470                 475                 480

Ala Thr Gly Cys Ala Cys Thr Gly Gly Gly Thr Gly Ala Gly Gly Cys
                485                 490                 495

Ala Ala Gly Cys Thr Cys Cys Gly Gly Thr Cys Ala Ala Gly Gly
            500                 505                 510

Ala Cys Thr Gly Gly Ala Gly Thr Gly Gly Ala Thr Gly Gly Gly Cys
            515                 520                 525

Ala Cys Cys Ala Thr Cys Gly Ala Cys Cys Cys Gly Ala Ala Ala
            530                 535                 540

Cys Thr Gly Gly Thr Gly Gly Cys Ala Cys Ala Gly Cys Cys Thr Ala
545                 550                 555                 560

Cys Ala Ala Cys Cys Ala Gly Ala Ala Gly Thr Thr Cys Ala Ala Gly
                565                 570                 575

Gly Gly Thr Cys Gly Thr Gly Thr Gly Ala Cys Cys Ala Thr Cys Ala
                580                 585                 590

Cys Cys Gly Cys Cys Gly Ala Thr Ala Ala Gly Ala Gly Cys Ala Cys
                595                 600                 605

Cys Thr Cys Cys Ala Cys Cys Gly Cys Cys Thr Ala Cys Ala Thr Gly
                610                 615                 620

Gly Ala Gly Cys Thr Gly Ala Gly Cys Thr Cys Thr Thr Ala Ala
625                 630                 635                 640

Gly Gly Ala Gly Cys Gly Ala Gly Gly Ala Cys Ala Cys Cys Gly Cys
                645                 650                 655

Cys Gly Thr Gly Thr Ala Thr Thr Ala Cys Thr Gly Cys Ala Cys Cys
                660                 665                 670

Ala Gly Cys Thr Thr Cys Thr Ala Cys Thr Ala Cys Ala Cys Cys Thr
                675                 680                 685

Ala Cys Ala Gly Cys Ala Ala Cys Thr Ala Cys Gly Ala Cys Gly Thr
                690                 695                 700

Gly Gly Gly Cys Thr Thr Cys Gly Cys Cys Thr Ala Cys Thr Gly Gly
705                 710                 715                 720

Gly Gly Cys Cys Ala Ala Gly Gly Thr Ala Cys Thr Thr Thr Ala Gly
                725                 730                 735

Thr Gly Ala Cys Cys Gly Thr Gly Thr Cys Cys Ala Gly Cys
                740                 745                 750

<210> SEQ ID NO 87
<211> LENGTH: 750
<212> TYPE: PRT
<213> ORGANISM: Homo sapiens

<400> SEQUENCE: 87

Gly Ala Cys Ala Thr Cys Gly Thr Gly Ala Thr Gly Ala Cys Cys Cys
1                 5                   10                  15

Ala Gly Ala Gly Cys Cys Cys Thr Cys Thr Gly Thr Cys Thr Thr Thr
                20                  25                  30

Ala Cys Cys Cys Gly Thr Gly Ala Cys Ala Cys Cys Cys Gly Gly Thr
                35                  40                  45

Gly Ala Gly Cys Cys Cys Gly Cys Thr Ala Gly Cys Ala Thr Thr Ala
            50                  55                  60

Gly Cys Thr Gly Thr Cys Gly Thr Thr Cys Cys Ala Cys Cys Ala Ala
65                  70                  75                  80

Gly Thr Cys Thr Thr Thr Ala Cys Thr Gly Cys Ala Cys Thr Cys Cys

-continued

```
                     85                  90                  95
Ala Ala Cys Gly Gly Cys Ala Ala Cys Ala Cys Thr Ala Thr Thr
                    100                 105                 110
Thr Ala Thr Ala Cys Thr Gly Gly Thr Ala Thr Thr Ala Cys Ala
                    115                 120                 125
Gly Ala Ala Gly Cys Cys Gly Gly Cys Cys Ala Gly Ala Gly Cys
                    130                 135                 140
Cys Cys Cys Cys Ala Gly Cys Thr Gly Cys Thr Gly Ala Thr Cys Thr
145                 150                 155                 160
Ala Thr Ala Gly Gly Ala Thr Gly Ala Gly Cys Ala Ala Thr Thr Thr
                    165                 170                 175
Ala Gly Cys Cys Ala Gly Cys Gly Gly Cys Gly Thr Gly Cys Cys Cys
                    180                 185                 190
Gly Ala Thr Ala Gly Ala Thr Thr Cys Ala Gly Cys Gly Gly Cys Ala
                    195                 200                 205
Gly Cys Gly Gly Ala Ala Gly Cys Gly Gly Cys Ala Cys Cys Gly Ala
                    210                 215                 220
Cys Thr Thr Cys Ala Cys Thr Thr Thr Ala Ala Ala Gly Ala Thr Cys
225                 230                 235                 240
Ala Gly Cys Ala Gly Ala Gly Thr Gly Gly Ala Ala Gly Cys Cys Gly
                    245                 250                 255
Ala Gly Gly Ala Cys Gly Thr Gly Gly Thr Gly Thr Gly Thr Ala
                    260                 265                 270
Cys Thr Ala Cys Thr Gly Cys Ala Thr Gly Cys Ala Gly Cys Ala Thr
                    275                 280                 285
Thr Thr Ala Gly Ala Gly Thr Ala Cys Cys Cys Cys Thr Thr Cys Ala
                    290                 295                 300
Cys Cys Thr Thr Cys Gly Gly Cys Gly Gly Cys Gly Gly Ala Ala Cys
305                 310                 315                 320
Cys Ala Ala Gly Gly Thr Gly Gly Ala Gly Ala Thr Cys Ala Ala Gly
                    325                 330                 335
Gly Gly Cys Gly Gly Cys Gly Gly Cys Gly Gly Cys Ala Gly Cys Gly
                    340                 345                 350
Gly Cys Gly Gly Ala Gly Gly Ala Gly Gly Ala Ala Gly Cys Gly Gly
                    355                 360                 365
Ala Gly Gly Cys Gly Gly Cys Gly Gly Cys Thr Cys Cys Gly Ala Gly
                    370                 375                 380
Ala Thr Thr Cys Ala Gly Cys Thr Gly Cys Ala Gly Cys Ala Ala Ala
385                 390                 395                 400
Gly Cys Gly Gly Cys Gly Cys Cys Gly Ala Gly Gly Thr Gly Ala Ala
                    405                 410                 415
Ala Ala Ala Gly Cys Cys Cys Gly Gly Thr Ala Gly Cys Ala Gly Cys
                    420                 425                 430
Gly Thr Gly Ala Ala Gly Gly Thr Gly Ala Gly Cys Thr Gly Thr Ala
                    435                 440                 445
Ala Gly Gly Cys Cys Ala Gly Cys Gly Gly Cys Thr Ala Cys Ala Cys
                    450                 455                 460
Cys Thr Thr Cys Ala Cys Cys Gly Ala Cys Thr Ala Cys Gly Ala Thr
465                 470                 475                 480
Ala Thr Gly Cys Ala Cys Thr Gly Gly Gly Thr Gly Ala Ala Gly Cys
                    485                 490                 495
Ala Ala Gly Cys Cys Cys Cys Gly Gly Thr Cys Ala Cys Gly Gly
                    500                 505                 510
```

```
Ala Cys Thr Gly Gly Ala Gly Thr Gly Gly Ala Thr Cys Gly Gly Cys
            515                 520                 525

Ala Cys Cys Ala Thr Thr Gly Ala Cys Cys Cys Gly Ala Gly Ala
            530                 535                 540

Cys Thr Gly Gly Thr Gly Gly Cys Ala Cys Gly Cys Cys Thr Ala
545                 550                 555                 560

Cys Ala Ala Cys Cys Ala Gly Ala Ala Thr Thr Cys Ala Ala Gly
                565                 570                 575

Gly Gly Cys Ala Ala Gly Gly Cys Cys Ala Cys Ala Cys Thr Gly Ala
            580                 585                 590

Cys Cys Gly Cys Cys Gly Ala Thr Cys Gly Thr Thr Cys Cys Ala Cys
            595                 600                 605

Cys Ala Gly Cys Ala Cys Ala Gly Cys Cys Thr Ala Thr Ala Thr Gly
            610                 615                 620

Gly Ala Gly Cys Thr Gly Ala Gly Cys Thr Cys Thr Thr Ala Ala
625                 630                 635                 640

Cys Cys Ala Gly Cys Gly Ala Gly Gly Ala Cys Ala Cys Cys Gly Cys
                645                 650                 655

Cys Gly Thr Gly Thr Ala Thr Ala Cys Thr Gly Cys Ala Cys Cys
            660                 665                 670

Thr Cys Cys Thr Thr Thr Thr Ala Cys Thr Ala Cys Ala Cys Cys Thr
            675                 680                 685

Ala Cys Ala Gly Cys Ala Ala Cys Thr Ala Cys Gly Ala Cys Gly Thr
            690                 695                 700

Gly Gly Gly

```
                130                 135                 140
Cys Cys Cys Cys Ala Gly Cys Thr Gly Cys Thr Gly Ala Thr Thr Thr
145                 150                 155                 160

Ala Thr Cys Gly Thr Ala Thr Gly Ala Gly Cys Ala Ala Thr Thr Thr
                165                 170                 175

Ala Gly Cys Cys Ala Gly Cys Gly Gly Cys Gly Thr Gly Cys Cys Cys
                180                 185                 190

Gly Ala Thr Cys Gly Thr Thr Thr Thr Thr Cys Cys Gly Gly Cys Ala
                195                 200                 205

Gly Cys Gly Gly Cys Ala Gly Cys Gly Gly Cys Ala Cys Ala Gly Ala
                210                 215                 220

Cys Thr Thr Cys Ala Cys Thr Thr Thr Ala Ala Gly Ala Thr Thr Cys
225                 230                 235                 240

Ala Gly Cys Ala G

Cys Ala Ala Cys Cys Ala Gly Ala Ala Gly Thr Thr Cys Ala Ala Ala
                565                 570                 575

Gly Gly Cys Ala Ala Gly Gly Cys Cys Ala Cys Thr Thr Ala Ala
            580                 585                 590

Cys Cys Gly Cys Gly Ala Cys Ala Gly Ala Ala Gly Cys Ala Cys
            595                 600                 605

Ala Ala Gly Cys Ala Cys Cys Gly Cys Thr Thr Ala Cys Ala Thr Gly
610                 615                 620

Gly Ala Gly Cys Thr Gly Thr Cys Cys Thr Cys Thr Thr Ala Ala
625                 630                 635                 640

Gly Ala Thr Cys Cys Gly Ala Gly Gly Ala Cys Ala Cys Cys Gly Cys
                645                 650                 655

Cys Gly Thr Gly Thr Ala Thr Thr Ala Cys Thr Gly Cys Ala Cys Ala
                660                 665                 670

Ala Gly Cys Thr Thr Cys Thr Ala Cys Thr Ala Cys Ala Cys Cys Thr
                675                 680                 685

Ala Cys Thr Cys Cys Ala Ala Cys Thr Ala Cys Gly Ala Cys Gly Thr
                690                 695                 700

Cys Gly Gly Cys Thr Thr Cys Gly Cys Cys Thr Ala Cys Thr Gly Gly
705                 710                 715                 720

Gly Gly Cys Cys Ala Ala Gly Gly Cys Ala Cys Thr Thr Thr Ala Gly
                725                 730                 735

Thr Gly Ala Cys Ala Gly Thr Gly Ala Gly Cys Ala Gly Cys
                740                 745                 750

<210> SEQ ID NO 89
<211> LENGTH: 750
<212> TYPE: PRT
<213> ORGANISM: Homo sapiens

<400> SEQUENCE: 89

Gly Ala Cys Ala Thr Cys Gly Thr Gly Ala Thr Gly Ala Cys Cys Cys
1               5                   10                  15

Ala Gly Ala Gly Cys Cys Cys Thr Cys Thr Gly Thr Cys Thr Thr Thr
                20                  25                  30

Ala Cys Cys Cys Gly Thr Gly Ala Cys Ala Cys Cys Cys Gly Gly Thr
                35                  40                  45

Gly Ala Gly Cys Cys Gly Cys Cys Thr Cys Cys Cys Thr Cys Cys Cys
            50                  55                  60

Gly Cys Thr Gly Thr Cys Gly Thr Cys Thr Cys Ala Cys Cys Ala Ala
65                  70                  75                  80

Gly Thr Cys Thr Thr Thr Ala Cys Thr Gly Cys Ala Cys Thr Cys Cys
                85                  90                  95

Ala Ala Cys Gly Gly Cys Ala Ala Cys Ala Cys Cys Thr Ala Thr Thr
                100                 105                 110

Thr Ala Thr Ala Cys Thr Gly Gly Thr Thr Cys Thr Thr Ala Cys Ala
            115                 120                 125

Gly Ala Ala Gly Cys Cys Gly Gly Cys Cys Ala Gly Ala Gly Cys Cys
            130                 135                 140

Cys Cys Cys Cys Ala Gly Cys Thr Gly Cys Thr Gly Ala Thr Cys Thr
145                 150                 155                 160

Ala Thr Ala Gly Gly Ala Thr Gly Ala Gly Cys Ala Ala Thr Thr Thr
                165                 170                 175

Ala Gly Cys Cys Ala Gly Cys Gly Gly Cys Gly Thr Gly Cys Cys Cys

```
            180                 185                 190
Gly Ala Thr Ala Gly Ala Thr Thr Cys Ala Gly Cys Gly Gly Cys Ala
            195                 200                 205
Gly Cys Gly Gly Ala Ala Gly Cys Gly Gly Cys Ala Cys Cys Gly Ala
            210                 215                 220
Cys Thr Thr Cys Ala Cys Thr Thr Ala Ala Gly Ala Thr Cys
225                 230                 235                 240
Ala Gly Cys Ala Gly Ala Gly Thr Gly Gly Ala Ala Gly Cys Cys Gly
                245                 250                 255
Ala Gly Gly Ala Cys Gly Thr Gly Gly Thr Gly Thr Gly Thr Ala
                260                 265                 270
Cys Thr Ala Cys Thr Gly Cys Ala Thr Gly Cys Ala Gly Cys Ala Thr
    275                 280                 285
Thr Thr Ala Gly Ala Gly Thr Ala Cys Cys Cys Thr Thr Cys Ala
            290                 295                 300
Cys Cys Thr Thr Cys Gly Gly Cys Gly Gly Cys Gly Gly Ala Ala Cys
305                 310                 315                 320
Cys Ala Ala Gly Gly Thr Gly Ala Gly Ala Thr Cys Ala Ala Gly
                325                 330                 335
Gly Gly Cys Gly Gly Cys Gly Gly Cys Gly Gly Cys Ala Gly Cys Gly
                340                 345                 350
Gly Cys Gly Gly Ala Gly Gly Ala Gly Gly Ala Ala Gly Cys Gly Gly
                355                 360                 365
Ala Gly Gly Cys Gly Gly Cys Gly Gly Cys Thr Cys Cys Gly Ala Gly
                370                 375                 380
Ala Thr Thr Cys Ala Gly Cys Thr Gly Cys Ala Gly Cys Ala Ala Ala
385                 390                 395                 400
Gly Cys Gly Gly Cys Gly Cys Cys Gly Ala Gly Gly Thr Gly Ala Ala
                405                 410                 415
Ala Ala Ala Gly Cys Cys Cys Gly Gly Thr Ala Gly Cys Ala Gly Cys
                420                 425                 430
Gly Thr Gly Ala Ala Gly Gly Thr Gly Ala Gly Cys Thr Gly Thr Ala
                435                 440                 445
Ala Gly Gly Cys Cys Ala Gly Cys Gly Gly Cys Thr Ala Cys Ala Cys
                450                 455                 460
Cys Thr Thr Cys Ala Cys Cys Gly Ala Cys Thr Ala Cys Gly Ala Thr
465                 470                 475                 480
Ala Thr Gly Cys Ala Cys Thr Gly Gly Gly Thr Gly Ala Ala Gly Cys
                485                 490                 495
Ala Ala Gly Cys Cys Cys Cys Gly Gly Thr Cys Ala Cys Gly Gly
                500                 505                 510
Ala Cys Thr Gly Gly Ala Gly Thr Gly Gly Ala Thr Gly Gly Gly Cys
                515                 520                 525
Ala Cys Cys Ala Thr Thr Gly Ala Cys Cys Cys Gly Ala Gly Ala
                530                 535                 540
Cys Thr Gly Gly Thr Gly Gly Cys Ala Cys Cys Gly Cys Cys Thr Ala
545                 550                 555                 560
Cys Ala Ala Cys Cys Ala Gly Ala Ala Thr Thr Cys Ala Ala Gly
                565                 570                 575
Gly Gly Cys Ala Ala Gly Gly Cys Cys Ala Ala Cys Thr Gly Ala
                580                 585                 590
Cys Cys Gly Cys Cys Gly Ala Thr Cys Gly Thr Thr Cys Cys Ala Cys
            595                 600                 605
```

```
Cys Ala Gly Cys Ala Cys Ala Gly Cys Cys Thr Ala Thr Ala Thr Gly
            610                 615                 620

Gly Ala Gly Cys Thr Gly Ala Gly Cys Thr Cys Thr Thr Thr Ala Ala
625                 630                 635                 640

Cys Cys Ala Gly Cys Gly Ala Gly Gly Ala Cys Ala Cys Cys Gly Cys
                645                 650                 655

Cys Gly Thr Gly Thr Ala Thr Thr Ala Cys Thr Gly Cys Ala Cys Cys
            660                 665                 670

Thr Cys Cys Thr Thr Thr Thr Ala Cys Thr Ala Cys Ala Cys Cys Thr
        675                 680                 685

Ala Cys Ala Gly Cys Ala Ala Cys Thr Ala Cys Gly Ala Cys Gly Thr
    690                 695                 700

Gly Gly Gly Cys Thr Thr Cys Gly Cys Cys Thr Ala Cys Thr Gly Gly
705                 710                 715                 720

Gly Gly Cys Cys Ala Ala Gly Gly Thr Ala Cys Thr Thr Thr Ala Gly
                725                 730                 735

Thr Gly Ala Cys Cys Gly Thr Gly Ala Gly Cys Thr Cys Cys
            740                 745                 750

<210> SEQ ID NO 90
<211> LENGTH: 714
<212> TYPE: PRT
<213> ORGANISM: Homo sapiens

<400> SEQUENCE: 90

Ala Gly Cys Ala Gly Cys Gly Ala Gly Cys Thr Gly Ala Cys Cys Cys
1               5                   10                  15

Ala Ala Gly Ala Thr Cys Cys Gly Cys Thr Gly Thr Gly Thr Gly Cys
            20                  25                  30

Cys Gly Thr Gly Gly Cys Thr Thr Ala Gly Gly Cys Cys Ala Gly Gly
        35                  40                  45

Ala Cys Cys Gly Thr Gly Ala Gly Gly Ala Thr Cys Ala Cys Thr Thr
    50                  55                  60

Gly Thr Cys Gly Thr Gly Gly Cys Gly Ala Cys Thr Cys Thr Thr Thr
65                  70                  75                  80

Ala Ala Gly Gly Ala Ala Gly Thr Ala Cys Thr Ala Cys Gly Cys Cys
                85                  90                  95

Ala Gly Cys Thr Gly Gly Thr Ala Cys Cys Ala Gly Cys Ala Gly Ala
            100                 105                 110

Ala Gly Cys Cys Ala Gly Ala Cys Ala Ala Gly Cys Thr Cys Cys
        115                 120                 125

Thr Cys Ala Gly Cys Thr Gly Gly Thr Gly Ala Thr Cys Thr Ala Cys
    130                 135                 140

Cys Ala Cys Ala Ala Gly Ala Ala Cys Ala Cys Ala Gly Ala Gly
145                 150                 155                 160

Cys Cys Ala Gly Cys Gly Gly Cys Ala Thr Cys Cys Cys Cys Gly Ala
                165                 170                 175

Thr Cys Gly Thr Thr Cys Thr Cys Cys Gly Gly Cys Thr Cys Cys
            180                 185                 190

Ala Thr Cys Ala Gly Cys Gly Gly Cys Ala Ala Cys Ala Cys Cys Gly
        195                 200                 205

Cys Cys Thr Cys Thr Thr Thr Ala Ala Cys Ala Thr Cys Ala Cys
    210                 215                 220

Cys Gly Gly Ala Gly Cys Thr Cys Ala Ala Gly Cys Thr Gly Ala Gly
```

-continued

```
225                 230                 235                 240

Gly Ala Cys Gly Ala Ala Gly Cys Cys Gly Cys Cys Thr Ala Cys Thr
                245                 250                 255
Thr Cys Thr Gly Cys Ala Ala Cys Thr Cys Thr Cys Gly Thr Gly Ala
            260                 265                 270

Cys Ala Cys Cys Ala Gly Cys Gly Gly Cys Ala Ala Cys Thr Ala Thr
        275                 280                 285

Thr Thr Ala Gly Thr Gly Thr Thr Cys Gly Gly Cys Gly Gly Ala Gly
    290                 295                 300

Gly Cys Ala Cys Cys Ala Ala Gly Gly Thr Gly Ala Cys Cys Gly Thr
305                 310                 315                 320

Gly Cys Thr Gly Gly Gly Ala Gly Gly Cys Gly Gly Ala Gly Gly Ala
                325                 330                 335
Gly Gly Cys Ala Gly Cys Gly Gly Cys Gly Gly Cys Gly Gly Cys Gly
            340                 345                 350

Gly Cys Thr Cys Cys Gly Gly Ala Gly Gly Ala Gly Gly Cys Gly Gly
        355                 360                 365

Cys Thr Cys Cys Cys Ala Gly Cys Thr Gly Cys Ala Ala Cys Thr Gly
    370                 375                 380

Cys Ala Ala Gly Ala Ala Ala Gly Cys Gly Gly Ala Cys Cys Cys Gly
385                 390                 395                 400

Gly Thr Thr Thr Ala Gly Thr Gly Ala Ala Ala Cys Cys Cys Thr Cys
                405                 410                 415

Cys Gly Ala Gly Ala Cys Thr Thr Thr Ala Thr Cys Thr Thr Thr Ala
            420                 425                 430

Ala Cys Thr Thr Gly Thr Gly Cys Thr Gly Thr Gly Thr Cys Cys Gly
        435                 440                 445

Gly Ala Gly Cys Cys Ala Gly Cys Ala Thr Cys Ala Gly Cys Ala Ala
    450                 455                 460

Cys Thr Gly Gly Thr Gly Gly Thr Cys Thr Thr Gly Gly Gly Thr Gly
465                 470                 475                 480

Ala Gly Ala Cys Ala Gly Cys Cys Cys Cys Cys Cys Gly Gly Cys Ala
                485                 490                 495

Ala Ala Gly Gly Ala Cys Thr Gly Gly Ala Gly Thr Gly Gly Ala Thr
            500                 505                 510

Cys Gly Gly Cys Gly Ala Gly Gly Thr Gly Cys Ala Cys Cys Ala Cys
        515                 520                 525

Ala Gly Cys Gly Gly Cys Gly Thr Gly Ala Cys Cys Ala Cys Cys Thr
    530                 535                 540

Ala Cys Ala Ala Gly Cys Cys Cys Thr Cys Thr Thr Thr Ala Ala Ala
545                 550                 555                 560

Gly Thr Cys Thr Cys Gly Thr Gly Thr Gly Ala Cys Cys Ala Thr Cys
                565                 570                 575

Ala Gly Cys Gly Thr Gly Gly Ala Cys Ala Ala Cys Ala Gly Cys Ala
            580                 585                 590

Ala Gly Ala Ala Cys Cys Ala Gly Cys Thr Gly Thr Cys Thr Thr Thr
        595                 600                 605

Ala Ala Ala Gly Cys Thr Gly Ala Cys Ala Ala Gly Cys Gly Thr Gly
    610                 615                 620

Ala Cys Cys Gly Cys Cys Gly Cys Thr Gly Ala Cys Ala Cys Cys Gly
625                 630                 635                 640

Cys Cys Gly Thr Gly Thr Ala Cys Thr Ala Cys Thr Gly Cys Gly Cys
                645                 650                 655

```
Cys Ala Gly Ala Gly Ala Gly Thr Thr Cys Gly Cys Gly Ala Thr
                660                 665                 670

Gly Ala Cys Gly Cys Cys Thr Thr Cys Gly Ala Cys Ala Thr Cys Thr
        675                 680                 685

Gly Gly Gly Gly Ala Ala Gly Gly Gly Cys Ala Cys Cys Ala Thr
        690                 695                 700

Gly Gly Thr Gly Ala Cys Cys Gly Thr Gly
705                 710

<210> SEQ ID NO 91
<211> LENGTH: 750
<212> TYPE: PRT
<213> ORGANISM: Homo sapiens

<400> SEQUENCE: 91

Gly Ala Cys Ala Thr Cys Gly Thr Gly Ala Thr Gly Ala Cys Cys Cys
1               5                   10                  15

Ala Gly Ala Gly Cys Cys Cys Cys Thr Cys Thr Cys Thr Thr Thr
            20                  25                  30

Ala Cys Cys Cys Gly Thr Thr Ala Cys Ala Cys Cys Gly Gly Thr
            35                  40                  45

Gly Ala Gly Cys Cys Cys Gly Cys Thr Ala Gly Cys Ala Thr Cys Ala
    50                  55                  60

Gly Cys Thr Gly Thr Cys Gly Thr Ala Gly Cys Ala Cys Ala Ala
65                  70                  75                  80

Gly Thr Cys Cys Thr Thr Ala Thr Ala Cys Ala Cys Thr Cys Cys
                85                  90                  95

Ala Ala Cys Gly Gly Cys Ala Ala Cys Ala Cys Cys Thr Ala Thr Thr
            100                 105                 110

Thr Ala Thr Ala Cys Thr Gly Gly Thr Ala Cys Cys Thr Cys Cys Ala
        115                 120                 125

Gly Ala Ala Ala Cys Cys Gly Gly Cys Cys Ala Gly Thr Cys Cys
    130                 135                 140

Cys Cys Cys Cys Ala Gly Cys Thr Gly Cys Thr Gly Ala Thr Cys Thr
145                 150                 155                 160

Ala Thr Cys Gly Thr Ala Thr Gly Ala Gly Cys Ala Ala Thr Thr
            165                 170                 175

Ala Gly Cys Cys Thr Cys Cys Gly Gly Cys Gly Thr Gly Cys Cys Cys
        180                 185                 190

Gly Ala Thr Ala Gly Ala Thr Thr Ala Gly Cys Gly Gly Cys Ala
    195                 200                 205

Gly Cys Gly Gly Thr Ala Gly Cys Gly Gly Cys Ala Cys Cys Gly Ala
        210                 215                 220

Cys Thr Thr Thr Ala Cys Thr Thr Ala Ala Ala Gly Ala Thr Cys
225                 230                 235                 240

Thr Cys Thr Cys Gly Thr Gly Thr Gly Gly Ala Gly Gly Cys Cys Gly
                245                 250                 255

Ala Gly Gly Ala Cys Gly Thr Gly Gly Thr Gly Thr Gly Thr Ala
            260                 265                 270

Cys Thr Ala Cys Thr Gly Cys Ala Thr Gly Cys Ala Gly Cys Ala Thr
        275                 280                 285

Thr Thr Ala Gly Ala Gly Thr Ala Cys Cys Cys Thr Thr Cys Ala
    290                 295                 300

Cys Cys Thr Thr Thr Gly Gly Cys Gly Gly Cys Gly Gly Cys Ala Cys
```

-continued

```
            305                 310                 315                 320
        Cys Ala Ala Gly Gly Thr Gly Ala Gly Ala Thr Cys Ala Ala Ala
                        325                 330                 335
        Gly Gly Cys Gly Gly Cys Gly Ala Gly Ala Ala Gly Cys Gly
                    340                 345                 350
        Gly Cys Gly Gly Cys Gly Gly Cys Gly Gly Cys Thr Cys Gly Gly
                    355                 360                 365
        Cys Gly Gly Cys Gly Ala Gly Gly Cys Thr Cys Gly Ala Gly
                    370                 375                 380
        Ala Thr Thr Cys Ala Gly Cys Thr Cys Ala Gly Cys Ala Gly Ala
        385                 390                 395                 400
        Gly Cys Gly Gly Cys Gly Cys Gly Ala Gly Thr Gly Ala Ala
                        405                 410                 415
        Ala Ala Ala Ala Cys Cys Cys Gly Gly Cys Thr Cys Thr Cys Cys
                    420                 425                 430
        Gly Thr Gly Ala Ala Gly Gly Thr Gly Cys Thr Thr Gly Thr Ala
                    435                 440                 445
        Ala Gly Gly Cys Cys Ala Gly Cys Gly Thr Ala Cys Ala Cys
                    450                 455                 460
        Cys Thr Thr Cys Ala Cys Ala Gly Ala Cys Thr Ala Cys Gly Ala Cys
        465                 470                 475                 480
        Ala Thr Gly Cys Ala Cys Thr Gly Gly Thr Gly Ala Gly Gly Cys
                        485                 490                 495
        Ala Ala Gly Cys Thr Cys Cys Gly Gly Thr Cys Ala Ala Gly Gly
                    500                 505                 510
        Ala Cys Thr Gly Gly Ala Gly Thr Gly Gly Ala Thr Gly Gly Gly Cys
                    515                 520                 525
        Ala Cys Cys Ala Thr Cys Gly Ala Cys Cys Cys Gly Ala Ala Ala
                    530                 535                 540
        Cys Thr Gly Gly Thr Gly Gly Cys Ala Cys Ala Gly Cys Cys Thr Ala
        545                 550                 555                 560
        Cys Ala Ala Cys Cys Ala Gly Ala Ala Gly Thr Thr Cys Ala Ala Gly
                        565                 570                 575
        Gly Gly Thr Cys Gly Thr Gly Thr Gly Ala Cys Cys Ala Thr Cys Ala
                    580                 585                 590
        Cys Cys Gly Cys Cys Gly Ala Cys Ala Ala Gly Ala Gly Cys Ala Cys
                    595                 600                 605
        Cys Thr Cys Cys Ala Cys Cys Gly Cys Cys Thr Ala Cys Ala Thr Gly
                    610                 615                 620
        Gly Ala Gly Cys Thr Gly Ala Gly Cys Thr Cys Thr Ala Ala
        625                 630                 635                 640
        Gly Gly Ala Gly Cys Gly Ala Gly Gly Ala Cys Ala Cys Cys Gly Cys
                        645                 650                 655
        Cys Gly Thr Gly Thr Ala Thr Thr Ala Cys Thr Gly Cys Ala Cys Cys
                    660                 665                 670
        Ala Gly Cys Thr Thr Cys Thr Ala Cys Thr Ala Cys Cys Thr
                    675                 680                 685
        Ala Cys Ala Gly Cys Ala Ala Cys Thr Ala Cys Gly Ala Cys Gly Thr
                    690                 695                 700
        Gly Gly Gly Cys Thr Thr Cys Gly Cys Thr Ala Cys Thr Gly Gly
        705                 710                 715                 720
        Gly Gly Cys Cys Ala Ala Gly Gly Thr Ala Cys Thr Thr Ala Gly
                        725                 730                 735
```

-continued

Thr Gly Ala Cys Cys Gly Thr Gly Thr Cys Cys Ala Gly Cys
             740                 745                 750

<210> SEQ ID NO 92
<211> LENGTH: 750
<212> TYPE: PRT
<213> ORGANISM: Homo sapiens

<400> SEQUENCE: 92

Gly Ala Cys Ala Thr Cys Gly Thr Gly Ala Thr Gly Ala Cys Cys Cys
1               5                   10                  15

Ala Gly Thr Cys Cys Cys Cys Thr Cys Thr Gly Thr Cys Thr Thr Thr
                20                  25                  30

Ala Cys Cys Cys Gly Thr Thr Ala Cys Ala Cys Cys Cys Gly Gly Thr
            35                  40                  45

Gly Ala Ala Cys Cys Cys Gly Cys Cys Ala Gly Cys Ala Thr Thr Ala
50                  55                  60

Gly Cys Thr Gly Thr Ala Gly Gly Thr Cys Cys Ala Cys Cys Ala Ala
65                  70                  75                  80

Gly Thr Cys Thr Thr Thr Ala Cys Thr Gly Cys Ala Cys Ala Gly Cys
                85                  90                  95

Ala Ala Cys Gly Gly Cys Ala Ala Cys Ala Cys Cys Thr Ala Thr Thr
            100                 105                 110

Thr Ala Thr Ala Cys Thr Gly Gly Thr Ala Thr Thr Thr Ala Cys Ala
            115                 120                 125

Gly Ala Ala Gly Cys Cys Cys Gly Gly Cys Cys Ala Ala Thr Cys Cys
130                 135                 140

Cys Cys Cys Cys Ala Gly Cys Thr Gly Cys Thr Gly Ala Thr Cys Thr
145                 150                 155                 160

Ala Thr Cys Gly Thr Ala Thr Gly Ala Gly Cys Ala Ala Thr Thr Thr
                165                 170                 175

Ala Gly Cys Thr Ala Gly Cys Gly Gly Cys Gly Thr Gly Cys Cys Cys
            180                 185                 190

Gly Ala Cys Ala Gly Ala Thr Thr Cys Ala Gly Cys Gly Gly Cys Ala
            195                 200                 205

Gly Cys Gly Gly Cys Thr Cys Cys Gly Gly Ala Ala Cys Cys Gly Ala
            210                 215                 220

Cys Thr Thr Cys Ala Cys Thr Thr Ala Ala Ala Gly Ala Thr Cys
225                 230                 235                 240

Thr Cys Cys Ala Gly Ala Gly Thr Gly Gly Ala Gly Gly Cys Cys Gly
                245                 250                 255

Ala Gly Gly Ala Cys Gly Thr Gly Gly Gly Cys Gly Thr Thr Thr Ala
            260                 265                 270

Cys Thr Ala Cys Thr Gly Cys Ala Thr Gly Cys Ala Gly Cys Ala Thr
            275                 280                 285

Thr Thr Ala Gly Ala Gly Thr Ala Cys Cys Cys Thr Thr Cys Ala
            290                 295                 300

Cys Cys Thr Thr Cys Gly Gly Cys Gly Gly Cys Gly Gly Cys Ala Cys
305                 310                 315                 320

Cys Ala Ala Gly Gly Thr Gly Gly Ala Gly Ala Thr Cys Ala Ala Gly
                325                 330                 335

Gly Gly Thr Gly Gly Cys Gly Gly Cys Gly Cys Ala Gly Cys Gly
            340                 345                 350

Gly Cys Gly Gly Cys Gly Gly Thr Gly Gly Cys Ala Gly Cys Gly Gly

```
                    355                 360                 365
Ala Gly Gly Cys Gly Gly Ala Gly Gly Cys Ala Gly Cys Gly Ala Gly
            370                 375                 380
Ala Thr Cys Cys Ala Gly Cys Thr Gly Cys Ala Gly Cys Ala Ala Ala
385                 390                 395                 400
Gly Cys Gly Gly Cys Gly Cys Cys Gly Ala Gly Thr Gly Ala Gly Ala
                405                 410                 415
Ala Ala Ala Gly Cys Cys Gly Gly Cys Ala Gly Cys Ala Gly Cys
            420                 425                 430
Gly Thr Cys Ala Ala Gly Gly Thr Gly Ala Gly Cys Thr Gly Cys Ala
                435                 440                 445
Ala Gly Gly Cys Cys Ala Gly Cys Gly Gly Cys Thr Ala Cys Ala Cys
            450                 455                 460
Cys Thr Thr Cys Ala Cys Cys Gly Ala Thr Thr Ala Cys Gly Ala Cys
465                 470                 475                 480
Ala Thr Gly Cys Ala Cys Thr Gly Gly Thr Gly Ala Gly Ala Cys
                485                 490                 495
Ala Ala Gly Cys Thr Cys Cys Gly Gly Thr Cys Ala Ala Gly Gly
            500                 505                 510
Thr Thr Thr Ala Gly Ala Gly Thr Gly Ala Thr Cys Gly Gly Cys
            515                 520                 525
Ala Cys Ala Ala Thr Cys Gly Ala Cys Cys Cys Gly Ala Gly Ala
530                 535                 540
Cys Cys Gly Gly Cys Gly Gly Cys Ala Cys Ala Gly Cys Cys Thr Ala
545                 550                 555                 560
Cys Ala Ala Cys Cys Ala Gly Ala Ala Gly Thr Thr Ala Ala Gly Gly
                565                 570                 575
Gly Gly Thr Cys Gly Thr Gly Cys Cys Ala Cys Thr Thr Ala Ala
            580                 585                 590
Cys Ala Gly Cys Cys Gly Ala Thr Cys Gly Thr Thr Cys Cys Ala Cys
            595                 600                 605
Cys Ala Gly Cys Ala Cys Cys Gly Cys Cys Thr Ala Cys Ala Thr Gly
            610                 615                 620
Gly Ala Gly Cys Thr Gly Ala Gly Cys Thr Cys Thr Thr Thr Ala Ala
625                 630                 635                 640
Gly Gly Thr Cys Cys Gly Ala Gly Gly Ala Cys Ala Cys Cys Gly Cys
                645                 650                 655
Thr Gly Thr Gly Thr Ala Cys Thr Ala Thr Gly Cys Ala Cys Cys
            660                 665                 670
Ala Gly Cys Thr Thr Cys Thr Ala Thr Thr Ala Cys Ala Cys Cys Thr
            675                 680                 685
Ala Cys Ala Gly Cys Ala Cys Thr Ala Cys Gly Ala Cys Gly Gly Thr
            690                 695                 700
Gly Gly Gly Cys Thr Thr Thr Gly Cys Cys Thr Ala Cys Thr Gly Gly
705                 710                 715                 720
Gly Gly Cys Cys Ala Ala Gly Gly Thr Ala Cys Cys Thr Cys Gly
                725                 730                 735
Thr Gly Ala Cys Ala Gly Thr Cys Ala Gly Cys Ala Gly Cys
            740                 745                 750

<210> SEQ ID NO 93
<211> LENGTH: 742
<212> TYPE: PRT
<213> ORGANISM: Homo sapiens
```

<400> SEQUENCE: 93

| Met | Asp | Lys | Phe | Trp | Trp | His | Ala | Ala | Trp | Gly | Leu | Cys | Leu | Val | Pro |
|---|---|---|---|---|---|---|---|---|---|---|---|---|---|---|---|
| 1 | | | | 5 | | | | | 10 | | | | | 15 | |

Leu Ser Leu Ala Gln Ile Asp Leu Asn Ile Thr Cys Arg Phe Ala Gly
            20                  25                  30

Val Phe His Val Glu Lys Asn Gly Arg Tyr Ser Ile Ser Arg Thr Glu
        35                  40                  45

Ala Ala Asp Leu Cys Lys Ala Phe Asn Ser Thr Leu Pro Thr Met Ala
    50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175

Asp Val Ser Ser Gly Ser Ser Ser Glu Arg Ser Ser Thr Ser Gly Gly
            180                 185                 190

Tyr Ile Phe Tyr Thr Phe Ser Thr Val His Pro Ile Pro Asp Glu Asp
        195                 200                 205

Ser Pro Trp Ile Thr Asp Ser Thr Asp Arg Ile Pro Ala Thr Thr Leu
    210                 215                 220

Met Ser Thr Ser Ala Thr Ala Thr Glu Thr Ala Thr Lys Arg Gln Glu
225                 230                 235                 240

Thr Trp Asp Trp Phe Ser Trp Leu Phe Leu Pro Ser Glu Ser Lys Asn
                245                 250                 255

His Leu His Thr Thr Thr Gln Met Ala Gly Thr Ser Ser Asn Thr Ile
            260                 265                 270

Ser Ala Gly Trp Glu Pro Asn Glu Glu Asn Glu Asp Glu Arg Asp Arg
        275                 280                 285

His Leu Ser Phe Ser Gly Ser Gly Ile Asp Asp Asp Glu Asp Phe Ile
    290                 295                 300

Ser Ser Thr Ile Ser Thr Thr Pro Arg Ala Phe Asp His Thr Lys Gln
305                 310                 315                 320

Asn Gln Asp Trp Thr Gln Trp Asn Pro Ser His Ser Asn Pro Glu Val
                325                 330                 335

Leu Leu Gln Thr Thr Thr Arg Met Thr Asp Val Asp Arg Asn Gly Thr
            340                 345                 350

Thr Ala Tyr Glu Gly Asn Trp Asn Pro Glu Ala His Pro Pro Leu Ile
        355                 360                 365

His His Glu His His Glu Glu Glu Thr Pro His Ser Thr Ser Thr
    370                 375                 380

Ile Gln Ala Thr Pro Ser Ser Thr Thr Glu Glu Thr Ala Thr Gln Lys
385                 390                 395                 400

Glu Gln Trp Phe Gly Asn Arg Trp His Glu Gly Tyr Arg Gln Thr Pro

```
            405                 410                 415
Lys Glu Asp Ser His Ser Thr Thr Gly Thr Ala Ala Ser Ala His
            420                 425                 430

Thr Ser His Pro Met Gln Gly Arg Thr Thr Pro Ser Pro Glu Asp Ser
        435                 440                 445

Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
            500                 505                 510

Phe Ser Thr Ser His Glu Gly Leu Glu Glu Asp Lys Asp His Pro Thr
        515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
            580                 585                 590

Asp Ser Asn Ser Asn Val Asn Arg Ser Leu Ser Gly Asp Gln Asp Thr
        595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
            660                 665                 670

Arg Arg Arg Cys Gly Gln Lys Lys Lys Leu Val Ile Asn Ser Gly Asn
        675                 680                 685

Gly Ala Val Glu Asp Arg Lys Pro Ser Gly Leu Asn Gly Glu Ala Ser
    690                 695                 700

Lys Ser Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                725                 730                 735

Asp Met Lys Ile Gly Val
            740

<210> SEQ ID NO 94
<211> LENGTH: 675
<212> TYPE: PRT
<213> ORGANISM: Artificial Sequence
<220> FEATURE:
<223> OTHER INFORMATION: Syntheized

<400> SEQUENCE: 94

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
```

```
            20                  25                  30
Val Phe His Val Glu Lys Asn Gly Arg Tyr Ser Ile Ser Arg Thr Glu
            35                  40                  45
Ala Ala Asp Leu Cys Lys Ala Phe Asn Ser Thr Leu Pro Thr Met Ala
50                  55                  60
Gln Met Glu Lys Ala Leu Ser Ile Gly Phe Glu Thr Cys Arg Tyr Gly
65                  70                  75                  80
Phe Ile Glu Gly His Val Val Ile Pro Arg Ile His Pro Asn Ser Ile
                    85                  90                  95
Cys Ala Ala Asn Asn Thr Gly Val Tyr Ile Leu Thr Ser Asn Thr Ser
                100                 105                 110
Gln Tyr Asp Thr Tyr Cys Phe Asn Ala Ser Ala Pro Pro Glu Glu Asp
                115                 120                 125
Cys Thr Ser Val Thr Asp Leu Pro Asn Ala Phe Asp Gly Pro Ile Thr
                130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                165                 170                 175
Asp Val Ser Ser Gly Ser Ser Ser Glu Arg Ser Ser Thr Ser Gly Gly
                180                 185                 190
Tyr Ile Phe Tyr Thr Phe Ser Thr Val His Pro Ile Pro Asp Glu Asp
                195                 200                 205
Ser Pro Trp Ile Thr Asp Ser Thr Asp Arg Ile Pro Ala Thr Thr Leu
                210                 215                 220
Met Ser Thr Ser Ala Thr Ala Thr Glu Thr Ala Thr Lys Arg Gln Glu
225                 230                 235                 240
Thr Trp Asp Trp Phe Ser Trp Leu Phe Leu Pro Ser Glu Ser Lys Asn
                245                 250                 255
His Leu His Thr Thr Thr Gln Met Ala Gly Thr Ser Ser Asn Thr Ile
                260                 265                 270
Ser Ala Gly Trp Glu Pro Asn Glu Glu Asn Glu Asp Glu Arg Asp Arg
                275                 280                 285
His Leu Ser Phe Ser Gly Ser Gly Ile Asp Asp Asp Glu Asp Phe Ile
                290                 295                 300
Ser Ser Thr Ile Ser Thr Thr Pro Arg Ala Phe Asp His Thr Lys Gln
305                 310                 315                 320
Asn Gln Asp Trp Thr Gln Trp Asn Pro Ser His Ser Asn Pro Glu Val
                325                 330                 335
Leu Leu Gln Thr Thr Thr Arg Met Thr Asp Val Asp Arg Asn Gly Thr
                340                 345                 350
Thr Ala Tyr Glu Gly Asn Trp Asn Pro Glu Ala His Pro Pro Leu Ile
                355                 360                 365
His His Glu His His Glu Glu Glu Thr Pro His Ser Thr Ser Thr
                370                 375                 380
Ile Gln Ala Thr Pro Ser Ser Thr Glu Glu Thr Ala Thr Gln Lys
385                 390                 395                 400
Glu Gln Trp Phe Gly Asn Arg Trp His Glu Gly Tyr Arg Gln Thr Pro
                405                 410                 415
Lys Glu Asp Ser His Ser Thr Thr Gly Thr Ala Ala Ala Ser Ala His
                420                 425                 430
Thr Ser His Pro Met Gln Gly Arg Thr Thr Pro Ser Pro Glu Asp Ser
                435                 440                 445
```

```
Ser Trp Thr Asp Phe Phe Asn Pro Ile Ser His Pro Met Gly Arg Gly
    450                 455                 460

His Gln Ala Gly Arg Arg Met Asp Met Asp Ser Ser His Ser Ile Thr
465                 470                 475                 480

Leu Gln Pro Thr Ala Asn Pro Asn Thr Gly Leu Val Glu Asp Leu Asp
                485                 490                 495

Arg Thr Gly Pro Leu Ser Met Thr Thr Gln Gln Ser Asn Ser Gln Ser
                500                 505                 510

Phe Ser Thr Ser His Glu Gly Leu Glu Glu Asp Lys Asp His Pro Thr
            515                 520                 525

Thr Ser Thr Leu Thr Ser Ser Asn Arg Asn Asp Val Thr Gly Gly Arg
    530                 535                 540

Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
                565                 570                 575

Thr Ser Ala Lys Thr Gly Ser Phe Gly Val Thr Ala Val Thr Val Gly
                580                 585                 590

Asp Ser Asn Ser Asn Val Asn Arg Ser Leu Ser Gly Asp Gln Asp Thr
            595                 600                 605

Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
                660                 665                 670

Arg Arg Arg
        675

<210> SEQ ID NO 95
<211> LENGTH: 736
<212> TYPE: PRT
<213> ORGANISM: Artificial Sequence
<220> FEATURE:
<223> OTHER INFORMATION: Syntheized

<400> SEQUENCE: 95

Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
                20                  25                  30

Val Phe His Val Glu Lys Asn Gly Arg Tyr Ser Ile Ser Arg Thr Glu
            35                  40                  45

Ala Ala Asp Leu Cys Lys Ala Phe Asn Ser Thr Leu Pro Thr Met Ala
        50                  55                  60

Gln Met Glu Lys Ala Leu Ser Ile Gly Phe Glu Thr Cys Arg Tyr Gly
65              70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125
```

-continued

```
Cys Thr Ser Val Thr Asp Leu Pro Asn Ala Phe Asp Gly Pro Ile Thr
    130                 135                 140
Ile Thr Ile Val Asn Arg Asp Gly Thr Arg Tyr Val Gln Lys Gly Glu
145                 150                 155                 160
Tyr Arg Thr Asn Pro Glu Asp Ile Tyr Pro Ser Asn Pro Thr Asp Asp
                165                 170                 175
Asp Val Ser Ser Gly Ser Ser Glu Arg Ser Ser Thr Ser Gly Gly
            180                 185                 190
Tyr Ile Phe Tyr Thr Phe Ser Thr Val His Pro Ile Pro Asp Glu Asp
        195                 200                 205
Ser Pro Trp Ile Thr Asp Ser Thr Asp Arg Ile Pro Ala Thr Thr Leu
210                 215                 220
Met Ser Thr Ser Ala Thr Ala Thr Glu Thr Ala Thr Lys Arg Gln Glu
225                 230                 235                 240
Thr Trp Asp Trp Phe Ser Trp Leu Phe Leu Pro Ser Glu Ser Lys Asn
                245                 250                 255
His Leu His Thr Thr Thr Gln Met Ala Gly Thr Ser Ser Asn Thr Ile
            260                 265                 270
Ser Ala Gly Trp Glu Pro Asn Glu Glu Asn Glu Asp Glu Arg Asp Arg
        275                 280                 285
His Leu Ser Phe Ser Gly Ser Gly Ile Asp Asp Asp Glu Asp Phe Ile
290                 295                 300
Ser Ser Thr Ile Ser Thr Thr Pro Arg Ala Phe Asp His Thr Lys Gln
305                 310                 315                 320
Asn Gln Asp Trp Thr Gln Trp Asn Pro Ser His Ser Asn Pro Glu Val
                325                 330                 335
Leu Leu Gln Thr Thr Thr Arg Met Thr Asp Val Asp Arg Asn Gly Thr
            340                 345                 350
Thr Ala Tyr Glu Gly Asn Trp Asn Pro Glu Ala His Pro Pro Leu Ile
        355                 360                 365
His His Glu His His Glu Glu Glu Thr Pro His Ser Thr Ser Thr
370                 375                 380
Ile Gln Ala Thr Pro Ser Ser Thr Thr Glu Glu Thr Ala Thr Gln Lys
385                 390                 395                 400
Glu Gln Trp Phe Gly Asn Arg Trp His Glu Gly Tyr Arg Gln Thr Pro
                405                 410                 415
Lys Glu Asp Ser His Ser Thr Thr Gly Thr Ala Ala Ala Ser Ala His
            420                 425                 430
Thr Ser His Pro Met Gln Gly Arg Thr Thr Pro Ser Pro Glu Asp Ser
        435                 440                 445
Ser Trp Thr Asp Phe Phe Asn Pro Ile Ser His Pro Met Gly Arg Gly
450                 455                 460
His Gln Ala Gly Arg Arg Met Asp Met Asp Ser Ser His Ser Ile Thr
465                 470                 475                 480
Leu Gln Pro Thr Ala Asn Pro Asn Thr Gly Leu Val Glu Asp Leu Asp
                485                 490                 495
Arg Thr Gly Pro Leu Ser Met Thr Thr Gln Gln Ser Asn Ser Gln Ser
            500                 505                 510
Phe Ser Thr Ser His Glu Gly Leu Glu Glu Asp Lys Asp His Pro Thr
        515                 520                 525
Thr Ser Thr Leu Thr Ser Ser Asn Arg Asn Asp Val Thr Gly Gly Arg
530                 535                 540
```

```
Arg Asp Pro Asn His Ser Glu Gly Ser Thr Thr Leu Leu Glu Gly Tyr
545                 550                 555                 560

Thr Ser His Tyr Pro His Thr Lys Glu Ser Arg Thr Phe Ile Pro Val
            565                 570                 575

Thr Ser Ala Lys Thr Gly Ser Phe Gly Val Thr Ala Val Thr Val Gly
        580                 585                 590

Asp Ser Asn Ser Asn Val Asn Arg Ser Leu Ser Gly Asp Gln Asp Thr
    595                 600                 605

Phe His Pro Ser Gly Gly Ser His Thr Thr His Gly Ser Glu Ser Asp
610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Gly Gly Gly Ser Pro Ala
                645                 650                 655

Pro Arg Pro Pro Thr Pro Ala Pro Thr Ile Ala Ser Gln Pro Leu Ser
                660                 665                 670

Leu Arg Pro Glu Ala Cys Arg Pro Ala Ala Gly Gly Ala Val His Thr
            675                 680                 685

Arg Gly Leu Asp Phe Ala Cys Asp Ile Tyr Ile Trp Ala Pro Leu Ala
690                 695                 700

Gly Thr Cys Gly Val Leu Leu Leu Ser Leu Val Ile Thr Leu Tyr Cys
705                 710                 715                 720

Asn His Arg Asn Arg Arg Val Cys Lys Cys Pro Arg Pro Val Val
                725                 730                 735
```

<210> SEQ ID NO 96
<211> LENGTH: 742
<212> TYPE: PRT
<213> ORGANISM: Artificial Sequence
<220> FEATURE:
<223> OTHER INFORMATION: Syntheized

<400> SEQUENCE: 96

```
Met Asp Lys Phe Trp Trp His Ala Ala Trp Gly Leu Cys Leu Val Pro
1               5                   10                  15

Leu Ser Leu Ala Gln Ile Asp Leu Asn Ile Thr Cys Arg Phe Ala Gly
                20                  25                  30

Val Phe His Val Glu Lys Asn Gly Arg Tyr Ser Ile Ser Arg Thr Glu
            35                  40                  45

Ala Ala Asp Leu Cys Lys Ala Phe Asn Ser Thr Leu Pro Thr Met Ala
        50                  55                  60

Gln Met Glu Lys Ala Leu Ser Ile Gly Phe Glu Thr Cys Arg Tyr Gly
65                  70                  75                  80

Phe Ile Glu Gly His Val Val Ile Pro Arg Ile His Pro Asn Ser Ile
                85                  90                  95

Cys Ala Ala Asn Asn Thr Gly Val Tyr Ile Leu Thr Ser Asn Thr Ser
            100                 105                 110

Gln Tyr Asp Thr Tyr Cys Phe Asn Ala Ser Ala Pro Pro Glu Glu Asp
        115                 120                 125

Cys Thr Ser Val Thr Asp Leu Pro Asn Ala Phe Asp Gly Pro Ile Thr
130                 135                 140

Ile Thr Ile Val Asn Arg Asp Gly Thr Arg Tyr Val Gln Lys Gly Glu
145                 150                 155                 160

Tyr Arg Thr Asn Pro Glu Asp Ile Tyr Pro Ser Asn Pro Thr Asp Asp
                165                 170                 175
```

```
Asp Val Ser Ser Gly Ser Ser Glu Arg Ser Ser Thr Ser Gly Gly
            180             185             190

Tyr Ile Phe Tyr Thr Phe Ser Thr Val His Pro Ile Pro Asp Glu Asp
        195             200             205

Ser Pro Trp Ile Thr Asp Ser Thr Asp Arg Ile Pro Ala Thr Thr Leu
    210             215             220

Met Ser Thr Ser Ala Thr Ala Thr Glu Thr Ala Thr Lys Arg Gln Glu
225             230             235             240

Thr Trp Asp Trp Phe Ser Trp Leu Phe Leu Pro Ser Glu Ser Lys Asn
                245             250             255

His Leu His Thr Thr Thr Gln Met Ala Gly Thr Ser Ser Asn Thr Ile
            260             265             270

Ser Ala Gly Trp Glu Pro Asn Glu Glu Asn Glu Asp Glu Arg Asp Arg
        275             280             285

His Leu Ser Phe Ser Gly Ser Gly Ile Asp Asp Asp Glu Asp Phe Ile
    290             295             300

Ser Ser Thr Ile Ser Thr Thr Pro Arg Ala Phe Asp His Thr Lys Gln
305             310             315             320

Asn Gln Asp Trp Thr Gln Trp Asn Pro Ser His Ser Asn Pro Glu Val
                325             330             335

Leu Leu Gln Thr Thr Thr Arg Met Thr Asp Val Asp Arg Asn Gly Thr
            340             345             350

Thr Ala Tyr Glu Gly Asn Trp Asn Pro Glu Ala His Pro Pro Leu Ile
        355             360             365

His His Glu His His Glu Glu Glu Thr Pro His Ser Thr Ser Thr
    370             375             380

Ile Gln Ala Thr Pro Ser Ser Thr Thr Glu Glu Thr Ala Thr Gln Lys
385             390             395             400

Glu Gln Trp Phe Gly Asn Arg Trp His Glu Gly Tyr Arg Gln Thr Pro
                405             410             415

Lys Glu Asp Ser His Ser Thr Thr Gly Thr Ala Ala Ala Ser Ala His
            420             425             430

Thr Ser His Pro Met Gln Gly Arg Thr Thr Pro Ser Pro Glu Asp Ser
        435             440             445

Ser Trp Thr Asp Phe Phe Asn Pro Ile Ser His Pro Met Gly Arg Gly
    450             455             460

His Gln Ala Gly Arg Arg Met Asp Met Asp Ser Ser His Ser Ile Thr
465             470             475             480

Leu Gln Pro Thr Ala Asn Pro Asn Thr Gly Leu Val Glu Asp Leu Asp
                485             490             495

Arg Thr Gly Pro Leu Ser Met Thr Thr Gln Gln Ser Asn Ser Gln Ser
            500             505             510

Phe Ser Thr Ser His Glu Gly Leu Glu Glu Asp Lys Asp His Pro Thr
        515             520             525

Thr Ser Thr Leu Thr Ser Ser Asn Arg Asn Asp Val Thr Gly Gly Arg
    530             535             540

Arg Asp Pro Asn His Ser Glu Gly Ser Thr Thr Leu Leu Glu Gly Tyr
545             550             555             560

Thr Ser His Tyr Pro His Thr Lys Glu Ser Arg Thr Phe Ile Pro Val
                565             570             575

Thr Ser Ala Lys Thr Gly Ser Phe Gly Val Thr Ala Val Thr Val Gly
            580             585             590

Asp Ser Asn Ser Asn Val Asn Arg Ser Leu Ser Gly Asp Gln Asp Thr
```

```
                    595                 600                 605
Phe His Pro Ser Gly Gly Ser His Thr Thr His Gly Ser Glu Ser Asp
    610                 615                 620

Gly His Ser His Gly Ser Gln Glu Gly Gly Ala Asn Thr Thr Ser Gly
625                 630                 635                 640

Pro Ile Arg Thr Pro Gln Ile Pro Glu Trp Leu Ile Ile Leu Ala Ser
                645                 650                 655

Leu Leu Ala Leu Ala Leu Ile Leu Ala Val Cys Ile Ala Val Asn Ser
                660                 665                 670

Arg Arg Arg Cys Gly Gln Lys Lys Lys Leu Val Ile Asn Ser Gly Asn
                675                 680                 685

Gly Ala Val Glu Asp Arg Lys Pro Ser Gly Leu Asn Gly Glu Ala Gly
                690                 695                 700

Lys Ala Gln Glu Met Val His Leu Val Asn Lys Glu Ser Ser Glu Thr
705                 710                 715                 720

Pro Asp Gln Phe Met Thr Ala Asp Glu Thr Arg Asn Leu Gln Asn Val
                    725                 730                 735

Asp Met Lys Ile Gly Val
                740

<210> SEQ ID NO 97
<211> LENGTH: 380
<212> TYPE: PRT
<213> ORGANISM: Artificial Sequence
<220> FEATURE:
<223> OTHER INFORMATION: Synthesized

<400> SEQUENCE: 97

Pro Cys Leu Gly Gly Asn Pro Cys Tyr Asn Gln Gly Thr Cys Glu Pro
1               5                   10                  15

Thr Ser Glu Ser Pro Phe Tyr Arg Cys Leu Cys Pro Ala Lys Phe Asn
                20                  25                  30

Gly Leu Leu Cys His Ile Leu Asp Tyr Ser Phe Gly Gly Gly Ala Gly
                35                  40                  45

Arg Asp Ile Pro Pro Pro Leu Ile Glu Glu Ala Cys Glu Leu Pro Glu
50                  55                  60

Cys Gln Glu Asp Ala Gly Asn Lys Val Cys Ser Leu Gln Cys Asn Asn
65                  70                  75                  80

His Ala Cys Gly Trp Asp Gly Gly Asp Cys Ser Leu Asn Phe Asn Asp
                85                  90                  95

Pro Trp Lys Asn Cys Thr Gln Ser Leu Gln Cys Trp Lys Tyr Phe Ser
                100                 105                 110

Asp Gly His Cys Asp Ser Gln Cys Asn Ser Ala Gly Cys Leu Phe Asp
                115                 120                 125

Gly Phe Asp Cys Gln Arg Ala Glu Gly Gln Cys Asn Pro Leu Tyr Asp
                130                 135                 140

Gln Tyr Cys Lys Asp His Phe Ser Asp Gly His Cys Asp Gln Gly Cys
145                 150                 155                 160

Asn Ser Ala Glu Cys Glu Trp Asp Gly Leu Asp Cys Ala Glu His Val
                165                 170                 175

Pro Glu Arg Leu Ala Ala Gly Thr Leu Val Val Val Leu Met Pro
                180                 185                 190

Pro Glu Gln Leu Arg Asn Ser Ser Phe His Phe Leu Arg Glu Leu Ser
                195                 200                 205

Arg Val Leu His Thr Asn Val Val Phe Lys Arg Asp Ala His Gly Gln
```

```
            210                 215                 220
Gln Met Ile Phe Pro Tyr Tyr Gly Arg Glu Glu Leu Arg Lys His
225                 230                 235                 240

Pro Ile Lys Arg Ala Ala Glu Gly Trp Ala Ala Pro Asp Ala Leu Leu
                245                 250                 255

Gly Gln Val Lys Ala Ser Leu Leu Pro Gly Gly Ser Glu Gly Gly Arg
                260                 265                 270

Arg Arg Arg Glu Leu Asp Pro Met Asp Val Arg Gly Ser Ile Val Tyr
            275                 280                 285

Leu Glu Ile Asp Asn Arg Gln Cys Val Gln Ala Ser Ser Gln Cys Phe
        290                 295                 300

Gln Ser Ala Thr Asp Val Ala Ala Phe Leu Gly Ala Leu Ala Ser Leu
305                 310                 315                 320

Gly Ser Leu Asn Ile Pro Tyr Lys Ile Glu Ala Val Gln Ser Glu Thr
                325                 330                 335

Val Glu Pro Pro Pro Ala Gln Leu His Phe Met Tyr Val Ala Ala
            340                 345                 350

Ala Ala Phe Val Leu Leu Phe Phe Val Gly Cys Gly Val Leu Leu Ser
                355                 360                 365

Arg Lys Arg Arg Arg Gln Leu Cys Ile Gln Lys Leu
            370                 375                 380

<210> SEQ ID NO 98
<211> LENGTH: 370
<212> TYPE: PRT
<213> ORGANISM: Artificial Sequence
<220> FEATURE:
<223> OTHER INFORMATION: Synthesized

<400> SEQUENCE: 98

Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
                20                  25                  30

Gly Leu Leu Cys His Ile Leu Asp Tyr Ser Phe Thr Gly Gly Ala Gly
            35                  40                  45

Arg Asp Ile Pro Pro Gln Ile Glu Glu Ala Cys Glu Leu Pro Glu
        50                  55                  60

Cys Gln Val Asp Ala Gly Asn Lys Val Cys Asn Leu Gln Cys Asn Asn
65                  70                  75                  80

His Ala Cys Gly Trp Asp Gly Gly Asp Cys Ser Leu Asn Phe Asn Asp
                85                  90                  95

Pro Trp Lys Asn Cys Thr Gln Ser Leu Gln Cys Trp Lys Tyr Phe Ser
                100                 105                 110

Asp Gly His Cys Asp Ser Gln Cys Asn Ser Ala Gly Cys Leu Phe Asp
            115                 120                 125

Gly Phe Asp Cys Gln Leu Thr Glu Gly Gln Cys Asn Pro Leu Tyr Asp
        130                 135                 140

Gln Tyr Cys Lys Asp His Phe Ser Asp Gly His Cys Asp Gln Gly Cys
145                 150                 155                 160

Asn Ser Ala Glu Cys Glu Trp Asp Gly Leu Asp Cys Ala Glu His Val
                165                 170                 175

Pro Glu Arg Leu Ala Ala Gly Thr Leu Val Leu Val Val Leu Leu Pro
            180                 185                 190

Pro Asp Gln Leu Arg Asn Asn Ser Phe His Phe Leu Arg Glu Leu Ser
```

```
                195                 200                 205
His Val Leu His Thr Asn Val Val Phe Lys Arg Asp Ala Gln Gly Gln
210                 215                 220

Gln Met Ile Phe Pro Tyr Tyr Gly His Glu Glu Leu Arg Lys His
225                 230                 235                 240

Pro Ile Lys Arg Ser Thr Val Gly Trp Ala Thr Ser Ser Leu Leu Pro
                245                 250                 255

Gly Thr Ser Gly Gly Arg Gln Arg Arg Glu Leu Asp Pro Met Asp Ile
                260                 265                 270

Arg Gly Ser Ile Val Tyr Leu Glu Ile Asp Asn Arg Gln Cys Val Gln
                275                 280                 285

Ser Ser Ser Gln Cys Phe Gln Ser Ala Thr Asp Val Ala Ala Phe Leu
290                 295                 300

Gly Ala Leu Ala Ser Leu Gly Ser Leu Asn Ile Pro Tyr Lys Ile Glu
305                 310                 315                 320

Ala Val Lys Ser Glu Pro Val Glu Pro Pro Leu Pro Ser Gln Leu His
                325                 330                 335

Leu Met Tyr Val Ala Ala Ala Phe Val Leu Leu Phe Phe Val Gly
                340                 345                 350

Cys Gly Val Leu Leu Ser Arg Lys Arg Arg Arg Gln Leu Cys Ile Gln
                355                 360                 365

Lys Leu
    370

<210> SEQ ID NO 99
<211> LENGTH: 186
<212> TYPE: PRT
<213> ORGANISM: Homo sapiens

<400> SEQUENCE: 99

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
    130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln
            180                 185
```

```
<210> SEQ ID NO 100
<211> LENGTH: 193
<212> TYPE: PRT
<213> ORGANISM: Homo sapiens

<400> SEQUENCE: 100

Met Val Arg Leu Pro Leu Gln Cys Val Leu Trp Gly Cys Leu Leu Thr
1               5                   10                  15

Ala Val His Pro Glu Pro Thr Ala Cys Arg Glu Lys Gln Tyr Leu
            20                  25                  30

Ile Asn Ser Gln Cys Cys Ser Leu Cys Gln Pro Gly Gln Lys Leu Val
        35                  40                  45

Ser Asp Cys Thr Glu Phe Thr Glu Thr Glu Cys Leu Pro Cys Gly Glu
    50                  55                  60

Ser Glu Phe Leu Asp Thr Trp Asn Arg Glu Thr His Cys His Gln His
65                  70                  75                  80

Lys Tyr Cys Asp Pro Asn Leu Gly Leu Arg Val Gln Gln Lys Gly Thr
                85                  90                  95

Ser Glu Thr Asp Thr Ile Cys Thr Cys Glu Glu Gly Trp His Cys Thr
            100                 105                 110

Ser Glu Ala Cys Glu Ser Cys Val Leu His Arg Ser Cys Ser Pro Gly
        115                 120                 125

Phe Gly Val Lys Gln Ile Ala Thr Gly Val Ser Asp Thr Ile Cys Glu
    130                 135                 140

Pro Cys Pro Val Gly Phe Phe Ser Asn Val Ser Ser Ala Phe Glu Lys
145                 150                 155                 160

Cys His Pro Trp Thr Ser Cys Glu Thr Lys Asp Leu Val Val Gln Gln
                165                 170                 175

Ala Gly Thr Asn Lys Thr Asp Val Val Cys Gly Pro Gln Asp Arg Leu
            180                 185                 190

Arg

<210> SEQ ID NO 101
<211> LENGTH: 186
<212> TYPE: PRT
<213> ORGANISM: Homo sapiens

<400> SEQUENCE: 101

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
            20                  25                  30

Ala Gly Thr Phe Cys Asp Asn Asn Arg Asn Gln Ile Cys Ser Pro Cys
        35                  40                  45

Pro Pro Asn Ser Phe Ser Ser Ala Gly Gly Gln Arg Thr Cys Asp Ile
    50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
            85                  90                  95

Ala Gly Cys Ser Met Cys Glu Gln Asp Cys Lys Gln Gly Gln Glu Leu
        100                 105                 110

Thr Lys Lys Gly Cys Lys Asp Cys Cys Phe Gly Thr Phe Asn Asp Gln
    115                 120                 125

Lys Arg Gly Ile Cys Arg Pro Trp Thr Asn Cys Ser Leu Asp Gly Lys
```

```
               130             135              140
Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln
            180                 185

<210> SEQ ID NO 102
<211> LENGTH: 652
<212> TYPE: PRT
<213> ORGANISM: Homo sapiens

<400> SEQUENCE: 102

Met Glu Leu Ala Ala Leu Cys Arg Trp Gly Leu Leu Leu Ala Leu Leu
1               5                  10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320
```

```
Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
        435                 440                 445

Gly Ile Ser Trp Leu Gly Leu Arg Ser Leu Arg Glu Leu Gly Ser Gly
450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
        515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
        595                 600                 605

Ser Tyr Met Pro Ile Trp Lys Phe Pro Asp Glu Glu Gly Ala Cys Gln
610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr
                645                 650

<210> SEQ ID NO 103
<211> LENGTH: 162
<212> TYPE: PRT
<213> ORGANISM: Homo sapiens

<400> SEQUENCE: 103

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45
```

Cys Cys Arg Val His Thr Thr Arg Cys Cys Arg Asp Tyr Pro Gly Glu
             50                  55                  60

Glu Cys Cys Ser Glu Trp Asp Cys Met Cys Val Gln Pro Glu Phe His
 65                  70                  75                  80

Cys Gly Asp Pro Cys Cys Thr Thr Cys Arg His His Pro Cys Pro Pro
                 85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
            115                 120                 125

Lys Pro Trp Thr Asp Cys Thr Gln Phe Gly Phe Leu Thr Val Phe Pro
            130                 135                 140

Gly Asn Lys Thr His Asn Ala Val Cys Val Pro Gly Ser Pro Pro Ala
145                 150                 155                 160

Glu Pro

<210> SEQ ID NO 104
<211> LENGTH: 152
<212> TYPE: PRT
<213> ORGANISM: Homo sapiens

<400> SEQUENCE: 104

Met Leu Arg Leu Leu Ala Leu Asn Leu Phe Pro Ser Ile Gln Val
 1               5                  10                  15

Thr Gly Asn Lys Ile Leu Val Lys Gln Ser Pro Met Leu Val Ala Tyr
                 20                  25                  30

Asp Asn Ala Val Asn Leu Ser Cys Lys Tyr Ser Tyr Asn Leu Phe Ser
             35                  40                  45

Arg Glu Phe Arg Ala Ser Leu His Lys Gly Leu Asp Ser Ala Val Glu
         50                  55                  60

Val Cys Val Val Tyr Gly Asn Tyr Ser Gln Gln Leu Gln Val Tyr Ser
 65                  70                  75                  80

Lys Thr Gly Phe Asn Cys Asp Gly Lys Leu Gly Asn Glu Ser Val Thr
                 85                  90                  95

Phe Tyr Leu Gln Asn Leu Tyr Val Asn Gln Thr Asp Ile Tyr Phe Cys
            100                 105                 110

Lys Ile Glu Val Met Tyr Pro Pro Pro Tyr Leu Asp Asn Glu Lys Ser
            115                 120                 125

Asn Gly Thr Ile Ile His Val Lys Gly Lys His Leu Cys Pro Ser Pro
130                 135                 140

Leu Phe Pro Gly Pro Ser Lys Pro
145                 150

<210> SEQ ID NO 105
<211> LENGTH: 140
<212> TYPE: PRT
<213> ORGANISM: Homo sapiens

<400> SEQUENCE: 105

Met Lys Ser Gly Leu Trp Tyr Phe Phe Leu Phe Cys Leu Arg Ile Lys
 1               5                  10                  15

Val Leu Thr Gly Glu Ile Asn Gly Ser Ala Asn Tyr Glu Met Phe Ile
                 20                  25                  30

Phe His Asn Gly Gly Val Gln Ile Leu Cys Lys Tyr Pro Asp Ile Val
             35                  40                  45

```
Gln Gln Phe Lys Met Gln Leu Leu Lys Gly Gly Gln Ile Leu Cys Asp
        50                  55                  60

Leu Thr Lys Thr Lys Gly Ser Gly Asn Thr Val Ser Ile Lys Ser Leu
 65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
                100                 105                 110

Ile Phe Asp Pro Pro Pro Phe Lys Val Thr Leu Thr Gly Gly Tyr Leu
                115                 120                 125

His Ile Tyr Glu Ser Gln Leu Cys Cys Gln Leu Lys
                130                 135                 140
```

<210> SEQ ID NO 106
<211> LENGTH: 819
<212> TYPE: PRT
<213> ORGANISM: Homo sapiens

<400> SEQUENCE: 106

```
Met Met Ile Ile Ser Met Trp Met Ser Ile Ser Arg Gly Leu Trp Asp
 1               5                   10                  15

Ser Ser Ser Ile Trp Ser Val Leu Leu Ile Leu Ala Cys Met Ala Ser
                20                  25                  30

Ile Thr Thr Ser Ser Ser Val Ser Asn Ala Gly Tyr Val Asp Asn Gly
                35                  40                  45

Asn Met Lys Val Cys Ile Gly Thr Lys Ser Arg Leu Ser Val Pro Ser
 50                  55                  60

Asn Lys Glu His His Tyr Arg Asn Leu Arg Asp Arg Tyr Thr Asn Cys
 65                  70                  75                  80

Thr Tyr Val Asp Gly Asn Leu Glu Leu Thr Trp Leu Pro Asn Glu Asn
                85                  90                  95

Leu Asp Leu Ser Phe Leu Asp Asn Ile Arg Glu Val Thr Gly Tyr Ile
                100                 105                 110

Leu Ile Ser His Val Asp Val Lys Lys Val Val Phe Pro Lys Leu Gln
                115                 120                 125

Ile Ile Arg Gly Arg Thr Leu Phe Ser Leu Ser Val Glu Glu Glu Lys
                130                 135                 140

Tyr Ala Leu Phe Val Thr Tyr Ser Lys Met Tyr Thr Leu Glu Ile Pro
145                 150                 155                 160

Asp Leu Arg Asp Val Leu Asn Gly Gln Val Gly Phe His Asn Asn Tyr
                165                 170                 175

Asn Leu Cys His Met Arg Thr Ile Gln Trp Ser Glu Ile Val Ser Asn
                180                 185                 190

Gly Thr Asp Ala Tyr Tyr Asn Tyr Asp Phe Thr Ala Pro Glu Arg Glu
                195                 200                 205

Cys Pro Lys Cys His Glu Ser Cys Thr His Gly Cys Trp Gly Glu Gly
                210                 215                 220

Pro Lys Asn Cys Gln Lys Phe Ser Lys Leu Thr Cys Ser Pro Gln Cys
225                 230                 235                 240

Ala Gly Gly Arg Cys Tyr Gly Pro Lys Pro Arg Glu Cys Cys His Leu
                245                 250                 255

Phe Cys Ala Gly Gly Cys Thr Gly Pro Thr Gln Lys Asp Cys Ile Ala
                260                 265                 270

Cys Lys Asn Phe Phe Asp Glu Gly Val Cys Lys Glu Glu Cys Pro Pro
                275                 280                 285
```

-continued

```
Met Arg Lys Tyr Asn Pro Thr Thr Tyr Val Leu Glu Thr Asn Pro Glu
    290                 295                 300

Gly Lys Tyr Ala Tyr Gly Ala Thr Cys Val Lys Glu Cys Pro Gly His
305                 310                 315                 320

Leu Leu Arg Asp Asn Gly Ala Cys Val Arg Ser Cys Pro Gln Asp Lys
                325                 330                 335

Met Asp Lys Gly Gly Glu Cys Val Pro Cys Asn Gly Pro Cys Pro Lys
            340                 345                 350

Thr Cys Pro Gly Val Thr Val Leu His Ala Gly Asn Ile Asp Ser Phe
        355                 360                 365

Arg Asn Cys Thr Val Ile Asp Gly Asn Ile Arg Ile Leu Asp Gln Thr
    370                 375                 380

Phe Ser Gly Phe Gln Asp Val Tyr Ala Asn Tyr Thr Met Gly Pro Arg
385                 390                 395                 400

Tyr Ile Pro Leu Asp Pro Glu Arg Leu Glu Val Phe Ser Thr Val Lys
                405                 410                 415

Glu Ile Thr Gly Tyr Leu Asn Ile Glu Gly Thr His Pro Gln Phe Arg
            420                 425                 430

Asn Leu Ser Tyr Phe Arg Asn Leu Glu Thr Ile His Gly Arg Gln Leu
        435                 440                 445

Met Glu Ser Met Phe Ala Ala Leu Ala Ile Val Lys Ser Ser Leu Tyr
    450                 455                 460

Ser Leu Glu Met Arg Asn Leu Lys Gln Ile Ser Ser Gly Ser Val Val
465                 470                 475                 480

Ile Gln His Asn Arg Asp Leu Cys Tyr Val Ser Asn Ile Arg Trp Pro
                485                 490                 495

Ala Ile Gln Lys Glu Pro Glu Gln Lys Val Trp Val Asn Glu Asn Leu
            500                 505                 510

Arg Ala Asp Leu Cys Glu Lys Asn Gly Thr Ile Cys Ser Asp Gln Cys
        515                 520                 525

Asn Glu Asp Gly Cys Trp Gly Ala Gly Thr Asp Gln Cys Leu Thr Cys
    530                 535                 540

Lys Asn Phe Asn Phe Asn Gly Thr Cys Ile Ala Asp Cys Gly Tyr Ile
545                 550                 555                 560

Ser Asn Ala Tyr Lys Phe Asp Asn Arg Thr Cys Lys Ile Cys His Pro
                565                 570                 575

Glu Cys Arg Thr Cys Asn Gly Ala Gly Ala Asp His Cys Gln Glu Cys
            580                 585                 590

Val His Val Arg Asp Gly Gln His Cys Val Ser Glu Cys Pro Lys Asn
        595                 600                 605

Lys Tyr Asn Asp Arg Gly Val Cys Arg Glu Cys His Ala Thr Cys Asp
    610                 615                 620

Gly Cys Thr Gly Pro Lys Asp Thr Ile Gly Ile Gly Ala Cys Thr Thr
625                 630                 635                 640

Cys Asn Leu Ala Ile Ile Asn Asn Asp Ala Thr Val Lys Arg Cys Leu
                645                 650                 655

Leu Lys Asp Asp Lys Cys Pro Asp Gly Tyr Phe Trp Glu Tyr Val His
            660                 665                 670

Pro Gln Glu Gln Gly Ser Leu Lys Pro Leu Ala Gly Arg Ala Val Cys
        675                 680                 685

Arg Lys Cys His Pro Leu Cys Glu Leu Cys Thr Asn Tyr Gly Tyr His
    690                 695                 700
```

```
Glu Gln Val Cys Ser Lys Cys Thr His Tyr Lys Arg Arg Glu Gln Cys
705                 710                 715                 720
Glu Thr Glu Cys Pro Ala Asp His Tyr Thr Asp Glu Glu Gln Arg Glu
                725                 730                 735
Cys Phe Gln Cys His Pro Glu Cys Asn Gly Cys Thr Gly Pro Gly Ala
            740                 745                 750
Asp Asp Cys Lys Ser Cys Arg Asn Phe Lys Leu Phe Asp Ala Asn Glu
        755                 760                 765
Thr Gly Pro Tyr Val Asn Ser Thr Met Phe Asn Cys Thr Ser Lys Cys
    770                 775                 780
Pro Leu Glu Met Arg His Val Asn Tyr Gln Tyr Thr Ala Ile Gly Pro
785                 790                 795                 800
Tyr Cys Ala Ala Ser Pro Pro Arg Ser Ser Lys Ile Thr Ala Asn Leu
                805                 810                 815
Asp Val Asn

<210> SEQ ID NO 107
<211> LENGTH: 191
<212> TYPE: PRT
<213> ORGANISM: Homo sapiens

<400> SEQUENCE: 107

Met Ala Arg Pro His Pro Trp Trp Leu Cys Val Leu Gly Thr Leu Val
1               5                   10                  15
Gly Leu Ser Ala Thr Pro Ala Pro Lys Ser Cys Pro Glu Arg His Tyr
            20                  25                  30
Trp Ala Gln Gly Lys Leu Cys Cys Gln Met Cys Glu Pro Gly Thr Phe
        35                  40                  45
Leu Val Lys Asp Cys Asp Gln His Arg Lys Ala Ala Gln Cys Asp Pro
    50                  55                  60
Cys Ile Pro Gly Val Ser Phe Ser Pro Asp His His Thr Arg Pro His
65                  70                  75                  80
Cys Glu Ser Cys Arg His Cys Asn Ser Gly Leu Leu Val Arg Asn Cys
                85                  90                  95
Thr Ile Thr Ala Asn Ala Glu Cys Ala Cys Arg Asn Gly Trp Gln Cys
            100                 105                 110
Arg Asp Lys Glu Cys Thr Glu Cys Asp Pro Leu Pro Asn Pro Ser Leu
        115                 120                 125
Thr Ala Arg Ser Ser Gln Ala Leu Ser Pro His Pro Gln Pro Thr His
    130                 135                 140
Leu Pro Tyr Val Ser Glu Met Leu Glu Ala Arg Thr Ala Gly His Met
145                 150                 155                 160
Gln Thr Leu Ala Asp Phe Arg Gln Leu Pro Ala Arg Thr Leu Ser Thr
                165                 170                 175
His Trp Pro Pro Gln Arg Ser Leu Cys Ser Ser Asp Phe Ile Arg
            180                 185                 190

<210> SEQ ID NO 108
<211> LENGTH: 960
<212> TYPE: PRT
<213> ORGANISM: Homo sapiens

<400> SEQUENCE: 108

Met Trp Arg Leu Arg Arg Ala Ala Val Ala Cys Glu Val Cys Gln Ser
1               5                   10                  15
Leu Val Lys His Ser Ser Gly Ile Lys Gly Ser Leu Pro Leu Gln Lys
```

```
            20                  25                  30
Leu His Leu Val Ser Arg Ser Ile Tyr His His Pro Thr Leu
            35                  40                  45
Lys Leu Gln Arg Pro Gln Leu Arg Thr Ser Phe Gln Gln Phe Ser Ser
        50                  55                  60
Leu Thr Asn Leu Pro Leu Arg Lys Leu Lys Phe Ser Pro Ile Lys Tyr
65                  70                  75                  80
Gly Tyr Gln Pro Arg Arg Asn Phe Trp Pro Ala Arg Leu Ala Thr Arg
                85                  90                  95
Leu Leu Lys Leu Arg Tyr Leu Ile Leu Gly Ser Ala Val Gly Gly Gly
            100                 105                 110
Tyr Thr Ala Lys Lys Thr Phe Asp Gln Trp Lys Asp Met Ile Pro Asp
            115                 120                 125
Leu Ser Glu Tyr Lys Trp Ile Val Pro Asp Ile Val Trp Glu Ile Asp
            130                 135                 140
Glu Tyr Ile Asp Phe Glu Lys Ile Arg Lys Ala Leu Pro Ser Ser Glu
145                 150                 155                 160
Asp Leu Val Lys Leu Ala Pro Asp Phe Asp Lys Ile Val Glu Ser Leu
            165                 170                 175
Ser Leu Leu Lys Asp Phe Phe Thr Ser Gly Ser Pro Glu Glu Thr Ala
            180                 185                 190
Phe Arg Ala Thr Asp Arg Gly Ser Glu Ser Asp Lys His Phe Arg Lys
            195                 200                 205
Val Ser Asp Lys Glu Lys Ile Asp Gln Leu Gln Glu Glu Leu Leu His
            210                 215                 220
Thr Gln Leu Lys Tyr Gln Arg Ile Leu Glu Arg Leu Glu Lys Glu Asn
225                 230                 235                 240
Lys Glu Leu Arg Lys Leu Val Leu Gln Lys Asp Lys Gly Ile His
            245                 250                 255
His Arg Lys Leu Lys Lys Ser Leu Ile Asp Met Tyr Ser Glu Val Leu
            260                 265                 270
Asp Val Leu Ser Asp Tyr Asp Ala Ser Tyr Asn Thr Gln Asp His Leu
            275                 280                 285
Pro Arg Val Val Val Gly Asp Gln Ser Ala Gly Lys Thr Ser Val
            290                 295                 300
Leu Glu Met Ile Ala Gln Ala Arg Ile Phe Pro Arg Gly Ser Gly Glu
305                 310                 315                 320
Met Met Thr Arg Ser Pro Val Lys Val Thr Leu Ser Glu Gly Pro His
            325                 330                 335
His Val Ala Leu Phe Lys Asp Ser Ser Arg Glu Phe Asp Leu Thr Lys
            340                 345                 350
Glu Glu Asp Leu Ala Ala Leu Arg His Glu Ile Glu Leu Arg Met Arg
            355                 360                 365
Lys Asn Val Lys Glu Gly Cys Thr Val Ser Pro Glu Thr Ile Ser Leu
            370                 375                 380
Asn Val Lys Gly Pro Gly Leu Gln Arg Met Val Leu Val Asp Leu Pro
385                 390                 395                 400
Gly Val Ile Asn Thr Val Thr Ser Gly Met Ala Pro Asp Thr Lys Glu
            405                 410                 415
Thr Ile Phe Ser Ile Ser Lys Ala Tyr Met Gln Asn Pro Asn Ala Ile
            420                 425                 430
Ile Leu Cys Ile Gln Asp Gly Ser Val Asp Ala Glu Arg Ser Ile Val
            435                 440                 445
```

-continued

```
Thr Asp Leu Val Ser Gln Met Asp Pro His Gly Arg Arg Thr Ile Phe
    450                 455                 460
Val Leu Thr Lys Val Asp Leu Ala Glu Lys Asn Val Ala Ser Pro Ser
465                 470                 475                 480
Arg Ile Gln Gln Ile Ile Glu Gly Lys Leu Phe Pro Met Lys Ala Leu
                485                 490                 495
Gly Tyr Phe Ala Val Val Thr Gly Lys Gly Asn Ser Ser Glu Ser Ile
                500                 505                 510
Glu Ala Ile Arg Glu Tyr Glu Glu Phe Phe Gln Asn Ser Lys Leu
                515                 520                 525
Leu Lys Thr Ser Met Leu Lys Ala His Gln Val Thr Thr Arg Asn Leu
530                 535                 540
Ser Leu Ala Val Ser Asp Cys Phe Trp Lys Met Val Arg Glu Ser Val
545                 550                 555                 560
Glu Gln Gln Ala Asp Ser Phe Lys Ala Thr Arg Phe Asn Leu Glu Thr
                565                 570                 575
Glu Trp Lys Asn Asn Tyr Pro Arg Leu Arg Glu Leu Asp Arg Asn Glu
                580                 585                 590
Leu Phe Glu Lys Ala Lys Asn Glu Ile Leu Asp Glu Val Ile Ser Leu
                595                 600                 605
Ser Gln Val Thr Pro Lys His Trp Glu Glu Ile Leu Gln Gln Ser Leu
        610                 615                 620
Trp Glu Arg Val Ser Thr His Val Ile Glu Asn Ile Tyr Leu Pro Ala
625                 630                 635                 640
Ala Gln Thr Met Asn Ser Gly Thr Phe Asn Thr Thr Val Asp Ile Lys
                645                 650                 655
Leu Lys Gln Trp Thr Asp Lys Gln Leu Pro Asn Lys Ala Val Glu Val
                660                 665                 670
Ala Trp Glu Thr Leu Gln Glu Glu Phe Ser Arg Phe Met Thr Glu Pro
                675                 680                 685
Lys Gly Lys Glu His Asp Asp Ile Phe Asp Lys Leu Lys Glu Ala Val
        690                 695                 700
Lys Glu Glu Ser Ile Lys Arg His Lys Trp Asn Asp Phe Ala Glu Asp
705                 710                 715                 720
Ser Leu Arg Val Ile Gln His Asn Ala Leu Glu Asp Arg Ser Ile Ser
                725                 730                 735
Asp Lys Gln Gln Trp Asp Ala Ala Ile Tyr Phe Met Glu Glu Ala Leu
                740                 745                 750
Gln Ala Arg Leu Lys Asp Thr Glu Asn Ala Ile Glu Asn Met Val Gly
                755                 760                 765
Pro Asp Trp Lys Lys Arg Trp Leu Tyr Trp Lys Asn Arg Thr Gln Glu
770                 775                 780
Gln Cys Val His Asn Glu Thr Lys Asn Glu Leu Glu Lys Met Leu Lys
785                 790                 795                 800
Cys Asn Glu Glu His Pro Ala Tyr Leu Ala Ser Asp Glu Ile Thr Thr
                805                 810                 815
Val Arg Lys Asn Leu Glu Ser Arg Gly Val Glu Val Asp Pro Ser Leu
                820                 825                 830
Ile Lys Asp Thr Trp His Gln Val Tyr Arg Arg His Phe Leu Lys Thr
        835                 840                 845
Ala Leu Asn His Cys Asn Leu Cys Arg Arg Gly Phe Tyr Tyr Tyr Gln
850                 855                 860
```

```
Arg His Phe Val Asp Ser Glu Leu Glu Cys Asn Asp Val Val Leu Phe
865                 870                 875                 880

Trp Arg Ile Gln Arg Met Leu Ala Ile Thr Ala Asn Thr Leu Arg Gln
            885                 890                 895

Gln Leu Thr Asn Thr Glu Val Arg Arg Leu Glu Lys Asn Val Lys Glu
        900                 905                 910

Val Leu Glu Asp Phe Ala Glu Asp Gly Glu Lys Lys Ile Lys Leu Leu
    915                 920                 925

Thr Gly Lys Arg Val Gln Leu Ala Glu Asp Leu Lys Lys Val Arg Glu
930                 935                 940

Ile Gln Glu Lys Leu Asp Ala Phe Ile Glu Ala Leu His Gln Glu Lys
945                 950                 955                 960

<210> SEQ ID NO 109
<211> LENGTH: 741
<212> TYPE: PRT
<213> ORGANISM: Homo sapiens

<400> SEQUENCE: 109

Met Ala Glu Pro Val Ser Pro Leu Lys His Phe Val Leu Ala Lys Lys
1               5                   10                  15

Ala Ile Thr Ala Ile Phe Asp Gln Leu Leu Glu Phe Val Thr Glu Gly
            20                  25                  30

Ser His Phe Val Glu Ala Thr Tyr Lys Asn Pro Glu Leu Asp Arg Ile
        35                  40                  45

Ala Thr Glu Asp Asp Leu Val Glu Met Gln Gly Tyr Lys Asp Lys Leu
    50                  55                  60

Ser Ile Ile Gly Glu Val Leu Ser Arg Arg His Met Lys Val Ala Phe
65                  70                  75                  80

Phe Gly Arg Thr Ser Ser Gly Lys Ser Ser Val Ile Asn Ala Met Leu
                85                  90                  95

Trp Asp Lys Val Leu Pro Ser Gly Ile Gly His Ile Thr Asn Cys Phe
            100                 105                 110

Leu Ser Val Glu Gly Thr Asp Gly Asp Lys Ala Tyr Leu Met Thr Glu
        115                 120                 125

Gly Ser Asp Glu Lys Lys Ser Val Lys Thr Val Asn Gln Leu Ala His
    130                 135                 140

Ala Leu His Met Asp Lys Asp Leu Lys Ala Gly Cys Leu Val Arg Val
145                 150                 155                 160

Phe Trp Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ser Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Arg Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His
                245                 250                 255

Met Glu Arg Cys Leu His Phe Leu Val Glu Glu Leu Lys Val Val Asn
            260                 265                 270

Ala Leu Glu Ala Gln Asn Arg Ile Phe Phe Val Ser Ala Lys Glu Val
        275                 280                 285
```

```
Leu Ser Ala Arg Lys Gln Lys Ala Gln Gly Met Pro Glu Ser Gly Val
    290                 295                 300

Ala Leu Ala Glu Gly Phe His Ala Arg Leu Gln Glu Phe Gln Asn Phe
305                 310                 315                 320

Glu Gln Ile Phe Glu Glu Cys Ile Ser Gln Ser Ala Val Lys Thr Lys
                325                 330                 335

Phe Glu Gln His Thr Ile Arg Ala Lys Gln Ile Leu Ala Thr Val Lys
                340                 345                 350

Asn Ile Met Asp Ser Val Asn Leu Ala Ala Glu Asp Lys Arg His Tyr
                355                 360                 365

Ser Val Glu Glu Arg Glu Asp Gln Ile Asp Arg Leu Asp Phe Ile Arg
    370                 375                 380

Asn Gln Met Asn Leu Leu Thr Leu Asp Val Lys Lys Ile Lys Glu
385                 390                 395                 400

Val Thr Glu Glu Val Ala Asn Lys Val Ser Cys Ala Met Thr Asp Glu
                405                 410                 415

Ile Cys Arg Leu Ser Val Leu Val Asp Glu Phe Cys Ser Glu Phe His
            420                 425                 430

Pro Asn Pro Asp Val Leu Lys Ile Tyr Lys Ser Glu Leu Asn Lys His
                435                 440                 445

Ile Glu Asp Gly Met Gly Arg Asn Leu Ala Asp Arg Cys Thr Asp Glu
    450                 455                 460

Val Asn Ala Leu Val Leu Gln Thr Gln Gln Glu Ile Ile Glu Asn Leu
465                 470                 475                 480

Lys Pro Leu Leu Pro Ala Gly Ile Gln Asp Lys Leu His Thr Leu Ile
                485                 490                 495

Pro Cys Lys Lys Phe Asp Leu Ser Tyr Asn Leu Asn Tyr His Lys Leu
                500                 505                 510

Cys Ser Asp Phe Gln Glu Asp Ile Val Phe Arg Phe Ser Leu Gly Trp
            515                 520                 525

Ser Ser Leu Val His Arg Phe Leu Gly Pro Arg Asn Ala Gln Arg Val
    530                 535                 540

Leu Leu Gly Leu Ser Glu Pro Ile Phe Gln Leu Pro Arg Ser Leu Ala
545                 550                 555                 560

Ser Thr Pro Thr Ala Pro Thr Thr Pro Ala Thr Pro Asp Asn Ala Ser
                565                 570                 575

Gln Glu Glu Leu Met Ile Thr Leu Val Thr Gly Leu Ala Ser Val Thr
                580                 585                 590

Ser Arg Thr Ser Met Gly Ile Ile Ile Val Gly Gly Val Ile Trp Lys
    595                 600                 605

Thr Ile Gly Trp Lys Leu Leu Ser Val Ser Leu Thr Met Tyr Gly Ala
    610                 615                 620

Leu Tyr Leu Tyr Glu Arg Leu Ser Trp Thr Thr His Ala Lys Glu Arg
625                 630                 635                 640

Ala Phe Lys Gln Gln Phe Val Asn Tyr Ala Thr Glu Lys Leu Arg Met
                645                 650                 655

Ile Val Ser Ser Thr Ser Ala Asn Cys Ser His Gln Val Lys Gln Gln
            660                 665                 670

Ile Ala Thr Thr Phe Ala Arg Leu Cys Gln Gln Val Asp Ile Thr Gln
            675                 680                 685

Lys Gln Leu Glu Glu Glu Ile Ala Arg Leu Pro Lys Glu Ile Asp Gln
    690                 695                 700
```

-continued

```
Leu Glu Lys Ile Gln Asn Asn Ser Lys Leu Leu Arg Asn Lys Ala Val
705                 710                 715                 720

Gln Leu Glu Asn Glu Leu Glu Asn Phe Thr Lys Gln Phe Leu Pro Ser
            725                 730                 735

Ser Asn Glu Glu Ser
            740

<210> SEQ ID NO 110
<211> LENGTH: 757
<212> TYPE: PRT
<213> ORGANISM: Homo sapiens

<400> SEQUENCE: 110

Met Ser Leu Leu Phe Ser Arg Cys Asn Ser Ile Val Thr Val Lys Lys
1               5                   10                  15

Asn Lys Arg His Met Ala Glu Val Asn Ala Ser Pro Leu Lys His Phe
            20                  25                  30

Val Thr Ala Lys Lys Lys Ile Asn Gly Ile Phe Glu Gln Leu Gly Ala
        35                  40                  45

Tyr Ile Gln Glu Ser Ala Thr Phe Leu Glu Asp Thr Tyr Arg Asn Ala
    50                  55                  60

Glu Leu Asp Pro Val Thr Thr Glu Glu Gln Val Leu Asp Val Lys Gly
65                  70                  75                  80

Tyr Leu Ser Lys Val Arg Gly Ile Ser Glu Val Leu Ala Arg His His
                85                  90                  95

Met Lys Val Ala Phe Phe Gly Arg Thr Ser Asn Gly Lys Ser Thr Val
            100                 105                 110

Ile Asn Ala Met Leu Trp Asp Lys Val Leu Pro Ser Gly Ile Gly His
        115                 120                 125

Thr Thr Asn Cys Phe Leu Arg Val Glu Gly Thr Asp Gly His Glu Ala
    130                 135                 140

Phe Leu Leu Thr Glu Gly Ser Glu Glu Lys Arg Ser Ala Lys Thr Val
145                 150                 155                 160

Asn Gln Leu Ala His Ala Leu His Gln Asp Lys Gln Leu His Ala Gly
                165                 170                 175

Ser Leu Val Ser Val Met Trp Pro Asn Ser Lys Cys Pro Leu Leu Lys
            180                 185                 190

Asp Asp Leu Val Leu Met Asp Ser Pro Gly Ile Asp Val Thr Thr Glu
        195                 200                 205

Leu Asp Ser Trp Ile Asp Lys Phe Cys Leu Asp Ala Asp Val Phe Val
    210                 215                 220

Leu Val Ala Asn Ser Glu Ser Thr Leu Met Gln Thr Glu Lys His Phe
225                 230                 235                 240

Phe His Lys Val Ser Glu Arg Leu Ser Arg Pro Asn Ile Phe Ile Leu
                245                 250                 255

Asn Asn Arg Trp Asp Ala Ser Ala Ser Glu Pro Glu Tyr Met Glu Glu
            260                 265                 270

Val Arg Arg Gln His Met Glu Arg Cys Thr Ser Phe Leu Val Asp Glu
        275                 280                 285

Leu Gly Val Val Asp Arg Ser Gln Ala Gly Asp Arg Ile Phe Phe Val
    290                 295                 300

Ser Ala Lys Glu Val Leu Asn Ala Arg Ile Gln Lys Ala Gln Gly Met
305                 310                 315                 320

Pro Glu Gly Gly Gly Ala Leu Ala Glu Gly Phe Gln Val Arg Met Phe
                325                 330                 335
```

```
Glu Phe Gln Asn Phe Glu Arg Arg Phe Glu Cys Ile Ser Gln Ser
                340                 345                 350

Ala Val Lys Thr Lys Phe Glu Gln His Thr Val Arg Ala Lys Gln Ile
            355                 360                 365

Ala Glu Ala Val Arg Leu Ile Met Asp Ser Leu His Met Ala Ala Arg
        370                 375                 380

Glu Gln Gln Val Tyr Cys Glu Glu Met Arg Glu Glu Arg Gln Asp Arg
385                 390                 395                 400

Leu Lys Phe Ile Asp Lys Gln Leu Glu Leu Leu Ala Gln Asp Tyr Lys
                405                 410                 415

Leu Arg Ile Lys Gln Ile Thr Glu Glu Val Arg Gln Val Ser Thr
            420                 425                 430

Ala Met Ala Glu Glu Ile Arg Arg Leu Ser Val Leu Val Asp Asp Tyr
        435                 440                 445

Gln Met Asp Phe His Pro Ser Pro Val Val Leu Lys Val Tyr Lys Asn
    450                 455                 460

Glu Leu His Arg His Ile Glu Glu Gly Leu Gly Arg Asn Met Ser Asp
465                 470                 475                 480

Arg Cys Ser Thr Ala Ile Thr Asn Ser Leu Gln Thr Met Gln Gln Asp
                485                 490                 495

Met Ile Asp Gly Leu Lys Pro Leu Leu Pro Val Ser Val Arg Ser Gln
            500                 505                 510

Ile Asp Met Leu Val Pro Arg Gln Cys Phe Ser Leu Asn Tyr Asp Leu
        515                 520                 525

Asn Cys Asp Lys Leu Cys Ala Asp Phe Gln Glu Asp Ile Glu Phe His
    530                 535                 540

Phe Ser Leu Gly Trp Thr Met Leu Val Asn Arg Phe Leu Gly Pro Lys
545                 550                 555                 560

Asn Ser Arg Arg Ala Leu Met Gly Tyr Asn Asp Gln Val Gln Arg Pro
                565                 570                 575

Ile Pro Leu Thr Pro Ala Asn Pro Ser Met Pro Pro Leu Pro Gln Gly
            580                 585                 590

Ser Leu Thr Gln Glu Glu Phe Met Val Ser Met Val Thr Gly Leu Ala
        595                 600                 605

Ser Leu Thr Ser Arg Thr Ser Met Gly Ile Leu Val Val Gly Gly Val
    610                 615                 620

Val Trp Lys Ala Val Gly Trp Arg Leu Ile Ala Leu Ser Phe Gly Leu
625                 630                 635                 640

Tyr Gly Leu Leu Tyr Val Tyr Glu Arg Leu Thr Trp Thr Thr Lys Ala
                645                 650                 655

Lys Glu Arg Ala Phe Lys Arg Gln Phe Val Glu His Ala Ser Glu Lys
            660                 665                 670

Leu Gln Leu Val Ile Ser Tyr Thr Gly Ser Asn Cys Ser His Gln Val
        675                 680                 685

Gln Gln Glu Leu Ser Gly Thr Phe Ala His Leu Cys Gln Gln Val Asp
    690                 695                 700

Val Thr Arg Glu Asn Leu Glu Gln Glu Ile Ala Ala Met Asn Lys Lys
705                 710                 715                 720

Ile Glu Val Leu Asp Ser Leu Gln Ser Lys Ala Lys Leu Leu Arg Asn
                725                 730                 735

Lys Ala Gly Trp Leu Asp Ser Glu Leu Asn Met Phe Thr His Gln Tyr
            740                 745                 750
```

```
Leu Gln Pro Ser Arg
        755

<210> SEQ ID NO 111
<211> LENGTH: 736
<212> TYPE: PRT
<213> ORGANISM: Homo sapiens

<400> SEQUENCE: 111

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60

Leu Gln Leu Val His Val Ser Gln Glu Asp Lys Arg Lys Thr Thr Gly
65                  70                  75                  80

Glu Glu Asn Gly Val Glu Ala Glu Glu Trp Gly Lys Phe Leu His Thr
                85                  90                  95

Lys Asn Lys Leu Tyr Thr Asp Phe Asp Glu Ile Arg Gln Glu Ile Glu
            100                 105                 110

Asn Glu Thr Glu Arg Ile Ser Gly Asn Lys Gly Val Ser Pro Glu
        115                 120                 125

Pro Ile His Leu Lys Ile Phe Ser Pro Asn Val Val Asn Leu Thr Leu
    130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
            180                 185                 190

Thr Ser Glu Ala Leu Lys Ile Ser Arg Glu Val Asp Pro Asp Gly Arg
        195                 200                 205

Arg Thr Leu Ala Val Ile Thr Lys Leu Asp Leu Met Asp Ala Gly Thr
    210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
            260                 265                 270

Tyr Pro Ser Leu Ala Asn Arg Asn Gly Thr Lys Tyr Leu Ala Arg Thr
        275                 280                 285

Leu Asn Arg Leu Leu Met His His Ile Arg Asp Cys Leu Pro Glu Leu
    290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
                325                 330                 335

Ile Thr Lys Phe Ala Thr Glu Tyr Cys Asn Thr Ile Glu Gly Thr Ala
            340                 345                 350

Lys Tyr Ile Glu Thr Ser Glu Leu Cys Gly Gly Ala Arg Ile Cys Tyr
        355                 360                 365
```

Ile Phe His Glu Thr Phe Gly Arg Thr Leu Glu Ser Val Asp Pro Leu
        370                 375                 380
Gly Gly Leu Asn Thr Ile Asp Ile Leu Thr Ala Ile Arg Asn Ala Thr
385                 390                 395                 400
Gly Pro Arg Pro Ala Leu Phe Val Pro Glu Val Ser Phe Glu Leu Leu
                405                 410                 415
Val Lys Arg Gln Ile Lys Arg Leu Glu Glu Pro Ser Leu Arg Cys Val
            420                 425                 430
Glu Leu Val His Glu Glu Met Gln Arg Ile Ile Gln His Cys Ser Asn
        435                 440                 445
Tyr Ser Thr Gln Glu Leu Leu Arg Phe Pro Lys Leu His Asp Ala Ile
    450                 455                 460
Val Glu Val Val Thr Cys Leu Leu Arg Lys Arg Leu Pro Val Thr Asn
465                 470                 475                 480
Glu Met Val His Asn Leu Val Ala Ile Glu Leu Ala Tyr Ile Asn Thr
                485                 490                 495
Lys His Pro Asp Phe Ala Asp Ala Cys Gly Leu Met Asn Asn Asn Ile
            500                 505                 510
Glu Glu Gln Arg Arg Asn Arg Leu Ala Arg Glu Leu Pro Ser Ala Val
        515                 520                 525
Ser Arg Asp Lys Ser Ser Lys Val Pro Ser Ala Leu Ala Pro Ala Ser
    530                 535                 540
Gln Glu Pro Ser Pro Ala Ala Ser Ala Glu Ala Asp Gly Lys Leu Ile
545                 550                 555                 560
Gln Asp Ser Arg Arg Glu Thr Lys Asn Val Ala Ser Gly Gly Gly Gly
                565                 570                 575
Val Gly Asp Gly Val Gln Glu Pro Thr Thr Gly Asn Trp Arg Gly Met
            580                 585                 590
Leu Lys Thr Ser Lys Ala Glu Glu Leu Leu Ala Glu Glu Lys Ser Lys
        595                 600                 605
Pro Ile Pro Ile Met Pro Ala Ser Pro Gln Lys Gly His Ala Val Asn
    610                 615                 620
Leu Leu Asp Val Pro Val Pro Val Ala Arg Lys Leu Ser Ala Arg Glu
625                 630                 635                 640
Gln Arg Asp Cys Glu Val Ile Glu Arg Leu Ile Lys Ser Tyr Phe Leu
                645                 650                 655
Ile Val Arg Lys Asn Ile Gln Asp Ser Val Pro Lys Ala Val Met His
            660                 665                 670
Phe Leu Val Asn His Val Lys Asp Thr Leu Gln Ser Glu Leu Val Gly
        675                 680                 685
Gln Leu Tyr Lys Ser Ser Leu Leu Asp Asp Leu Leu Thr Glu Ser Glu
    690                 695                 700
Asp Met Ala Gln Arg Arg Lys Glu Ala Ala Asp Met Leu Lys Ala Leu
705                 710                 715                 720
Gln Gly Ala Ser Gln Ile Ile Ala Glu Ile Arg Glu Thr His Leu Trp
                725                 730                 735

<210> SEQ ID NO 112
<211> LENGTH: 415
<212> TYPE: PRT
<213> ORGANISM: Homo sapiens

<400> SEQUENCE: 112

Met Arg Ile Pro Val Asp Pro Ser Thr Ser Arg Arg Phe Thr Pro Pro

```
            1               5                    10                        15
        Ser Pro Ala Phe Pro Cys Gly Gly Gly Gly Lys Met Gly Glu Asn
                        20                      25                    30

Ser Gly Ala Leu Ser Ala Gln Ala Ala Val Gly Pro Gly Arg Ala
                        35                      40                    45

Arg Pro Glu Val Arg Ser Met Val Asp Val Leu Ala Asp His Ala Gly
                    50                      55                    60

Glu Leu Val Arg Thr Asp Ser Pro Asn Phe Leu Cys Ser Val Leu Pro
        65                      70                      75                    80

Ser His Trp Arg Cys Asn Lys Thr Leu Pro Val Ala Phe Lys Val Val
                            85                      90                    95

Ala Leu Gly Asp Val Pro Asp Gly Thr Val Thr Val Met Ala Gly
                        100                     105                   110

Asn Asp Glu Asn Tyr Ser Ala Glu Leu Arg Asn Ala Ser Ala Val Met
                        115                     120                   125

Lys Asn Gln Val Ala Arg Phe Asn Asp Leu Arg Phe Val Gly Arg Ser
                    130                     135                   140

Gly Arg Gly Lys Ser Phe Thr Leu Thr Ile Thr Val Phe Thr Asn Pro
        145                     150                     155                   160

Thr Gln Val Ala Thr Tyr His Arg Ala Ile Lys Val Thr Val Asp Gly
                            165                     170                   175

Pro Arg Glu Pro Arg Arg His Arg Gln Lys Leu Glu Asp Gln Thr Lys
                        180                     185                   190

Pro Phe Pro Asp Arg Phe Gly Asp Leu Glu Arg Leu Arg Met Arg Val
                        195                     200                   205

Thr Pro Ser Thr Pro Ser Pro Arg Gly Ser Leu Ser Thr Thr Ser His
                    210                     215                   220

Phe Ser Ser Gln Pro Gln Thr Pro Ile Gln Gly Thr Ser Glu Leu Asn
        225                     230                     235                   240

Pro Phe Ser Asp Pro Arg Gln Phe Asp Arg Ser Phe Pro Thr Leu Pro
                        245                     250                   255

Thr Leu Thr Glu Ser Arg Phe Pro Asp Pro Arg Met His Tyr Pro Gly
                        260                     265                   270

Ala Met Ser Ala Ala Phe Pro Tyr Ser Ala Thr Pro Ser Gly Thr Ser
                    275                     280                   285

Ile Ser Ser Leu Ser Val Ala Gly Met Pro Ala Thr Ser Arg Phe His
        290                     295                     300

His Thr Tyr Leu Pro Pro Pro Tyr Pro Gly Ala Pro Gln Asn Gln Ser
        305                     310                     315                   320

Gly Pro Phe Gln Ala Asn Pro Ser Pro Tyr His Leu Tyr Tyr Gly Thr
                    325                     330                   335

Ser Ser Gly Ser Tyr Gln Phe Ser Met Val Ala Gly Ser Ser Gly
                        340                     345                   350

Gly Asp Arg Ser Pro Thr Arg Met Leu Ala Ser Cys Thr Ser Ser Ala
                    355                     360                   365

Ala Ser Val Ala Ala Gly Asn Leu Met Asn Pro Ser Leu Gly Gly Gln
                370                     375                     380

Ser Asp Gly Val Glu Ala Asp Gly Ser His Ser Asn Ser Pro Thr Ala
        385                     390                     395                   400

Leu Ser Thr Pro Gly Arg Met Asp Glu Ala Val Trp Arg Pro Tyr
                        405                     410                   415

<210> SEQ ID NO 113
```

```
<211> LENGTH: 686
<212> TYPE: PRT
<213> ORGANISM: Homo sapiens

<400> SEQUENCE: 113
```

| Met<br>1 | Gln | Leu | Gly | Glu<br>5 | Gln | Leu | Leu | Val | Ser<br>10 | Ser | Val | Asn | Leu | Pro<br>15 | Gly |
|---|---|---|---|---|---|---|---|---|---|---|---|---|---|---|---|
| Ala | His | Phe | Tyr<br>20 | Pro | Leu | Glu | Ser<br>25 | Ala | Arg | Gly | Gly<br>30 | Ser | Gly | Gly | Ser |
| Ala | Gly | His<br>35 | Leu | Pro | Ser | Ala<br>40 | Pro | Ser | Pro | Gln<br>45 | Lys | Leu | Asp | Leu |
| Asp<br>50 | Lys | Ala | Ser | Lys<br>55 | Lys | Phe | Ser | Gly | Ser<br>60 | Leu | Ser | Cys | Glu | Ala | Val |
| Ser<br>65 | Gly | Glu | Pro | Ala<br>70 | Ala | Ser | Ala | Gly<br>75 | Ala | Pro | Ala | Ala | Met<br>80 | Leu |
| Ser | Asp | Thr | Asp<br>85 | Ala | Gly | Asp | Ala<br>90 | Phe | Ala | Ser | Ala | Ala<br>95 | Val | Ala |
| Lys | Pro<br>100 | Gly | Pro | Pro | Asp<br>105 | Gly | Arg | Lys | Gly<br>110 | Ser | Pro | Cys | Gly | Glu | Glu |
| Glu | Leu | Pro<br>115 | Ser | Ala | Ala | Ala<br>120 | Ala | Ala | Ala | Ala<br>125 | Ala | Ala | Ala | Ala |
| Ala | Ala<br>130 | Thr | Ala | Arg | Tyr<br>135 | Ser | Met | Asp | Ser | Leu<br>140 | Ser | Ser | Glu | Arg | Tyr |
| Tyr<br>145 | Leu | Gln | Ser | Pro<br>150 | Gly | Pro | Gln | Gly | Ser<br>155 | Glu | Leu | Ala | Ala | Pro<br>160 | Cys |
| Ser | Leu | Phe | Pro<br>165 | Tyr | Gln | Ala | Ala<br>170 | Ala | Gly | Ala | Pro | His<br>175 | Gly | Pro | Val |
| Tyr | Pro<br>180 | Ala | Pro | Asn | Gly<br>185 | Ala | Arg | Tyr | Pro<br>190 | Tyr | Gly | Ser | Met | Leu<br>| Pro |
| Pro | Gly<br>195 | Gly | Phe | Pro | Ala<br>200 | Ala | Val | Cys | Pro<br>205 | Pro | Gly | Arg | Ala | Gln | Phe |
| Gly<br>210 | Pro | Gly | Ala | Gly<br>215 | Ala | Gly | Ser | Gly<br>220 | Ala | Gly | Ser | Ser | Gly | Gly |
| Gly<br>225 | Gly | Gly | Pro | Gly<br>230 | Thr | Tyr | Gln | Tyr<br>235 | Ser | Gln | Gly | Ala | Pro<br>240 | Leu | Tyr |
| Gly | Pro | Tyr<br>245 | Pro | Gly | Ala | Ala<br>250 | Ala | Ala | Gly | Ser | Cys<br>255 | Gly | Gly | Leu | Gly |
| Gly | Leu<br>260 | Gly | Val | Pro | Gly<br>265 | Ser | Gly | Phe | Arg<br>270 | Ala | His | Val | Tyr | Leu | Cys |
| Asn | Arg<br>275 | Pro | Leu | Trp | Leu<br>280 | Lys | Phe | His | Arg<br>285 | His | Gln | Thr | Glu | Met | Ile |
| Ile<br>290 | Thr | Lys | Gln | Gly<br>295 | Arg | Arg | Met | Phe<br>300 | Pro | Phe | Leu | Ser | Phe | Asn | Ile |
| Asn<br>305 | Gly | Leu | Asn | Pro<br>310 | Thr | Ala | His | Tyr<br>315 | Asn | Val | Phe | Val | Glu<br>320 | Val | Val |
| Leu | Ala | Asp<br>325 | Pro | Asn | His | Trp<br>330 | Arg | Phe | Gln | Gly | Gly<br>335 | Lys | Trp | Val | Thr |
| Cys | Gly<br>340 | Lys | Ala | Asp | Asn<br>345 | Asn | Met | Gln | Gly<br>350 | Asn | Lys | Met | Tyr | Val | His |
| Pro | Glu | Ser<br>355 | Pro | Asn | Thr | Gly<br>360 | Ser | His | Trp | Met<br>365 | Arg | Gln | Glu | Ile | Ser |
| Phe | Gly<br>370 | Lys | Leu | Lys | Leu<br>375 | Thr | Asn | Asn | Lys<br>380 | Gly | Ala | Asn | Asn | Asn | Asn |
| Thr | Gln | Met | Ile | Val | Leu | Gln | Ser | Leu | His | Lys | Tyr | Gln | Pro | Arg | Leu |

```
                385                 390                 395                 400
His Ile Val Glu Val Thr Glu Asp Gly Val Glu Asp Leu Asn Glu Pro
                    405                 410                 415

Ser Lys Thr Gln Thr Phe Thr Phe Ser Glu Thr Gln Phe Ile Ala Val
                    420                 425                 430

Thr Ala Tyr Gln Asn Thr Asp Ile Thr Gln Leu Lys Ile Asp His Asn
                    435                 440                 445

Pro Phe Ala Lys Gly Phe Arg Asp Asn Tyr Asp Ser Ser His Gln Ile
            450                 455                 460

Val Pro Gly Gly Arg Tyr Gly Val Gln Ser Phe Phe Pro Glu Pro Phe
465                 470                 475                 480

Val Asn Thr Leu Pro Gln Ala Arg Tyr Tyr Asn Gly Glu Arg Thr Val
                        485                 490                 495

Pro Gln Thr Asn Gly Leu Leu Ser Pro Gln Ser Glu Glu Val Ala
                500                 505                 510

Asn Pro Pro Gln Arg Trp Leu Val Thr Pro Val Gln Gln Pro Gly Thr
                515                 520                 525

Asn Lys Leu Asp Ile Ser Ser Tyr Glu Ser Glu Tyr Thr Ser Ser Thr
            530                 535                 540

Leu Leu Pro Tyr Gly Ile Lys Ser Leu Pro Leu Gln Thr Ser His Ala
545                 550                 555                 560

Leu Gly Tyr Tyr Pro Asp Pro Thr Phe Pro Ala Met Ala Gly Trp Gly
                565                 570                 575

Gly Arg Gly Ser Tyr Gln Arg Lys Met Ala Ala Gly Leu Pro Trp Thr
                580                 585                 590

Ser Arg Thr Ser Pro Thr Val Phe Ser Glu Asp Gln Leu Ser Lys Glu
            595                 600                 605

Lys Val Lys Glu Glu Ile Gly Ser Ser Trp Ile Glu Thr Pro Pro Ser
610                 615                 620

Ile Lys Ser Leu Asp Ser Asn Asp Ser Gly Val Tyr Thr Ser Ala Cys
625                 630                 635                 640

Lys Arg Arg Arg Leu Ser Pro Ser Asn Ser Ser Asn Glu Asn Ser Pro
                        645                 650                 655

Ser Ile Lys Cys Glu Asp Ile Asn Ala Glu Glu Tyr Ser Lys Asp Thr
                660                 665                 670

Ser Lys Gly Met Gly Gly Tyr Tyr Ala Phe Tyr Thr Thr Pro
            675                 680                 685

<210> SEQ ID NO 114
<211> LENGTH: 586
<212> TYPE: PRT
<213> ORGANISM: Artificial Sequence
<220> FEATURE:
<223> OTHER INFORMATION: Synthesized

<400> SEQUENCE: 114

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
                20                  25                  30

Asn Thr Glu Val His Ser Ser Pro Ala Gln Arg Trp Ser Met Gln Val
            35                  40                  45

Pro Pro Glu Val Ser Ala Glu Ala Gly Asp Ala Ala Val Leu Pro Cys
        50                  55                  60

Thr Phe Thr His Pro His Arg His Tyr Asp Gly Pro Leu Thr Ala Ile
```

```
               65                  70                  75                  80
Trp Arg Ala Gly Glu Pro Tyr Ala Gly Pro Gln Val Phe Arg Cys Ala
                    85                  90                  95
Ala Ala Arg Gly Ser Glu Leu Cys Gln Thr Ala Leu Ser Leu His Gly
                   100                 105                 110
Arg Phe Arg Leu Leu Gly Asn Pro Arg Arg Asn Asp Leu Ser Leu Arg
                   115                 120                 125
Val Glu Arg Leu Ala Leu Ala Asp Asp Arg Arg Tyr Phe Cys Arg Val
        130                 135                 140
Glu Phe Ala Gly Asp Val His Asp Arg Tyr Glu Ser Arg His Gly Val
145                 150                 155                 160
Arg Leu His Val Thr Ala Ala Pro Arg Ile Val Asn Ile Ser Val Leu
                    165                 170                 175
Pro Ser Pro Ala His Ala Phe Arg Ala Leu Cys Thr Ala Glu Gly Glu
            180                 185                 190
Pro Pro Pro Ala Leu Ala Trp Ser Gly Pro Ala Leu Gly Asn Ser Leu
        195                 200                 205
Ala Ala Val Arg Ser Pro Arg Glu Gly His Gly His Leu Val Thr Ala
210                 215                 220
Glu Leu Pro Ala Leu Thr His Asp Gly Arg Tyr Thr Cys Thr Ala Ala
225                 230                 235                 240
Asn Ser Leu Gly Arg Ser Glu Ala Ser Val Tyr Leu Phe Arg Phe His
                245                 250                 255
Gly Ala Ser Gly Ala Ser Thr Val Ala Leu Leu Leu Gly Ala Leu Gly
            260                 265                 270
Phe Lys Ala Leu Leu Leu Leu Gly Val Leu Ala Ala Arg Ala Ala Arg
        275                 280                 285
Arg Arg Pro Glu His Leu Asp Thr Pro Asp Thr Pro Pro Arg Ser Gln
    290                 295                 300
Ala Gln Glu Ser Asn Tyr Glu Asn Leu Ser Gln Met Asn Pro Arg Ser
305                 310                 315                 320
Pro Pro Ala Thr Met Cys Ser Pro Ala Thr Asn Phe Ser Leu Leu Lys
                325                 330                 335
Gln Ala Gly Asp Val Glu Glu Asn Pro Gly Pro Met Val Ser Lys Gly
            340                 345                 350
Glu Glu Leu Phe Thr Gly Val Val Pro Ile Leu Val Glu Leu Asp Gly
        355                 360                 365
Asp Val Asn Gly His Lys Phe Ser Val Ser Gly Glu Gly Glu Gly Asp
    370                 375                 380
Ala Thr Tyr Gly Lys Leu Thr Leu Lys Phe Ile Cys Thr Thr Gly Lys
385                 390                 395                 400
Leu Pro Val Pro Trp Pro Thr Leu Val Thr Thr Leu Thr Tyr Gly Val
                405                 410                 415
Gln Cys Phe Ser Arg Tyr Pro Asp His Met Lys Gln His Asp Phe Phe
            420                 425                 430
Lys Ser Ala Met Pro Glu Gly Tyr Val Gln Glu Arg Thr Ile Phe Phe
        435                 440                 445
Lys Asp Asp Gly Asn Tyr Lys Thr Arg Ala Glu Val Lys Phe Glu Gly
    450                 455                 460
Asp Thr Leu Val Asn Arg Ile Glu Leu Lys Gly Ile Asp Phe Lys Glu
465                 470                 475                 480
Asp Gly Asn Ile Leu Gly His Lys Leu Glu Tyr Asn Tyr Asn Ser His
                485                 490                 495
```

```
Asn Val Tyr Ile Met Ala Asp Lys Gln Lys Asn Gly Ile Lys Val Asn
                500                 505                 510

Phe Lys Ile Arg His Asn Ile Glu Asp Gly Ser Val Gln Leu Ala Asp
            515                 520                 525

His Tyr Gln Gln Asn Thr Pro Ile Gly Asp Gly Pro Val Leu Leu Pro
        530                 535                 540

Asp Asn His Tyr Leu Ser Thr Gln Ser Ala Leu Ser Lys Asp Pro Asn
545                 550                 555                 560

Glu Lys Arg Asp His Met Val Leu Leu Glu Phe Val Thr Ala Ala Gly
                565                 570                 575

Ile Thr Leu Gly Met Asp Glu Leu Tyr Lys
            580                 585

<210> SEQ ID NO 115
<211> LENGTH: 276
<212> TYPE: PRT
<213> ORGANISM: Artificial Sequence
<220> FEATURE:
<223> OTHER INFORMATION: Synthesized

<400> SEQUENCE: 115

Met Glu Thr Pro Ala Gln Leu Leu Phe Leu Leu Leu Leu Trp Leu Pro
1               5                   10                  15

Asp Thr Thr Gly Glu Ile Gln Leu Gln Gln Ser Gly Ala Glu Val Lys
            20                  25                  30

Lys Pro Gly Ser Ser Val Lys Val Ser Cys Ala Lys Ser Gly Tyr Thr
        35                  40                  45

Phe Thr Asp Tyr Asp Met His Trp Val Arg Gln Ala Pro Gly Gln Gly
    50                  55                  60

Leu Glu Trp Met Gly Thr Ile Asp Pro Glu Thr Gly Gly Thr Ala Tyr
65                  70                  75                  80

Asn Gln Lys Phe Lys Gly Arg Val Thr Ile Thr Ala Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Thr Ser Phe Tyr Thr Tyr Ser Asn Tyr Asp Val
        115                 120                 125

Gly Phe Ala Tyr Trp Gly Gln Gly Thr Leu Val Thr Val Ser Ser Gly
    130                 135                 140

Gly Gly Gly Ser Gly Gly Gly Ser Gly Gly Gly Gly Ser Asp Ile
145                 150                 155                 160

Val Met Thr Gln Ser Pro Leu Ser Leu Pro Val Thr Pro Gly Glu Pro
                165                 170                 175

Ala Ser Ile Ser Cys Arg Ser Thr Lys Ser Leu Leu His Ser Asn Gly
            180                 185                 190

Asn Thr Tyr Leu Tyr Trp Tyr Leu Gln Lys Pro Gly Gln Ser Pro Gln
        195                 200                 205

Leu Leu Ile Tyr Arg Met Ser Asn Leu Ala Ser Gly Val Pro Asp Arg
    210                 215                 220

Phe Ser Gly Ser Gly Ser Gly Thr Asp Phe Thr Leu Lys Ile Ser Arg
225                 230                 235                 240

Val Glu Ala Glu Asp Val Gly Val Tyr Tyr Cys Met Gln His Leu Glu
                245                 250                 255

Tyr Pro Phe Thr Phe Gly Gly Gly Thr Lys Val Glu Ile Lys His His
            260                 265                 270
```

His His His His
        275

<210> SEQ ID NO 116
<211> LENGTH: 271
<212> TYPE: PRT
<213> ORGANISM: Artificial Sequence
<220> FEATURE:
<223> OTHER INFORMATION: Synthesized

<400> SEQUENCE: 116

Met Glu Thr Pro Ala Gln Leu Leu Phe Leu Leu Leu Trp Leu Pro
1               5                   10                  15

Asp Thr Thr Gly Gln Val Gln Leu Gln Gln Ser Gly Ala Glu Val Lys
                20                  25                  30

Lys Pro Gly Ser Ser Val Lys Val Ser Cys Lys Ala Ser Gly Tyr Thr
            35                  40                  45

Phe Thr Ser Tyr Trp Met His Trp Val Arg Gln Ala Pro Gly Gln Gly
        50                  55                  60

Leu Glu Trp Met Gly Leu Ile Asn Pro Ser Asn Ala Arg Thr Asn Tyr
65                  70                  75                  80

Asn Glu Lys Phe Asn Thr Arg Val Thr Ile Thr Ala Asp Lys Ser Thr
                85                  90                  95

Ser Thr Ala Tyr Met Glu Leu Ser Ser Leu Arg Ser Glu Asp Thr Ala
            100                 105                 110

Val Tyr Tyr Cys Ala Arg Gly Gly Asp Gly Asp Tyr Phe Asp Tyr Trp
        115                 120                 125

Gly Gln Gly Thr Thr Val Thr Val Ser Ser Gly Gly Gly Ser Gly
    130                 135                 140

Gly Gly Gly Ser Gly Gly Gly Ser Asp Ile Val Met Thr Ala Thr
145                 150                 155                 160

Pro Leu Ser Leu Pro Val Thr Pro Glu Gly Pro Ala Ser Ile Ser Cys
                165                 170                 175

Arg Ser Ser Lys Ser Leu Leu His Ser Asn Gly Ile Thr Tyr Leu Tyr
            180                 185                 190

Trp Tyr Leu Gln Lys Pro Gly Gln Ser Pro Gln Leu Leu Ile Tyr Gln
        195                 200                 205

Met Ser Asn Leu Ala Ser Gly Val Pro Asp Arg Phe Ser Gly Ser Gly
    210                 215                 220

Ser Gly Thr Asp Phe Thr Leu Lys Ile Ser Arg Val Glu Ala Glu Asp
225                 230                 235                 240

Val Gly Val Tyr Tyr Cys Ala Gln Asn Leu Glu Leu Pro Tyr Thr Phe
                245                 250                 255

Gly Gly Gly Thr Lys Val Glu Ile Lys His His His His His His
            260                 265                 270

<210> SEQ ID NO 117
<211> LENGTH: 710
<212> TYPE: PRT
<213> ORGANISM: Homo sapiens

<400> SEQUENCE: 117

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Gly
                20                  25                  30

Thr Gln Ser Ser Gly Lys Ser Ser Val Leu Glu Ser Leu Val Gly Arg
                35                  40                  45

Asp Leu Leu Pro Arg Gly Thr Gly Ile Val Thr Arg Arg Pro Leu Ile
 50                  55                  60

Leu Gln Leu Val His Val Ser Gln Glu Asp Lys Arg Lys Thr Thr Gly
 65                  70                  75                  80

Glu Glu Asn Gly Val Glu Ala Glu Trp Gly Lys Phe Leu His Thr
                85                  90                  95

Lys Asn Lys Leu Tyr Thr Asp Phe Asp Glu Ile Arg Gln Glu Ile Glu
                100                 105                 110

Asn Glu Thr Glu Arg Ile Ser Gly Asn Asn Lys Gly Val Ser Pro Glu
                115                 120                 125

Pro Ile His Leu Lys Ile Phe Ser Pro Asn Val Val Asn Leu Thr Leu
                130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
                180                 185                 190

Thr Ser Glu Ala Leu Lys Ile Ser Arg Glu Val Asp Pro Asp Gly Arg
                195                 200                 205

Arg Thr Leu Ala Val Ile Thr Lys Leu Asp Leu Met Asp Ala Gly Thr
                210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
                260                 265                 270

Tyr Pro Ser Leu Ala Asn Arg Asn Gly Thr Lys Tyr Leu Ala Arg Thr
                275                 280                 285

Leu Asn Arg Leu Leu Met His His Ile Arg Asp Cys Leu Pro Glu Leu
                290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
                325                 330                 335

Ile Thr Lys Phe Ala Thr Glu Tyr Cys Asn Thr Ile Glu Gly Thr Ala
                340                 345                 350

Lys Tyr Ile Glu Thr Ser Glu Leu Cys Gly Gly Ala Arg Ile Cys Tyr
                355                 360                 365

Ile Phe His Glu Thr Phe Gly Arg Thr Leu Glu Ser Val Asp Pro Leu
                370                 375                 380

Gly Gly Leu Asn Thr Ile Asp Ile Leu Thr Asp Ile Arg Asn Ala Thr
385                 390                 395                 400

Gly Pro Arg Pro Ala Leu Phe Val Pro Glu Val Ser Phe Glu Leu Leu
                405                 410                 415

Val Lys Arg Gln Ile Lys Arg Leu Glu Glu Pro Ser Leu Arg Cys Val
                420                 425                 430

Glu Leu Val His Glu Glu Met Gln Arg Ile Ile Gln His Cys Ser Asn
                435                 440                 445

Tyr Ser Thr Gln Glu Leu Leu Arg Phe Pro Lys Leu His Asp Ala Ile

```
            450                 455                 460
Val Glu Val Val Thr Cys Leu Leu Arg Lys Arg Leu Pro Val Thr Asn
465                 470                 475                 480

Glu Met Val His Asn Leu Val Ala Ile Glu Leu Ala Tyr Ile Asn Thr
                485                 490                 495

Lys His Pro Asp Phe Ala Asp Ala Cys Gly Leu Met Asn Asn Asn Ile
            500                 505                 510

Glu Glu Gln Arg Arg Asn Arg Leu Ala Arg Glu Leu Pro Ser Ala Val
        515                 520                 525

Ser Arg Asp Lys Leu Ile Gln Asp Ser Arg Arg Glu Thr Lys Asn Val
530                 535                 540

Ala Ser Gly Gly Gly Val Gly Asp Gly Val Gln Glu Pro Thr Thr
545                 550                 555                 560

Gly Asn Trp Arg Gly Met Leu Lys Thr Ser Lys Ala Glu Glu Leu Leu
                565                 570                 575

Ala Glu Glu Lys Ser Lys Pro Ile Pro Ile Met Pro Ala Ser Pro Gln
            580                 585                 590

Lys Gly His Ala Val Asn Leu Leu Asp Val Pro Val Pro Val Ala Arg
        595                 600                 605

Lys Leu Ser Ala Arg Glu Gln Arg Asp Cys Glu Val Ile Glu Arg Leu
        610                 615                 620

Ile Lys Ser Tyr Phe Leu Ile Val Arg Lys Asn Ile Gln Asp Ser Val
625                 630                 635                 640

Pro Lys Ala Val Met His Phe Leu Val Asn His Val Lys Asp Thr Leu
                645                 650                 655

Gln Ser Glu Leu Val Gly Gln Leu Tyr Lys Ser Ser Leu Leu Asp Asp
            660                 665                 670

Leu Leu Thr Glu Ser Glu Asp Met Ala Gln Arg Lys Glu Ala Ala
        675                 680                 685

Asp Met Leu Lys Ala Leu Gln Gly Ala Ser Gln Ile Ile Ala Glu Ile
        690                 695                 700

Arg Glu Thr His Leu Trp
705                 710

<210> SEQ ID NO 118
<211> LENGTH: 1215
<212> TYPE: PRT
<213> ORGANISM: Artificial Sequence
<220> FEATURE:
<223> OTHER INFORMATION: Synthesized

<400> SEQUENCE: 118

Met Ala Leu Pro Val Thr Ala Leu Leu Leu Pro Leu Ala Leu Leu Leu
1               5                   10                  15

His Ala Ala Arg Pro Asp Ile Gln Met Thr Gln Thr Thr Ser Ser Leu
                20                  25                  30

Ser Ala Ser Leu Gly Asp Arg Val Thr Ile Ser Cys Arg Ala Ser Gln
            35                  40                  45

Asp Ile Ser Lys Tyr Leu Asn Trp Tyr Gln Gln Lys Pro Asp Gly Thr
        50                  55                  60

Val Lys Leu Leu Ile Tyr His Thr Ser Arg Leu His Ser Gly Val Pro
65                  70                  75                  80

Ser Arg Phe Ser Gly Ser Gly Ser Gly Thr Asp Tyr Ser Leu Thr Ile
                85                  90                  95

Ser Asn Leu Glu Gln Glu Asp Ile Ala Thr Tyr Phe Cys Gln Gln Gly
```

```
                  100                 105                 110
Asn Thr Leu Pro Tyr Thr Phe Gly Gly Gly Thr Lys Leu Glu Ile Thr
            115                 120                 125
Gly Gly Gly Gly Ser Gly Gly Gly Ser Gly Gly Gly Ser Glu
            130                 135             140
Val Lys Leu Gln Glu Ser Gly Pro Gly Leu Val Ala Pro Ser Gln Ser
145                 150                 155                 160
Leu Ser Val Thr Cys Thr Val Ser Gly Val Ser Leu Pro Asp Tyr Gly
                165                 170                 175
Val Ser Trp Ile Arg Gln Pro Pro Arg Lys Gly Leu Glu Trp Leu Gly
                180                 185                 190
Val Ile Trp Gly Ser Glu Thr Thr Tyr Tyr Asn Ser Ala Leu Lys Ser
            195                 200                 205
Arg Leu Thr Ile Ile Lys Asp Asn Ser Lys Ser Gln Val Phe Leu Lys
            210                 215                 220
Met Asn Ser Leu Gln Thr Asp Asp Thr Ala Ile Tyr Tyr Cys Ala Lys
225                 230                 235                 240
His Tyr Tyr Tyr Gly Gly Ser Tyr Ala Met Asp Tyr Trp Gly Gln Gly
                245                 250                 255
Thr Ser Val Thr Val Ser Ser Lys Ile Glu Val Met Tyr Pro Pro Pro
                260                 265                 270
Tyr Leu Asp Asn Glu Lys Ser Asn Gly Thr Ile Ile His Val Lys Gly
                275                 280                 285
Lys His Leu Cys Pro Ser Pro Leu Phe Pro Gly Pro Ser Lys Pro Phe
            290                 295                 300
Trp Val Leu Val Val Val Gly Gly Val Leu Ala Cys Tyr Ser Leu Leu
305                 310                 315                 320
Val Thr Val Ala Phe Ile Ile Phe Trp Val Arg Ser Lys Arg Ser Arg
                325                 330                 335
Leu Leu His Ser Asp Tyr Met Asn Met Thr Pro Arg Arg Pro Gly Pro
            340                 345                 350
Thr Arg Lys His Tyr Gln Pro Tyr Ala Pro Pro Arg Asp Phe Ala Ala
            355                 360                 365
Tyr Arg Ser Arg Val Lys Phe Ser Arg Ser Ala Asp Ala Pro Ala Tyr
            370                 375                 380
Gln Gln Gly Gln Asn Gln Leu Tyr Asn Glu Leu Asn Leu Gly Arg Arg
385                 390                 395                 400
Glu Glu Tyr Asp Val Leu Asp Lys Arg Gly Arg Asp Pro Glu Met
                405                 410                 415
Gly Gly Lys Pro Arg Arg Lys Asn Pro Gln Glu Gly Leu Tyr Asn Glu
            420                 425                 430
Leu Gln Lys Asp Lys Met Ala Glu Ala Tyr Ser Glu Ile Gly Met Lys
            435                 440                 445
Gly Glu Arg Arg Arg Gly Lys Gly His Asp Gly Leu Tyr Gln Gly Leu
            450                 455                 460
Ser Thr Ala Thr Lys Asp Thr Tyr Asp Ala Leu His Met Gln Ala Leu
465                 470                 475                 480
Pro Pro Arg Gly Ser Gly Ala Thr Asn Phe Ser Leu Leu Lys Gln Ala
                485                 490                 495
Gly Asp Val Glu Glu Asn Pro Gly Pro Met Glu Ala Leu Ile Pro Val
                500                 505                 510
Ile Asn Lys Leu Gln Asp Val Phe Asn Thr Val Gly Ala Asp Ile Ile
            515                 520                 525
```

```
Gln Leu Pro Gln Ile Val Val Gly Thr Gln Ser Ser Gly Lys Ser
    530                 535                 540

Ser Val Leu Glu Ser Leu Val Gly Arg Asp Leu Leu Pro Arg Gly Thr
545                 550                 555                 560

Gly Ile Val Thr Arg Arg Pro Leu Ile Leu Gln Leu Val His Val Ser
                565                 570                 575

Gln Glu Asp Lys Arg Lys Thr Thr Gly Glu Glu Asn Gly Val Glu Ala
            580                 585                 590

Glu Glu Trp Gly Lys Phe Leu His Thr Lys Asn Lys Leu Tyr Thr Asp
        595                 600                 605

Phe Asp Glu Ile Arg Gln Glu Ile Glu Asn Glu Thr Glu Arg Ile Ser
    610                 615                 620

Gly Asn Asn Lys Gly Val Ser Pro Glu Pro Ile His Leu Lys Ile Phe
625                 630                 635                 640

Ser Pro Asn Val Val Asn Leu Thr Leu Val Asp Leu Pro Gly Met Thr
                645                 650                 655

Lys Val Pro Val Gly Asp Gln Pro Lys Asp Ile Glu Leu Gln Ile Arg
            660                 665                 670

Glu Leu Ile Leu Arg Phe Ile Ser Asn Pro Asn Ser Ile Ile Leu Ala
        675                 680                 685

Val Thr Ala Ala Asn Thr Asp Met Ala Thr Ser Glu Ala Leu Lys Ile
    690                 695                 700

Ser Arg Glu Val Asp Pro Asp Gly Arg Arg Thr Leu Ala Val Ile Thr
705                 710                 715                 720

Lys Leu Asp Leu Met Asp Ala Gly Thr Asp Ala Met Asp Val Leu Met
                725                 730                 735

Gly Arg Val Ile Pro Val Lys Leu Gly Ile Ile Gly Val Val Asn Arg
            740                 745                 750

Ser Gln Leu Asp Ile Asn Asn Lys Lys Ser Val Thr Asp Ser Ile Arg
        755                 760                 765

Asp Glu Tyr Ala Phe Leu Gln Lys Lys Tyr Pro Ser Leu Ala Asn Arg
    770                 775                 780

Asn Gly Thr Lys Tyr Leu Ala Arg Thr Leu Asn Arg Leu Leu Met His
785                 790                 795                 800

His Ile Arg Asp Cys Leu Pro Glu Leu Lys Thr Arg Ile Asn Val Leu
                805                 810                 815

Ala Ala Gln Tyr Gln Ser Leu Leu Asn Ser Tyr Gly Glu Pro Val Asp
            820                 825                 830

Asp Lys Ser Ala Thr Leu Leu Gln Leu Ile Thr Lys Phe Ala Thr Glu
        835                 840                 845

Tyr Cys Asn Thr Ile Glu Gly Thr Ala Lys Tyr Ile Glu Thr Ser Glu
    850                 855                 860

Leu Cys Gly Gly Ala Arg Ile Cys Tyr Ile Phe His Glu Thr Phe Gly
865                 870                 875                 880

Arg Thr Leu Glu Ser Val Asp Pro Leu Gly Gly Leu Asn Thr Ile Asp
                885                 890                 895

Ile Leu Thr Asp Ile Arg Asn Ala Thr Gly Pro Arg Pro Ala Leu Phe
            900                 905                 910

Val Pro Glu Val Ser Phe Glu Leu Leu Val Lys Arg Gln Ile Lys Arg
        915                 920                 925

Leu Glu Glu Pro Ser Leu Arg Cys Val Glu Leu Val His Glu Glu Met
930                 935                 940
```

Gln Arg Ile Ile Gln His Cys Ser Asn Tyr Ser Thr Gln Glu Leu Leu
945                 950                 955                 960

Arg Phe Pro Lys Leu His Asp Ala Ile Glu Val Val Thr Cys Leu
            965                 970                 975

Leu Arg Lys Arg Leu Pro Val Thr Asn Glu Met Val His Asn Leu Val
            980                 985                 990

Ala Ile Glu Leu Ala Tyr Ile Asn Thr Lys His Pro Asp Phe Ala Asp
        995                 1000                1005

Ala Cys Gly Leu Met Asn Asn Asn Ile Glu Glu Gln Arg Arg Asn
    1010                1015                1020

Arg Leu Ala Arg Glu Leu Pro Ser Ala Val Ser Arg Asp Lys Leu
    1025                1030                1035

Ile Gln Asp Ser Arg Arg Glu Thr Lys Asn Val Ala Ser Gly Gly
    1040                1045                1050

Gly Gly Val Gly Asp Gly Val Gln Glu Pro Thr Thr Gly Asn Trp
    1055                1060                1065

Arg Gly Met Leu Lys Thr Ser Lys Ala Glu Glu Leu Leu Ala Glu
    1070                1075                1080

Glu Lys Ser Lys Pro Ile Pro Ile Met Pro Ala Ser Pro Gln Lys
    1085                1090                1095

Gly His Ala Val Asn Leu Leu Asp Val Pro Val Pro Val Ala Arg
    1100                1105                1110

Lys Leu Ser Ala Arg Glu Gln Arg Asp Cys Glu Val Ile Glu Arg
    1115                1120                1125

Leu Ile Lys Ser Tyr Phe Leu Ile Val Arg Lys Asn Ile Gln Asp
    1130                1135                1140

Ser Val Pro Lys Ala Val Met His Phe Leu Val Asn His Val Lys
    1145                1150                1155

Asp Thr Leu Gln Ser Glu Leu Val Gly Gln Leu Tyr Lys Ser Ser
    1160                1165                1170

Leu Leu Asp Asp Leu Leu Thr Glu Ser Glu Asp Met Ala Gln Arg
    1175                1180                1185

Arg Lys Glu Ala Ala Asp Met Leu Lys Ala Leu Gln Gly Ala Ser
    1190                1195                1200

Gln Ile Ile Ala Glu Ile Arg Glu Thr His Leu Trp
    1205                1210                1215

<210> SEQ ID NO 119
<211> LENGTH: 1234
<212> TYPE: PRT
<213> ORGANISM: Artificial Sequence
<220> FEATURE:
<223> OTHER INFORMATION: Synthesized

<400> SEQUENCE: 119

Ala Thr Asn Phe Ser Leu Leu Lys Gln Ala Gly Asp Val Glu Glu Asn
1               5                   10                  15

Pro Gly Pro Met Ala Leu Pro Val Thr Ala Leu Leu Leu Pro Leu Ala
                20                  25                  30

Leu Leu Leu His Ala Ala Arg Pro Asp Ile Gln Met Thr Gln Thr Thr
                35                  40                  45

Ser Ser Leu Ser Ala Ser Leu Gly Asp Arg Val Thr Ile Ser Cys Arg
        50                  55                  60

Ala Ser Gln Asp Ile Ser Lys Tyr Leu Asn Trp Tyr Gln Gln Lys Pro
65                  70                  75                  80

```
Asp Gly Thr Val Lys Leu Leu Ile Tyr His Thr Ser Arg Leu His Ser
            85                  90                  95

Gly Val Pro Ser Arg Phe Ser Gly Ser Gly Ser Gly Thr Asp Tyr Ser
        100                 105                 110

Leu Thr Ile Ser Asn Leu Glu Gln Glu Asp Ile Ala Thr Tyr Phe Cys
        115                 120                 125

Gln Gln Gly Asn Thr Leu Pro Tyr Thr Phe Gly Gly Gly Thr Lys Leu
        130                 135                 140

Glu Ile Thr Gly Gly Gly Gly Ser Gly Gly Gly Gly Ser Gly Gly Gly
145                 150                 155                 160

Gly Ser Glu Val Lys Leu Gln Glu Ser Gly Pro Gly Leu Val Ala Pro
                165                 170                 175

Ser Gln Ser Leu Ser Val Thr Cys Thr Val Ser Gly Val Ser Leu Pro
        180                 185                 190

Asp Tyr Gly Val Ser Trp Ile Arg Gln Pro Pro Arg Lys Gly Leu Glu
        195                 200                 205

Trp Leu Gly Val Ile Trp Gly Ser Glu Thr Thr Tyr Tyr Asn Ser Ala
210                 215                 220

Leu Lys Ser Arg Leu Thr Ile Ile Lys Asp Asn Ser Lys Ser Gln Val
225                 230                 235                 240

Phe Leu Lys Met Asn Ser Leu Gln Thr Asp Asp Thr Ala Ile Tyr Tyr
                245                 250                 255

Cys Ala Lys His Tyr Tyr Gly Gly Ser Tyr Ala Met Asp Tyr Trp
                260                 265                 270

Gly Gln Gly Thr Ser Val Thr Val Ser Ser Lys Ile Glu Val Met Tyr
        275                 280                 285

Pro Pro Pro Tyr Leu Asp Asn Glu Lys Ser Asn Gly Thr Ile Ile His
        290                 295                 300

Val Lys Gly Lys His Leu Cys Pro Ser Pro Leu Phe Pro Gly Pro Ser
305                 310                 315                 320

Lys Pro Phe Trp Val Leu Val Val Val Gly Gly Val Leu Ala Cys Tyr
                325                 330                 335

Ser Leu Leu Val Thr Val Ala Phe Ile Ile Phe Trp Val Arg Ser Lys
        340                 345                 350

Arg Ser Arg Leu Leu His Ser Asp Tyr Met Asn Met Thr Pro Arg Arg
        355                 360                 365

Pro Gly Pro Thr Arg Lys His Tyr Gln Pro Tyr Ala Pro Pro Arg Asp
        370                 375                 380

Phe Ala Ala Tyr Arg Ser Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
                405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
            435                 440                 445

Tyr Asn Glu Leu Gln Lys Asp Lys Met Ala Glu Ala Tyr Ser Glu Ile
450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
            485                 490                 495

Gln Ala Leu Pro Pro Arg Gly Ser Gly Ala Thr Asn Phe Ser Leu Leu
```

```
              500                 505                 510
Lys Gln Ala Gly Asp Val Glu Glu Asn Pro Gly Pro Met Glu Ala Leu
            515                 520                 525

Ile Pro Val Ile Asn Lys Leu Gln Asp Val Phe Asn Thr Val Gly Ala
        530                 535                 540

Asp Ile Ile Gln Leu Pro Gln Ile Val Val Gly Thr Gln Ser Ser
545                 550                 555                 560

Gly Lys Ser Ser Val Leu Glu Ser Leu Val Gly Arg Asp Leu Leu Pro
                565                 570                 575

Arg Gly Thr Gly Ile Val Thr Arg Arg Pro Leu Ile Leu Gln Leu Val
            580                 585                 590

His Val Ser Gln Glu Asp Lys Arg Lys Thr Thr Gly Glu Glu Asn Gly
        595                 600                 605

Val Glu Ala Glu Glu Trp Gly Lys Phe Leu His Thr Lys Asn Lys Leu
    610                 615                 620

Tyr Thr Asp Phe Asp Glu Ile Arg Gln Glu Ile Glu Asn Glu Thr Glu
625                 630                 635                 640

Arg Ile Ser Gly Asn Asn Lys Gly Val Ser Pro Glu Pro Ile His Leu
                645                 650                 655

Lys Ile Phe Ser Pro Asn Val Val Asn Leu Thr Leu Val Asp Leu Pro
            660                 665                 670

Gly Met Thr Lys Val Pro Val Gly Asp Gln Pro Lys Asp Ile Glu Leu
        675                 680                 685

Gln Ile Arg Glu Leu Ile Leu Arg Phe Ile Ser Asn Pro Asn Ser Ile
    690                 695                 700

Ile Leu Ala Val Thr Ala Ala Asn Thr Asp Met Ala Thr Ser Glu Ala
705                 710                 715                 720

Leu Lys Ile Ser Arg Glu Val Asp Pro Asp Gly Arg Arg Thr Leu Ala
                725                 730                 735

Val Ile Thr Lys Leu Asp Leu Met Asp Ala Gly Thr Asp Ala Met Asp
            740                 745                 750

Val Leu Met Gly Arg Val Ile Pro Val Lys Leu Gly Ile Ile Gly Val
        755                 760                 765

Val Asn Arg Ser Gln Leu Asp Ile Asn Asn Lys Lys Ser Val Thr Asp
    770                 775                 780

Ser Ile Arg Asp Glu Tyr Ala Phe Leu Gln Lys Lys Tyr Pro Ser Leu
785                 790                 795                 800

Ala Asn Arg Asn Gly Thr Lys Tyr Leu Ala Arg Thr Leu Asn Arg Leu
                805                 810                 815

Leu Met His His Ile Arg Asp Cys Leu Pro Glu Leu Lys Thr Arg Ile
            820                 825                 830

Asn Val Leu Ala Ala Gln Tyr Gln Ser Leu Leu Asn Ser Tyr Gly Glu
        835                 840                 845

Pro Val Asp Asp Lys Ser Ala Thr Leu Leu Gln Leu Ile Thr Lys Phe
    850                 855                 860

Ala Thr Glu Tyr Cys Asn Thr Ile Glu Gly Thr Ala Lys Tyr Ile Glu
865                 870                 875                 880

Thr Ser Glu Leu Cys Gly Gly Ala Arg Ile Cys Tyr Ile Phe His Glu
                885                 890                 895

Thr Phe Gly Arg Thr Leu Glu Ser Val Asp Pro Leu Gly Gly Leu Asn
            900                 905                 910

Thr Ile Asp Ile Leu Thr Asp Ile Arg Asn Ala Thr Gly Pro Arg Pro
        915                 920                 925
```

```
Ala Leu Phe Val Pro Glu Val Ser Phe Glu Leu Leu Val Lys Arg Gln
        930                 935                 940

Ile Lys Arg Leu Glu Glu Pro Ser Leu Arg Cys Val Glu Leu Val His
945                 950                 955                 960

Glu Glu Met Gln Arg Ile Ile Gln His Cys Ser Asn Tyr Ser Thr Gln
                965                 970                 975

Glu Leu Arg Phe Pro Lys Leu His Asp Ala Ile Val Glu Val Val
            980                 985                 990

Thr Cys Leu Leu Arg Lys Arg Leu Pro Val Thr Asn Glu Met Val His
        995                 1000                1005

Asn Leu Val Ala Ile Glu Leu Ala Tyr Ile Asn Thr Lys His Pro
        1010                1015                1020

Asp Phe Ala Asp Ala Cys Gly Leu Met Asn Asn Asn Ile Glu Glu
        1025                1030                1035

Gln Arg Arg Asn Arg Leu Ala Arg Glu Leu Pro Ser Ala Val Ser
        1040                1045                1050

Arg Asp Lys Leu Ile Gln Asp Ser Arg Arg Glu Thr Lys Asn Val
        1055                1060                1065

Ala Ser Gly Gly Gly Val Gly Asp Gly Val Gln Glu Pro Thr
        1070                1075                1080

Thr Gly Asn Trp Arg Gly Met Leu Lys Thr Ser Lys Ala Glu Glu
        1085                1090                1095

Leu Leu Ala Glu Glu Lys Ser Lys Pro Ile Pro Ile Met Pro Ala
        1100                1105                1110

Ser Pro Gln Lys Gly His Ala Val Asn Leu Leu Asp Val Pro Val
        1115                1120                1125

Pro Val Ala Arg Lys Leu Ser Ala Arg Glu Gln Arg Asp Cys Glu
        1130                1135                1140

Val Ile Glu Arg Leu Ile Lys Ser Tyr Phe Leu Ile Val Arg Lys
        1145                1150                1155

Asn Ile Gln Asp Ser Val Pro Lys Ala Val Met His Phe Leu Val
        1160                1165                1170

Asn His Val Lys Asp Thr Leu Gln Ser Glu Leu Val Gly Gln Leu
        1175                1180                1185

Tyr Lys Ser Ser Leu Leu Asp Asp Leu Leu Thr Glu Ser Glu Asp
        1190                1195                1200

Met Ala Gln Arg Arg Lys Glu Ala Ala Asp Met Leu Lys Ala Leu
        1205                1210                1215

Gln Gly Ala Ser Gln Ile Ile Ala Glu Ile Arg Glu Thr His Leu
        1220                1225                1230

Trp

<210> SEQ ID NO 120
<211> LENGTH: 15
<212> TYPE: PRT
<213> ORGANISM: Artificial Sequence
<220> FEATURE:
<223> OTHER INFORMATION: Synthesized

<400> SEQUENCE: 120

Gly Gly Gly Gly Ser Gly Gly Gly Ser Gly Gly Gly Gly Ser
1               5                   10                  15
```